US012799129B2

(12) United States Patent
Wagner et al.

(10) Patent No.: US 12,799,129 B2
(45) Date of Patent: Nov. 17, 2026

(54) ISOTRYPTAMINE PSYCHOPLASTOGENS AND USES THEREOF

(71) Applicant: Delix Therapeutics, Inc., Bedford, MA (US)

(72) Inventors: Florence Wagner, Ashland, MA (US); Noel Aaron Powell, Westford, MA (US); Milan Chytil, Acton, MA (US); David E. Olson, Davis, CA (US)

(73) Assignee: DELIX THERAPEUTICS, INC., Concord, MA (US)

( * ) Notice: Subject to any disclaimer, the term of this patent is extended or adjusted under 35 U.S.C. 154(b) by 918 days.

(21) Appl. No.: 18/001,191

(22) PCT Filed: Jun. 9, 2021

(86) PCT No.: PCT/US2021/036693

§ 371 (c)(1),
(2) Date: Dec. 8, 2022

(87) PCT Pub. No.: WO2021/252692

PCT Pub. Date: Dec. 16, 2021

(65) Prior Publication Data

US 2023/0219969 A1 Jul. 13, 2023

Related U.S. Application Data

(60) Provisional application No. 63/070,502, filed on Aug. 26, 2020, provisional application No. 63/037,478, filed on Jun. 10, 2020.

(51) Int. Cl.

| | |
|---|---|
| ***C07D 491/147*** | (2006.01) |
| ***A61P 25/28*** | (2006.01) |
| ***C07D 209/08*** | (2006.01) |
| ***C07D 403/04*** | (2006.01) |
| ***C07D 403/08*** | (2006.01) |
| ***C07D 471/04*** | (2006.01) |
| ***C07D 471/08*** | (2006.01) |
| ***C07D 487/04*** | (2006.01) |
| ***C07D 491/056*** | (2006.01) |
| ***C07D 491/107*** | (2006.01) |

(52) U.S. Cl.

CPC .......... *C07D 491/147* (2013.01); *A61P 25/28* (2018.01); *C07D 209/08* (2013.01); *C07D 403/04* (2013.01); *C07D 403/08* (2013.01); *C07D 471/04* (2013.01); *C07D 471/08* (2013.01); *C07D 487/04* (2013.01); *C07D 491/056* (2013.01); *C07D 491/107* (2013.01)

(58) Field of Classification Search

CPC ..... A61P 25/28; C07D 209/08; C07D 403/04; C07D 471/04; C07D 487/04; C07D 491/056

See application file for complete search history.

(56) References Cited

U.S. PATENT DOCUMENTS

| | | | | |
|---|---|---|---|---|
| 3,525,750 | A | | 8/1970 | Renner |
| 3,553,232 | A | | 1/1971 | Hester, Jr. |
| 3,637,744 | A | | 1/1972 | Yardley et al. |
| 3,652,588 | A | | 3/1972 | Hester, Jr. |
| 4,088,647 | A | * | 5/1978 | Glushkov ............ C07D 471/04 546/81 |
| 4,478,750 | A | | 10/1984 | Gadient |
| 4,581,354 | A | | 4/1986 | Bell |
| 4,841,056 | A | | 6/1989 | Hunter |
| 5,068,234 | A | | 11/1991 | D'Ambra et al. |
| 5,219,859 | A | | 6/1993 | Festal et al. |
| 5,494,928 | A | | 2/1996 | Bos |
| 5,627,077 | A | | 5/1997 | Dyllick-Brenzinger et al. |
| 5,714,495 | A | * | 2/1998 | Viaud ................. C07D 471/04 546/116 |
| 5,843,682 | A | | 12/1998 | Sigler et al. |
| 5,852,046 | A | | 12/1998 | Lang et al. |
| 6,017,945 | A | | 1/2000 | Rawson et al. |
| 6,380,238 | B1 | | 4/2002 | Adams et al. |
| 6,380,242 | B1 | | 4/2002 | Arora et al. |
| 6,407,092 | B1 | | 6/2002 | Hester et al. |
| 6,468,999 | B1 | | 10/2002 | Jacobsen et al. |
| 6,548,493 | B1 | | 4/2003 | Robichaud et al. |
| 6,552,017 | B1 | | 4/2003 | Robichaud et al. |
| 6,586,421 | B2 | | 7/2003 | Frank et al. |
| 6,635,639 | B2 | | 10/2003 | Arora et al. |

(Continued)

FOREIGN PATENT DOCUMENTS

| | | | |
|---|---|---|---|
| AU | 614343 | B2 | 8/1991 |
| AU | 2006244914 | A1 | 11/2006 |

(Continued)

OTHER PUBLICATIONS

E. Mutschler et al. 1978, Arch. Pharm. (Weinheim)3II, 248-255. (Year: 1978).*

Azimov, V. et al. (Khimiya Geterotsiklicheskikh Soedinenii (1976), (6), 848-52 CODEN: KGSSAQ; ISSN: 0132-6244. (Year: 1976).*

J M. Burger et al. (J. Med. Chem. 2006, 49, 1730-1743. (Year: 2006).*

(Continued)

*Primary Examiner* — James H Alstrum-Acevedo

*Assistant Examiner* — Manahil Mirghani Ali Abdalhameed

(74) *Attorney, Agent, or Firm* — WILSON SONSINI GOODRICH & ROSATI

(57) ABSTRACT

Disclosed herein are compounds, compositions, and methods for promoting neuronal growth and/or improving neuronal structure with the compounds and compositions disclosed herein. Also described are methods of treating diseases or disorders that are mediated by the loss of synaptic connectivity and/or plasticity, such as neurological diseases and disorders, with non-hallucinogenic psychoplastogens.

16 Claims, No Drawings

(56) References Cited

U.S. PATENT DOCUMENTS 6,716,837 B1 4/2004 Edwards et al.
6,828,314 B2 12/2004 Frank et al.
6,903,090 B2 6/2005 Frank et al.
7,411,064 B2 8/2008 Bernotas et al.
7,585,873 B2 * 9/2009 Bernotas ................. A61P 25/28 514/249
8,338,447 B2 12/2012 Hung et al.
8,367,655 B2 2/2013 Rajagopalan
8,481,731 B2 7/2013 Tran et al.
9,481,676 B2 11/2016 Hung et al.
10,583,123 B2 3/2020 Yang et al.
10,889,569 B2 1/2021 Li et al.
11,254,640 B2 2/2022 Olson et al.
11,414,423 B1 8/2022 Olson et al.
11,697,651 B2 7/2023 Muratore et al.
12,325,710 B2 6/2025 Olson et al.
2002/0019531 A1 2/2002 Kitazawa et al.
2002/0022616 A1 2/2002 Fu
2002/0169322 A1 11/2002 Arora et al.
2002/0173503 A1 11/2002 Robichaud et al.
2003/0199491 A1 10/2003 Hennequin
2003/0212055 A1 11/2003 Hennequin
2003/0220321 A1 11/2003 Frank et al.
2003/0225058 A1 12/2003 Frank et al.
2003/0232828 A1 12/2003 Bernotas et al.
2003/0236278 A1 12/2003 Bernotas et al.
2004/0023947 A1 2/2004 Martin et al.
2004/0092502 A1 5/2004 Fevig et al.
2004/0242884 A1 12/2004 Larsen et al.
2005/0070558 A1 3/2005 Vidal Juan et al.
2005/0250767 A1 11/2005 Weiner et al.
2006/0105030 A1 5/2006 Windt-Hanke et al.
2006/0148808 A1 7/2006 Robichaud et al.
2006/0199829 A1 9/2006 Anandan et al.
2006/0247228 A1 11/2006 Umeda et al.
2007/0027178 A1 2/2007 Lee
2007/0197603 A1 8/2007 Consonni et al.
2007/0213359 A1 9/2007 Burstein et al.
2007/0254875 A1 11/2007 Zhi et al.
2008/0119518 A1 5/2008 Suzuki et al.
2009/0318446 A1 12/2009 Fischer et al.
2010/0152163 A1 6/2010 Hung et al.
2010/0317863 A1 12/2010 Kuzmich et al.
2011/0003793 A1 1/2011 Guzzo et al.
2011/0003836 A1 1/2011 McKnight et al.
2011/0003840 A1 1/2011 Rajagopalan
2011/0229555 A1 9/2011 Helson et al.
2011/0245222 A1 10/2011 Payan et al.
2012/0214815 A1 * 8/2012 Kenda ..................... A61P 25/06 514/363
2012/0245161 A1 9/2012 Choi-Sledeski et al.
2012/0296569 A1 11/2012 Shahaf et al.
2013/0018038 A1 1/2013 Axten et al.
2013/0040977 A1 2/2013 McKnight et al.
2013/0178618 A1 7/2013 Boulanger
2013/0190293 A1 7/2013 Chakravarty et al.
2013/0195866 A1 8/2013 Bacskai et al.
2013/0217675 A1 8/2013 Chakravarty et al.
2013/0225558 A1 8/2013 Chakravarty et al.
2014/0155384 A1 6/2014 Protter et al.
2014/0206711 A1 7/2014 Chakravarty et al.
2014/0228353 A1 8/2014 Protter et al.
2014/0275531 A1 9/2014 Bollu et al.
2014/0275548 A1 9/2014 Basinger et al.
2014/0296209 A1 10/2014 Protter et al.
2014/0303144 A1 10/2014 Protter et al.
2014/0343018 A1 11/2014 McKnight et al.
2015/0057301 A1 2/2015 McKnight et al.
2015/0141345 A1 5/2015 Gozes et al.
2015/0266884 A1 9/2015 Protter et al.
2015/0315198 A1 11/2015 Li et al.
2016/0002237 A1 1/2016 Rajagopalan
2016/0168140 A1 6/2016 Jones et al.
2018/0263964 A1 9/2018 Bamdad et al.
2020/0017466 A1 1/2020 Li et al.
2020/0030309 A1 1/2020 Olson
2020/0087305 A1 3/2020 Tomesch et al.
2020/0375967 A1 12/2020 Stamets
2022/0251040 A1 8/2022 Olson et al.
2022/0304980 A1 9/2022 Arnold et al.
2023/0150963 A1 5/2023 Baggott
2023/0202965 A1 6/2023 Short et al.
2023/0295106 A1 9/2023 Olson et al.
2023/0322735 A1 10/2023 Kruegel
2024/0208973 A1 6/2024 Olson et al.
2025/0051276 A1 2/2025 Powell et al.
2025/0057822 A1 2/2025 Olson et al.
2025/0059184 A1 2/2025 Powell et al.
2025/0101001 A1 3/2025 Powell et al.
2025/0122164 A1 4/2025 Olson et al.

FOREIGN PATENT DOCUMENTS

CA 2715282 A1 8/2009
CN 102977091 A 3/2013
CN 102977092 A 3/2013
CN 117586171 A 2/2024
EP 0473550 A1 3/1992
GB 2550110 A 11/2017
JP 2004509074 A 3/2004
JP 2017031088 A 2/2017
NL 6515701 A 6/1966
WO WO-9423720 A1 10/1994
WO WO-9524200 A1 9/1995
WO WO-9623783 A1 8/1996
WO WO-9747598 A1 12/1997
WO WO-9840102 A1 9/1998
WO WO-0012475 A1 3/2000
WO WO-0038677 A1 7/2000
WO WO-0064899 A1 11/2000
WO WO-0112603 A1 2/2001
WO WO-0140183 A1 6/2001
WO WO-0170223 A1 9/2001
WO WO-0224701 A2 3/2002
WO WO-03044017 A1 5/2003
WO WO-03101990 A1 12/2003
WO WO-2004005389 A1 1/2004
WO WO-2004024730 A1 3/2004
WO WO-2004064738 A2 8/2004
WO WO-2006024535 A1 3/2006
WO WO-2006038773 A1 4/2006
WO WO-2006056600 A1 6/2006
WO WO-2007118314 A1 10/2007
WO WO-2007131907 A2 11/2007
WO WO-2008117935 A1 10/2008
WO WO-2008157845 A1 12/2008
WO WO-2009035473 A2 3/2009
WO WO-2009036996 A2 3/2009
WO WO-2009103022 A1 8/2009
WO WO-2009118305 A1 10/2009
WO WO-2011076708 A1 6/2011
WO WO-2011103433 A1 8/2011
WO WO-2012112966 A1 8/2012
WO WO-2012143726 A1 10/2012
WO WO-2012154261 A1 11/2012
WO WO-2013007698 A1 1/2013
WO WO-2016187667 A1 12/2016
WO WO-2017001812 A1 1/2017
WO WO-2017197240 A1 11/2017
WO WO-2017216279 A1 12/2017
WO WO-2018045178 A1 3/2018
WO WO-2018064465 A1 4/2018
WO WO-2018149986 A1 * 8/2018 ........... C07D 471/04
WO WO-2018209341 A1 11/2018
WO WO-2019099402 A1 5/2019
WO WO-2020169851 A1 8/2020
WO WO-2020176597 A1 9/2020
WO WO-2020176599 A1 9/2020
WO WO-2020181050 A1 9/2020
WO WO-2020181194 A1 9/2020
WO WO-2020186027 A1 9/2020
WO WO-2021076572 A1 4/2021
WO WO-2021178691 A1 9/2021
WO WO-2021252692 A1 12/2021

(56) References Cited

FOREIGN PATENT DOCUMENTS

| | | | |
|---|---|---|---|
| WO | WO-2022020352 | A1 | 1/2022 |
| WO | WO-2022051670 | A1 | 3/2022 |
| WO | WO-2022067165 | A1 | 3/2022 |
| WO | WO-2022081631 | A1 | 4/2022 |
| WO | WO-2022120181 | A1 | 6/2022 |
| WO | WO-2022120475 | A1 | 6/2022 |
| WO | WO-2022170268 | A1 | 8/2022 |
| WO | WO-2022221415 | A2 | 10/2022 |
| WO | WO-2022246554 | A1 | 12/2022 |
| WO | WO-2023283364 | A2 | 1/2023 |
| WO | WO-2023018480 | A1 | 2/2023 |
| WO | WO-2023018864 | A1 | 2/2023 |
| WO | WO-2023023298 | A1 | 2/2023 |
| WO | WO-2023059546 | A1 | 4/2023 |
| WO | WO-2023073423 | A1 | 5/2023 |
| WO | WO-2023077127 | A2 | 5/2023 |
| WO | WO-2023081306 | A1 | 5/2023 |
| WO | WO-2023081753 | A1 | 5/2023 |
| WO | WO-2023092195 | A1 | 6/2023 |
| WO | WO-2023108164 | A2 | 6/2023 |
| WO | WO-2023108165 | A2 | 6/2023 |
| WO | WO-2023108174 | A1 | 6/2023 |
| WO | WO-2023114238 | A1 | 6/2023 |
| WO | WO-2023114325 | A1 | 6/2023 |
| WO | WO-2023114472 | A1 | 6/2023 |
| WO | WO-2023114844 | A1 | 6/2023 |
| WO | WO-2023115006 | A1 | 6/2023 |
| WO | WO-2023115060 | A1 | 6/2023 |
| WO | WO-2023115165 | A1 | 6/2023 |
| WO | WO-2023115166 | A1 | 6/2023 |
| WO | WO-2023122135 | A1 | 6/2023 |
| WO | WO-2023141595 | A2 | 7/2023 |
| WO | WO-2023150547 | A2 | 8/2023 |
| WO | WO-2023183613 | A2 | 9/2023 |
| WO | WO-2023201421 | A1 | 10/2023 |
| WO | WO-2023201423 | A1 | 10/2023 |
| WO | WO-2024044847 | A1 | 3/2024 |
| WO | WO-2024044848 | A1 | 3/2024 |
| WO | WO-2024059495 | A1 | 3/2024 |
| WO | WO-2024077203 | A1 | 4/2024 |
| WO | WO-2024213032 | A1 | 10/2024 |
| WO | WO-2024258988 | A2 | 12/2024 |
| WO | WO-2024258995 | A2 | 12/2024 |
| WO | WO-2025080608 | A1 | 4/2025 |
| WO | WO-2025080609 | A1 | 4/2025 |

OTHER PUBLICATIONS

Abate et al. Interaction of Chiral MS-245 Analogs at h5-HT6 Receptors. Bioorg Med Chem Letter 15(15):3510-3513 (2005).

CAS Registry No. 1416330-38-5; Entry Date Oct. 20, 2020; 9-Bromo-1,2,3,4,5,6-hexahydroazepino[4,5-b]indole. p. 1.

CAS Registry No. 802581-10-8; Entry Date Mar. 26, 2005; 9-Methoxy-3-methyl-1,2,3,4,5,6-hexahydroazepino[4,5-b]indole. p. 1.

Chemical Abstracts Services. CAS Registry No. 405312-66-5, 2 Pages.

Chemical Abstracts Services. CAS Registry No. 7546-69-2, 2 Pages (No date given).

Chemical Abstracts Services. CAS Registry No. 7546-72-7, 2 Pages (No date given).

Chemical Abstracts Services. CAS Registry No. 7546-73-8, 2 Pages (No date given).

Chemical Abstracts Services. CAS Registry No. 7546-75-0, 2 Pages (No date given).

Chemical Abstracts Services. CAS Registry No. 7546-76-1, 2 Pages (No date given).

Chen et al. Iboga-type alkaloids with Indolizidino[8,7-b]Indole scaffold and bisindole alkaloids from *Tabernaemontana bufalina* Lour. Phytochemistry 196:113089 (2022).

Church, et al. 'Ecstasy' enhances noise-induced hearing loss. Hear Res 302:96-106 (2013).

Dong, et al. Psychedelic-inspired drug discovery using an engineered biosensor. Cell 184(10):2779-2792.e18 (2021).

Eiter et al. Zur Konstitution des Folicanthins: II. Mitteilung uber Folicanthin, ein neues Alkaloid aus den Blattern des *Calycanthus floridus* L, Monastshefte Fur Chemies—Chemical Monthyl 83(6):1453-1476 (1952).

Fitzgerald et al. High-Affinity Agonist Binding Correlates with Efficacy (Intrinsic Activity) at the Human Serotonin 5-HT2A and 5-HT2C Receptors: Evidence Favouring the Ternary Complex and Two-State Models of Agonist Action. J Neurochem 72(5):2127-2134 (1999).

Huang, et al. Comparison of the use of aqueous and nonaqueous buffers in association with cyclodextrin for the chiral separation of 3,4-methylenedioxymethamphetamine and related compounds. Electrophoresis 26(20):3904-3909 (2005).

Macor, John E. et al. 3-(1, 2, 5, 6-Tetrahydropyrid-4-yl) pyrrolo [3, 2-b] pyrid-5-one: a potent and selective serotonin (5-HT1) agonist and rotationally restricted phenolic analog of 5-methoxy-3-(1, 2, 5, 6-tetrahydropyrid-4-yl) indole. Journal of Medicinal Chemistry 33(8):2087-2093 (1990).

Masuda et al. The Effect of Globopentaosylceramide on a Depression Model, Mouse Forced Swimming. J Exper Med 191:47-54 (2000).

Niswender, C. M. et al. GenBank Accession No. AAF35842. Version No. AAF35842.1. edited 5-hydroxytryptamine receptor 2C [*Homo sapiens*]: pp. 1-2. Record created Feb. 24, 2000. Retrieved Jun. 18, 2024. Retrieved from: https://www.ncbi.nlm.nih.gov/protein/AAF35842.1.

PCT/US2022/024626 International Search Report and Written Opinion dated Jul. 1, 2022.

PCT/US2022/079217 International Search Report and Written Opinion dated Feb. 1, 2023.

PCT/US2022/081927 International Search Report and Written Opinion dated Apr. 17, 2023.

PCT/US2024/033644 International Search Report and Written Opinion dated Oct. 30, 2024.

PCT/US2024/033644 Invitation to Pay Additional Fees dated Aug. 19, 2024.

Pieroni, et al. Rational Design and Synthesis of Thioridazine Analogues as Enhancers of the Antituberculosis Therapy. J Med Chem 58(15):1-43(2015).

PubChem CID:62785545. 1-(Azetidin-3-yl)indoline. STN Entry Date Oct. 22, 2012. Retrieved Nov. 14, 2024 at URL: https://pubchem.ncbi.nlm.nih.gov/compound/62785545. pp. 1-8.

PubChem SID: 274223890, 5-[(R)-2-(Dimethylamino)propyl]-1,3-benzodioxole. 1-5 (2016).

Sanches et al. Antidepressant Effects of a Single Dose of Ayahuasca in Patients with Recurrent Depression. J Clin Psychopharmacol 36(1):77-81 (2016).

Seki. Studies on 2-benzimidazolethiol derivatives. V. Structure-activity relationship on analgesic action of 1-(dialkylamino-alkyl)-2-(p-ethoxyphenylthio)benzimidazole. Journal of the Pharmaceutical Society of Japan 87(3):301-309 (1967) (English Abstract).

Whitehouse, et al. Development of Inhibitors against *Mycobacterium abscessus* tRNA (m1G37) Methyltransferase (TrmD) Using Fragment-Based Approaches. J Med Chem 62(15):7210-7232 (2019).

Zubenko et al. Pyridine-Azepine Structural Modification of 3, 4-Dihydro-nor-isoharmine. Russian Journal of Organic Chemistry 55(1):74-82 (Apr. 17, 2019).

Lacivita et al. Selective Agents for Serotonin(2C)(5-HT2C) Receptor. Current Topics in Medicinal Chemistry 6(18):1927-1970 (2006).

Anderson. The process of structure-based drug design. Chem and Biol 10:787-797 (2003).

Antonaci et al. Recent Advances in Migraine Therapy. SpringerPlus 5:1-14 (May 17, 2016).

Berge et al. Pharmaceutical Salts. Journal of Pharmaceutical Sciences 66(1): 1-19 (Jan. 1977).

Borovac. Side Effects of a Dopamine Agonist Therapy for Parkinson's Disease: A Mini-review of Clinical Pharmacology. Yale J Biol Med 89:37-47 (Mar. 24, 2016).

Bundgaard. Design and Application of Prodrugs. Textbook of Drug Design and Development. Krosgaard-Larsen and Bundgaard. Chapter 5. pp.113-191 (1991).

(56) References Cited

OTHER PUBLICATIONS

Bundgaard. (C) Means to enhance penetration. (1) Prodrugs as a means to improve the delivery of peptide drugs. Advanced Drug Delivery Reviews, 8:1-38 (1992).
Cameron et al. A Non-hallucinogenic Psychedelic Analogue With Therapeutic Potential. Nature 589:474-479 (Jan. 21, 2021).
Cameron et al.: Chronic, Intermittent Microdoses of the Psychedelic N, N-Dimethyltryptamine (DMT) Produce Positive Effects on Mood and Anxiety in Rodents. CS Chem Neurosci. 10(7):3261-3270 doi: 10.1021/acschemneuro.8b00692 (2019).
Cameron et al. Dark Classics in Chemical Neuroscience: N,N-Dimethyltryptamine (DMT). ACS Chemical Neuroscience 9(10):2344-2357 (Oct. 2018).
Cameron et al. Effects of N,N-Dimethyltryptamine on Rat Behaviors Relevant to Anxiety and Depression. ACS Chemical Neuroscience 9(7):1582-1590 (Jul. 2018).
Cameron et al. Psychedelic Microdosing: Prevalence and Subjective Effects, Journal of Psychoactive Drugs, 52(2):113-122 (Apr.-Jun. 2020).
CAS RN:1501472-60-1. 3-[2-(1-Piperazinyl)ethyl]imidazo[1,2-a]pyridine. (2013).
CAS RN:1555386-21-4. 2-Methyl-3-[2-(1-piperazinyl)propyl]imidazo[1,2-a]pyridine. (2014).
CAS RN: 1780584-97-5. β,2-Dimethyl-β-4-morpholinylimidazo[1,2-a]pyridine-3-propanamine. (2015).
CAS RN:1895314-76-7. 1-bromo-3-[2-(1-piperazinyl)propyl]imidazo[1,5-a]pyridine. (2016).
CAS RN:2515504-68-2. 3-[2-(2,5-Dimethyl-1H-pyrrol-1-yl)ethyl]-7-methylimidazo[1,2-a]pyridine. (2020).
Chang-Fong et al. Evaluation of Isotryptamine Derivatives at 5-HT2 Serotonin Receptors. Bioorg Med Chem Letters 12(2):155-158 (Jan. 21, 2002).
Chiba et al. Cabergoline, a Dopamine Receptor Agaonist, has an Antidepressant-like Property and Enhances Brain-derived Neurotrophic Factor Signaling. Psychpharmacology 211(3):291-301 (May 23, 2010).
Coe et al., Convenient preparation of N-substituted indoles by modified Leimgruber-Batcho indole synthesis. Tetrahedron Letters 37(34), 6045-6048 (1996).
Depression The National Institute of Mental Health: www.nimh.nih.gov, 13 pages (2018).
Dunlap et al., Identification of psychoplastogenic N,N-dimethylaminoisotryptamine (isoDMT) analogues through structure-activity relationship studies. J Med Chem. 63(3):1142-1155 (2020).
Glennon et al. Binding of Beta-Carbolines and Related Agents at Serotonin (5-HT(2) and 5-HT(1A)), Dopamine (D(2)) and Benzodiazepine Receptors. Drug & Alcohol Dependence 60(2):121-132 (2000).
Glennon et al. DOM-stimulus Generalization to LSD and other Hallucinogenic Indolealkylamines. Eur J Pharmacol 86:453-459 (1983).
Glennon et al. Synthesis and Evaluation of a Novel Series of N ,N -Dimethylisotryptamines. J Med Chem 27(1):41-45 (1984).
Goadsby et al. Comparative Efficacy of Eletriptan and Sumatriptan in Reducing Headache Recurrence in High-Risk Migraine Patients. J Neurolog Sci 238(Suppl. 1):5940 (Nov. 11, 2005).
Golda et al. Animal Model of Depression: Drug Induced Changes Independent of Changes in Exploratory Activity. Activitas Nervosa Superior 29(2):114-115 (Jun. 1987).
Golda et al. Animal Model of Depression: Imipramine, Bromocriptine and Lisuride Alleviate Motor Depression. Activitas Nervosa Superior 28(1):26-27 (1986).
Golda et al. Reactivity to the Electric Shocks and Motor Depression as a Consequence of Inescapable Shocking: the Effect of Acute Lisuride Treatment. Sb Ved Pr Lek Fak Karlovy Univerzity Hradci Kralov 27(4):377-392 (1984).
Halford. Ibogaine Inspires Potential Neuropsychiatric Treatment. C&E News (3 pgs.) (Dec. 2020).
Harris et al. Cabergoline Associated with First Episode Mania. Psychosomatics 53(6):595-600 (2012).
Heloire, et al., Exploring 6-(substituted sulfonyl) imidazopyridines as a potential scaffold for the design of 5-HT 6 ligands. Monatshefte für Chemie-Chemical Monthly 144:429-435 (2013).
Hester et al. Azepinoindoles. I. Hexahydroazepino[4,5-b]indoles, J Med Chem 11:101-106 (Jan. 1, 1968).
Hougaku et al. Therapeutic Effect of Lisuride Maleate on Post-stroke Depression. Japanese Journal of Geriatrics 31:52-59 (Jan. 1994).
Izumi et al. Open Pergolide Treatment of Tricyclic and Heterocyclic Antidepressant-resistant Depression. Journal of Affective Disorders 61:127-132 (2000).
Konopaske et al. Prefrontal Cortical Dendritic Spine Pathology in Schizophrenia and Bipolar disorder. JAMA Psychiatry 71(12):1323-1331 (Dec. 2014).
Lieberman et al. Use of Lisuride in Advanced Parkinson's Disease. Potent Dopamine and Serotonin Agonist. New York State Journal of Medicine, 81(12):1751-1755 (Nov. 1981).
Luquin et al. Parenteral Administration of Lisuride In Parkinson's Disease. Advances in Neurology 45:561-568 (1987).
Ly et al., Psychedelics promote structural and functional neural plasticity. Cell Rep. 23(11):3170-3182 (2018).
Meintzschel et al. Modification of Practice-dependent Plasticity in Human Motor Cortex by Neuromodulators. Cerebral Cortex 16(8):1106-1115 (Oct. 12, 2005).
Meyer et al. The Effect of Paroxetine on 5-HT 2A Receptors in Depression: An [18F]Setoperone PET Imaging Study. The American Journal of Psychiatry 158(1):78-85 (Jan. 2001).
Moyer et al. Dendritic Spine Alterations in Schizophrenia. Neuroscience Letters 601:46-53 (2015).
Nakamura et al. Effects in Animal Models of Depression of Lisuride Along and Upon Co-administration with antidepressants. Nihon Yakurigaku zasshi. Folia Pharmacolgica Japonica 94(1):81-89 (1989).
Nichols, Structure-activity relationships of serotonin 5-HT2A agonists. WIREs Membr. Transp. Signal 1:559-579 (2012).
Odaka et al. Cabergoline, Dopamine D2 REceptor Agonist, Prevents Neuronal Cell Death under Oxidative Stress via Reducing Excitotoxicity. PLoS One 9(6):e99271 (Jun. 2014).
PCT/US2017/054277 International Search Report and Written Opinion dated Dec. 14, 2017.
PCT/US2020/019856 International Search Report and Written Opinion dated Jun. 26, 2020.
PCT/US2020/019858 International Search Report and Written Opinion dated Jul. 15, 2020.
PCT/US2020/055507 International Search Report and Written Opinion dated Mar. 1, 2021.
PCT/US2021/036693 International Search Report and Written Opinion dated Sep. 29, 2021.
PCT/US2022/052753 International Search Report and Written Opinion dated Mar. 9, 2023.
PCT/US2022/052888 International Search Report and Written Opinion dated Apr. 11, 2023.
PCT/US2022/081555 International Search Report and Written Opinion dated Dec. 14, 2022.
Penzes et al. Dendritic Spine Pathology in Neuropsychiatric Disorders. Nature Neuroscience Review 14(3):285-293 (Mar. 2011).
Pfizer Canana, Inc. Product Monograph, Pfizer Cananda Inc. (pp. 1-2) (Jul. 23, 2013).
PubChem CID 314981250. 3,4-Trimethylen-inden (Jun. 16, 2016).
PubChem CID 43403. Carbazole, 9-(1-methyl-2-piperidyl)methyl-, (Aug. 8, 2005).
PubChem CID 82415753. 1,2,3,4-Tetrahydropyrrolo[2,3-b]Indole, (Oct. 20, 2014).
Pumphrey et al. Rhll2-Catalyzed Synthesis of a-, [3-, or 6-Carbolines from Aryl Azides. Angew Chem Int Ed Engl 51(24):5920-5923 (Jun. 11, 2012).
Qian et al., Counterion-Induced Asymmetric Control in Ring-Opening of Azetidiniums: Facile Access to Chiral Amines. Angewandte Chemie, International Edition, 57(14):3763-3766 (2018).
Sasakura et al., Simple synthesis of 1-(azacycloalkyl)indoles using exclusiveortho α-chloroacetylation of N-(azacycloalkyl)anilines. Synthetic Communications 18(3):265-273 (1988).

(56) References Cited

OTHER PUBLICATIONS

Sharma et al. Intranasal Cabergoline: Pharmacokinetic and Pharmacodynamic Studies. AAPS PharmSciTech 10(4):1321-1330 (Dec. 2009).
Thiel. Structure-aided drug design's next generation. Nat Biotechnol 22(5):513-319 (2004).
Tittarelli et al., Recreational use, analysis and toxicity of tryptamines. Cut Neuropharmacol. 13:26-46 (2015).
Vargas et al. Psychedelics and Other Psychoplastogens for Treating Mental Illness. Front Psychiatry 12:727117 (2021).
Widder et al. Section III: Prodrugs Kinetics. Method in Enzymology. 112:309-396 (1985).
Zetler et al. Die Wirkung von 11 Indol-Alkaloiden auf das Meerschweinchen-Herz in vivo und in vitro, verglichen mit 2 synthetischen Azepinoindolen, Chinidin und Quindonium. Naunyn-Schmiedebergs Archiv filr Pharmakologie und experimentelle Pathologie 260:26-49 (Jan. 1968).
Zetler et al. Inhibition of Cardiac Effects of Noradrenaline by Eleven Indole Alkaloids, Two Azepinoindoles, Quinidine, Quindonium, and Propranolol. Pharmacology 4:129-142 (1970).
Zetler et al. Refractory Period and Strophanthin Actions, as Influenced by Four Indole Alkaloids and Two Synthetic Azepinoindoles. Pharmacology 8:235-243 (1972).
Blair, et al. Effect of ring fluorination on the pharmacology of hallucinogenic tryptamines. J Med Chem.43(24):4701-4710 (2000).
Carman, et al. Negative effects of melatonin on depression. Am J Psychiatry.133(10):1181-1186 (1976).
Chemical Abstracts Service. CAS Registry No. 1347326-94-6. STN Entry Date Dec. 2, 2011.
Chemical Abstracts Service. CAS Registry No. 1499823-45-8. STN Entry Date Dec. 20, 2013.
Chemical Abstracts Service. CAS Registry No. 1501213-32-6. Azepino[4,5-b]-1,3-dioxolo[4,5-flindole, 5,6,7,8,9, 10-hexahydro-5-methyl-. STN Entry Date Dec. 23, 2013.
Chemical Abstracts Service. CAS Registry No. 1502739-86-7. Azepino[4,5-b]-1,3-dioxolo[4,5-flindole, 5,6,7,8,9,10-hexahydro-. STN Entry Date Dec. 24, 2013.
Chemical Abstracts Service. CAS Registry No. 1503723-45-2. STN Entry Date Dec. 25, 2013.
Chemical Abstracts Service. CAS Registry No. 1505385-98-7. STN Entry Date Dec. 27, 2013.
Chemical Abstracts Service. CAS Registry No. 1509251-72-2. STN Entry Date Jan. 2, 2014.
Chemical Abstracts Service. CAS Registry No. 1513834-45-1. STN Entry Date Jan. 7, 2014.
Chemical Abstracts Service. CAS Registry No. 1513937-46-6. Azepino[4,5-b]-1,4-dioxino[2,3-f]indole, 2,3,6,7,8,9,10,11-octahydro-. STN Entry Date Jan. 8, 2014.
Chemical Abstracts Service. CAS Registry No. 1514378-08-5. STN Entry Date Jan. 8, 2014.
Chemical Abstracts Service. CAS Registry No. 1515073-46-7. STN Entry Date Jan. 9, 2014.
Chemical Abstracts Service. CAS Registry No. 1515565-33-9. STN Entry Date Jan. 9, 2014.
Chemical Abstracts Service. CAS Registry No. 1516490-69-9. STN Entry Date Jan. 10, 2014.
Chemical Abstracts Service. CAS Registry No. 1519408-31-1. STN Entry Date Jan. 14, 2014.
Chemical Abstracts Service. CAS Registry No. 1521620-08-5. STN Entry Date Jan. 16, 2014.
Chemical Abstracts Service. CAS Registry No. 1523634-22-1. STN Entry Date Jan. 19, 2014.
Chemical Abstracts Service. CAS Registry No. 1524903-93-2. Azepino[4,5-b]-1,4-dioxino[2,3-f]indole, 2,3,6,7,8,9,10,11-octahydro-6-methyl-. STN Entry Date Jan. 20, 2014.
Chemical Abstracts Service. CAS Registry No. 1525468-14-7. STN Entry Date Jan. 20, 2014.
Chemical Abstracts Service. CAS Registry No. 1533723-14-6. STN Entry Date Jan. 30, 2014.
Chemical Abstracts Service. CAS Registry No. 1533998-25-2. STN Entry Date Jan. 30, 2014.
Chemical Abstracts Service. CAS Registry No. 1540077-46-0. STN Entry Date Feb. 9, 2014.
Chemical Abstracts Service. CAS Registry No. 1540652-24-1. STN Entry Date Feb. 10, 2014.
Chemical Abstracts Service. CAS Registry No. 15918-68-0. STN Entry Date Nov. 16, 1984.
Chemical Abstracts Service. CAS Registry No. 15918-91-9. STN Entry Date Nov. 16, 1984.
Chemical Abstracts Service. CAS Registry No. 15923-19-0. STN Entry Date Nov. 16, 1984.
Chemical Abstracts Service. CAS Registry No. 1779925-03-9. Azepino[4,5-b]indol-8-ol, 1,2,3,4,5,6-hexahydro-6-methyl-. STN Entry Date Jun. 14, 2015.
Chemical Abstracts Service. CAS Registry No. 1781710-62-0. Azepino[4,5-b]indole, 8-bromo-1,2,3,4,5,6-hexahydro-6-methyl-. STN Entry Date Jun. 17, 2015.
Chemical Abstracts Service. CAS Registry No. 1781798-70-6. STN Entry Date Jun. 17, 2015.
Chemical Abstracts Service. CAS Registry No. 1781904-21-9. STN Entry Date Jun. 17, 2015.
Chemical Abstracts Service. CAS Registry No. 1781908-34-6. Azepino[4,5-b]indole, 8-bromo-1,2,3,4,5,6-hexahydro. STN Entry Date Jun. 17, 2015.
Chemical Abstracts Service. CAS Registry No. 1782881-47-3. STN Entry Date Jun. 17, 2015.
Chemical Abstracts Service. CAS Registry No. 1784120-59-7. STN Entry Date Jun. 19, 2015.
Chemical Abstracts Service. CAS Registry No. 1785609-23-5. STN Entry Date Jun. 21, 2015.
Chemical Abstracts Service. CAS Registry No. 2072109-20-5. STN Entry Date Feb. 17, 2017.
Chemical Abstracts Service. CAS Registry No. 2072109-30-7. STN Entry Date Feb. 17, 2017.
Chemical Abstracts Service. CAS Registry No. 405305-92-2. STN Entry Date Apr. 16, 2002.
Chemical Abstracts Service. CAS Registry No. 405305-95-5. Azepino[4,5-b]indole, 1,2,3,4,5,6-hexahydro-8-phenyl-. STN Entry Date Apr. 16, 2002.
Chemical Abstracts Service. CAS Registry No. 405311-77-5 . STN Entry Date Apr. 16, 2002.
Chemical Abstracts Service. CAS Registry No. 685503-57-5 . STN Entry Date May 24, 2004.
Chemical Abstracts Service. CAS Registry No. 736129-10-5 . STN Entry Date Aug. 31, 2004.
Chemical Abstracts Service. CAS Registry No. 755746-20-4 . STN Entry Date Oct. 1, 2004.
Chemical Abstracts Service. CAS Registry No. 757934-75-1 . STN Entry Date Oct. 7, 2004.
Chemical Abstracts Service. CAS Registry No. 770702-18-6 . STN Entry Date Oct. 28, 2004.
Chemical Abstracts Service. CAS Registry No. 778568-40-4 . STN Entry Date Nov. 11, 2004.
Chemical Abstracts Service. CAS Registry No. 780030-99-1 . STN Entry Date Nov. 14, 2004.
Colley, Claire. This Is What It Feels Like to Treat Depression with Magic Mushrooms. Vice.com (2015); [retrieved on Jun. 19, 2024]. Available atURL:https://www.vice.com/en/article/8gk5wz/microdosing-psilocybin-depression-184 pp. 1-6.
Cooper, Anna G. et al. Alkyl Indole-based Cannabinoid Type 2 Receptor Tools: Exploration of Linker and Fluorophore Attachment. European Journal of Medicinal Chemistry 145:770-789 (2018).
Database Registry, Chemical Abstracts Services, CAS Registry No. 1711992-37-8 (Entered STN: May 25, 2015).
Database Registry, Chemical Abstracts Services, CAS Registry No. 1770193-31-1 (Entered STN: Jan. 1, 2015).
EP20170857489.3 Third Party Observations dated Jan. 10, 2024.
Gmeiner, P. et al. Enantiomerically Pure Amino Alcohols and Diamino Alcohols From L-aspartic Acid. Application to the Synthesis of Epi- and Diepislaframine. The Journal of Organic Chemistry 59(22):6766-6776 (1994).

(56) References Cited

OTHER PUBLICATIONS

Godyn, Justyna et al. Lipophilic Properties of Anti-alzheimer's Agents Determined by Micellar Electrokinetic Chromatography and Reversed-phase Thin-layer Chromatography. Electrophoresis 38(9-10):1268-1275 (2017).
Hao, Wei et al. Palladium-catalyzed One-pot Three- or Four-component Coupling of Aryl lodides, Alkynes, and Amines Through C—N Bond Cleavage: Efficient Synthesis of Indole Derivatives. Chemistry 20(9):2605-2612 (2014).
Marek, G. J., et al. Evidence for involvement of 5-hydroxytryptamine1 receptors in antidepressant-like drug effects on differential-reinforcement-of-low-rate 72-second behavior. Journal of Pharmacology and Experimental Therapeutics, 250(1):60-71 (1989).
PCT/US2023/073837 International Search Report and Written Opinion dated Jan. 26, 2024.
PCT/US2024/050417 International Search Report and Written Opinion dated Jan. 16, 2024.
PubChem SID: 441175770, 5-Bromo-6-chloro-N,N-diethylnicotinamide 1-5 (2022).
PUBCHEM-SID-368776104, modify date May 25, 2018. p. 2.
Ray., Psychedelics and the human receptorome. PLoS One 5(2):e9019 (2010).
Registry No. 137641-70-4, File Registry on STN, entered STN Nov. 29, 1991.
Registry No. 885479-51-6. , File Registry on CAPLUS, entered May 24, 2006.
Shi, Ying et al. Amidoalkylindoles as Potent and Selective Cannabinoid Type 2 Receptor Agonists With in Vivo Efficacy in a Mouse Model of Multiple Sclerosis. Journal of Medicinal Chemistry 60(16):7067-7083 (2017).
Turton, et al. A qualitative report on the subjective experience of intravenous psilocybin administered in an FMRI environment. Curr Drug Abuse Rev. 7(2):117-127 (2014).

* cited by examiner

ISOTRYPTAMINE PSYCHOPLASTOGENS AND USES THEREOF

FIELD OF THE INVENTION

This application is a § 371 U.S. National Stage Entry of International Application No. PCT/US2021/036693, filed Jun. 9, 2021, which claims the benefit of U.S. Provisional Application No. 63/037,478, filed on Jun. 10, 2020, and U.S. Provisional Application No. 63/070,502, filed on Aug. 26, 2020, all of which are incorporated herein by reference in their entireties.

FIELD OF THE INVENTION

Described herein are compounds, methods of making such compounds, pharmaceutical compositions and medicaments comprising such compounds, and methods of using such compounds for the treatment of conditions, diseases, or disorders that would benefit from promoting neuronal growth and/or improving neuronal structure.

BACKGROUND OF THE INVENTION

Altered synaptic connectivity and plasticity has been observed in the brains of individuals with neurological diseases and disorders. Psychoplastogens promote neuronal growth and improve neuronal architecture through mechanisms involving the activation of AMPA receptors, the tropomyosin receptor kinase B (TrkB), and the mammalian target of rapamycin (mTOR). Modulators of these biological targets, such as, for example, ketamine, scopolamine, N,N-dimethyltryptamine (DMT), and rapastinel have demonstrated psychoplastogenic properties. For example, ketamine is capable of rectifying deleterious changes in neuronal structure that are associated with neurological diseases and disorders. Such structural alterations include, for example, the loss of dendritic spines and synapses in the prefrontal cortex (PFC) as well as reductions in dendritic arbor complexity. Furthermore, pyramidal neurons in the PFC exhibit top-down control over areas of the brain controlling motivation, fear, and reward. Psychedelic psychoplastogens have demonstrated antidepressant, anxiolytic, and anti-addictive effects of in the clinic.

SUMMARY OF THE INVENTION

In some embodiments, provided herein is a compound of Formula (II), or a pharmaceutically acceptable salt or solvate thereof:

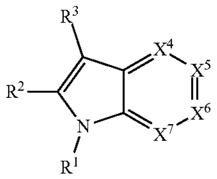

wherein, $R^1$ is

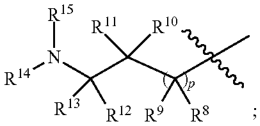

;

each $R^8$ and $R^9$ are independently hydrogen, halogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is optionally substituted;

or $R^8$ and $R^9$ are taken together with the atoms to which they are attached to form an optionally substituted heterocycloalkyl or cycloalkyl;

$R^{10}$-$R^{13}$ are each independently hydrogen, halogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is optionally substituted;

or two of $R^{10}$-$R^{13}$ are taken together with the atoms to which they are attached to form an optionally substituted heterocycloalkyl or cycloalkyl;

$R^{14}$ and $R^{15}$ are each independently hydrogen, alkyl, heteroalkyl, haloalkyl, cycloalkyl, or heterocycloalkyl, wherein each alkyl, heteroalkyl, cycloalkyl, or heterocycloalkyl is optionally substituted;

or $R^{14}$ and $R^{15}$ are taken together with the nitrogen atom to which they are attached to form an optionally substituted heterocycloalkyl;

or $R^{13}$ and $R^{14}$ are taken together with the nitrogen atom to which they are attached to form an optionally substituted heterocycloalkyl;

p is 0-4;

$R^2$ and $R^3$ are each independently hydrogen, alkyl, alkoxy, haloalkyl, cycloalkyl, or heterocycloalkyl, wherein each alkyl, alkoxy, cycloalkyl, or heterocycloalkyl is optionally substituted;

or $R^2$ and $R^3$ are taken together with the atoms to which they are attached to form a cycloalkyl or a heterocycloalkyl, wherein each cycloalkyl and heterocycloalkyl is optionally substituted;

$X^4$ is N or $CR^4$;

$X^5$ is N or $CR^5$;

$X^6$ is N or $CR^6$;

$X^7$ is N or $CR^7$;

wherein $R^4$-$R^7$ are each independently hydrogen, halogen, —CN, —$OR^a$, —$SR^a$, —$S(=O)R^a$, —$S(=O)_2R^a$, —$NO_2$, —$NR^bR^c$, —$NHS(=O)_2R^a$, —$S(=O)_2NR^bR^c$, —$C(=O)R^a$, —$OC(=O)R^a$, —$C(=O)OR^b$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, alkyl, heteroalkyl, haloalkyl, cycloalkyl, or heterocycloalkyl, wherein each alkyl, heteroalkyl, cycloalkyl, or heterocycloalkyl is optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl); and each $R^a$-$R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl, provided that:

(a) if p is 0 or 1, $R^{12}$ and $R^{13}$ are H, and $R^2$ and $R^3$ are each independently hydrogen, alkyl, alkoxy, haloalkyl, cycloalkyl, or heterocycloalkyl, then at least one of $X^4$—$X^7$ is N;

(b) if p is 0, $R^{12}$ is H, $R^{13}$ is alkyl, and $R^2$ and $R^3$ are each independently hydrogen, alkyl, alkoxy, haloalkyl, cycloalkyl, or heterocycloalkyl, then at least one of $X^4$—$X^7$ is N; and (c) if $R^{13}$ and $R^{14}$ are taken together with the nitrogen atom to which they are attached to form an optionally substituted heterocycloalkyl and $R^2$ and $R^3$ are each independently hydrogen, alkyl, alkoxy, haloalkyl, cycloalkyl, or heterocycloalkyl, then at least one of $X^4$—$X^7$ is N.

In another aspect, described herein is a compound of Formula (III), or a pharmaceutically acceptable salt or solvate thereof:

Formula (III)

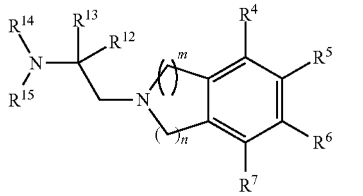

wherein:

$R^4$-$R^7$ are each independently hydrogen, halogen, —CN, —$OR^a$, —$SR^a$, —S(═O)$R^a$, —S(═O)$_2R^a$, —$NO_2$, —$NR^bR^c$, —NHS(═O)$_2R^a$, —S(═O)$_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl are optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl);

each $R^a$, $R^b$, and $R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, haloalkyl, cycloalkyl, or heterocycloalkyl, wherein each alkyl, alkoxy, heteroalkyl, cycloalkyl, or heterocycloalkyl is optionally substituted;

$R^{14}$ and $R^{15}$ are each independently alkyl, heteroalkyl, haloalkyl, cycloalkyl, or heterocycloalkyl, wherein each alkyl, heteroalkyl, cycloalkyl, or heterocycloalkyl is optionally substituted;

or $R^{14}$ and $R^{15}$ are taken together with the nitrogen atom to which they are attached to form an optionally substituted heterocycloalkyl;

m is 1, 2, or 3;

n is 0 or 1; and wherein (n+m) is an integer ranging from 5-7;

provided that (a) at least one of $R^{12}$ or $R^{13}$ is halogen, alkyl, haloalkyl, cycloalkyl, or heterocycloalkyl; and (b) when n and m are each 1, then $R^4$-$R^7$ are not —$NH_2$.

Provided in certain embodiments herein is a compound of Formula (V), or a pharmaceutically acceptable salt or solvate thereof:

Formula (V)

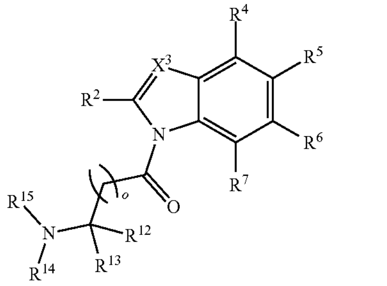

wherein:

$X^3$ is N or $CR^3$;

$R^2$ is hydrogen, alkyl, alkoxy, haloalkyl, cycloalkyl, or heterocycloalkyl, wherein each alkyl, alkoxy, cycloalkyl, or heterocycloalkyl is independently optionally substituted;

$R^3$ is hydrogen, alkyl, alkoxy, haloalkyl, cycloalkyl, or heterocycloalkyl, wherein each alkoxy, cycloalkyl, or heterocycloalkyl is independently optionally substituted;

$R^4$-$R^7$ are each independently hydrogen, —F, —Cl, —CN, —$OR^a$, —$SR^a$, —S(═O)$R^a$, —S(═O)$_2R^a$, —$NO_2$, —$NR^bR^c$, —NHS(═O)$_2R^a$, —S(═O)$_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl is independently optionally substituted;

each $R^a$-$R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is independently optionally substituted;

or $R^{12}$ and $R^{13}$ are taken together with the atoms to which they are attached to form an optionally substituted heterocycloalkyl or an optionally substituted cycloalkyl;

$R^{14}$ and $R^{15}$ are each independently hydrogen, alkyl, haloalkyl, cycloalkyl, or heterocycloalkyl, wherein each alkyl, cycloalkyl, or heterocycloalkyl is independently optionally substituted;

or $R^{14}$ and $R^{15}$ are taken together with the nitrogen atom to which they are attached to form a heterocycloalkyl (e.g., an optionally substituted heterocycloalkyl);

or $R^{13}$ and $R^{14}$ are taken together with the nitrogen atom to which they are attached to form an optionally substituted heterocycloalkyl; and is 0-3;

wherein:

one or more $R^4$-$R^7$ is —F, —Cl, —CN, —$OR^a$, —$SR^a$, —S(═O)$R^a$, —S(═O)$_2R^a$, —$NO_2$, —$NR^bR^c$, —NHS(═O)$_2R^a$, —S(═O)$_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl is independently optionally substituted;

$R^4$-$R^7$ are each hydrogen and $R^{12}$ is alkyl, haloalkyl, cycloalkyl, or heterocycloalkyl;

$R^4$-$R^7$ are each hydrogen and $R^{12}$ and $R^{13}$ are each hydrogen; or any of $R^4$ and $R^5$, $R^5$ and $R^6$, or $R^6$ and $R^7$ are taken together with the atoms to which they are attached to form an optionally substituted cycloalkyl or an optionally substituted heterocycloalkyl (e.g., an optionally substituted 5- or 6-membered ring);

provided that:

(a) if $X^3$ is CH and $R^4$, $R^5$, $R^6$, or $R^7$ is —$NR^bR^c$, then $R^b$ is alkyl, haloalkyl, heteroalkyl, cycloalkyl, or heterocycloalkyl or $R^b$ and $R^c$ are taken together with the nitrogen atom to which they are attached to form an optionally substituted heterocycloalkyl; and (b) if $R^4$-$R^7$ are each hydrogen and $R^{12}$ and $R^{13}$ are each hydrogen, then $R^{14}$ and $R^{15}$ are each methyl.

In one aspect, provided herein is a pharmaceutical composition comprising a compound disclosed herein, or a pharmaceutically acceptable salt, or solvate thereof, and at least one pharmaceutically acceptable excipient.

In some embodiments, the compounds disclosed herein, or a pharmaceutically acceptable salt thereof, are formulated for administration to a mammal by intravenous administration, subcutaneous administration, oral administration, inhalation, nasal administration, dermal administration, or ophthalmic administration. In some embodiments, the compound disclosed herein, or a pharmaceutically acceptable salt thereof, is in the form of a tablet, a pill, a capsule, a liquid, a suspension, a gel, a dispersion, a solution, an emulsion, an ointment, or a lotion.

In one aspect, described herein is a method of promoting neuronal growth in a mammal comprising administering to the mammal a compound described herein, or any pharmaceutically acceptable salt or solvate thereof.

In another aspect, described herein is a method of improving neuronal structure comprising administering to the mammal a compound provided herein, or a pharmaceutically acceptable salt or solvate thereof.

In another aspect, described herein is a method of method of modulating the activity of 5-hydroxytryptamine receptor 2A (5-$HT_{2A}$) receptor in a mammal comprising administering to the mammal a compound provided herein, or any pharmaceutically acceptable salt or solvate thereof.

In another aspect, described herein is a method of treating a disease or disorder in a mammal that is mediated by the action of 5-hydroxytryptamine (5-HT) at 5-hydroxytryptamine receptor 2A (5-$HT_{2A}$) comprising administering to the mammal a compound provided herein, or any pharmaceutically acceptable salt or solvate thereof.

In another aspect, described herein is a method of treating a disease or disorder in a mammal that is mediated by the loss of synaptic connectivity, plasticity, or a combination thereof comprising administering to the mammal a compound provided herein, or a pharmaceutically acceptable salt or solvate thereof.

In some embodiments, the disease or disorder is neurological disease or disorder.

In another aspect, described herein is a method for treating neurological disease or disorder in a mammal, the method comprising administering to the mammal a compound of Formula (II), Formula (III), Formula (IV), or Formula (V), or a pharmaceutically acceptable salt or solvate thereof.

In some embodiments, the neurological disease or disorder is a neurodegenerative, a neuropsychiatric, or a substance use disease or disorder.

In some embodiments, the neurological disease or disorder is an injury.

In some embodiments, the neurological disease or disorder is selected from the group consisting of an anxiety disorder, a mood disorder, a psychotic disorder, a personality disorder, an eating disorder, a sleep disorder, a sexuality disorder, an impulse control disorder, a substance use disorder, a dissociative disorder, a cognitive disorder, a developmental disorder, and a factitious disorder.

In some embodiments, the neurological disease or disorder is selected from the group consisting of Alzheimer's disease, Parkinson's disease, Huntington's disease, a phobia, brain cancer, depression, treatment resistant depression, obsessive compulsive disorder (OCD), dependence, addiction, anxiety, post-traumatic stress disorder (PTSD), suicidal ideation, major depressive disorder, bipolar disorder, schizophrenia, stroke, and traumatic brain injury. In some embodiments, the neurological disease or disorder is schizophrenia, depression, treatment resistant depression, anxiety, obsessive compulsive disorder (OCD), post-traumatic stress disorder (PTSD), suicidal ideation, major depressive disorder, or bipolar disorder. In some embodiments, the neurological disease or disorder is Alzheimer's disease, Parkinson's disease, or Huntington's disease. In some embodiments, the neurological disease or disorder is a phobia. In some embodiments, the neurological disease or disorder is a brain cancer. In some embodiments, the neurological disease or disorder is dependence or addiction. In some embodiments, he neurological disease or disorder is stroke or traumatic brain injury.

In some embodiments, the mammal is a human.

In any of the aforementioned aspects are further embodiments in which an effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal.

In any of the aforementioned aspects are further embodiments comprising single administrations of an effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

Articles of manufacture, which include packaging material, a formulation within the packaging material (e.g. a formulation suitable for topical administration), and a label that indicates that the compound or composition, or pharmaceutically acceptable salt, or solvate thereof, is used for promoting neuronal growth and/or improving neuronal structure, or for the treatment, prevention or amelioration of one or more symptoms of a disease or disorder that is associated with promoting neuronal growth and/or improving neuronal structure, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

The present invention provides non-hallucinogenic compounds useful for the treatment of a variety of neurological diseases and disorders as well as increasing neuronal plasticity.

Psychedelic compounds promote structural and functional neural plasticity in key circuits, elicit therapeutic responses in multiple neuropsychiatric disorders, and produce beneficial neurological effects that can last for months following a single administration. Compounds capable of modifying neural circuits that control motivation, anxiety, and drug-seeking behavior have potential for treating neurological diseases and disorders that are mediated by the loss of synaptic connectivity and/or plasticity. Moreover, such compounds are likely to produce sustained therapeutic effects because, for example, of the potential to treat the underlying pathological changes in circuitry.

5-$HT_{2A}$ antagonists abrogate the neuritogenesis and spinogenesis effects of hallucinogenic compounds with 5-$HT_{2A}$ agonist activity, e.g., DMT, LSD, and DOI, demonstrating the correlation of 5-$HT_{2A}$ agonism and the promotion of neural plasticity (Ly et al., 2018; Dunlap et al., 2020). However, the hallucinogenic and dissociative potential of such compounds has limited the use of these compounds in the clinic for neurological diseases, such as, for example, neuropsychiatric diseases. (Ly et al., 2018)

In addition, non-hallucinogenic analogs of psychedelic compounds, such as, for example, lisuride and sumatriptan, have been examined as treatments for various neurological diseases and disorders, such as, but not limited to, neurodegenerative diseases (e.g., Alzheimer's disease and Parkinson's disease) and headaches (e.g., migraines).

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ . . . $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

"Alkyl" generally refers to a straight or branched hydrocarbon chain radical consisting solely of carbon and hydrogen atoms, such as having from one to fifteen carbon atoms (e.g., $C_1$-$C_{15}$ alkyl). Unless otherwise state, alkyl is saturated or unsaturated (e.g., an alkenyl, which comprises at least one carbon-carbon double bond). Disclosures provided herein of an "alkyl" are intended to include independent recitations of a saturated "alkyl," unless otherwise stated. Alkyl groups described herein are generally monovalent, but may also be divalent (which may also be described herein as "alkylene" or "alkylenyl" groups). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. In general, alkyl groups are each independently substituted or unsubstituted. Each recitation of "alkyl" provided herein, unless otherwise stated, includes a specific and explicit recitation of an unsaturated "alkyl" group.

Similarly, unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^x$, —$N(R^x)_2$, —C(O)$R^x$, —C(O)O$R^x$, —C(O)N$(R^x)_2$, —N($R^x$)C(O)O$R^x$, —OC(O)—N$(R^x)_2$, —N($R^x$)C(O)$R^x$, —N($R^x$)S$(O)_t$$R^x$ (where t is 1 or 2), —S$(O)_t$O$R^x$ (where t is 1 or 2), —S$(O)_t$$R^x$ (where t is 1 or 2) and —S$(O)_t$N$(R^x)_2$ (where t is 1 or 2) where each $R^x$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_6$alkylene. In other embodiments, an alkylene is a $C_1$-$C_4$alkylene. Typical alkylene groups include, but are not limited to, $—CH_2—$, $—CH(CH_3)—$, $—C(CH_3)_2—$, $—CH_2CH_2—$, $—CH_2CH(CH_3)—$, $—CH_2C(CH_3)_2—$, $—CH_2CH_2CH_2—$, $—CH_2CH_2CH_2CH_2—$, and the like. Unless stated otherwise specifically in the specification, an alkylene chain is optionally substituted as described for alkyl groups herein.

The term "alkenyl" refers to a type of alkyl group in which at least one carbon-carbon double bond is present. In one embodiment, an alkenyl group has the formula —C(R)$=CR^2$, wherein R refers to the remaining portions of the alkenyl group, which may be the same or different. In some embodiments, R is H or an alkyl. Non-limiting examples of an alkenyl group include $—CH{=}CH_2$, $—C(CH_3){=}CH_2$, $—CH{=}CHCH_3$, $—C(CH_3){=}CHCH_3$, and $—CH_2CH{=}CH_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. Non-limiting examples of an alkynyl group include —C≡CH, $—C≡CCH_3$$—C≡CCH_2CH_3$, $—CH_2C≡CH$.

An "alkoxy" group refers to a (alkyl)O— group, where alkyl is as defined herein.

The term "alkylamine" refers to —NH(alkyl), or $—N(alkyl)_2$.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl or cycloalkyl is saturated (i.e., containing single C—C bonds only) or unsaturated (i.e., containing one or more double bonds or triple bonds). Examples of saturated cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $—R^y—OR^x$, $—R^y—OC(O)—R^y$, $—R^y—OC(O)—OR^y$, $—R^y—OC(O)—N(R^x)_2$, $—R^y—N(R^x)_2$, $—R^y—C(O)R^x$, $—R^y—C(O)OR^x$, $—R^y—C(O)N(R^x)_2$, $—R^y—O—R^z—C(O)N(R^x)_2$, $—R^y—N(R^x)C(O)OR^x$, $—R^y—N(R^x)C(O)R^x$, $—R^y—N(R^x)S(O)_tR^x$ (where t is 1 or 2), $—R^y—S(O)_tR^x$ (where t is 1 or 2), $—R^y—S(O)_tOR^x$ (where t is 1 or 2) and $—R^y—S(O)_tN(R^x)_2$ (where t is 1 or 2), where each IV is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^y$ is independently a direct bond or a straight or branched alkylene or alkenylene chain, and $R^z$ is a straight or branched alkylene or alkenylene chain, and where each of the above substituents is unsubstituted unless otherwise indicated.

As used herein, the term "aryl" refers to an aromatic ring wherein each of the atoms forming the ring is a carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroaryl alkyl, $—R^y—OR^x$, $—R^y—OC(O)—R^x$, $—R^y—OC(O)—OR^x$, $—R^y—OC(O)—N(R^x)_2$, $—R^y—N(R^x)_2$, $—R^y—C(O)R^x$, $—R^y—C(O)OR^x$, $—R^y—C(O)N(R^x)_2$, $—R^y—O—R^z—C(O)N(R^x)_2$, $—R^y—N(R^x)C(O)OR^x$, $—R^y—N(R^x)C(O)R^x$, $—R^y—N(R^x)S(O)_tR^x$ (where t is 1 or 2), $—R^y—S(O)_tR^x$ (where t is 1 or 2), $—R^y—S(O)_tOR^x$ (where t is 1 or 2) and $—R^y—S(O)_tN(R^x)_2$ (where t is 1 or 2), where each $R^x$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^y$ is independently a direct bond or a straight or branched alkylene or alkenylene chain, and $R^z$ is a straight or branched alkylene or alkenylene chain, and where each of the above substituents is unsubstituted unless otherwise indicated.

"Aralkyl" or "aryl-alkyl" refers to a radical of the formula —W-aryl where $R^z$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

The term "cycloalkyl" refers to a monocyclic or polycyclic aliphatic, non-aromatic radical, wherein each of the atoms forming the ring (i.e., skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1]pentyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, adamantyl, norbornyl, and decalinyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom, such as, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group. In one aspect, a fluoralkyl is a $C_1$-$C_6$fluoroalkyl.

The term "heteroalkyl" refers to an alkyl group as defined above in which one or more skeletal carbon atoms of the alkyl are substituted with a heteroatom (with the appropriate number of substituents or valencies—for example, $—CH_2—$ may be replaced with —NH—, —S—, or —O—). For example, each substituted carbon atom is independently substituted with a heteroatom, such as wherein the carbon is substituted with a nitrogen, oxygen, selenium, or other suitable heteroatom. In some instances, each substituted carbon atom is independently substituted for an oxygen, nitrogen (e.g. —NH—, —N(alkyl)-, or —N(aryl)- or having another substituent contemplated herein), or sulfur (e.g. —S—, —S(═O)—, or $—S(═O)_2—$). In some embodiments, a heteroalkyl is attached to the rest of the molecule at a carbon atom of the heteroalkyl. In some embodiments, a heteroalkyl is attached to the rest of the molecule at a heteroatom of the heteroalkyl. In some embodiments, a heteroalkyl is a $C_1$-$C_{18}$ heteroalkyl. In some embodiments, a heteroalkyl is a $C_1$-$C_{12}$ heteroalkyl. In some embodiments, a heteroalkyl is a $C_1$-$C_6$ heteroalkyl. In some embodiments, a heteroalkyl is a $C_1$-$C_4$ heteroalkyl. Representative heteroalkyl groups include, but are not limited to $—OCH_2OMe$, or $—CH_2CH_2OMe$. In some embodiments, heteroalkyl includes alkoxy, alkoxyalkyl, alkylamino, alkylaminoalkyl, aminoalkyl, heterocycloalkyl, heterocycloalkyl, and heterocycloalkylalkyl, as defined herein. Unless stated otherwise specifically in the specification, a heteroalkyl group is optionally substituted as defined above for an alkyl group. In one aspect, a heteroalkyl is a $C_1$-$C_6$heteroalkyl.

Examples of such heteroalkyl are, for example, $—CH_2OCH_3$, $—CH_2CH_2OCH_3$, $—CH_2CH_2OCH_2CH_2OCH_3$, $—CH(CH_3)OCH_3$, $—CH_2NHCH_3$, $—CH_2N(CH_3)_2$, and $—CH_2SCH_3$.

"Heteroalkylene" refers to a divalent heteroalkyl group defined above which links one part of the molecule to another part of the molecule. Unless stated specifically otherwise, a heteroalkylene is optionally substituted, as defined above for an alkyl group.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^y$—$OR^x$, —$R^y$—OC(O)—$R^x$, —$R^y$—OC(O)—OR', —$R^y$—OC(O)—$N(R^x)_2$, —$R^y$—$N(R^x)_2$, —$R^y$—C(O)$R^x$, —$R^y$—C(O)O$R^x$, —$R^y$—C(O)$N(R^x)_2$, —$R^y$—O—$R^z$—C(O)$N(R^x)_2$, —$R^y$—N($R^x$)C(O)O$R^x$, —$R^y$—N($R^x$)C(O)$R^x$, —$R^y$—N($R^x$)$S(O)_tR^x$ (where t is 1 or 2), —$R^y$—$S(O)_tR^x$ (where t is 1 or 2), —$R^y$—$S(O)_tOR^x$ (where t is 1 or 2) and —$R^y$—$S(O)_tN(R^x)_2$ (where t is 1 or 2), where each $R^x$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^y$ is independently a direct bond or a straight or branched alkylene or alkenylene chain, and $R^z$ is a straight or branched alkylene or alkenylene chain, and where each of the above substituents is unsubstituted unless otherwise indicated.

"Heterocyclylalkyl" refers to a radical of the formula —$R^z$-heterocyclyl where $R^z$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^z$-heterocyclyl where $R^z$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclcic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl. Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^y$—$OR^x$, —$R^y$—OC(O)—$R^z$, —$R^y$—OC(O)—$OR^z$, —$R^y$—OC(O)—$N(R^x)_2$, —$R^y$—$N(R^x)_2$, —$R^y$—C(O)$R^x$, —$R^y$—C(O)O$R^x$, —$R^y$—C(O)$N(R^x)_2$, —$R^y$—O—$R^z$—C(O)$N(R^x)_2$, —$R^y$—N($R^x$)C(O)O$R^x$, —$R^y$—N($R^x$)C(O)$R^x$, —$R^y$—N($R^x$)$S(O)_tR^x$ (where t is 1 or 2), —$R^y$—$S(O)_tR^x$ (where t is 1 or 2), —$R^y$—$S(O)_tOR^x$ (where t is 1 or 2) and —$R^y$—$S(O)_tN(R^x)_2$ (where t is 1 or 2), where each $R^x$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^y$ is independently a direct bond or a straight or branched alkylene or alkenylene chain, and $R^z$ is a straight or branched alkylene or alkenylene chain, and where each of the above substituents is unsubstituted unless otherwise indicated.

"Heteroarylalkyl" refers to a radical of the formula —$R^z$-heteroaryl, where $R^z$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^z$-heteroaryl, where $R^z$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

In general, optionally substituted groups are each independently substituted or unsubstituted. Each recitation of an optionally substituted group provided herein, unless otherwise stated, includes an independent and explicit recitation of both an unsubstituted group and a substituted group (e.g., substituted in certain embodiments, and unsubstituted in certain other embodiments). Unless otherwise stated, substituted groups may be substituted by one or more of the following substituents: halo, cyano, nitro, oxo, thioxo, imino, oximo, trimethylsilanyl, —$OR^x$, —$SR^x$, —OC(O)—$R^x$, —$N(R^x)_2$, —$C(O)R^x$, —$C(O)OR^x$, —$C(O)N(R^x)_2$, —$N(R^x)C(O)OR^x$, —OC(O)—$N(R^x)_2$, —$N(R^x)C(O)R^x$, —$N(R^x)S(O)_tR^x$ (where t is 1 or 2), —$S(O)_tOR^x$ (where t is 1 or 2), —$S(O)_tR^x$ (where t is 1 or 2) and —$S(O)_tN(R^x)_2$ (where t is 1 or 2) where each $R^x$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl). In some other embodiments, optional substituents are independently selected from halogen, —CN, —$NH_2$, —NH$(CH_3)$, —$N(CH_3)_2$, —OH, —$CO_2H$, —$CO_2(C_1$-$C_4$alkyl), —C(═O)$NH_2$, —C(═O)NH($C_1$-$C_4$alkyl), —C(═O)N($C_1$-$C_4$alkyl)$_2$, —S(═O)$_2NH_2$, —S(═O)$_2$NH($C_1$-$C_4$alkyl), —S(═O)$_2$N($C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(═O)$C_1$-$C_4$alkyl, and —S(═O)$_2C_1$-$C_4$alkyl. In some embodiments, optional substituents are independently selected from halogen, —CN, —$NH_2$, —OH, —NH$(CH_3)$, —$N(CH_3)_2$, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (═O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target. In some embodiments, "modulate" means to interact with a target either directly or indirectly so as to decrease or inhibit receptor activity. In some instances. modulation is an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT_{2A}$) are modulators of the receptor.

The term "modulator" as used herein, refers to a molecule that interacts with a target either directly or indirectly. The interactions include, but are not limited to, the interactions of an agonist, partial agonist, an inverse agonist, antagonist, or combinations thereof. In some embodiments, a modulator is an antagonist. Receptor antagonists are inhibitors of receptor activity. Antagonists mimic ligands that bind to a receptor and prevent receptor activation by a natural ligand. Preventing activation may have many effects. If a natural agonist binding to a receptor leads to an increase in cellular function, an antagonist that binds and blocks this receptor decreases the function.

The term "agonism," as used herein, generally refers to the activation of a receptor or enzyme by a modulator, or agonist, to produce a biological response.

The term "agonist," as used herein, generally refers to a modulator that binds to a receptor or enzyme and activates the receptor to produce a biological response. By way of example only, a "$5HT_{2A}$ agonist" can be used to refer to a compound that exhibits an $EC_{50}$ with respect to $5HT_{2A}$ activity of no more than about 100 μM. In some embodiments, the term "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

The term "positive allosteric modulator," as used herein, generally refers to a modulator that binds to a site distinct from the orthosteric binding site and enhances or amplifies the effect of an agonist.

The term "antagonism," as used herein, generally refers to the inactivation of a receptor or enzyme by a modulator, or antagonist. Antagonism of a receptor, for example, is when a molecule binds to the receptor and does not allow activity to occur.

The term "antagonist" or "neutral antagonist," as used herein, generally refers to a modulator that binds to a receptor or enzyme and blocks a biological response. An antagonist has no activity in the absence of an agonist or inverse agonist but can block the activity of either, causing no change in the biological response.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "pharmaceutically acceptable," as used herein, generally refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt," as used herein, generally refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

Provided herein are non-hallucinogenic compounds that promote neuronal growth and/or improve neuronal structure.

In some embodiments, compounds provided herein possess comparable affinity for serotonin receptors (e.g., $5HT_{2A}$) as compared to their hallucinogenic counterparts. In some embodiments, the compounds provided herein have improved physiochemical properties as a result of the loss of a hydrogen bond donor, decreasing total polar surface area and improving central nervous system multiparameter optimization (MPO) scores. Described herein in some embodiments are non-hallucinogenic compounds that demonstrate similar therapeutic potential as hallucinogenic $5\text{-}HT_{2A}$ agonists. In some embodiments, the non-hallucinogenic compounds described herein provide better therapeutic potential than hallucinogenic $5\text{-}HT_{2A}$ agonists for neurological diseases.

Neurological Disorders

Neuronal plasticity, and changes thereof, have been attributed to many neurological diseases and disorders. For example, during development and in adulthood, changes in dendritic spine number and morphology (e.g., lengths, crossings, density) accompany synapse formation, maintenance and elimination; these changes are thought to establish and remodel connectivity within neuronal circuits. Furthermore, dendritic spine structural plasticity is coordinated with synaptic function and plasticity. For example, spine enlargement is coordinated with long-term potentiation in neuronal circuits, whereas long-term depression is associated with spine shrinkage.

In addition, dendritic spines undergo experience-dependent morphological changes in live animals, and even subtle changes in dendritic spines can affect synaptic function, synaptic plasticity, and patterns of connectivity in neuronal circuits. For example, disease-specific disruptions in dendritic spine shape, size, and/or number accompany neurological diseases and disorders, such as, for example, neurodegenerative (e.g., Alzheimer's disease or Parkinson's disease) and neuropsychiatric (e.g., depression or schizophrenia) diseases and disorders, suggesting that dendritic spines may serve as a common substrate in diseases that involve deficits in information processing.

In some embodiments, disclosed herein are methods of treating neurological diseases and disorders with a compound represented by a structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6, or a pharmaceutically acceptable salt or solvate thereof.

In some instances, a neurological disease or disorder is a disease or disorder of the central nervous system (CNS) (e.g., brain, spine, and/or nerves) of an individual.

Types of neurological diseases and disorders include, but are not limited to, neurodegenerative diseases (such as Alzheimer's disease, Parkinson's disease, and dementia), headaches (e.g., migraines), brain injury (e.g., stroke or traumatic brain injury), brain cancer, an anxiety disorder (e.g., post-traumatic stress disorder (PTSD) or obsessive-compulsive disorder (OCD)), a mood disorder (e.g., suicidal ideation, depression, or bipolar disorder), a psychotic disorder (e.g., schizophrenia or substance-induced psychotic disorder), a personality disorder, an eating disorder (e.g., binge eating disorder), a sleep disorder, a sexuality disorder, an impulse control disorder (e.g., gambling, compulsive sexuality, or kleptomania), a substance use disorder (e.g., alcohol dependence, opioid addiction, or cocaine addiction), a dissociative disorder (e.g., epilepsy, amnesia, or dissociative identity disorder), a cognitive disorder (e.g., substance-induced cognitive impairment), a developmental disorder (e.g., Attention-Deficit/Hyperactivity Disorder (ADHD)), an autoimmune disease (e.g., multiple sclerosis (MS)), pain (e.g., chronic pain), and a factitious disorder. In some embodiments, a mammal treated with a compound described herein has a disease or disorder that is or is associated with a disease or disorder of the CNS.

Neurodegenerative diseases or disorders include, but are not limited to, Alzheimer's disease (AD), Parkinson's disease (PD), prion disease, frontotemporal dementia, motor neuron disease (MND), Huntington's disease (HD), Lewy Body dementia (LBD), and the like.

Substance use disorders include, but are not limited to, substance abuse, addiction and dependence, such as addiction or dependence to alcohol, opioids (e.g., heroin, oxycodone, and hydrocodone), cocaine, amphetamines (e.g., methamphetamine), nicotine, cannabinoids (e.g., tetrahydrocannabinol (THC)), caffeine, phencyclidine, paint thinner, glue, steroids (e.g., anabolic steroids), barbiturates (e.g., phenobarbital), methadone, benzodiazepines (e.g., diazepam), and the like.

Impulse control disorders include, but are not limited to, gambling, kleptomania, trichotillomania, intermittent explosive disorder, pyromania, skin picking, compulsive buying, Tourette syndrome, compulsive sexual behavior, and the like.

Neuropsychiatric disorders include, but are not limited to, seizures (e.g., epilepsy), attention deficit disorders (e.g., ADHD and Autism), eating disorders (e.g., bulimia, anorexia, binge eating disorder, and pica), depression (e.g., clinical depression, persistent depressive disorder, bipolar disorder, postpartum depression, suicidal ideation, major depressive disorder, seasonal depression, and the like), anxiety (e.g., panic attacks, social anxiety disorder, panic disorder, and the like), schizophrenia, post-traumatic stress disorder (PTSD), obsessive-compulsive disorder (OCD), substance-induced psychotic disorder, substance-induced cognitive impairment, and the like.

Brain injury includes, but is not limited to, stroke, traumatic brain injury, dementia pugiliistica, chronic traumatic encephalopathy (CTE), or the like.

In some embodiments, a compound provided herein (e.g., a compound represented by the structure of Formula (II) (e.g., Formula (II), Formula (IIA'), Formula (IIA), Formula (IIB), Formula (ITC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6), or a pharmaceutically acceptable salt or solvate thereof, improves dendritic spine number and dendritic spine morphology that is lost in neurological diseases and disorders.

5-$HT_{2A}$

5-$HT_{2A}$ agonism has been correlated with the promotion of neural plasticity (Ly et al., 2018). 5-$HT_{2A}$ antagonists abrogate the neuritogenesis and spinogenesis effects of hallucinogenic compounds with 5-$HT_{2A}$ agonist activity, e.g., DMT, LSD, and DOI. Furthermore, DMT and other psychedelic compounds promote increased dendritic arbor complexity, dendritic spine density, and synaptogenesis through a 5-$HT_{2A}$-dependent process. Pretreating cortical cultures with a 5-$HT_{2A}$ antagonist blocked the ability of 5-MeO-DMT to increase dendritic growth. Importantly, the psychoplastogenic effects of compounds provided herein are also blocked under these conditions, implicating the 5-$HT_{2A}$ receptor in their mechanism of action.

Furthermore, non-hallucinogenic compounds (e.g., lisuride and 6-MeO-DMT) compete off 5-HT when an $5HT_{2A}$ sensor assay is run in antagonist mode. Additionally, compounds, such as, for example, 6-F-DET, Ketanserin, BOL148, which are non-hallucinogenic in animals (e.g., humans), compete with 5HT binding to $5HT_{2A}$ in an antagonist mode sensor assay. In some embodiments, a compound provided herein prevents binding of 5-HT to $5HT_{2A}$. In some embodiments, the $5HT_{2A}$ sensor assay is in an antagonist mode. In some embodiments, a compound provided herein prevents binding of 5-HT to $5HT_{2A}$ and has non-hallucinogenic potential. In some embodiments, a compound provided herein prevents binding of 5-HT to $5HT_{2A}$ and is non-hallucinogenic. In some embodiments, a compound provided herein prevents binding of 5-HT to $5HT_{2A}$ in antagonist mode has non-hallucinogenic potential. In some embodiments, a compound provided herein prevents binding of 5-HT in antagonist mode is a non-hallucinogenic compound. In some embodiments, a compound provided herein inhibits the response of a sensor assay in antagonist mode has non-hallucinogenic potential. In some embodiments, a compound provided herein inhibits the response of a sensor assay in antagonist mode is a non-hallucinogenic compound.

In some embodiments, the effect of a compound provided herein on an agonist mode sensor assay suggests the compound is a non-hallucinogenic ligand of the 5-$HT_{2A}$ receptor. In some embodiments, the effect of a compound provided herein on an antagonist mode sensor assay suggests the compound is a non-hallucinogenic ligand of the 5-$HT_{2A}$ receptor. In some embodiments, effect of a compound provided herein on an agonist mode and an antagonist mode sensor assay together suggest the compound is a non-hallucinogenic ligand of the 5-$HT_{2A}$ receptor.

Described in some embodiments are non-hallucinogenic compounds that demonstrate similar therapeutic potential as hallucinogenic 5-$HT_{2A}$ agonists. In some embodiments, the non-hallucinogenic compounds described herein provide better therapeutic potential than hallucinogenic 5-$HT_{2A}$ agonists for neurological diseases. In some embodiments, the compounds of the present invention are 5-$HT_{2A}$ modulators and promote neural plasticity (e.g., cortical structural plasticity).

Provided herein are compounds (e.g., a compound represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) useful for the treatment of a brain disorder and other conditions described herein. In some embodiments, a compound provided herein is 5-$HT_{2A}$ modulator and promote neural plasticity (e.g., cortical structural plasticity). In some embodiments, 5-$HT_{2A}$ modulators (e.g., 5-$HT_{2A}$ agonists) are used to treat a brain disorder. In some embodiments, the brain disorder or other conditions described herein comprise decreased neural plasticity, decreased cortical structural plasticity, decreased 5-$HT_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, the compounds provided herein have activity as 5-$HT_{2A}$ modulators. In some embodiments, the compounds provided herein elicit a biological response by activating the 5-$HT_{2A}$ receptor (e.g., allosteric modulation or modulation of a biological target that activates the 5-$HT_{2A}$ receptor). In some embodiments, the compounds provided herein are selective 5-$HT_{2A}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, the 5-$HT_{2A}$ modulators (e.g., 5-$HT_{2A}$ agonists) are non-hallucinogenic. In some embodiments, non-hallucinogenic 5-$HT_{2A}$ modulators (e.g., 5-$HT_{2A}$ agonists) are used to treat neurological diseases, which modulators do not elicit dissociative side-effects. In some embodiments, the hallucinogenic potential of the compounds described herein is assessed in vitro. In some embodiments, the hallucinogenic potential assessed in vitro of the compounds described herein is compared to the hallucinogenic potential assessed in vitro of hallucinogenic homologs. In some embodiments, the compounds provided herein elicit less hallucinogenic potential in vitro than the hallucinogenic homologs.

In some embodiments, non-hallucinogenic 5-$HT_{2A}$ modulators (e.g., 5-$HT_{2A}$ agonists) are used to treat neurological diseases. In some embodiments, the neurological diseases comprise decreased neural plasticity, decreased cortical structural plasticity, decreased 5-$HT_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, non-hallucinogenic 5-$HT_{2A}$ modulators (e.g., 5-$HT_{2A}$ agonists) are used for increasing neuronal plasticity. In some embodiments, non-hallucinogenic 5-$HT_{2A}$ modulators (e.g., 5-$HT_{2A}$ agonists) are used for treating a brain disorder. In some embodiments, non-hallucinogenic 5-$HT_{2A}$ modulators (e.g., 5-$HT_{2A}$ agonists) are used for increasing at least one of translation, transcription, or secretion of neurotrophic factors.

In some embodiments, the experiment or assay to determine increased neuronal plasticity of any compound of the present invention is a phenotypic assay, a dendritogenesis assay, a spinogenesis assay, a synaptogenesis assay, a Sholl analysis, a concentration-response experiment, a 5-$HT_{2A}$ agonist assay, a 5-$HT_{2A}$ antagonist assay, a 5-$HT_{2A}$ binding assay, or a 5-$HT_{2A}$ blocking experiment (e.g., ketanserin blocking experiments). In some embodiments, the experiment or assay to determine the hallucinogenic potential of a compound provided herein is a mouse head-twitch response (HTR) assay.

Compounds

In some instances, a compound described herein, including pharmaceutically acceptable salts, prodrugs, active metabolites and solvates thereof, is a non-hallucinogenic psychoplastogen. In some embodiments, a non-hallucinogenic psychoplastogen (e.g., described herein) promotes neuronal growth, improve neuronal structure, or a combination thereof.

In some embodiments, provided herein is a compound of Formula (II), or a pharmaceutically acceptable salt or solvate thereof:

Formula (II)

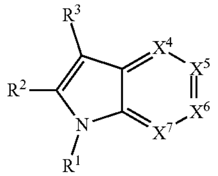

wherein:

$R^1$

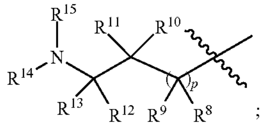

;

each $R^8$ and $R^9$ are independently hydrogen, halogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is optionally substituted;

or $R^8$ and $R^9$ are taken together with the atoms to which they are attached to form an optionally substituted heterocycloalkyl or cycloalkyl;

$R^{10}$-$R^{13}$ are each independently hydrogen, halogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is optionally substituted;

or two of $R^{10}$-$R^{13}$ are taken together with the atoms to which they are attached to form an optionally substituted heterocycloalkyl or cycloalkyl;

$R^{14}$ and $R^{15}$ are each independently hydrogen, alkyl, heteroalkyl, haloalkyl, cycloalkyl, or heterocycloalkyl, wherein each alkyl, heteroalkyl, cycloalkyl, or heterocycloalkyl is optionally substituted;

or $R^{14}$ and $R^{15}$ are taken together with the nitrogen atom to which they are attached to form an optionally substituted heterocycloalkyl;

or $R^{13}$ and $R^{14}$ are taken together with the nitrogen atom to which they are attached to form an optionally substituted heterocycloalkyl;

p is 0-4;

$R^2$ and $R^3$ are each independently hydrogen, alkyl, alkoxy, haloalkyl, cycloalkyl, or heterocycloalkyl, wherein each alkyl, alkoxy, cycloalkyl, or heterocycloalkyl is optionally substituted;

or $R^2$ and $R^3$ are taken together with the atoms to which they are attached to form a cycloalkyl or a heterocycloalkyl, wherein each cycloalkyl and heterocycloalkyl is optionally substituted;

$X^4$ is N or $CR^4$;

$X^5$ is N or $CR^5$;

$X^6$ is N or $CR^6$;

$X^7$ is N or $CR^7$;

wherein $R^4$-$R^7$ are each independently hydrogen, halogen, —CN, —$OR^a$, —$SR^a$, —S(═O)$R^a$, —S(═O)$_2R^a$, —$NO_2$, —$NR^bR^c$, —NHS(═O)$_2R^a$, —S(═O)$_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl is optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl); and each $R^a$-$R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl, provided that:

(a) if p is 0 or 1, $R^{12}$ and $R^{13}$ are H, and $R^2$ and $R^3$ are each independently hydrogen, alkyl, alkoxy, haloalkyl, cycloalkyl, or heterocycloalkyl, then at least one of $X^4$—$X^7$ is N;

(b) if p is 0, $R^{12}$ is H, $R^{13}$ is alkyl, and $R^2$ and $R^3$ are each independently hydrogen, alkyl, alkoxy, haloalkyl, cycloalkyl, or heterocycloalkyl, then at least one of $X^4$—$X^7$ is N; and (c) if $R^{13}$ and $R^{14}$ are taken together with the nitrogen atom to which they are attached to form an optionally substituted heterocycloalkyl and $R^2$ and $R^3$ are each independently hydrogen, alkyl, alkoxy, haloalkyl, cycloalkyl, or heterocycloalkyl, then at least one of $X^4$—$X^7$ is N.

For any and all of the embodiments, substituents are selected from among a subset of the listed alternatives. For example, in some embodiments, p is 0-2. In some embodiments, p is 0 or 1. In some embodiments, p is 1. In some embodiments, each $R^8$ and $R^9$ are independently hydrogen, halogen, alkyl, alkoxy, or haloalkyl. In some embodiments, each $R^8$ and $R^9$ are independently hydrogen, halogen, or $C_1$-$C_6$ alkyl. In some embodiments, each $R^8$ and $R^9$ are hydrogen.

In some embodiments, $R^8$ is hydrogen, halogen, alkyl, alkoxy, or haloalkyl. In some embodiments, $R^8$ is hydrogen, halogen, or $C_1$-$C_6$ alkyl. In some embodiments, $R^8$ is hydrogen.

In some embodiments, $R^9$ is hydrogen, halogen, alkyl, alkoxy, or haloalkyl. In some embodiments, $R^9$ is hydrogen, halogen, or $C_1$-$C_6$ alkyl. In some embodiments, $R^9$ is hydrogen.

In some embodiments, p is 0. In some embodiments, $R^{10}$ and $R^{11}$ are each independently hydrogen, halogen, alkyl, alkoxy, or haloalkyl. In some embodiments, $R^{10}$ and $R^{11}$ are each independently hydrogen, halogen, or $C_1$-$C_6$ alkyl. In some embodiments, $R^{10}$ and $R^{11}$ are hydrogen.

In some embodiments, $R^{10}$ is hydrogen, halogen, alkyl, alkoxy, or haloalkyl. In some embodiments, $R^{10}$ is hydrogen, halogen, or $C_1$-$C_6$ alkyl. In some embodiments, $R^{10}$ is hydrogen.

In some embodiments, $R^{11}$ is hydrogen, halogen, alkyl, alkoxy, or haloalkyl. In some embodiments, $R^{11}$ is hydrogen, halogen, or $C_1$-$C_6$ alkyl. In some embodiments, $R^{11}$ is hydrogen.

In some embodiments, $R^{12}$ and $R^{13}$ are each independently hydrogen, halogen, or optionally substituted alkyl. In some embodiments, $R^{12}$ and $R^{13}$ are each independently hydrogen, halogen, or optionally substituted alkyl, wherein at least one of $R^{12}$ and $R^{13}$ is halogen or optionally substituted alkyl. In some embodiments, $R^{12}$ and $R^{13}$ are each independently hydrogen, halogen, or optionally substituted alkyl, wherein at least one of $R^{12}$ and $R^{13}$ is $C_1$-$C_6$ alkyl. In some embodiments, $R^{12}$ and $R^{13}$ are each independently hydrogen or optionally substituted alkyl. In some embodiments, $R^{12}$ is hydrogen or optionally substituted alkyl and $R^{13}$ is optionally substituted alkyl. In some embodiments, $R^{12}$ and $R^{13}$ are each independently halogen or optionally substituted alkyl.

In some embodiments, $R^{12}$ and $R^{13}$ are each independently hydrogen or unsubstituted alkyl. In some embodiments, $R^{12}$ and $R^{13}$ are each independently hydrogen or $C_1$-$C_6$ alkyl. In some embodiments, $R^{12}$ and $R^{13}$ are each independently hydrogen or methyl. In some embodiments, $R^{12}$ is hydrogen and $R^{13}$ is methyl.

In some embodiments, $R^{12}$ and $R^{13}$ are each independently unsubstituted alkyl. In some embodiments, $R^{12}$ and $R^{13}$ are each independently $C_1$-$C_6$ alkyl.

In some embodiments, $R^{12}$ and $R^{13}$ are hydrogen.

In some embodiments, $R^{12}$ is hydrogen, halogen, or optionally substituted alkyl. In some embodiments, $R^{12}$ is hydrogen or optionally substituted alkyl. In some embodiments, $R^{12}$ is unsubstituted alkyl. In some embodiments, $R^{12}$ is $C_1$-$C_6$ alkyl. In some embodiments, $R^{12}$ is methyl.

In some embodiments, $R^{12}$ is hydrogen.

In some embodiments, $R^{13}$ is hydrogen, halogen, or optionally substituted alkyl. In some embodiments, $R^{13}$ is hydrogen or optionally substituted alkyl. In some embodiments, $R^{13}$ is unsubstituted alkyl. In some embodiments, $R^{13}$ is $C_1$-$C_6$ alkyl. In some embodiments, $R^{13}$ is methyl. In some embodiments, $R^{13}$ is hydrogen.

In some embodiments, $R^{12}$ and $R^{13}$ are taken together with the atoms to which they are attached to form an optionally substituted cycloalkyl.

In some embodiments, p is 0.

In some embodiments, $R^1$ is:

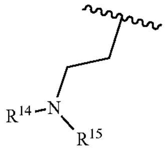 , 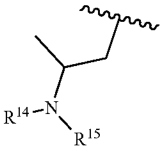 ,

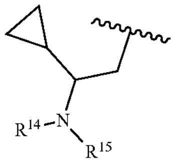 , 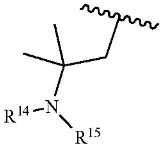 , or

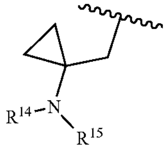 .

In some embodiments, $R^1$ is:

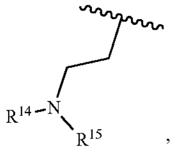 , 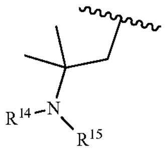 , or

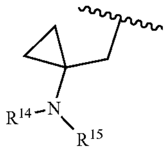 .

In some embodiments, $R^1$ is:

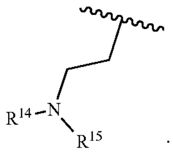 .

In some embodiments, $R^1$ is:

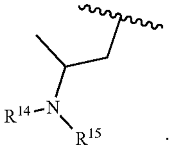 .

In some embodiments, $R^1$ is:

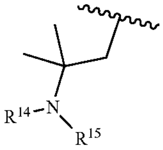 ,

In some embodiments, $R^1$ is:

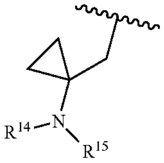 .

In some embodiments, $R^{14}$ and $R^{15}$ are each independently hydrogen, methyl, ethyl, or $R^{14}$ and $R^5$ are taken together with the nitrogen atom to which they are attached to form $C_2$-$C_5$ heterocycloalkyl.

In some embodiments, $R^{14}$ and $R^{15}$ are each independently methyl or ethyl, or $R^{14}$ and $R^{15}$ are taken together with the nitrogen atom to which they are attached to form $C_2$-$C_5$ heterocycloalkyl.

In some embodiments, $R^{14}$ and $R^{15}$ are each hydrogen.

In some embodiments, $R^{14}$ and $R^{15}$ are each methyl.

In some embodiments, $R^{14}$ is hydrogen and $R^{15}$ is methyl.

In some embodiments, $R^{14}$ is hydrogen or $C_1$-$C_6$ alkyl. In some embodiments, $R^{14}$ is hydrogen. In some embodiments, $R^{14}$ is $C_1$-$C_3$ alkyl. In some embodiments, $R^{14}$ is methyl, ethyl, or propyl.

In some embodiments, $R^{15}$ is hydrogen or $C_1$-$C_6$ alkyl. In some embodiments, $R^{15}$ is hydrogen. In some embodiments, $R^{15}$ is $C_1$-$C_3$ alkyl. In some embodiments, $R^{15}$ is methyl, ethyl, or propyl.

In some embodiments, $R^4$-$R^7$ are each independently selected from hydrogen, halogen, —$OR^a$, —$NR^bR^c$, $C_1$-$C_6$ alkyl, haloalkyl, $C_3$-$C_5$ cycloalkyl, or $C_2$-$C_4$ heterocycloalkyl. In some embodiments, $R^4$-$R^7$ are each independently selected from H, F, Cl, Br, —$CH_3$, —$CH_2CH_3$, —$CH(CH_3)_2$, —$C(CH_3)_3$, —$OCH_3$, —$OCH_2CH_3$, —$OCH(CH_3)_2$, —$OC(CH_3)_3$—$OC_3$-$C_5$cycloalkyl, —$CF_3$, —$OCF_3$, and —$NR^bR^c$, wherein $R^b$ and $R^c$ are taken together with the nitrogen atom to which they are attached to form an optionally substituted heterocycloalkyl. In some embodiments, $R^4$-$R^7$ are each independently selected from H, F, Cl, Br, —$CH_3$, —$OCH_3$, —$CF_3$, —$OCF_3$, and —$NR^bR^c$, wherein $R^b$ and $R^c$ are taken together with the nitrogen atom to which they are attached to form an optionally substituted heterocycloalkyl. In some embodiments, $R^4$-$R^7$ are each independently selected from H, F, Cl, Br, —$CH_3$, —$OCH_3$, —$CF_3$, —$OCF_3$, and —$NR^bR^c$, wherein $R^b$ and $R^c$ are taken together with the nitrogen atom to which they are attached to form an optionally substituted heterocycloalkyl, wherein at least one of $R^4$-$R^7$ is not H. In some embodiments, $R^4$, $R^6$, and $R^7$ are each independently selected from H, F, Cl, Br, —$CH_3$, —$OCH_3$, —$CF_3$, —$OCF_3$, and —$NR^bR^c$, wherein $R^b$ and $R^c$ are taken together with the nitrogen atom to which they are attached to form an optionally substituted heterocycloalkyl, wherein $R^5$ is F, Cl, Br, —$CH_3$, —$OCH_3$, —$CF_3$, —$OCF_3$, and —$NR^bR^c$, wherein $R^b$ and $R^c$ are taken together with the nitrogen atom to which they are attached to form an optionally substituted heterocycloalkyl. In some embodiments, $R^4$-$R^7$ are each independently hydrogen, —F, —Cl, —CN, —OH, —O—$C_1$-$C_3$alkyl, $C_1$-$C_4$alkyl, $C_1$-$C_3$haloalkyl, $C_3$-$C_6$cycloalkyl, or $C_2$-$C_5$heterocycloalkyl. In some embodiments, $R^4$-$R^7$ are each independently hydrogen, —F, —Cl, —OH, —$OCH_3$, —$OCF_3$, —$CH_3$, or —$CF_3$. In some embodiments, any of $R^4$ and $R^5$, $R^5$ and $R^6$, or $R^6$ and $R^7$ are taken together with the atoms to which they are attached to form an optionally substituted 5- or 6-membered heterocycloalkyl. In some embodiments, $R^5$ and $R^6$ are taken together with the atoms to which they are attached to form an optionally substituted heterocycloalkyl (e.g., an optionally substituted 5- or 6-membered ring). In some embodiments, $R^5$ and $R^6$ are taken together with the atoms to which they are attached to form an optionally substituted 5- or 6-membered ring. In some embodiments, $R^5$ and $R^6$ are taken together with the atoms to which they are attached to form a 6-membered heterocycloalkyl containing at least one O atom in the ring. In some embodiments, $R^5$ and $R^6$ are taken together with the atoms to which they are attached to form (e.g., an optionally substituted) dioxanyl or (e.g., an optionally substituted) dioxolanyl. In some embodiments, $R^5$ and $R^6$ are taken together with the atoms to which they are attached to form an unsubstituted 1,3-dioxolanyl. In some embodiments, $R^5$ and $R^6$ are taken together with the atoms to which they are attached to form a 2,2-difluoro-1,3-dioxolanyl.

In some embodiments, $R^4$ is selected from H, F, Cl, Br, —$CH_3$, —$OCH_3$, —$CF_3$, and —$OCF_3$. In some embodiments, $R^4$ is H. In some embodiments, $R^4$ is a halogen. In some embodiments, $R^4$ is methyl. In some embodiments, $R^4$ is $C_1$-$C_3$ alkyl. In some embodiments, $R^4$ is —$OCH_3$.

In some embodiments, $R^5$ is selected from H, F, Cl, Br, —$CH_3$, —$OCH_3$, —$CF_3$, and —$OCF_3$. In some embodiments, $R^5$ is H. In some embodiments, $R^5$ is a halogen. In some embodiments, $R^5$ is methyl. In some embodiments, $R^5$ is $C_1$-$C_3$ alkyl. In some embodiments, $R^5$ is —$OCH_3$.

In some embodiments, $R^6$ is selected from H, F, Cl, Br, —$CH_3$, —$OCH_3$, —$CF_3$, and —$OCF_3$. In some embodiments, $R^6$ is H. In some embodiments, $R^6$ is a halogen. In some embodiments, $R^6$ is methyl. In some embodiments, $R^6$ is $C_1$-$C_3$ alkyl. In some embodiments, $R^6$ is —$OCH_3$.

In some embodiments, $R^7$ is selected from H, F, Cl, Br, —$CH_3$, —$OCH_3$, —$CF_3$, and —$OCF_3$. In some embodiments, $R^7$ is H. In some embodiments, $R^7$ is a halogen. In some embodiments, $R^7$ is methyl. In some embodiments, $R^7$ is $C_1$-$C_3$ alkyl. In some embodiments, $R^7$ is —$OCH_3$.

In some embodiments, IV is hydrogen, alkyl, haloalkyl, heteroalkyl, cycloalkyl, or heterocycloalkyl. In some embodiments, IV is hydrogen. In some embodiments, IV is $C_1$-$C_3$ alkyl. In some embodiments, IV is methyl.

In some embodiments, $R^b$ is hydrogen, alkyl, haloalkyl, heteroalkyl, cycloalkyl, or heterocycloalkyl. In some embodiments, $R^b$ is hydrogen. In some embodiments, $R^b$ is $C_1$-$C_3$ alkyl. In some embodiments, $R^b$ is methyl.

In some embodiments, $R^c$ is hydrogen, alkyl, haloalkyl, heteroalkyl, cycloalkyl, or heterocycloalkyl. In some embodiments, $R^c$ is hydrogen. In some embodiments, $R^c$ is $C_1$-$C_3$ alkyl. In some embodiments, $R^c$ is methyl.

In some instances, any one of p, 10-$R^{15}$, $X^1$—$X^7$, and $R^a$-$R^c$, is described elsewhere herein.

In some embodiments, $R^2$ and $R^3$ are taken together with the atoms to which they are attached to form a 5-, 6-, or 7-membered heterocycloalkyl or a 5-, 6-, or 7-membered cycloalkyl. In some embodiments, the 5-, 6-, or 7-membered heterocycloalkyl is selected from the group consisting of tetrahydrofuranyl, dioxolanyl, dioxanyl, tetrahydropyranyl, dioxepanyl, oxepanyl, imidazolidinyl, pyrrolidinyl, piperidinyl, piperazinyl, azepanyl, diazepanyl, thiophenyl, dithiolanyl, thiopyranyl, dithianyl, thiepanyl, and dithiepanyl. In some embodiments, the 5-, 6-, or 7-membered heterocycloalkyl is selected from the group consisting of dioxolanyl, dioxanyl, tetrahydropyranyl, dioxepanyl, and oxepanyl. In some embodiments, the 5-, 6-, or 7-membered cycloalkyl is selected from the group consisting of cyclopentyl, cyclohexyl, and cycloheptyl.

In some embodiments, the compound of Formula (II) has the structure of Formula (IIA'), or a pharmaceutically acceptable salt or solvate thereof:

Formula (IIA')

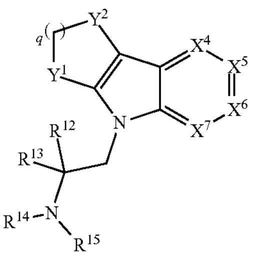

wherein:

$R^{12}$ and $R^{13}$ are each independently hydrogen, halogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is optionally substituted;

or $R^{12}$ and $R^{13}$ are taken together with the atoms to which they are attached to form an optionally substituted heterocycloalkyl or cycloalkyl;

$R^{14}$ and $R^{15}$ are each independently alkyl, heteroalkyl, haloalkyl, cycloalkyl, or heterocycloalkyl, wherein each alkyl, heteroalkyl, cycloalkyl, or heterocycloalkyl is optionally substituted;

or $R^{14}$ and $R^{15}$ are taken together with the nitrogen atom to which they are attached to form an optionally substituted heterocycloalkyl;

or $R^{13}$ and $R^{14}$ are taken together with the nitrogen atom to which they are attached to form an optionally substituted heterocycloalkyl;

$X^4$ is N or $CR^4$;

$X^5$ is N or $CR^5$;

$X^6$ is N or $CR^6$;

$X^7$ is N or $CR^7$;

wherein $R^4$-$R^7$ are each independently hydrogen, halogen, —CN, —$OR^a$, —$SR^a$, —S(═O)$R^a$, —$S(═O)_2R^a$, —$NO_2$, —$NR^bR^c$, —$NHS(═O)_2R^a$, —$S(═O)_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl is optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl); and each $R^a$-$R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$Y^1$ is $CH_2$ or O;

$Y^2$ is $CH_2$ or O; and q is 1, 2, or 3.

In some embodiments, the compound of Formula (II) has the structure of Formula (IIA), or a pharmaceutically acceptable salt or solvate thereof:

Formula (IIA)

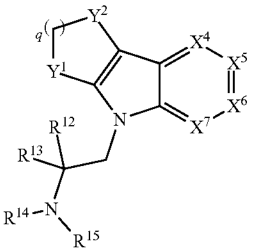

wherein:

$R^{12}$ and $R^{13}$ are each independently hydrogen, halogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is optionally substituted;

or $R^{12}$ and $R^{13}$ are taken together with the atoms to which they are attached to form an optionally substituted heterocycloalkyl or cycloalkyl;

$R^{14}$ and $R^{15}$ are each independently alkyl, heteroalkyl, haloalkyl, cycloalkyl, or heterocycloalkyl, wherein each alkyl, heteroalkyl, cycloalkyl, or heterocycloalkyl is optionally substituted;

or $R^{14}$ and $R^{15}$ are taken together with the nitrogen atom to which they are attached to form an optionally substituted heterocycloalkyl;

or $R^{13}$ and $R^{14}$ are taken together with the nitrogen atom to which they are attached to form an optionally substituted heterocycloalkyl;

$X^4$ is N or $CR^4$;

$X^5$ is N or $CR^5$;

$X^6$ is N or $CR^6$;

$X^7$ is N or $CR^7$;

wherein $R^4$-$R^7$ are each independently hydrogen, halogen, —CN, —$OR^a$, —$SR^a$, —$S(=O)R^a$, —$S(=O)_2R^a$, —$NO_2$, —$NR^bR^c$, —$NHS(=O)_2R^a$, —$S(=O)_2NR^bR^c$, —$C(=O)R^a$, —$OC(=O)R^a$, —$C(=O)OR^b$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, alkyl, heteroalkyl, haloalkyl, cycloalkyl, or heterocycloalkyl, wherein each alkyl, heteroalkyl, cycloalkyl, or heterocycloalkyl is optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl); and each $R^a$-$R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$Y^1$ is $CH_2$ or O;

$Y^2$ is $CH_2$ or O;

q is 1, 2, or 3;

provided that:

(a) when q is 3, at least one of $Y^1$ or $Y^2$ is 0 or at least one of $X^4$—$X^7$ is N; and (b) when q is 2, at least one of $Y^1$ or $Y^2$ is O.

In some embodiments, $Y^1$ is $CH_2$, $Y^2$ is $CH_2$, and q is 1. In some embodiments, $Y^1$ is $CH_2$, $Y^2$ is $CH_2$, and q is 2. In some embodiments, $Y^1$ is $CH_2$, $Y^2$ is $CH_2$, and q is 3.

In some embodiments, $Y^1$ is O, $Y^2$ is $CH_2$, and q is 1. In some embodiments, $Y^1$ is O, $Y^2$ is $CH_2$, and q is 2 or 3. In some embodiments, $Y^1$ is O, $Y^2$ is $CH_2$, and q is 2. In some embodiments, $Y^1$ is O, $Y^2$ is $CH_2$, and q is 2.

In some embodiments, $Y^1$ is $CH_2$, $Y^2$ is O, and q is 1. In some embodiments, $Y^1$ is $CH_2$, $Y^2$ is O, and q is 2 or 3. In some embodiments, $Y^1$ is $CH_2$, $Y^2$ is O, and q is 2. In some embodiments, $Y^1$ is $CH_2$, $Y^2$ is O, and q is 3.

In some embodiments, $Y^1$ is O, $Y^2$ is O, and q is 1, 2, or 3. In some embodiments, $Y^1$ is O, $Y^2$ is O, and q is 1. In some embodiments, $Y^1$ is O, $Y^2$ is O, and q is 2. In some embodiments, $Y^1$ is O, $Y^2$ is O, and q is 3.

In some embodiments, the compound of Formula (II) has the structure of Formula (IIB), or a pharmaceutically acceptable salt or solvate thereof:

Formula (IIB)

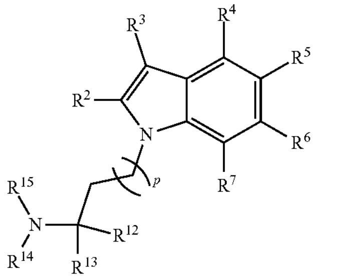

wherein:

$R^2$ and $R^3$ are each independently hydrogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is optionally substituted;

wherein $R^4$-$R^7$ are each independently hydrogen, halogen, —CN, —$OR^a$, —$SR^a$, —$S(=O)R^a$, —$S(=O)_2R^a$, —$NO_2$, —$NR^bR^c$, —$NHS(=O)_2R^a$, —$S(=O)_2NR^bR^c$, —$C(=O)R^a$, —$OC(=O)R^a$, —$C(=O)OR^b$, —$OC(=O)OR^b$, —$OC(=O)NR^bR^c$, —$NR^bC(=O)NR^bR^c$, —$NR^bC(=O)R^a$, —$NR^bC(=O)OR^b$, alkyl, heteroalkyl, haloalkyl, cycloalkyl, or heterocycloalkyl, wherein each alkyl, heteroalkyl, cycloalkyl, or heterocycloalkyl is optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl);

each $R^a$, $R^b$, and $R^c$ are independently hydrogen, alkyl, haloalkyl, heteroalkyl, cycloalkyl, or heterocycloalkyl, wherein each alkyl, heteroalkyl, cycloalkyl, or heterocycloalkyl is optionally substituted;

or $R^b$ and $R^c$ are taken together with the nitrogen atom to which they are attached to form an optionally substituted heterocycloalkyl;

$R^{12}$ and $R^{13}$ are each independently halogen, alkyl, alkoxy, heteroalkyl, haloalkyl, cycloalkyl, or heterocycloalkyl, wherein each alkyl, alkoxy heteroalkyl, cycloalkyl, or heterocycloalkyl is optionally substituted;

or $R^{12}$ and $R^{13}$ are taken together with the atoms to which they are attached to form an optionally substituted heterocycloalkyl or cycloalkyl;

$R^{14}$ and $R^{15}$ are each independently alkyl, haloalkyl, cycloalkyl, or heterocycloalkyl, wherein each alkyl, cycloalkyl, or heterocycloalkyl is optionally substituted;

or $R^{14}$ and $R^{15}$ are taken together with the nitrogen atom to which they are attached to form an optionally substituted heterocycloalkyl; and p is 0-2.

In some embodiments, p is 0.

In some embodiments, p is 1.

In some embodiments, p is 2.

In some embodiments, $R^2$ and $R^3$ are each independently hydrogen or optionally substituted alkyl. In some embodiments, $R^2$ and $R^3$ are each independently hydrogen or $C_1$-$C_6$ alkyl. In some embodiments, $R^2$ and $R^3$ are each independently hydrogen or $—CH_3$.

In some embodiments, $R^2$ and $R^3$ are each hydrogen.

In some embodiments, $R^2$ is hydrogen and $R^3$ is $—CH_3$.

In some embodiments, $R^2$ is hydrogen or optionally substituted alkyl. In some embodiments, $R^2$ is hydrogen or $C_1$-$C_6$ alkyl. In some embodiments, $R^2$ is hydrogen or $—CH_3$.

In some embodiments, $R^3$ is hydrogen or optionally substituted alkyl. In some embodiments, $R^3$ is hydrogen or $C_1$-$C_6$ alkyl. In some embodiments, $R^3$ is hydrogen or $—CH_3$.

In some embodiments, $R^5$ is F, Cl, Br, $—CH_3$, $—OCH_3$, $—CF_3$, or $—OCF_3$. In some embodiments, $R^5$ is F, Cl, or Br. In some embodiments, $R^5$ is F. In some embodiments, $R^5$ is $—CH_3$, $—OCH_3$, $—CF_3$, or $—OCF_3$. In some embodiments, $R^5$ is $—OCH_3$.

In some embodiments, $R^4$, $R^6$, and $R^7$ are each hydrogen and $R^5$ is F, Cl, Br, $—CH_3$, $—OCH_3$, $—CF_3$, or $—OCF_3$. In some embodiments, $R^4$, $R^6$, and $R^7$ are each hydrogen and $R^5$ is $—CH_3$, $—OCH_3$, $—CF_3$, or $—OCF_3$. In some embodiments, $R^4$, $R^6$, and $R^7$ are each hydrogen and $R^5$ is $—OCH_3$. In some embodiments, $R^4$, $R^6$, and $R^7$ are each hydrogen and $R^5$ is F, Cl, or Br. In some embodiments, $R^4$, $R^6$, and $R^7$ are each hydrogen and $R^5$ is F.

In some embodiments, $R^5$ is F, Cl, Br, $—CH_3$, $—OCH_3$, $—CF_3$, or $—OCF_3$ and $R^6$ is F, Cl, Br, $—CH_3$, $—OCH_3$, $—CF_3$, or $—OCF_3$. In some embodiments, $R^5$ is F, Cl, or Br and $R^6$ is F, Cl, or Br. In some embodiments, $R^5$ is F and $R^6$ is F.

In some embodiments, $R^4$ and $R^7$ are each hydrogen, $R^5$ is F, Cl, Br, $—CH_3$, $—OCH_3$, $—CF_3$, or $—OCF_3$, and $R^6$ is F, Cl, Br, $—CH_3$, $—OCH_3$, $—CF_3$, or $—OCF_3$. In some embodiments, $R^4$ and $R^7$ are each hydrogen, $R^5$ is F, Cl, or Br, and $R^6$ is F, Cl, or Br. In some embodiments, $R^4$ and $R^7$ are each hydrogen, $R^5$ is F and $R^6$ is F.

In some embodiments, $R^{12}$ and $R^{13}$ are each independently optionally substituted alkyl. In some embodiments, $R^{12}$ and $R^{13}$ are each independently $C_1$-$C_6$ alkyl. In some embodiments, $R^{12}$ and $R^{13}$ are each methyl.

In some embodiments, $R^{14}$ and $R^{15}$ are each independently optionally substituted alkyl. In some embodiments, $R^{14}$ and $R^{15}$ are each independently $C_1$-$C_6$ alkyl. In some embodiments, $R^{14}$ and $R^{15}$ are each methyl.

In some embodiments, $R^2$ and $R^3$ are each hydrogen, $R^4$, $R^6$, and $R^7$ are each hydrogen and $R^5$ is $—CH_3$, $—OCH_3$, $—CF_3$, or $—OCF_3$, $R^{12}$ and $R^{13}$ are each methyl, and $R^{14}$ and $R^{15}$ are each methyl.

In some embodiments, $R^2$ and $R^3$ are each hydrogen, $R^4$ and $R^7$ are each hydrogen, $R^5$ is F and $R^6$ is F, $R^{12}$ and $R^{13}$ are each methyl, and $R^{14}$ and $R^{15}$ are each methyl.

In some embodiments, $R^2$ is hydrogen and $R^3$ is $—CH_3$, $R^4$, $R^6$, and $R^7$ are each hydrogen and $R^5$ is F, $R^{12}$ and $R^{13}$ are each methyl, and $R^{14}$ and $R^{15}$ are each methyl.

In some embodiments, the compound of Formula (II) has the structure of Formula (IIC), or a pharmaceutically acceptable salt or solvate thereof:

Formula (IIC)

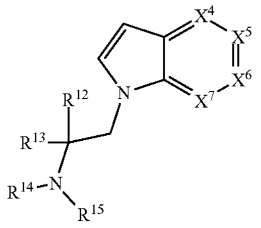

wherein:

$X^4$ is N or $CR^4$;

$X^5$ is N or $CR^5$;

$X^6$ is N or $CR^6$;

$X^7$ is N or $CR^7$;

wherein at least one of $X^4$—$X^7$ is N;

wherein $R^4$-$R^7$ are each independently hydrogen, halogen, —CN, $—OR^a$, $—SR^a$, $—S(=O)R^a$, $—S(=O)_2R^a$, $—NO_2$, $—NR^bR^c$, $—NHS(=O)_2R^a$, $—S(=O)_2NR^bR^c$, $—C(=O)R^a$, $—OC(=O)R^a$, $—C(=O)OR^b$, $—OC(=O)OR^b$, $—C(=O)NR^bR^c$, $—OC(=O)NR^bR^c$, $—NR^bC(=O)NR^bR^c$, $—NR^bC(=O)R^a$, $—NR^bC(=O)OR^b$, alkyl, heteroalkyl, haloalkyl, cycloalkyl, or heterocycloalkyl, wherein each alkyl, heteroalkyl, cycloalkyl, or heterocycloalkyl is optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl);

each $R^a$, $R^b$, and $R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, haloalkyl, cycloalkyl, or heterocycloalkyl, wherein each alkyl, alkoxy, cycloalkyl, or heterocycloalkyl is optionally substituted, wherein at least one of $R^{12}$ and $R^{13}$ is halogen, alkyl, alkoxy, haloalkyl, cycloalkyl, or heterocycloalkyl;

or $R^{12}$ and $R^{13}$ are taken together with the atoms to which they are attached to form an optionally substituted heterocycloalkyl or cycloalkyl;

$R^{14}$ and $R^{15}$ are each independently alkyl, haloalkyl, cycloalkyl, or heterocycloalkyl, wherein each alkyl, cycloalkyl, or heterocycloalkyl is optionally substituted;

or $R^{14}$ and $R^{15}$ are taken together with the nitrogen atom to which they are attached to form an optionally substituted heterocycloalkyl.

In some embodiments, $X^4$ is N and $R^5$ is F, Cl, Br, $—CH_3$, $—OCH_3$, $—CF_3$, or $—OCF_3$. In some embodiments, $X^4$ is N and $R^5$ is $—CH_3$, $—OCH_3$, $—CF_3$, or $—OCF_3$. In some embodiments, $X^4$ is N and $R^5$ is $—OCH_3$.

In some embodiments, $X^4$ is N, $R^6$ and $R^7$ are each hydrogen, and $R^5$ is F, Cl, Br, $—CH_3$, $—OCH_3$, $—CF_3$, or $—OCF_3$. In some embodiments, $X^4$ is N, $R^6$ and $R^7$ are each hydrogen, and $R^5$ is $—CH_3$, $—OCH_3$, $—CF_3$, or $—OCF_3$. In some embodiments, $X^4$ is N, $R^6$ and $R^7$ are each hydrogen, and $R^5$ is $—OCH_3$.

In some embodiments, $X^6$ is N and $R^5$ is F, Cl, Br, $—CH_3$, $—OCH_3$, $—CF_3$, or $—OCF_3$. In some embodiments, $X^6$ is N and $R^5$ is $—CH_3$, $—OCH_3$, $—CF_3$, or $—OCF_3$. In some embodiments, $X^6$ is N and $R^5$ is $—OCH_3$.

In some embodiments, $X^6$ is N, $R^4$ and $R^7$ are each hydrogen, and $R^5$ is F, Cl, Br, $—CH_3$, $—OCH_3$, $—CF_3$, or $—OCF_3$. In some embodiments, $X^6$ is N, $R^4$ and $R^7$ are each hydrogen, and $R^5$ is $—CH_3$, $—OCH_3$, $—CF_3$, or $—OCF_3$. In some embodiments, $X^6$ is N, $R^4$ and $R^7$ are each hydrogen, and $R^5$ is $—OCH_3$.

In some embodiments, $R^{12}$ and $R^{13}$ are each independently hydrogen or optionally substituted alkyl. In some embodiments, $R^{12}$ and $R^{13}$ are each independently optionally substituted alkyl. In some embodiments, $R^{12}$ and $R^{13}$ are each independently hydrogen or $C_1$-$C_6$ alkyl. In some embodiments, $R^{12}$ and $R^{13}$ are each independently $C_1$-$C_6$ alkyl. In some embodiments, $R^{12}$ and $R^{13}$ are each methyl. In some embodiments, $R^{12}$ and $R^{13}$ are each hydrogen. In some embodiments, $R^{12}$ is hydrogen and $R^{13}$ is methyl.

In some embodiments, $R^{14}$ and $R^{15}$ are each independently optionally substituted alkyl. In some embodiments, $R^{14}$ and $R^{15}$ are each independently $C_1$-$C_6$ alkyl. In some embodiments, $R^{14}$ and $R^{15}$ are each methyl.

In some embodiments, $X^4$ is N, $X^5$—$X^7$ is $R^5$-$R^7$, respectively, $R^5$ is $—OCH_3$, $R^{12}$ and $R^{13}$ are each methyl, and $R^{14}$ and $R^{15}$ are each methyl.

In some embodiments, $X^4$ is N, $X^5$—$X^7$ is $R^5$-$R^7$, respectively, $R^6$ and $R^7$ are each hydrogen, $R^5$ is $—OCH_3$, $R^{12}$ and $R^{13}$ are each hydrogen, and $R^{14}$ and $R^{15}$ are each methyl.

In some embodiments, $X^6$ is N, $X^4$, $X^5$ and $X^7$ are $R^4$, $R^5$, and $R^7$, respectively, $R^4$ and $R^7$ are each hydrogen, $R^5$ is $—OCH_3$, $R^{12}$ and $R^{13}$ are each hydrogen, and $R^{14}$ and $R^{15}$ are each methyl.

In some embodiments, $X^4$ is N, $X^5$—$X^7$ is $R^5$-$R^7$, respectively, $R^6$ and $R^7$ are each hydrogen, $R^5$ is $—OCH_3$, $R^{12}$ is hydrogen and $R^{13}$ is methyl, and $R^{14}$ and $R^{15}$ are each methyl.

In some embodiments, the compound of Formula (II) has the structure of Formula (IID'), or a pharmaceutically acceptable salt or solvate thereof:

Formula (IID')

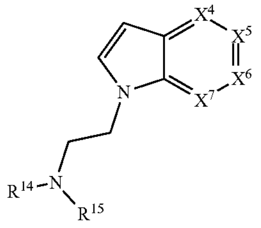

wherein:

$X^4$ is N or $CR^4$;

$X^5$ is N or $CR^5$;

$X^6$ is N or $CR^6$;

$X^7$ is N or $CR^7$;

wherein at least one of $X^4$—$X^7$ is N;

wherein $R^4$-$R^7$ are each independently hydrogen, halogen, —CN, $—OR^a$, $—SR^a$, $—S(=O)R^a$, $—S(=O)_2R^a$, $—NO_2$, $—NR^bR^c$, $—NHS(=O)_2R^a$, $—S(=O)_2NR^bR^c$, $—C(=O)R^a$, $—OC(=O)R^a$, $—C(=O)OR^b$, $—OC(=O)OR^b$, $—C(=O)NR^bR^c$, $—OC(=O)NR^bR^c$, $—NR^bC(=O)NR^bR^c$, $—NR^bC(=O)R^a$, $—NR^bC(=O)OR^b$, alkyl, heteroalkyl, haloalkyl, cycloalkyl, or heterocycloalkyl, wherein each alkyl, heteroalkyl, cycloalkyl, or heterocycloalkyl is optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl);

each $R^a$, $R^b$, and $R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl; and $R^{14}$ and $R^{15}$ are each independently alkyl, haloalkyl, cycloalkyl, or heterocycloalkyl, wherein each alkyl, heteroalkyl, cycloalkyl, or heterocycloalkyl is optionally substituted;

or $R^{14}$ and $R^{15}$ are taken together with the nitrogen atom to which they are attached to form an optionally substituted heterocycloalkyl.

In some embodiments, the compound of Formula (II) has the structure of Formula (IID), or a pharmaceutically acceptable salt or solvate thereof:

Formula (IID)

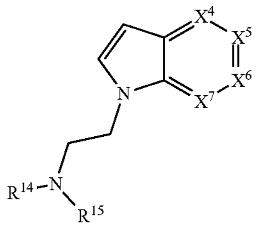

wherein:

$X^4$ is N or $CR^4$;

$X^5$ is N or $CR^5$;

$X^6$ is N or $CR^6$;
$X^7$ is N or $CR^7$;
wherein at least one of $X^4$—$X^7$ is N;
wherein $R^4$-$R^7$ are each independently hydrogen, halogen, —CN, —$OR^a$, —$SR^a$, —S(═O)$R^a$, —S(═O)$_2R^a$, —$NO_2$, —$NR^bR^c$, —NHS(═O)$_2R^a$, —S(═O)$_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl is optionally substituted;
or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl);
each $R^a$, $R^b$, and $R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;
or $R^b$ and $R^c$ are taken together with the nitrogen atom to which they are attached to form an optionally substituted heterocycloalkyl;
$R^{14}$ and $R^{15}$ are each independently alkyl, haloalkyl, cycloalkyl, or heterocycloalkyl, wherein each alkyl, heteroalkyl, cycloalkyl, or heterocycloalkyl is optionally substituted;
or $R^{14}$ and $R^{15}$ are taken together with the nitrogen atom to which they are attached to form an optionally substituted heterocycloalkyl;
provided that if:
(a) $X^7$ is N and $X^4$—$X^6$ are $CR^4$—$CR^6$, then $R^5$ is F, —CN, —$OR^a$, —$NO_2$, alkyl, heteroalkyl, haloalkyl, heterocycloalkyl, or cycloalkyl;
(b) $X^6$ is N, $X^4$ is $CR^4$, $X^5$ is $CR^5$, and $X^7$ is $CR^7$, then $R^5$ is H, F, Cl, —CN, —$OR^a$, —$NO_2$, alkyl, heteroalkyl, haloalkyl, heterocycloalkyl, or cycloalkyl;
(c) $X^5$ and $X^7$ are each N, $X^4$ is $CR^4$, and $X^6$ is $CR^6$, then $R^4$ is H, F, Br, —CN, —$OR^a$, —$NO_2$, heteroalkyl, haloalkyl, and cycloalkyl;
(d) $X^4$ and $X^6$ are each N, $X^5$ is $CR^5$, and $X^7$ is $CR^7$, then $R^7$ is H, F, Br, —CN, —$OR^a$, —$NO_2$, alkyl, haloalkyl, and cycloalkyl; and
(e) $X^4$ is N and $X^5$—$X^7$ are $CR^5$—$CR^7$, then $R^7$ is H, F, Cl, —CN, —$OR^a$, —$NO_2$, alkyl, heteroalkyl, haloalkyl, and cycloalkyl.

In some embodiments, $X^4$ is N and $R^5$ is F, Cl, Br, —$CH_3$, —$OCH_3$, —$CF_3$, or —$OCF_3$. In some embodiments, $X^4$ is N and $R^5$ is —$CH_3$, —$OCH_3$, —$CF_3$, or —$OCF_3$. In some embodiments, $X^4$ is N and $R^5$ is —$OCH_3$.

In some embodiments, $X^4$ is N, $R^6$ and $R^7$ are each hydrogen, and $R^5$ is F, Cl, Br, —$CH_3$, —$OCH_3$, —$CF_3$, or —$OCF_3$. In some embodiments, $X^4$ is N, $R^6$ and $R^7$ are each hydrogen, and $R^5$ is —$CH_3$, —$OCH_3$, —$CF_3$, or —$OCF_3$. In some embodiments, $X^4$ is N, $R^6$ and $R^7$ are each hydrogen, and $R^5$ is —$OCH_3$.

In some embodiments, $X^6$ is N and $R^5$ is F, Cl, Br, —$CH_3$, —$OCH_3$, —$CF_3$, or —$OCF_3$. In some embodiments, $X^6$ is N and $R^5$ is —$CH_3$, —$OCH_3$, —$CF_3$, or —$OCF_3$. In some embodiments, $X^6$ is N and $R^5$ is —$OCH_3$.

In some embodiments, $X^6$ is N, $R^4$ and $R^7$ are each hydrogen, and $R^5$ is F, Cl, Br, —$CH_3$, —$OCH_3$, —$CF_3$, or —$OCF_3$. In some embodiments, $X^6$ is N, $R^4$ and $R^7$ are each hydrogen, and $R^5$ is —$CH_3$, —$OCH_3$, —$CF_3$, or —$OCF_3$. In some embodiments, $X^6$ is N, $R^4$ and $R^7$ are each hydrogen, and $R^5$ is —$OCH_3$.

In some embodiments, $R^{12}$ and $R^{13}$ are each independently hydrogen or optionally substituted alkyl. In some embodiments, $R^{12}$ and $R^{13}$ are each independently optionally substituted alkyl. In some embodiments, $R^{12}$ and $R^{13}$ are each independently hydrogen or $C_1$-$C_6$ alkyl. In some embodiments, $R^{12}$ and $R^{13}$ are each independently $C_1$-$C_6$ alkyl. In some embodiments, $R^{12}$ and $R^{13}$ are each methyl. In some embodiments, $R^{12}$ and $R^{13}$ are each hydrogen. In some embodiments, $R^{12}$ is hydrogen and $R^{13}$ is methyl.

In some embodiments, $R^{14}$ and $R^{15}$ are each independently optionally substituted alkyl. In some embodiments, $R^{14}$ and $R^{15}$ are each independently $C_1$-$C_6$ alkyl. In some embodiments, $R^{14}$ and $R^{15}$ are each methyl.

In some embodiments, $X^4$ is N, $X^5$—$X^7$ is $R^5$-$R^7$, respectively, $R^5$ is —$OCH_3$, $R^{12}$ and $R^{13}$ are each methyl, and $R^{14}$ and $R^{15}$ are each methyl.

In some embodiments, $X^4$ is N, $X^5$—$X^7$ is $R^5$-$R^7$, respectively, $R^6$ and $R^7$ are each hydrogen, $R^5$ is —$OCH_3$, $R^{12}$ and $R^{13}$ are each hydrogen, and $R^{14}$ and $R^{15}$ are each methyl.

In some embodiments, $X^6$ is N, $X^4$, $X^5$ and $X^7$ are $R^4$, $R^5$, and $R^7$, respectively, $R^4$ and $R^7$ are each hydrogen, $R^5$ is —$OCH_3$, $R^{12}$ and $R^{13}$ are each hydrogen, and $R^{14}$ and $R^{15}$ are each methyl.

In some embodiments, $X^4$ is N, $X^5$—$X^7$ is $R^5$-$R^7$, respectively, $R^6$ and $R^7$ are each hydrogen, $R^5$ is —$OCH_3$, $R^{12}$ is hydrogen and $R^{13}$ is methyl, and $R^{14}$ and $R^{15}$ are each methyl.

In some embodiments, the compound of Formula (II) has the structure of Formula (IIF'), or a pharmaceutically acceptable salt or solvate thereof:

Formula (IIF')

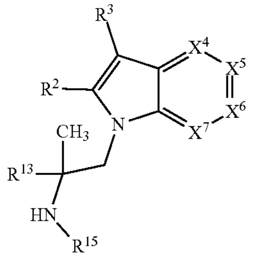

wherein:
$R^2$ and $R^3$ are each independently hydrogen or $CH_3$;
$R^{13}$ is hydrogen or $CH_3$;
$R^{15}$ is hydrogen or $CH_3$;
$X^4$ is N or $CR^4$;
$X^5$ is N or $CR^5$;
$X^6$ is N or $CR^6$;
$X^7$ is N or $CR^7$;
wherein $R^4$-$R^7$ are each independently hydrogen, halogen, —$OR^a$, alkyl, haloalkyl, cycloalkyl, or heterocycloalkyl, wherein each alkyl, cycloalkyl, or heterocycloalkyl is optionally substituted; and
$R^a$ is hydrogen, alkyl, haloalkyl, cycloalkyl, or heterocycloalkyl, wherein each alkyl, cycloalkyl, or heterocycloalkyl is independently optionally substituted.

In some embodiments, the compound of Formula (II) has the structure of Formula (IIF), or a pharmaceutically acceptable salt or solvate thereof:

Formula (IIF)

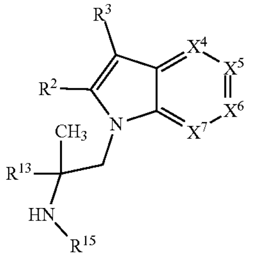

wherein:

$R^2$ and $R^3$ are each independently hydrogen or $CH_3$;

$R^{13}$ is hydrogen or $CH_3$;

$R^{15}$ is hydrogen or $CH_3$;

$X^4$ is N or $CR^4$;

$X^5$ is N or $CR^5$;

$X^6$ is N or $CR^6$;

$X^7$ is N or $CR^7$;

wherein $R^4$-$R^7$ are each independently hydrogen, halogen, —$OR^a$, alkyl, haloalkyl, cycloalkyl, or heterocycloalkyl, wherein each alkyl, cycloalkyl, or heterocycloalkyl is optionally substituted;

$R^a$ is hydrogen, alkyl, haloalkyl, cycloalkyl, or heterocycloalkyl, wherein each alkyl, cycloalkyl, or heterocycloalkyl is independently optionally substituted;

provided that:

(a) $R^{13}$ is $CH_3$ and at least one of $R^4$, $R^5$, $R^6$, or $R^7$ is halogen, —$OR^a$, alkyl, haloalkyl, cycloalkyl, or heterocycloalkyl;

(b) $R^{13}$ is hydrogen, at least one of $X^4$—$X^7$ is N, and $CR^5C$—$OR^a$.

In some embodiments, $R^2$ and $R^3$ are hydrogen.

In some embodiments, $R^2$ is hydrogen and $R^3$ is $CH_3$.

In some embodiments, $R^{13}$ is hydrogen. In some embodiments, $R^{15}$ is $CH_3$. In some embodiments, $R^{13}$ is hydrogen and $R^{15}$ is $CH_3$. In some embodiments, $R^{13}$ is hydrogen and $R^{15}$ is hydrogen. In some embodiments, $R^{13}$ is $CH_3$ and $R^{15}$ is hydrogen.

In some embodiments, $X^4$—$X^7$ are described elsewhere herein. In some embodiments, $R^4$-$R^7$ are described elsewhere herein. In some embodiments, IV is described elsewhere herein.

In some embodiments, $R^{11}$ and $R^{12}$ are taken together with the atoms to which they are attached to form a cycloalkyl, wherein the cycloalkyl is a Ring A, wherein Ring A is optionally substituted. In some embodiments, Ring A is substituted with alkyl, halogen, or haloalkyl. In some embodiments, the Ring A is cyclopropyl, cyclobutyl, cyclopentyl, or cyclohexyl, wherein the cyclopropyl, cyclobutyl, cyclopentyl, or cyclohexyl is optionally substituted. In some embodiments, the Ring A is cyclopropyl, cyclobutyl, cyclopentyl, or cyclohexyl, wherein the cyclopropyl, cyclobutyl, cyclopentyl, or cyclohexyl is unsubstituted.

In some embodiments, the compound of Formula (II) has the structure of Formula (IIE), or a pharmaceutically acceptable salt or solvate thereof:

Formula (IIE)

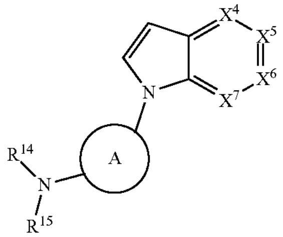

wherein:
Ring A is

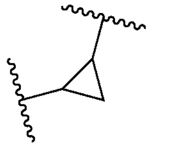

or

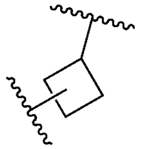

;

$R^{14}$ and $R^{15}$ are each independently hydrogen, alkyl, haloalkyl, cycloalkyl, or heterocycloalkyl, wherein each alkyl, cycloalkyl, or heterocycloalkyl is optionally substituted;

or $R^{14}$ and $R^{15}$ are taken together with the nitrogen atom to which they are attached to form an optionally substituted heterocycloalkyl;

$X^4$ is N or $CR^4$;
$X^5$ is N or $CR^5$;
$X^6$ is N or $CR^6$;
$X^7$ is N or $CR^7$;

wherein $R^4$-$R^7$ are each independently hydrogen, halogen, —CN, —$OR^a$, —$SR^a$, —$S(=O)R^a$, —$S(=O)_2R^a$, —$NO_2$, —$NR^bR^c$, —$NHS(=O)_2R^a$, —$S(=O)_2NR^bR^c$, —$C(=O)R^a$, —$OC(=O)R^a$, —$C(=O)OR^b$, —$OC(=O)OR^b$, —$C(=O)NR^bR^c$, —$OC(=O)NR^bR^c$, —$NR^bC(=O)NR^bR^c$, —$NR^bC(=O)R^a$, —$NR^bC(=O)OR^b$, alkyl, heteroalkyl, haloalkyl, cycloalkyl, or heterocycloalkyl, wherein each alkyl, heteroalkyl, cycloalkyl, or heterocycloalkyl is optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl); and each $R^a$-$R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl.

In some embodiments, $R^1$ is:

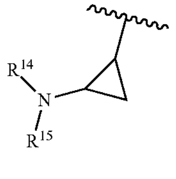

or

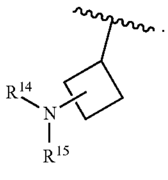

.

In some embodiments, $R^1$ is:

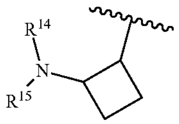

or

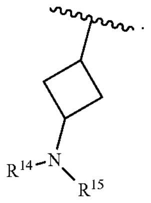

In some embodiments, $R^1$ is:

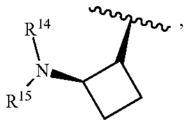

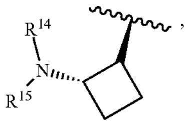

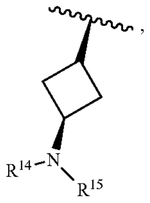

or

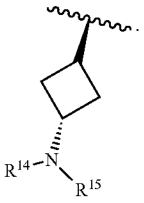

In some embodiments, $R^1$ is:

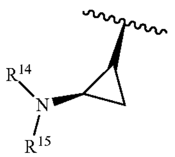

or

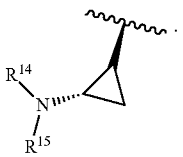

In some embodiments, $R^{14}$ and $R^{15}$ are each independently methyl or ethyl, or $R^{14}$ and $R^{15}$ are taken together with the nitrogen atom to which they are attached to form $C_2$-$C_5$ heterocycloalkyl.

In some embodiments, $X^4$ is N. In some embodiments, $X^4$ is $CR^4$.

In some embodiments, $X^5$ is N. In some embodiments, $X^5$ is $CR^5$.

In some embodiments, $X^6$ is N. In some embodiments, $X^6$ is $CR^6$.

In some embodiments, $X^7$ is N. In some embodiments, $X^7$ is $CR^7$.

In some embodiments, any one of $R^4$-$R^7$ is described elsewhere herein.

In some embodiments, the compound of Formula (II) has the structure of Formula (VI'), or a pharmaceutically acceptable salt or solvate thereof:

Formula (VI')

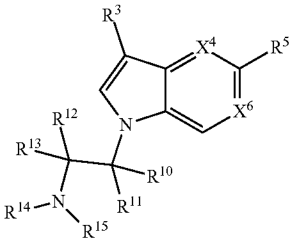

wherein:

$R^3$ is hydrogen or $C_1$-$C_3$ alkyl;

$X^4$ is N or $CR^4$;

$R^4$ is hydrogen or halo;

$X^6$ is N or CH;

$R^5$ is halo or $C_1$-$C_3$ alkoxy;

$R^{10}$ and $R^{11}$ are each hydrogen;

$R^{12}$ and $R^{13}$ are each independently hydrogen or $C_1$-$C_3$ alkyl;

or $R^{11}$ and $R^{12}$ are taken together with the atoms to which they are attached to form a cyclobutyl ring;

or $R^{12}$ and $R^{13}$ are taken together with the atoms to which they are attached to form a cyclopropyl ring;

$R^{14}$ is hydrogen or $C_1$-$C_3$ alkyl; and $R^{15}$ is $C_1$-$C_3$ alkyl.

In some embodiments, the compound of Formula (II) has the structure of Formula (VI), or a pharmaceutically acceptable salt or solvate thereof:

Formula (VI)

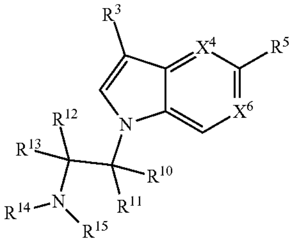

wherein:

$R^3$ is hydrogen or $C_1$-$C_3$ alkyl;

$X^4$ is N or $CR^4$;

$R^4$ is hydrogen or halo;

$X^6$ is N or CH;

$R^5$ is halo or $C_1$-$C_3$ alkoxy;

$R^{10}$ and $R^{11}$ are each hydrogen;

$R^{12}$ and $R^{13}$ are each independently hydrogen or $C_1$-$C_3$ alkyl;

or $R^{11}$ and $R^{12}$ are taken together with the atoms to which they are attached to form a cyclobutyl ring;

or $R^{12}$ and $R^{13}$ are taken together with the atoms to which they are attached to form a cyclopropyl ring;

$R^{14}$ is hydrogen or $C_1$-$C_3$ alkyl; and $R^{15}$ is $C_1$-$C_3$ alkyl, provided that:

(a) $X^4$ or $X^6$ is N;

(b) $R^{12}$ and $R^{13}$ are $C_1$-$C_3$ alkyl;

(c) $R^{11}$ and $R^{12}$ are taken together with the atoms to which they are attached to form a cyclobutyl ring; or (d) $R^{12}$ and $R^{13}$ are taken together with the atoms to which they are attached to form a cyclopropyl ring.

In some embodiments, $X^4$ is N.

In some embodiments, $X^4$ is N and $R^5$ is —$OCH_3$. In some embodiments, $X^4$ is N, $R^5$ is —$OCH_3$, and $R^{12}$ and $R^{13}$ are $C_1$-$C_3$ alkyl.

In some embodiments, $X^4$ is $CR^4$.

In some embodiments, $R^4$ is hydrogen or fluorine. In some embodiments, $X^4$ is $CR^4$, $R^4$ is hydrogen or fluorine, and $R^5$ is —$OCH_3$. In some embodiments, $X^4$ is $CR^4$, $R^4$ is hydrogen, and $R^5$ is —$OCH_3$. In some embodiments, $X^4$ is $CR^4$, $R^4$ is fluorine, and $R^5$ is —$OCH_3$.

In some embodiments, $X^6$ is N.

In some embodiments, $X^6$ is N and $R^5$ is —$OCH_3$. In some embodiments, $X^6$ is N, $R^5$ is —$OCH_3$, and $R^{12}$ and $R^{13}$ are hydrogen.

In some embodiments, $X^4$ is $CR^4$, $R^4$ is hydrogen or fluorine, $X^6$ is CH, and $R^5$ is fluorine or —$OCH_3$. In some embodiments, $X^4$ is $CR^4$, $R^4$ is hydrogen, $X^6$ is CH, and $R^5$ is fluorine. In some embodiments, $X^4$ is $CR^4$, $R^4$ is fluorine, $X^6$ is CH, and $R^5$ is fluorine. In some embodiments, $X^4$ is $CR^4$, $R^4$ is hydrogen, $X^6$ is CH, and $R^5$ is —$OCH_3$.

In some embodiments, $R^{10}$ and $R^{11}$ are hydrogen.

In some embodiments, $R^{10}$ and $R^{11}$ are hydrogen and $X^4$ is N. In some embodiments, $R^{10}$ and $R^{11}$ are hydrogen, $X^4$ is N, and $R^5$ is —$OCH_3$.

In some embodiments, $R^{10}$ and $R^{11}$ are hydrogen and $X^6$ is N. In some embodiments, $R^{10}$ and $R^{11}$ are hydrogen, $X^6$ is N, and $R^5$ is —$OCH_3$.

In some embodiments, $R^{11}$ and $R^{12}$ are taken together with the atoms to which they are attached to form a cyclobutyl ring.

In some embodiments, $R^3$ is —$CH_3$, $R^{11}$ and $R^{12}$ are taken together with the atoms to which they are attached to form a cyclobutyl ring, and $R^5$ is fluorine.

In some embodiments, $R^{12}$ is hydrogen and $R^{13}$ is $CH_3$.

In some embodiments, $R^{12}$ is hydrogen and $R^{13}$ is $CH_3$ and $X^4$ is N. In some embodiments, $R^{12}$ is hydrogen, $R^{13}$ is $CH_3$ and $X^4$ is N, and $R^5$ is —$OCH_3$. In some embodiments, $R^{12}$ is hydrogen and $R^{13}$ is $CH_3$ and $X^6$ is N. In some embodiments, $R^{12}$ is hydrogen and $R^{13}$ is $CH_3$, $X^6$ is N, and $R^5$ is —$OCH_3$.

In some embodiments, $R^{12}$ and $R^{13}$ are $CH_3$.

In some embodiments, $R^{12}$ and $R^{13}$ are taken together with the atoms to which they are attached to form a cyclopropyl ring.

In some embodiments, $R^{12}$ and $R^{13}$ are taken together with the atoms to which they are attached to form a cyclopropyl ring and $R^3$ is $CH_3$. In some embodiments, $R^{12}$ and $R^{13}$ are taken together with the atoms to which they are attached to form a cyclopropyl ring, $R^3$ is $CH_3$, and $R^5$ is fluorine.

In some embodiments, $R^3$ is hydrogen.

In some embodiments, $R^3$ is —$CH_3$.

In some embodiments, $R^{14}$ is hydrogen and $R^{15}$ is —$CH_3$.

In some embodiments, $R^{14}$ and $R^{15}$ are —$CH_3$.

Provided in certain embodiments herein is a compound of Formula (V'), or a pharmaceutically acceptable salt or solvate thereof:

Formula (V')

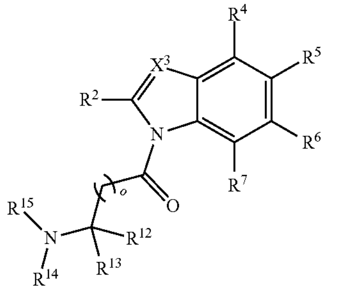

wherein:

$X^3$ is N or $CR^3$;

$R^2$ is hydrogen, alkyl, alkoxy, haloalkyl, cycloalkyl, or heterocycloalkyl, wherein each alkyl, alkoxy, cycloalkyl, or heterocycloalkyl is independently optionally substituted;

$R^3$ is hydrogen, alkyl, alkoxy, haloalkyl, cycloalkyl, or heterocycloalkyl, wherein each alkoxy, cycloalkyl, or heterocycloalkyl is independently optionally substituted;

$R^4$-$R^7$ are each independently hydrogen, —F, —Cl, —CN, —$OR^a$, —$SR^a$, —S(═O)$R^a$, —S(═O)$_2R^a$, —$NO_2$, —$NR^bR^c$, —NHS(═O)$_2R^a$, —S(═O)$_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl is independently optionally substituted;

each $R^a$-$R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is independently optionally substituted;

or $R^{12}$ and $R^{13}$ are taken together with the atoms to which they are attached to form an optionally substituted heterocycloalkyl or an optionally substituted cycloalkyl;

$R^{14}$ and $R^{15}$ are each independently hydrogen, alkyl, haloalkyl, cycloalkyl, or heterocycloalkyl, wherein each alkyl, cycloalkyl, or heterocycloalkyl is independently optionally substituted;

or $R^{14}$ and $R^{15}$ are taken together with the nitrogen atom to which they are attached to form a heterocycloalkyl (e.g., an optionally substituted heterocycloalkyl);

or $R^{13}$ and $R^{14}$ are taken together with the nitrogen atom to which they are attached to form an optionally substituted heterocycloalkyl; and is 0-3.

Provided in some embodiments herein is a compound of Formula (V), or a pharmaceutically acceptable salt or solvate thereof:

Formula (V)

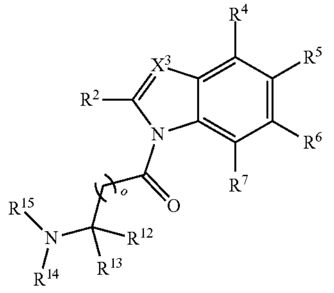

wherein:

$X^3$ is N or $CR^3$;

$R^2$ is hydrogen, alkyl, alkoxy, haloalkyl, cycloalkyl, or heterocycloalkyl, wherein each alkyl, alkoxy, cycloalkyl, or heterocycloalkyl is independently optionally substituted;

$R^3$ is hydrogen, alkyl, alkoxy, haloalkyl, cycloalkyl, or heterocycloalkyl, wherein each alkoxy, cycloalkyl, or heterocycloalkyl is independently optionally substituted;

$R^4$-$R^7$ are each independently hydrogen, —F, —Cl, —CN, —$OR^a$, —$SR^a$, —S(═O)$R^a$, —$S(═O)_2R^a$, —$NO_2$, —$NR^bR^c$, —$NHS(═O)_2R^a$, —$S(═O)_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl is independently optionally substituted;

each $R^a$-$R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is independently optionally substituted;

or $R^{12}$ and $R^{13}$ are taken together with the atoms to which they are attached to form an optionally substituted heterocycloalkyl or an optionally substituted cycloalkyl;

$R^{14}$ and $R^{15}$ are each independently hydrogen, alkyl, haloalkyl, cycloalkyl, or heterocycloalkyl, wherein each alkyl, cycloalkyl, or heterocycloalkyl is independently optionally substituted;

or $R^{14}$ and $R^{15}$ are taken together with the nitrogen atom to which they are attached to form a heterocycloalkyl (e.g., an optionally substituted heterocycloalkyl);

or $R^{13}$ and $R^{14}$ are taken together with the nitrogen atom to which they are attached to form an optionally substituted heterocycloalkyl; and o is 0-3;

wherein:

one or more $R^4$-$R^7$ is —F, —Cl, —CN, —$OR^a$, —$SR^a$, —S(═O)$R^a$, —$S(═O)_2R^a$, —$NO_2$, —$NR^bR^c$, —$NHS(═O)_2R^a$, —$S(═O)_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl is independently optionally substituted;

$R^4$-$R^7$ are each hydrogen and $R^{12}$ is alkyl, haloalkyl, cycloalkyl, or heterocycloalkyl;

$R^4$-$R^7$ are each hydrogen and $R^{12}$ and $R^{13}$ are each hydrogen; or any of $R^4$ and $R^5$, $R^5$ and $R^6$, or $R^6$ and $R^7$ are taken together with the atoms to which they are attached to form an optionally substituted cycloalkyl or an optionally substituted heterocycloalkyl (e.g., an optionally substituted 5- or 6-membered ring);

provided that:

(a) if $X^3$ is CH and $R^4$, $R^5$, $R^6$, or $R^7$ is —$NR^bR^c$, then $R^b$ is alkyl, haloalkyl, heteroalkyl, cycloalkyl, or heterocycloalkyl or $R^b$ and $R^c$ are taken together with the nitrogen atom to which they are attached to form an optionally substituted heterocycloalkyl; and (b) if $R^4$-$R^7$ are each hydrogen and $R^{12}$ and $R^{13}$ are each hydrogen, then $R^{14}$ and $R^{15}$ are each methyl.

In some embodiments, o is 2-0. In some embodiments, o is 0.

In some embodiments, $R^2$ is hydrogen, optionally substituted alkoxy, or haloalkyl. In some embodiments, $R^3$ is hydrogen, optionally substituted alkoxy, or haloalkyl. In some embodiments, $R^2$ and $R^3$ are each independently hydrogen, optionally substituted alkoxy, or haloalkyl. In some embodiments, $R^2$ is H. In some embodiments, $R^3$ is H. In some embodiments, $R^2$ and $R^3$ are each H.

In some embodiments, the compound of Formula (V) has the structure of Formula (V-A), or a pharmaceutically acceptable salt or solvate thereof:

Formula (V-A)

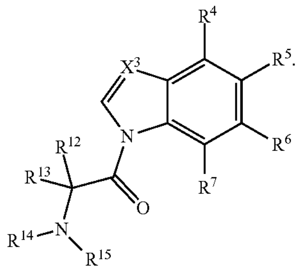

In some embodiments, one or more $R^4$-$R^7$ is —F, —Cl, —CN, —$OR^a$, —$SR^a$, —S(═O)$R^a$, —$S(═O)_2R^a$, —$NO_2$, —$NR^bR^c$, —$NHS(═O)_2R^a$, —$S(═O)_2NR^bR^c$, —C(═O)$R^a$, —OC(═O)$R^a$, —C(═O)$OR^b$, —OC(═O)$OR^b$, —C(═O)$NR^bR^c$—OC(═O)$NR^bR^c$—$NR^b$C(═O)$NR^bR^c$—$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl is independently optionally substituted. In some embodiments, one or more $R^4$-$R^7$ is —F, —Cl, —CN, —$OR^a$, —$SR^a$, —$NO_2$, —C(═O)$R^a$, —OC(═O)$R^a$, —C(═O)$OR^b$, —OC(═O)$OR^b$, —C(═O)$NR^bR^c$—OC(═O)$NR^bR^c$—$NR^b$C(═O)$NR^bR^c$—$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl is independently optionally substituted. In some embodiments, one or more $R^4$-$R^7$ is —F, —Cl, —CN, —$OR^a$, alkyl, haloalkyl, cycloalkyl, or heterocycloalkyl, wherein each alkyl, cycloalkyl, or heterocycloalkyl is independently optionally substituted. In some embodiments, one or more $R^4$-$R^7$ is —F, —Cl, —CN, —OH, —$OC_1$-$C_6$ alkyl, $C_1$-$C_6$ alkyl, or $C_1$-$C_6$ haloalkyl. In some embodiments, one or more $R^4$-$R^7$ is —F, —Cl, —OH, —$OCH_3$, —$OCF_3$, —$CH_3$, or —$CF_3$.

In some embodiments, one or more $R^5$-$R^7$ is —F, —Cl, —OH, —$OCH_3$, —$OCF_3$, —$CH_3$, or —$CF_3$.

In some embodiments, $X^3$ is N.

In some embodiments, $X^3$ is $CR^3$.

In some embodiments, $X^3$ is CH.

In some embodiments, $X^3$ is CH and $R^4$, $R^5$, $R^6$, or $R^7$ is —$NR^bR^c$ and $R^b$ is alkyl, haloalkyl, heteroalkyl, cycloalkyl, or heterocycloalkyl. In some embodiments, $X^3$ is CH and $R^4$, $R^5$, $R^6$, or $R^7$ is —$NR^bR^c$ and $R^b$ and $R^c$ are taken together with the nitrogen atom to which they are attached to form an optionally substituted heterocycloalkyl.

In some embodiments, $R^4$-$R^7$ are each hydrogen and $R^{12}$ is alkyl, haloalkyl, cycloalkyl, or heterocycloalkyl. In some embodiments, $R^4$-$R^7$ are each hydrogen and $R^{12}$ is $C_1$-$C_6$ alkyl or $C_3$-$C_6$ cycloalkyl. In some embodiments, $R^4$-$R^7$ are each hydrogen and $R^{12}$ is methyl.

In some embodiments, $R^4$-$R^7$ are each hydrogen and $R^{12}$ and $R^{13}$ are each hydrogen. In some embodiments, $R^4$-$R^7$ are each hydrogen, $R^{12}$ and $R^{13}$ are each hydrogen, and $R^{14}$ and $R^{15}$ are each methyl.

In some embodiments, any of $R^4$ and $R^5$, $R^5$ and $R^6$, or $R^6$ and $R^7$ are taken together with the atoms to which they are attached to form an optionally substituted cycloalkyl or an optionally substituted heterocycloalkyl (e.g., an optionally substituted 5- or 6-membered ring). In some embodiments, $R^5$ and $R^6$ are taken together with the atoms to which they are attached to form an optionally substituted heterocycloalkyl. In some embodiments, $R^5$ and $R^6$ are taken together with the atoms to which they are attached to form an optionally substituted $C_2$-$C_6$ heterocycloalkyl.

In some instances, provided herein is a compound of Formula (V-B), or a pharmaceutically acceptable salt or solvate thereof:

Formula (V-B)

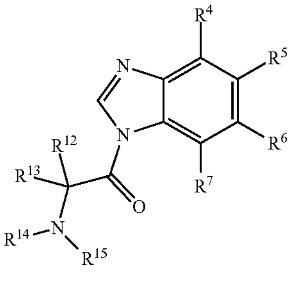

wherein:

$R^4$-$R^7$ are each independently hydrogen, halogen, —CN, —$OR^a$, —$SR^a$, —S(=O)$R^a$, —S(=O)$_2R^a$, —$NO_2$, —$NR^bR^c$, —NHS(=O)$_2R^a$, —S(=O)$_2$ $NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^b$C(=O)$NR^bR^c$, —$NR^b$C(=O)$R^a$, —$NR^b$C(=O)$OR^b$, alkyl, heteroalkyl, haloalkyl, cycloalkyl, or heterocycloalkyl, wherein each alkyl, heteroalkyl, cycloalkyl, or heterocycloalkyl is independently optionally substituted;

each $R^a$-$R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl; $R^{12}$ and $R^{13}$ are each independently hydrogen, halogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is independently optionally substituted;

or $R^{12}$ and $R^{13}$ are taken together with the atoms to which they are attached to form an optionally substituted heterocycloalkyl or an optionally substituted cycloalkyl; and $R^{14}$ and $R^{15}$ are each independently hydrogen, alkyl, haloalkyl, cycloalkyl, or heterocycloalkyl, wherein each alkyl, cycloalkyl, or heterocycloalkyl is independently optionally substituted;

or $R^{14}$ and $R^{15}$ are taken together with the nitrogen atom to which they are attached to form a heterocycloalkyl (e.g., an optionally substituted heterocycloalkyl).

In some instances, provided herein is a compound of Formula (V-C), or a pharmaceutically acceptable salt or solvate thereof:

Formula (V-C)

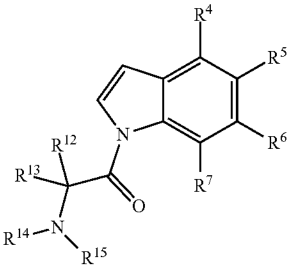

wherein:

$R^4$-$R^7$ are each independently hydrogen, —F, —Cl, —CN, —$OR^a$, —$SR^a$, —S(=O)$R^a$, —S(=O)$_2R^a$, —$NO_2$, —C(=O)$R^a$, —OC(=O)$R^a$, —C(=O)$OR^b$, —OC(=O)$OR^b$, —C(=O)$NR^bR^c$, alkyl, heteroalkyl, haloalkyl, cycloalkyl, or heterocycloalkyl, wherein each alkyl, heteroalkyl, cycloalkyl, or heterocycloalkyl is independently optionally substituted;

each $R^a$-$R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is independently optionally substituted;

or $R^{12}$ and $R^{13}$ are taken together with the atoms to which they are attached to form an optionally substituted heterocycloalkyl or an optionally substituted cycloalkyl; and $R^{14}$ and $R^{15}$ are each independently hydrogen, alkyl, haloalkyl, cycloalkyl, or heterocycloalkyl, wherein each alkyl, cycloalkyl, or heterocycloalkyl is independently optionally substituted;

or $R^{14}$ and $R^{15}$ are taken together with the nitrogen atom to which they are attached to form a heterocycloalkyl (e.g., an optionally substituted heterocycloalkyl).

In some instances, provided herein is a compound of Formula (V-C), or a pharmaceutically acceptable salt or solvate thereof:

Formula (V-C)

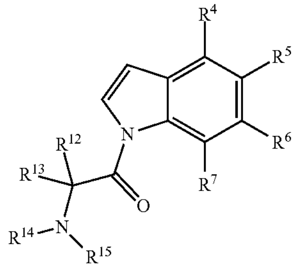

wherein:

$R^4$-$R^7$ are each independently hydrogen, —F, —Cl, —CN, —$OR^a$, —$SR^a$, —S(═O)$R^a$, —S(═O)$_2R^a$, —$NO_2$, —C(═O)$R^a$, —OC(═O)$R^a$, —C(═O)$OR^b$, —OC(═O)$OR^b$, —C(═O)$NR^bR^c$, alkyl, heteroalkyl, haloalkyl, cycloalkyl, or heterocycloalkyl, wherein each alkyl, heteroalkyl, cycloalkyl, or heterocycloalkyl is independently optionally substituted;

each $R^a$-$R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, heteroalkyl, haloalkyl, cycloalkyl, or heterocycloalkyl, wherein each alkyl, alkoxy, heteroalkyl, cycloalkyl, or heterocycloalkyl is independently optionally substituted;

or $R^{12}$ and $R^{13}$ are taken together with the atoms to which they are attached to form an optionally substituted heterocycloalkyl or an optionally substituted cycloalkyl; and $R^{14}$ and $R^{15}$ are each independently hydrogen, alkyl, haloalkyl, cycloalkyl, or heterocycloalkyl, wherein each alkyl, cycloalkyl, or heterocycloalkyl is independently optionally substituted;

or $R^{14}$ and $R^{15}$ are taken together with the nitrogen atom to which they are attached to form a heterocycloalkyl (e.g., an optionally substituted heterocycloalkyl);

provided that:

(a) one or more $R^5$-$R^7$ is —F, —Cl, —CN, —$OR^a$, —$SR^a$, —S(═O)$R^a$, —S(═O)$_2R^a$, —$NO_2$, —C(═O)$R^a$, —OC(═O)$R^a$, —C(═O)$OR^b$, —OC(═O)$OR^b$, —C(═O)$NR^bR^c$, alkyl, heteroalkyl, haloalkyl, cycloalkyl, or heterocycloalkyl, wherein each alkyl, heteroalkyl, cycloalkyl, or heterocycloalkyl is independently optionally substituted;

(b) any of $R^4$ and $R^5$, $R^5$ and $R^6$, or $R^6$ and $R^7$ are taken together with the atoms to which they are attached to form an optionally substituted cycloalkyl or an optionally substituted heterocycloalkyl (e.g., an optionally substituted 5- or 6-membered ring);

(c) $R^4$-$R^7$ are each hydrogen and $R^{12}$ is alkyl, haloalkyl, cycloalkyl, heterocycloalkyl, or $R^{12}$ and $R^{13}$ are taken together with the atoms to which they are attached to form an optionally substituted heterocycloalkyl or an optionally substituted cycloalkyl; or (d) $R^4$-$R^7$ are each hydrogen, $R^{12}$ and $R^{13}$ are each hydrogen, and $R^{14}$ and $R^{15}$ are each methyl or $R^{14}$ and $R^{15}$ are taken together with the nitrogen atom to which they are attached to form a heterocycloalkyl (e.g., an unsubstituted heterocycloalkyl).

In some embodiments, one or more $R^5$-$R^7$ is —F, —Cl, —CN, —$OR^a$, —$SR^a$, —S(═O)$R^a$, —S(═O)$_2R^a$, —$NO_2$, —C(═O)$R^a$, —OC(═O)$R^a$, —C(═O)$OR^b$, —OC(═O)$OR^b$, —C(═O)$NR^bR^c$, alkyl, heteroalkyl, haloalkyl, cycloalkyl, or heterocycloalkyl, wherein each alkyl, heteroalkyl, cycloalkyl, or heterocycloalkyl is independently optionally substituted. In some embodiments, one or more $R^5$-$R^7$ is —F, —Cl, —CN, —$OR^a$, alkyl, haloalkyl, cycloalkyl, or heterocycloalkyl, wherein each alkyl, cycloalkyl, or heterocycloalkyl is independently optionally substituted. In some embodiments, one or more $R^5$-$R^7$ is —F, —Cl, —CN, —OH, —$OC_1$-$C_6$ alkyl, $C_1$-$C_6$ alkyl, or $C_1$-$C_6$ haloalkyl. In some embodiments, one or more $R^5$-$R^7$ is —F, —Cl, —OH, —$OCH_3$, —$OCF_3$, —$CH_3$, or —$CF_3$.

In some embodiments, $R^4$-$R^7$ are each hydrogen and $R^{12}$ is alkyl, haloalkyl, cycloalkyl, heterocycloalkyl. In some embodiments, $R^4$-$R^7$ are each hydrogen and $R^{12}$ is $C_1$-$C_6$ alkyl. In some embodiments, $R^4$-$R^7$ are each hydrogen and $R^{12}$ is methyl. In some embodiments, $R^4$-$R^7$ are each hydrogen and $R^{12}$ and $R^{13}$ are taken together with the atoms to which they are attached to form an optionally substituted heterocycloalkyl or an optionally substituted cycloalkyl.

In some embodiments, $R^4$-$R^7$ are each hydrogen, $R^{12}$ and $R^{13}$ are each hydrogen, and $R^{14}$ and $R^{15}$ are each methyl. some embodiments, $R^4$-$R^7$ are each hydrogen, $R^{12}$ and $R^{13}$ are each hydrogen, and $R^{14}$ and $R^{15}$ are taken together with the nitrogen atom to which they are attached to form a heterocycloalkyl (e.g., an unsubstituted heterocycloalkyl).

In some embodiments, $R^{12}$ and $R^{13}$ are each independently hydrogen or $C_1$-$C_6$ alkyl. In some embodiments, $R^{12}$ and $R^{13}$ are each independently hydrogen, methyl, ethyl, or isopropyl.

In some embodiments,

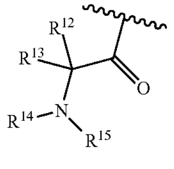

is

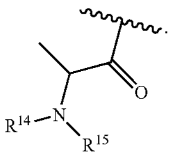

.

In some embodiments,

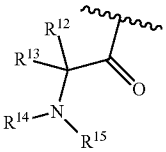 is 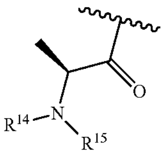 or

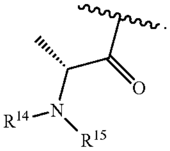.

In some embodiments, $R^{12}$ and $R^{13}$ are each hydrogen.

In some embodiments, $R^4$-$R^7$ are each independently selected from hydrogen, halogen, —$OR^a$, —$NR^bR^c$, $C_1$-$C_6$ alkyl, haloalkyl, $C_3$-$C_5$ cycloalkyl, or $C_2$-$C_4$ heterocycloalkyl. In some embodiments, $R^4$-$R^7$ are each independently selected from H, F, Cl, Br, —$CH_3$, —$CH_2CH_3$, —$CH(CH_3)_2$, —$C(CH_3)_3$, —$OCH_3$, —$OCH_2CH_3$, —$OCH(CH_3)_2$, —$OC(CH_3)_3$—$OC_3$-$C_5$cycloalkyl, —$CF_3$, —$OCF_3$, and —$NR^bR^c$, wherein $R^b$ and $R^c$ are taken together with the nitrogen atom to which they are attached to form an optionally substituted heterocycloalkyl. In some embodiments, $R^4$-$R^7$ are each independently selected from H, F, Cl, Br, —$CH_3$, —$OCH_3$, —$CF_3$, —$OCF_3$, and —$NR^bR^c$, wherein $R^b$ and $R^c$ are taken together with the nitrogen atom to which they are attached to form an optionally substituted heterocycloalkyl. In some embodiments, $R^4$-$R^7$ are each independently selected from H, F, Cl, Br, —$CH_3$, —$OCH_3$, —$CF_3$, —$OCF_3$, and —$NR^bR^c$, wherein $R^b$ and $R^c$ are taken together with the nitrogen atom to which they are attached to form an optionally substituted heterocycloalkyl, wherein at least one of $R^4$-$R^7$ is not H. In some embodiments, $R^4$, $R^6$, and $R^7$ are each independently selected from H, F, Cl, Br, —$CH_3$, —$OCH_3$, —$CF_3$, —$OCF_3$, and —$NR^bR^c$, wherein $R^b$ and $R^c$ are taken together with the nitrogen atom to which they are attached to form an optionally substituted heterocycloalkyl, wherein $R^5$ is F, Cl, Br, —$CH_3$, —$OCH_3$, —$CF_3$, —$OCF_3$, and —$NR^bR^c$, wherein $R^b$ and $R^c$ are taken together with the nitrogen atom to which they are attached to form an optionally substituted heterocycloalkyl.

In some embodiments, $R^4$-$R^7$ are each independently hydrogen, —F, —Cl, —CN, —OH, —O—$C_1$-$C_3$alkyl, $C_1$-$C_4$alkyl, $C_1$-$C_3$haloalkyl, $C_3$-$C_6$cycloalkyl, or $C_2$-$C_5$heterocycloalkyl. In some embodiments, $R^4$-$R^7$ are each independently hydrogen, —F, —Cl, —OH, —$OCH_3$, —$OCF_3$, —$CH_3$, or —$CF_3$.

In some embodiments, any of $R^4$ and $R^5$, $R^5$ and $R^6$, or $R^6$ and $R^7$ are taken together with the atoms to which they are attached to form an optionally substituted 5- or 6-membered heterocycloalkyl. In some embodiments, $R^5$ and $R^6$ are taken together with the atoms to which they are attached to form an optionally substituted heterocycloalkyl (e.g., an optionally substituted 5- or 6-membered ring). In some embodiments, $R^5$ and $R^6$ are taken together with the atoms to which they are attached to form an optionally substituted 5- or 6-membered ring. In some embodiments, $R^5$ and $R^6$ are taken together with the atoms to which they are attached to form a 6-membered heterocycloalkyl containing at least one O atom in the ring. In some embodiments, $R^5$ and $R^6$ are taken together with the atoms to which they are attached to form (e.g., an optionally substituted) dioxanyl or (e.g., an optionally substituted) dioxolanyl. In some embodiments, $R^5$ and $R^6$ are taken together with the atoms to which they are attached to form an unsubstituted 1,3-dioxolanyl. In some embodiments, $R^5$ and $R^6$ are taken together with the atoms to which they are attached to form a 2,2-difluoro-1,3-dioxolanyl.

In some embodiments, $X^4$ is $CR^4$, $X^5$ is $CR^5$, $X^6$ is $CR^6$, $X^7$ is $CR^7$, and $R^4$-$R^7$ are each independently selected from H, F, Cl, Br, —$CH_3$, —$OCH_3$, —$OCH(CH_3)_2$, —$CF_3$, —$OCF_3$,

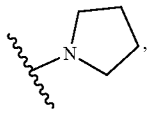, and 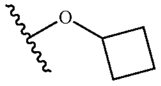.

In some embodiments, $X^4$ is N, $X^5$ is $CR^5$, $X^6$ is $CR^6$, $X^7$ is $CR^7$, and $R^5$-$R^7$ are each independently selected from H, F, Cl, Br, —$CH_3$, —$OCH_3$, —$OCH(CH_3)_2$, —$CF_3$, —$OCF_3$,

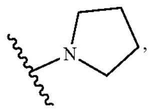, and 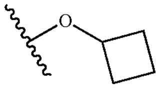.

In some embodiments, $X^4$ is $CR^4$, $X^5$ is N, $X^6$ is $CR^6$, $X^7$ is $CR^7$, and $R^4$, $R^6$, and $R^7$ are each independently selected from H, F, Cl, Br, —$CH_3$, —$OCH_3$, —$OCH(CH_3)_2$, —$CF_3$, —$OCF_3$,

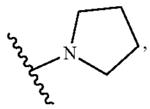, and 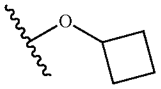.

In some embodiments, $X^4$ is $CR^4$, $X^5$ is $CR^5$, $X^6$ is N, $X^7$ is $CR^7$, and $R^4$, $R^5$, and $R^7$ are each independently selected from H, F, Cl, Br, —$CH_3$, —$OCH_3$, —$OCH(CH_3)_2$, —$CF_3$, —$OCF_3$,

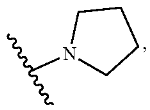, and 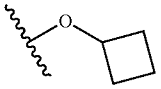.

In some embodiments, $X^4$ is $CR^4$, $X^5$ is $CR^5$, $X^6$ is $CR^6$, $X^7$ is N, and $R^4$-$R^6$ are each independently selected from H, F, Cl, Br, —$CH_3$, —$OCH_3$, —$OCH(CH_3)_2$, —$CF_3$, —$OCF_3$,

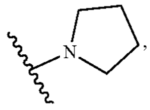, and 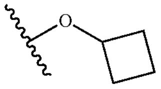.

In some embodiments, $X^4$ is N, $X^5$ is $CR^5$, $X^6$ is N, $X^7$ is $CR^7$, and $R^5$ and $R^7$ are each independently selected from H, F, Cl, Br, —$CH_3$, —$OCH_3$, —$OCH(CH_3)_2$, —$CF_3$, —$OCF_3$,

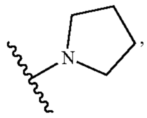, and 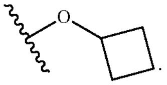.

In some embodiments, $X^4$ is $CR^4$, $X^5$ is N, $X^6$ is $CR^6$, $X^7$ is N, and $R^4$ and $R^6$ are each independently selected from H, F, Cl, Br, —$CH_3$, —$OCH_3$, —$OCH(CH_3)_2$, —$CF_3$, —$OCF_3$,

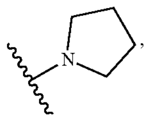, and 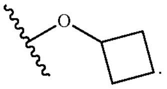.

In some embodiments, $X^4$ is N, $X^5$ is $CR^5$, $X^6$ is $CR^6$, $X^7$ is N, and $R^5$ and $R^6$ are each independently selected from H, F, Cl, Br, —$CH_3$, —$OCH_3$, —$OCH(CH_3)_2$, —$CF_3$, —$OCF_3$,

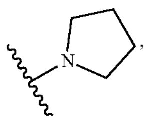, and 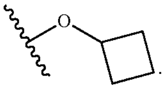.

In some embodiments, $R^5$ is F, Cl, Br, —$CH_3$, —$OCH_3$, —$OCH(CH_3)_2$, —$CF_3$, —$OCF_3$,

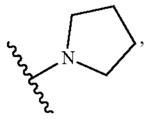, and 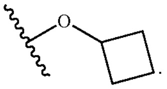.

In some embodiments, $R^5$ is F, Cl, Br, —$CH_3$, —$OCH_3$, —$CF_3$, or —$OCF_3$.

In some embodiments, $R^6$ and $R^7$ are each H and $R^4$ and $R^5$ are each independently selected from F, Cl, Br, —$CH_3$, —$OCH_3$, —$CF_3$, and —$OCF_3$. In some embodiments, $R^4$ and $R^7$ are each H and $R^5$ and $R^6$ are each independently selected from F, Cl, Br, —$CH_3$, —$OCH_3$, —$CF_3$, and —$OCF_3$. In some embodiments, $R^4$ and $R^5$ are each H and $R^6$ and $R^7$ are each independently selected from F, Cl, Br, —$CH_3$, —$OCH_3$, —$CF_3$, and —$OCF_3$.

In some embodiments, $R^4$ is H.

In some embodiments, $R^4$ is H; $R^5$ is H, —F, —Cl, —OH, —$OCH_3$, —$OCF_3$, —$CH_3$, or —$CF_3$; $R^6$ is H, —F, —$OCH_3$, —$OCF_3$, —$CH_3$, or —$CF_3$; and $R^7$ is H, —F, —$OCH_3$, —$OCF_3$, —$CH_3$, or —$CF_3$.

In some embodiments, $R^4$ is H; $R^5$ is —F, —Cl, —OH, —$OCH_3$, —$OCF_3$, —$CH_3$, or —$CF_3$; $R^6$ is H; and $R^7$ is H.

In some embodiments, $R^4$ is H; $R^5$ is H; $R^6$ is —F, —Cl, —OH, —$OCH_3$, —$OCF_3$, —$CH_3$, or —$CF_3$; and $R^7$ is H.

In some embodiments, $R^4$ is H; $R^5$ is H; $R^6$ is H; and $R^7$ is —F, —Cl, —OH, —$OCH_3$, —$OCF_3$, —$CH_3$, or —$CF_3$.

In some embodiments, $R^4$ is H; $R^5$ is —F, —Cl, —OH, —$OCH_3$, —$OCF_3$, —$CH_3$, or —$CF_3$; $R^6$ is —F, —Cl, —OH, —$OCH_3$, —$OCF_3$, —$CH_3$, or —$CF_3$; and $R^7$ is H.

In some embodiments, $R^4$ is H; $R^5$ is —F, —Cl, —OH, —$OCH_3$, —$OCF_3$, —$CH_3$, or —$CF_3$; $R^6$ is H; and $R^7$ is —F, —Cl, —OH, —$OCH_3$, —$OCF_3$, —$CH_3$, or —$CF_3$.

In some embodiments, $R^{13}$ and $R^{14}$ are taken together with the nitrogen atom to which they are attached to form an optionally substituted monocyclic $C_2$-$C_6$heterocycloalkyl. In some embodiments, $R^{13}$ and $R^{14}$ are taken together with the nitrogen atom to which they are attached to form an optionally substituted monocyclic $C_2$-$C_6$heterocycloalkyl and $R^{15}$ is $C_1$-$C_6$ alkyl. In some embodiments, $R^{13}$ and $R^{14}$ are taken together with the nitrogen atom to which they are attached to form an optionally substituted monocyclic $C_2$-$C_6$heterocycloalkyl and $R^{15}$ is methyl. In some embodiments, the monocyclic $C_2$-$C_6$heterocycloalkyl is aziridinyl, azetadinyl, oxazetidinyl, pyrrolidinyl, piperidinyl, piperazinyl, or morpholinyl. In some embodiments, the monocyclic $C_2$-$C_6$heterocycloalkyl is pyrrolidinyl or piperidinyl.

In some embodiments, $R^{14}$ and $R^{15}$ are each independently hydrogen or $C_1$-$C_6$-alkyl. In some embodiments, $R^{14}$ and $R^{15}$ are each independently optionally substituted alkyl. In some embodiments, $R^{14}$ and $R^{15}$ are each independently $C_1$-$C_6$ alkyl. In some embodiments, $R^{14}$ and $R^{15}$ are each methyl, ethyl, propyl, isopropyl, or t-butyl. In some embodiments, $R^{14}$ and $R^{15}$ are each independently hydrogen, methyl, ethyl, or isopropyl. In some embodiments, $R^{14}$ and $R^{15}$ are each independently methyl or ethyl. In some embodiments, $R^{14}$ and $R^{15}$ are each methyl.

In some embodiments, $R^{14}$ and $R^{15}$ are taken together with the nitrogen atom to which they are attached to form an optionally substituted heterocycloalkyl. In some embodiments, the optionally substituted heterocycloalkyl is substituted with one or more substituent, each substituent selected from the group consisting of $C_1$-$C_6$ alkyl, halogen, or $C_1$-$C_6$ haloalkyl. In some embodiments, $R^{14}$ and $R^{15}$ are taken together with the nitrogen atom to which they are attached to form a heterocycloalkyl. In some embodiments, the heterocycloalkyl is a monocyclic $C_2$-$C_6$heterocycloalkyl or a bicyclic $C_5$-$C_8$heterocycloalkyl containing at least 1 N atom in the ring.

In some embodiments, $R^{14}$ and $R^{15}$ are taken together with the nitrogen atom to which they are attached to form aziridinyl, azetadinyl, oxazetidinyl, pyrrolidinyl, piperidinyl, piperazinyl, or morpholinyl. In some embodiments, $R^{14}$ and $R^{15}$ are taken together with the nitrogen atom to which they are attached to form aziridinyl or azetadinyl.

In some embodiments, the heterocycloalkyl is a monocyclic $C_2$-$C_6$heterocycloalkyl containing 1 N atom in the ring. In some embodiments, the heterocycloalkyl is a monocyclic $C_2$-$C_6$heterocycloalkyl containing 2 N atom in the ring. In some embodiments, the heterocycloalkyl is a monocyclic $C_2$-$C_6$heterocycloalkyl containing 1 N atom and 1 O atom in the ring. In some embodiments, the heterocycloalkyl is a monocyclic $C_2$-$C_6$heterocycloalkyl containing 1 N atom and 1 S atom in the ring. In some embodiments, the monocyclic $C_2$-$C_6$heterocycloalkyl is selected from aziridinyl, azetidinyl, pyrrolidinyl, morpholinyl, thiomorpholinyl, piperidinyl, piperazinyl, and azepanyl.

In some embodiments, the heterocycloalkyl is a bicyclic $C_5$-$C_8$heterocycloalkyl containing 1 N atom in the ring. In some embodiments, the heterocycloalkyl is a bicyclic $C_5$-$C_8$heterocycloalkyl containing 2 N atom in the ring. In some embodiments, the heterocycloalkyl is a bicyclic $C_5$-$C_8$heterocycloalkyl containing 1 N atom and 1 O atom in the ring. In some embodiments, the heterocycloalkyl is a bicyclic $C_5$-$C_8$heterocycloalkyl containing 1 N atom and 1 S atom in the ring. In some embodiments, the bicyclic $C_5$-$C_8$heterocycloalkyl is a fused bicyclic $C_5$-$C_8$heterocycloalkyl, bridged bicyclic $C_5$-$C_8$heterocycloalkyl, or spiro bicyclic $C_5$-$C_8$heterocycloalkyl. In some embodiments, the bicyclic $C_5$-$C_8$heterocycloalkyl is selected from azabicyclo[2.1.1]hexane, azabicyclo[3.2.1]heptane, azabicyclo[3.2.1]octane, azaspiro[3.3]heptane, and oxa-6-azaspiro[3.3]heptane.

In some embodiments,

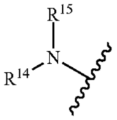

is

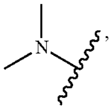, 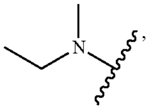, 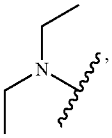, 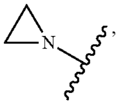, 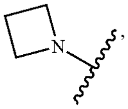, 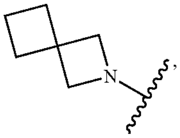, 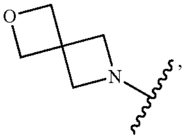, 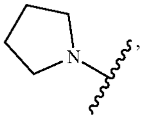, 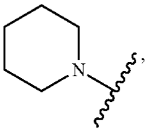, 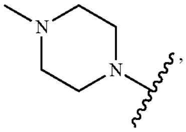, 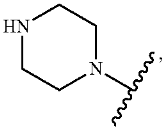, 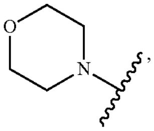, 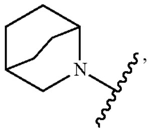, or 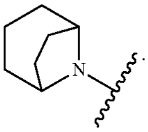.

In some embodiments,

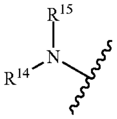

is

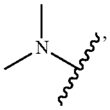, 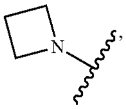, 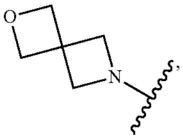,

-continued

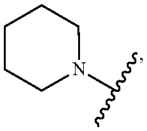, or 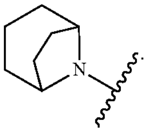.

In some embodiments, $R^1$ is:

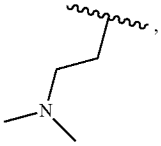, 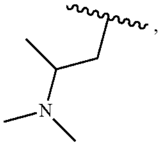, 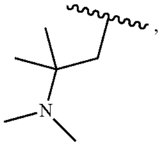, 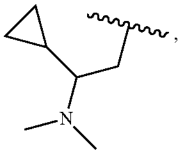, 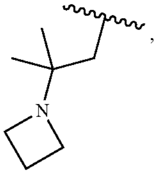, 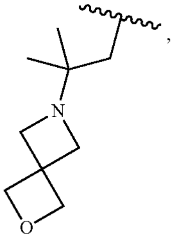, 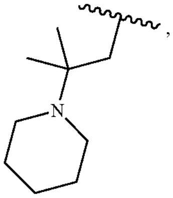, 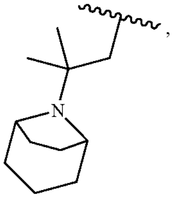, 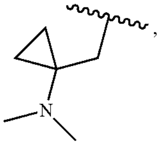, 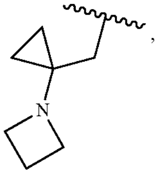, 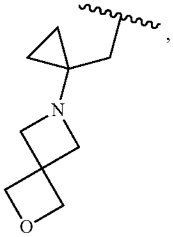, 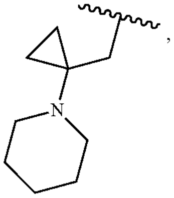, 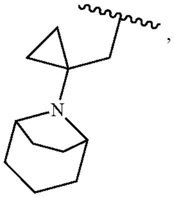, 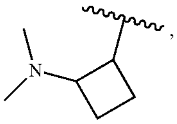, 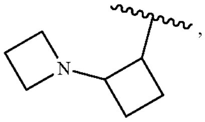, 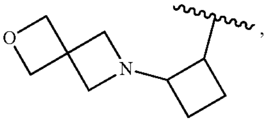, 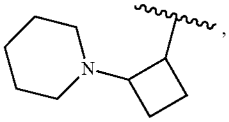, 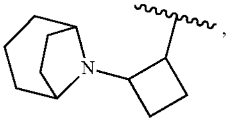, -continued

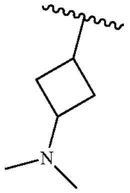, 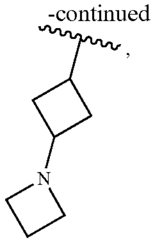, 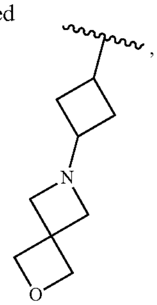,

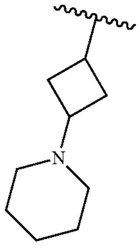, 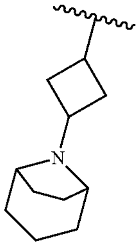, 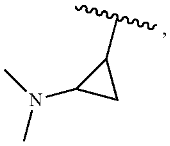,

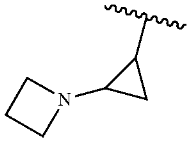, 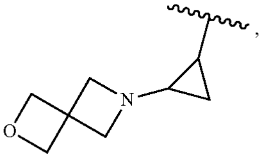,

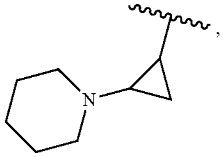, or 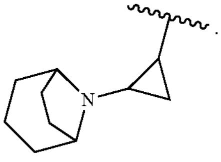.

In another aspect, described herein is a compound of Formula (IV), or a pharmaceutically acceptable salt or solvate thereof:

Formula (IV)

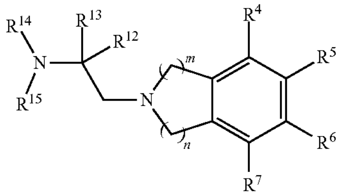

wherein:

$R^4$-$R^7$ are each independently hydrogen, halogen, —CN, —$OR^a$, —$SR^a$, —S(═O)$R^a$, —S(═O)$_2R^a$, —$NO_2$, —$NR^bR^c$, —NHS(═O)$_2R^a$, —S(═O)$_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl are optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl);

each $R^a$, $R^b$, and $R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, haloalkyl, cycloalkyl, or heterocycloalkyl, wherein each alkyl, alkoxy, heteroalkyl, cycloalkyl, or heterocycloalkyl is optionally substituted;

or $R^{12}$ and $R^{13}$ are taken together with the atoms to which they are attached to form an optionally substituted heterocycloalkyl or cycloalkyl;

$R^{14}$ and $R^{15}$ are each independently alkyl, heteroalkyl, haloalkyl, cycloalkyl, or heterocycloalkyl, wherein each alkyl, heteroalkyl, cycloalkyl, or heterocycloalkyl is optionally substituted;

or $R^{14}$ and $R^{15}$ are taken together with the nitrogen atom to which they are attached to form an optionally substituted heterocycloalkyl;

m is 1, 2, or 3;

n is 0 or 1; and wherein (n+m) is an integer ranging from 5-7.

In some embodiments, provided herein is a compound of Formula (IV'), or a pharmaceutically acceptable salt or solvate thereof:

Formula (IV')

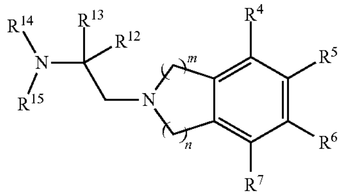

wherein:

$R^4$-$R^7$ are each independently hydrogen, halogen, —CN, —$OR^a$, —$SR^a$, —S(═O)$R^a$, —S(═O)$_2R^a$, —$NO_2$, —$NR^bR^c$, —NHS(═O)$_2R^a$, —S(═O)$_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl are optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl);

each $R^a$, $R^b$, and $R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, haloalkyl, cycloalkyl, or heterocycloalkyl, wherein each alkyl, alkoxy, heteroalkyl, cycloalkyl, or heterocycloalkyl is optionally substituted;

or $R^{12}$ and $R^{13}$ are taken together with the atoms to which they are attached to form an optionally substituted heterocycloalkyl or cycloalkyl;

$R^{14}$ and $R^{15}$ are each independently alkyl, heteroalkyl, haloalkyl, cycloalkyl, or heterocycloalkyl, wherein each alkyl, heteroalkyl, cycloalkyl, or heterocycloalkyl is optionally substituted;

or $R^{14}$ and $R^{15}$ are taken together with the nitrogen atom to which they are attached to form an optionally substituted heterocycloalkyl;

m is 1, 2, or 3;

n is 0 or 1; and wherein (n+m) is an integer ranging from 2-4.

In another aspect, described herein is a compound of Formula (III-1), or a pharmaceutically acceptable salt or solvate thereof:

Formula (III-1)

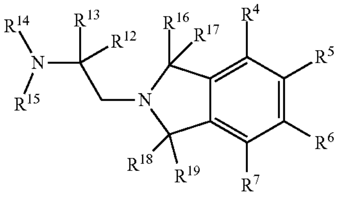

wherein:

$R^4$-$R^7$ are each independently hydrogen, halogen, —CN, —$OR^a$, —$SR^a$, —S(=O)$R^a$, —S(=O)$_2R^a$, —$NO_2$, —$NR^bR^c$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^b$C(=O)$NR^bR^c$, —$NR^b$C(=O)$R^a$, —$NR^b$C(=O)$OR^b$, alkyl, heteroalkyl, haloalkyl, cycloalkyl, or heterocycloalkyl, wherein each alkyl, heteroalkyl, cycloalkyl, or heterocycloalkyl are optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl);

each $R^a$, $R^b$, and $R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, haloalkyl, cycloalkyl, or heterocycloalkyl, wherein each alkyl, alkoxy, heteroalkyl, cycloalkyl, or heterocycloalkyl is optionally substituted;

$R^{14}$ and $R^{15}$ are each independently alkyl, heteroalkyl, haloalkyl, cycloalkyl, or heterocycloalkyl, wherein each alkyl, heteroalkyl, cycloalkyl, or heterocycloalkyl is optionally substituted;

or $R^{14}$ and $R^{15}$ are taken together with the nitrogen atom to which they are attached to form an optionally substituted heterocycloalkyl;

each $R^{16}$-$R^{19}$ is independently hydrogen or alkyl;

or any of $R^{16}$ and $R^{17}$, $R^{18}$ and $R^{19}$, or $R^{16}$ and $R^{18}$ are taken together with the atoms to which they are attached to form an optionally substituted cycloalkyl;

m is 1, 2, or 3;

n is 0 or 1; and wherein (n+m) is an integer ranging from 5-7, provided that (a) at least one of $R^{12}$ or $R^{13}$ is halogen, alkyl, haloalkyl, cycloalkyl, or heterocycloalkyl; and (b) when n and m are each 1, then $R^4$-$R^7$ are not —$NH_2$.

In another aspect, described herein is a compound of Formula (III-1'), or a pharmaceutically acceptable salt or solvate thereof:

Formula (III-1')

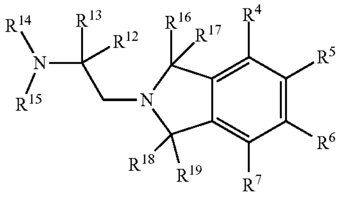

wherein:

$R^4$-$R^7$ are each independently hydrogen, halogen, —CN, —$OR^a$, —$SR^a$, —S(=O)$R^a$, —S(=O)$_2R^a$, —$NO_2$, —$NR^bR^c$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^b$C(=O)$NR^bR^c$, —$NR^b$C(=O)$R^a$, —$NR^b$C(=O)$OR^b$, alkyl, heteroalkyl, haloalkyl, cycloalkyl, or heterocycloalkyl, wherein each alkyl, heteroalkyl, cycloalkyl, or heterocycloalkyl are optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl);

each $R^a$, $R^b$, and $R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, haloalkyl, cycloalkyl, or heterocycloalkyl, wherein each alkyl, alkoxy, heteroalkyl, cycloalkyl, or heterocycloalkyl is optionally substituted;

$R^{14}$ and $R^{15}$ are each independently alkyl, heteroalkyl, haloalkyl, cycloalkyl, or heterocycloalkyl, wherein each alkyl, heteroalkyl, cycloalkyl, or heterocycloalkyl is optionally substituted;

or $R^{14}$ and $R^{15}$ are taken together with the nitrogen atom to which they are attached to form an optionally substituted heterocycloalkyl;

each $R^{16}$-$R^{19}$ is independently hydrogen or alkyl;

or any of $R^{16}$ and $R^{17}$, $R^{18}$ and $R^{19}$, or $R^{16}$ and $R^{18}$ are taken together with the atoms to which they are attached to form an optionally substituted cycloalkyl;

m is 1, 2, or 3;

n is 0 or 1; and wherein (n+m) is an integer ranging from 2-4, provided that (a) at least one of $R^{12}$ or $R^{13}$ is halogen, alkyl, haloalkyl, cycloalkyl, or heterocycloalkyl; and (b) when n and m are each 1, then $R^4$-$R^7$ are not —$NH_2$.

In some embodiments, each $R^{16}$-$R^{19}$ is independently hydrogen or alkyl. In some embodiments, each $R^{16}$-$R^{19}$ is independently hydrogen or $C_1$-$C_6$ alkyl. In some embodiments, each $R^{16}$-$R^{19}$ is hydrogen In another aspect, described herein is a compound of Formula (III'), or a pharmaceutically acceptable salt or solvate thereof:

Formula (III')

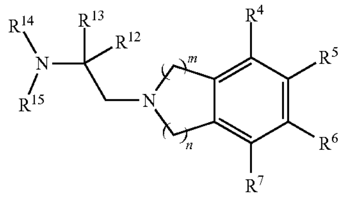

wherein:

$R^4$-$R^7$ are each independently hydrogen, halogen, —CN, —$OR^a$, —$SR^a$, —S(═O)$R^a$, —S(═O)$_2R^a$, —$NO_2$, —$NR^bR^c$, —NHS(═O)$_2R^a$, —S(═O)$_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl are optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl);

each $R^a$, $R^b$, and $R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, haloalkyl, cycloalkyl, or heterocycloalkyl, wherein each alkyl, alkoxy, heteroalkyl, cycloalkyl, or heterocycloalkyl is optionally substituted;

$R^{14}$ and $R^{15}$ are each independently alkyl, heteroalkyl, haloalkyl, cycloalkyl, or heterocycloalkyl, wherein each alkyl, heteroalkyl, cycloalkyl, or heterocycloalkyl is optionally substituted;

or $R^{14}$ and $R^{15}$ are taken together with the nitrogen atom to which they are attached to form an optionally substituted heterocycloalkyl;

m is 1, 2, or 3;

n is 0 or 1; and wherein (n+m) is an integer ranging from 5-7, provided that (a) at least one of $R^{12}$ or $R^{13}$ is halogen, alkyl, haloalkyl, cycloalkyl, or heterocycloalkyl; and (b) when n and m are each 1, then $R^4$-$R^7$ are not —$NH_2$.

In another aspect, described herein is a compound of Formula (III), or a pharmaceutically acceptable salt or solvate thereof:

Formula (III)

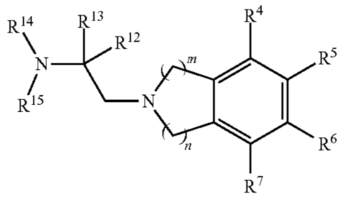

wherein:

$R^4$-$R^7$ are each independently hydrogen, halogen, —CN, —$OR^a$, —$SR^a$, —S(═O)$R^a$, —S(═O)$_2R^a$, —$NO_2$, —$NR^bR^c$, —NHS(═O)$_2R^a$, —S(═O)$_2NR^bR^c$, —C(═O)$R^a$, —OC(═O)$R^a$, —C(═O)$OR^b$, —OC(═O)$OR^b$, —C(═O)$NR^bR^c$, —OC(═O)$NR^bR^c$, —$NR^b$C(═O)$NR^bR^c$, —$NR^b$C(═O)$R^a$, —$NR^b$C(═O)$OR^b$, alkyl, heteroalkyl, haloalkyl, cycloalkyl, or heterocycloalkyl, wherein each alkyl, heteroalkyl, cycloalkyl, or heterocycloalkyl are optionally substituted;

or any of $R^4$ and $R^5$, $R^5$ and $R^6$, or $R^6$ and $R^7$ are taken together with the atoms to which they are attached to form an optionally substituted 5- or 6-membered ring (e.g., cycloalkyl or heterocycloalkyl);

each $R^a$, $R^b$, and $R^c$ are independently hydrogen, alkyl, haloalkyl, heteroalkyl, cycloalkyl, or heterocycloalkyl, wherein each alkyl, heteroalkyl, cycloalkyl, or heterocycloalkyl is independently optionally substituted;

or $R^b$ and $R^c$ are taken together with the nitrogen atom to which they are attached to form an optionally substituted heterocycloalkyl;

$R^{12}$ and $R^{13}$ are each independently hydrogen, halogen, alkyl, alkoxy, haloalkyl, cycloalkyl, or heterocycloalkyl, wherein each alkyl, alkoxy, heteroalkyl, cycloalkyl, or heterocycloalkyl is optionally substituted;

$R^{14}$ and $R^{15}$ are each independently alkyl, heteroalkyl, haloalkyl, cycloalkyl, or heterocycloalkyl, wherein each alkyl, heteroalkyl, cycloalkyl, or heterocycloalkyl is optionally substituted;

or $R^{14}$ and $R^{15}$ are taken together with the nitrogen atom to which they are attached to form an optionally substituted heterocycloalkyl;

m is 1, 2, or 3;

n is 0 or 1; and wherein (n+m) is an integer ranging from 2-4, provided that (a) at least one of $R^{12}$ or $R^{13}$ is halogen, alkyl, haloalkyl, cycloalkyl, or heterocycloalkyl; and (b) when n and m are each 1, then $R^4$-$R^7$ are not —$NH_2$.

In some embodiments, (n+m) is 5. In some embodiments, (n+m) is 6. In some embodiments, (n+m) is 7.

In some embodiments, (n+m) is 2. In some embodiments, (n+m) is 3. In some embodiments, (n+m) is 4.

In some embodiments, m is 1. In some embodiments, m is 2. In some embodiments, m is 3. In some embodiments, n is 0. In some embodiments, n is 1. In some embodiments, n is 0 and m is 2. In some embodiments, n is 1 and m is 1. In some embodiments, n is 0 and m is 3. In some embodiments, n is 1 and m is 2.

In some embodiments, at least one of $R^{12}$ or $R^{13}$ is halogen or $C_1$-$C_6$ alkyl. In some embodiments, at least one of $R^{12}$ or $R^{13}$ is $C_1$-$C_6$ alkyl. In some embodiments, at least one of $R^{12}$ or $R^{13}$ is methyl.

Representative compounds of Formula (II) include, but are not limited to:
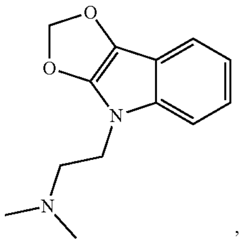
,
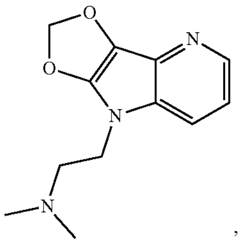
,
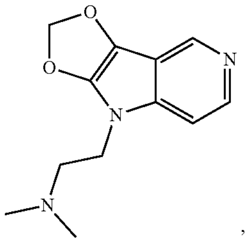
,
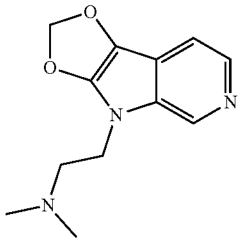
,
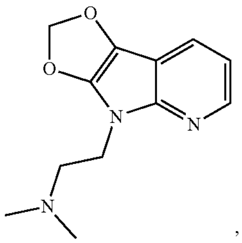
,
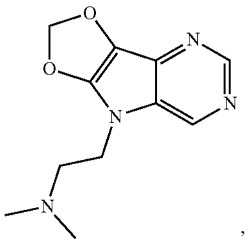
,
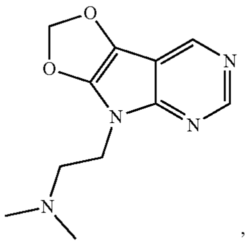
,
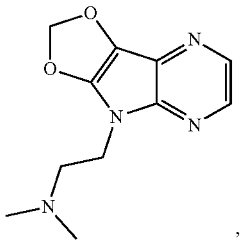
,
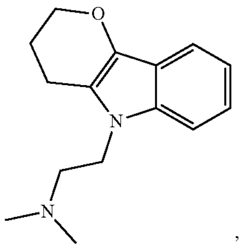
,
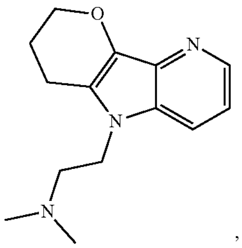
,
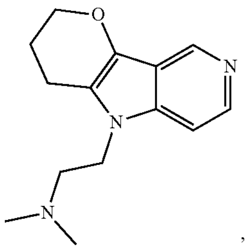
,
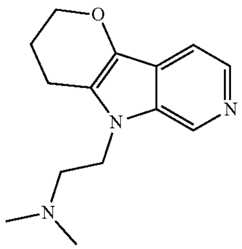
,
-continued
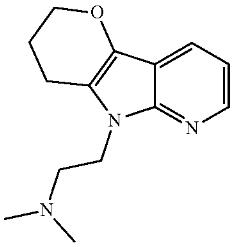
,
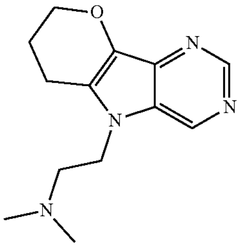
,
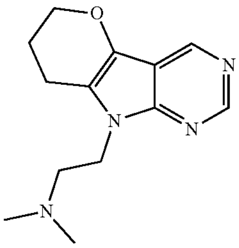
,
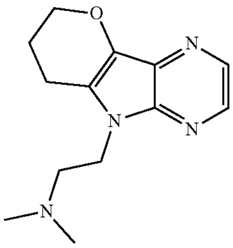
,
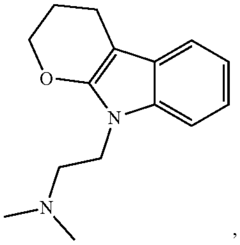
,
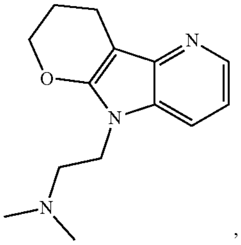
,
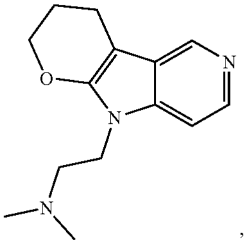
,
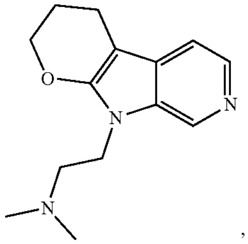
,
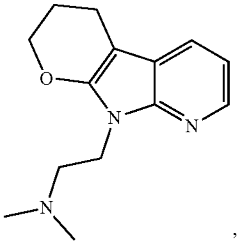
,
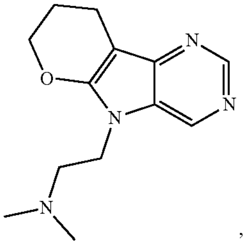
,
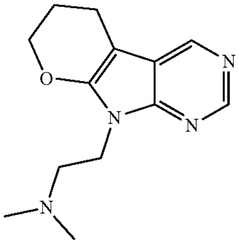
,
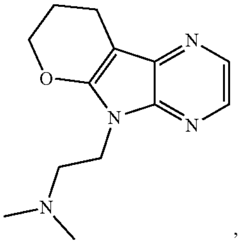
,
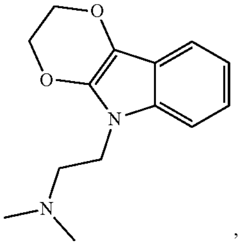
,
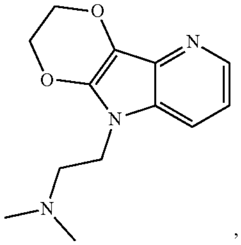
, -continued
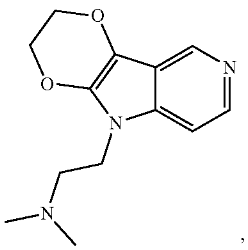,
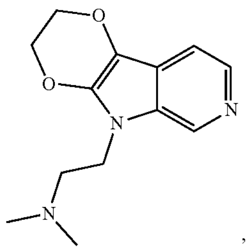,
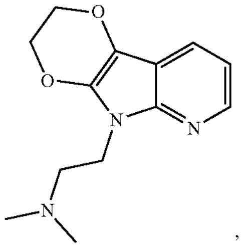,
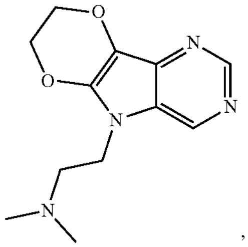,
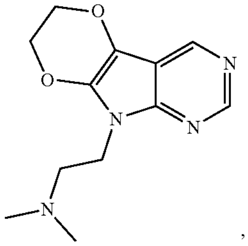,
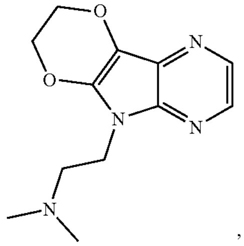,
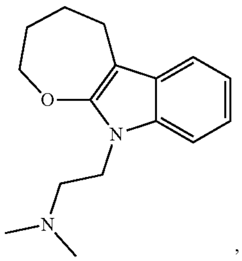,
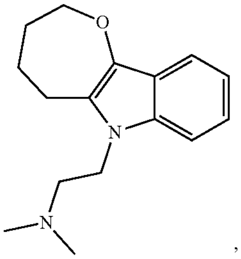,
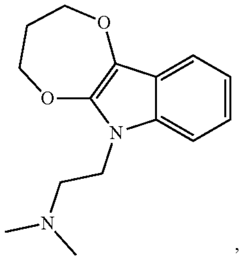,
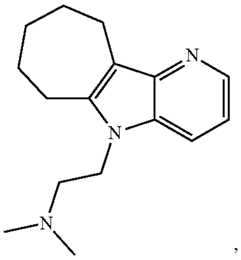,
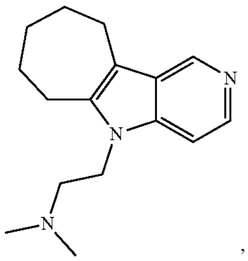,
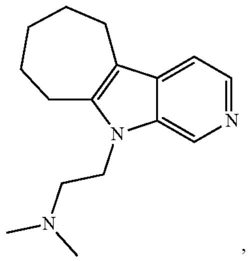,
-continued
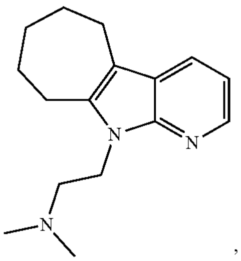,
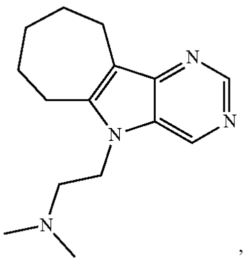,
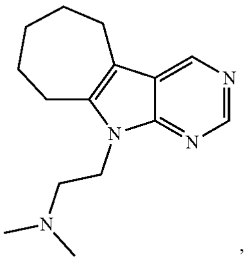,
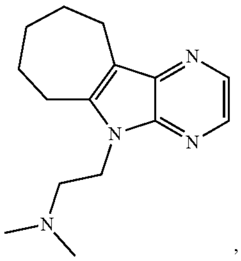,
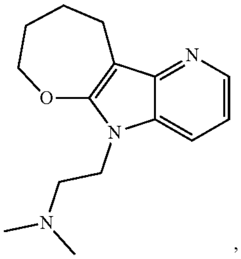,
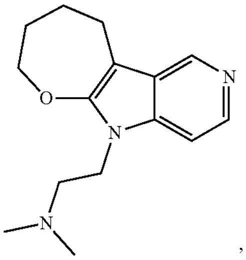,
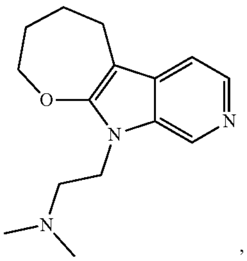,
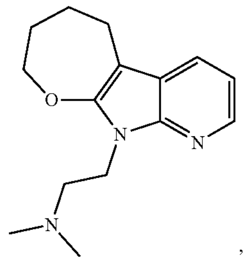,
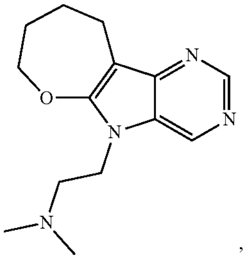,
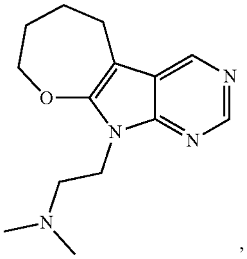,
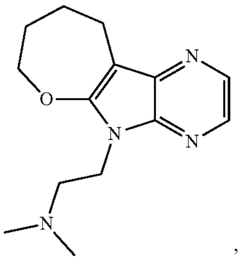,
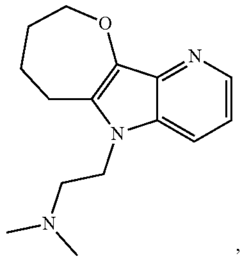, -continued
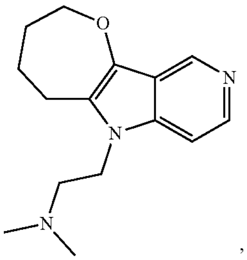,
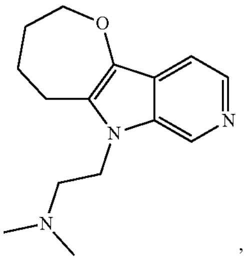,
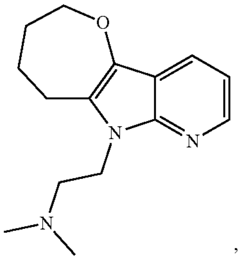,
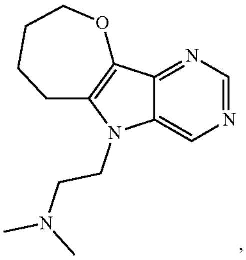,
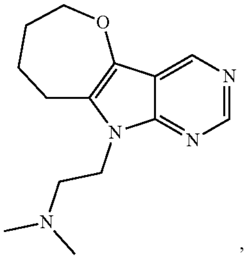,
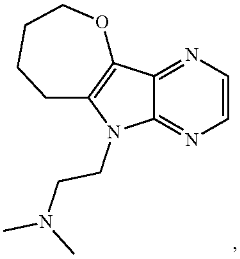,
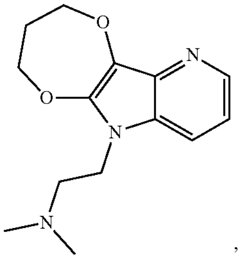,
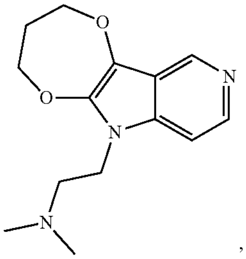,
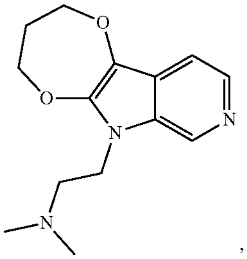,
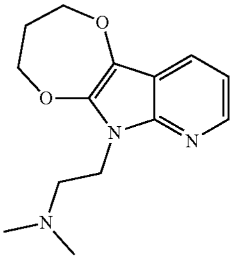,
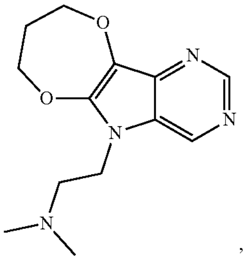,
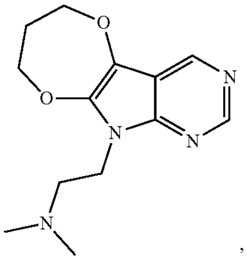,
-continued
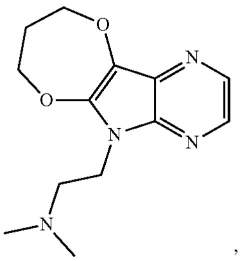,
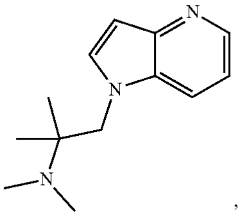,
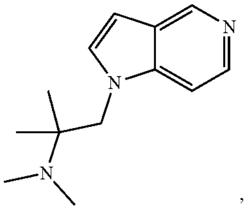,
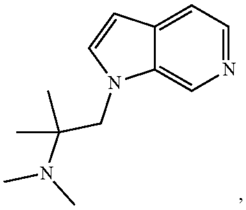,
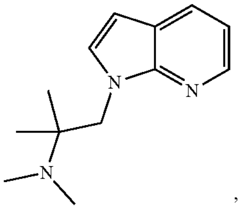,
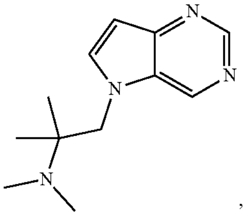,
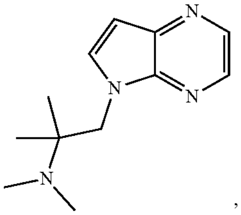,
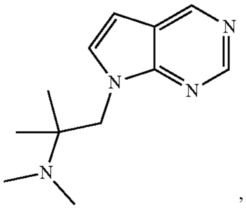,
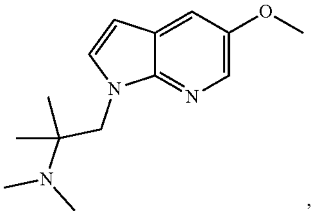,
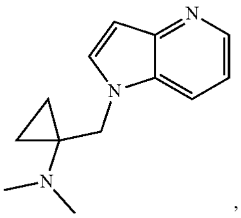,
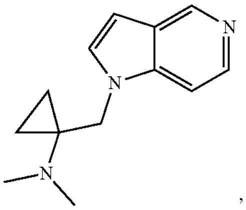,
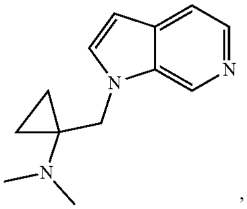,
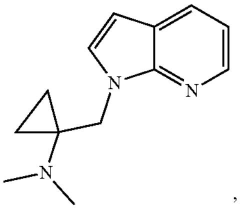, -continued
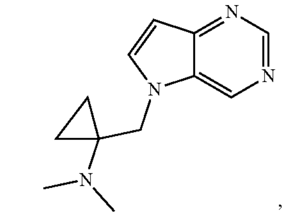
,
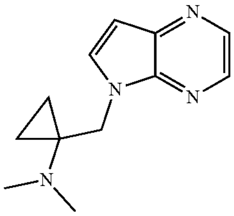
,
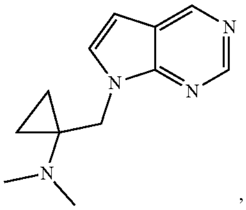
,
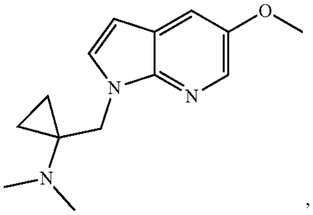
,
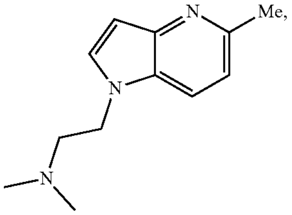
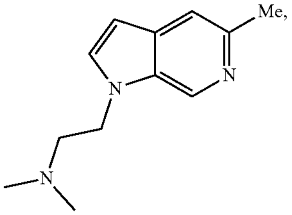
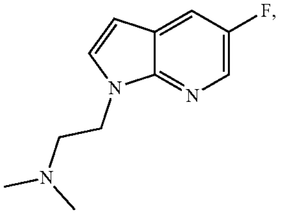
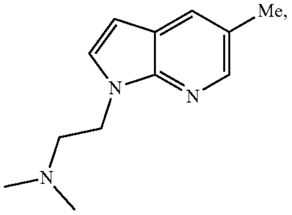
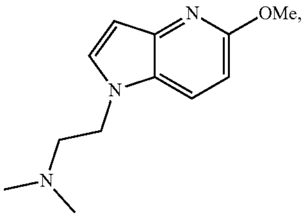
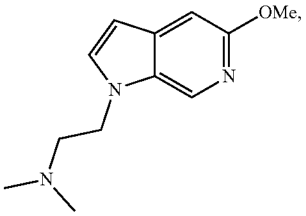
-continued
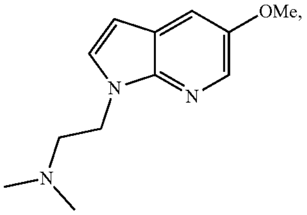
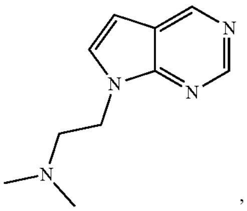
,
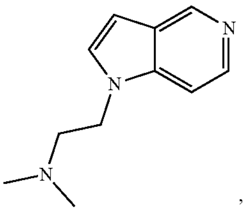
,
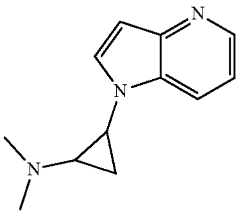
,
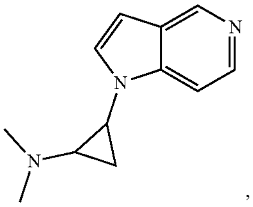
,
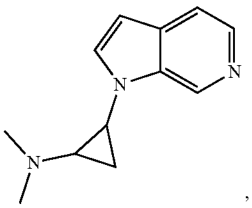
,
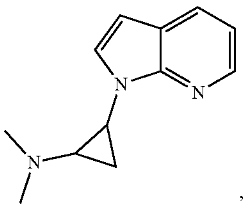
,
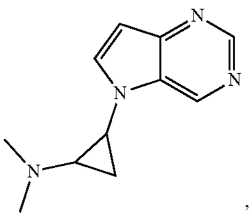
,
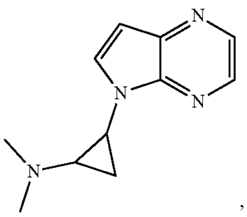
,
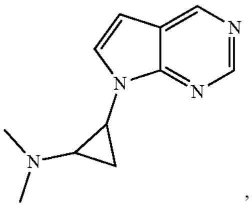
,
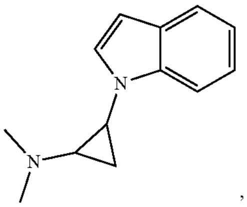
,
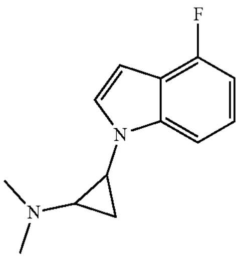
,
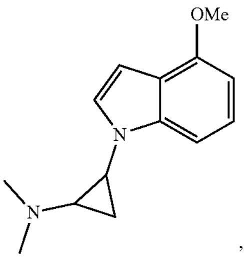
, -continued
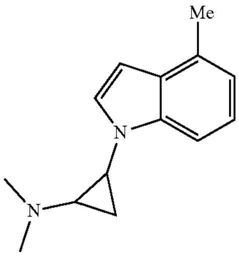
,
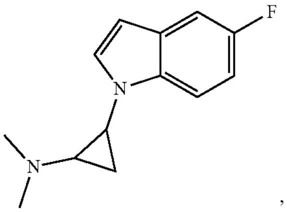
,
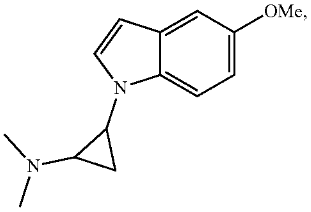
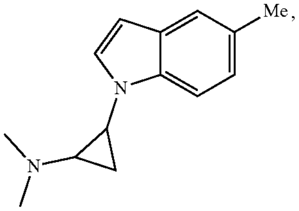
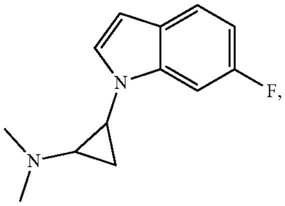
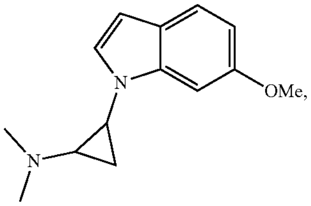
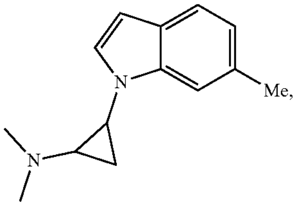
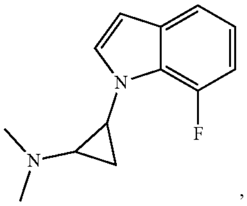
,
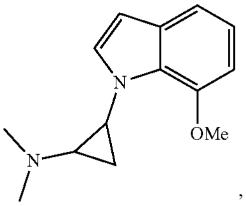
,
-continued
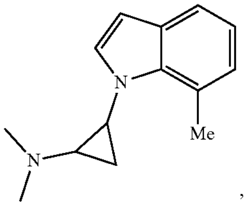
,
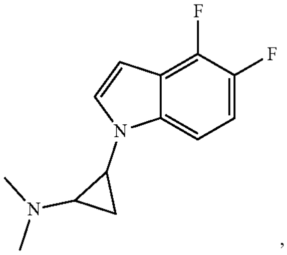
,
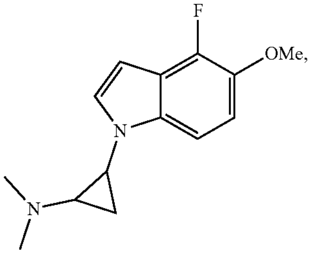
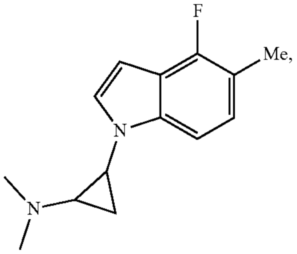
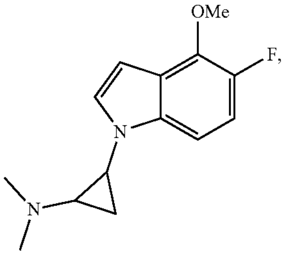
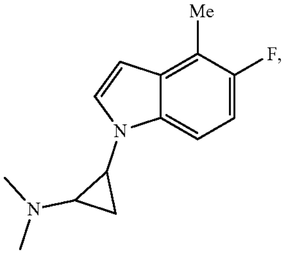
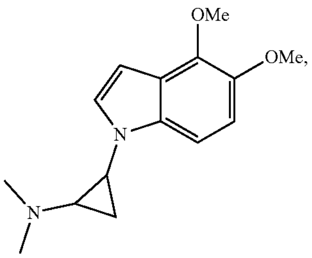

-continued
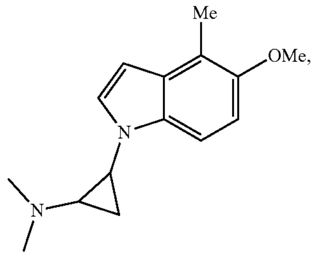
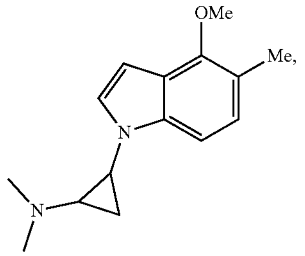
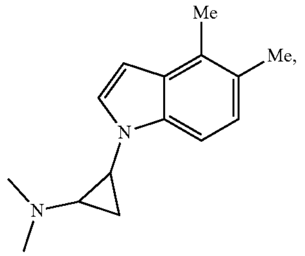
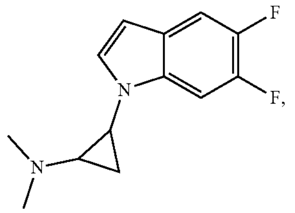
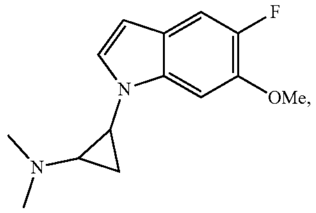
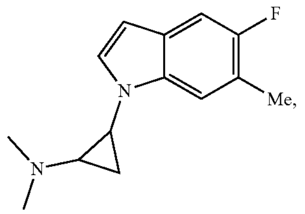
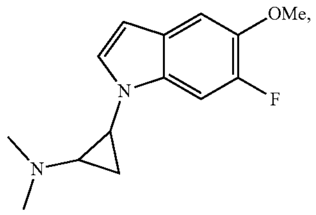
-continued
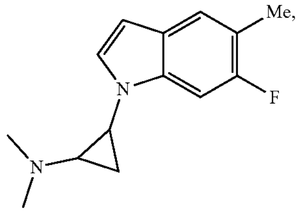
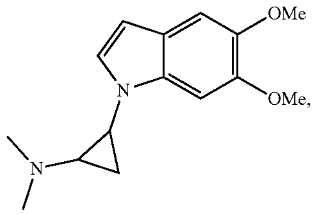
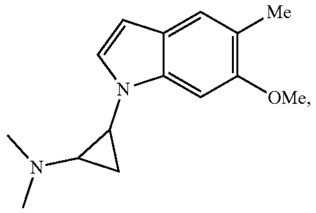
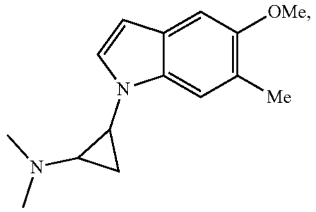
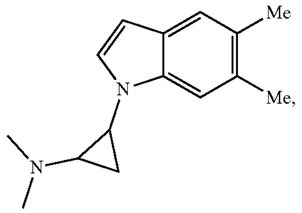
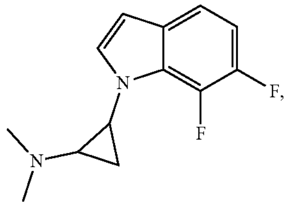
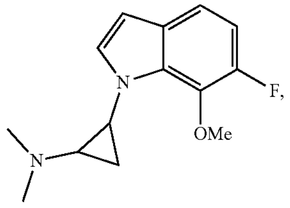
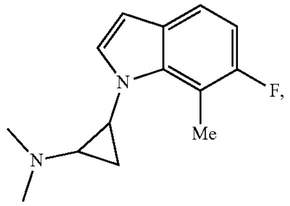

-continued
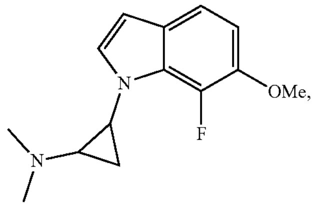
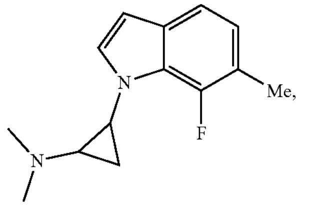
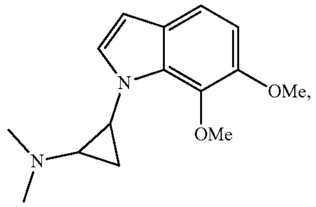
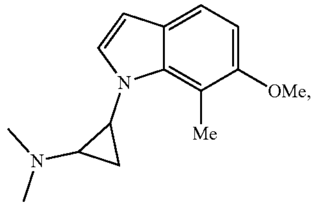
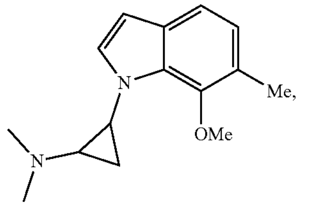
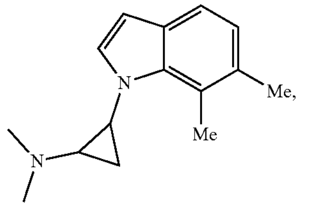
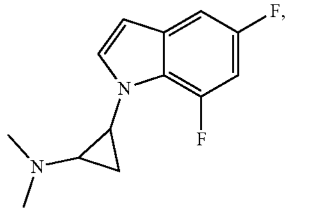
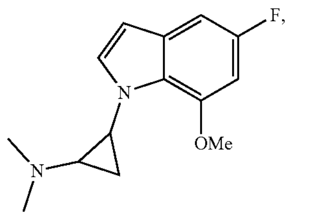
-continued
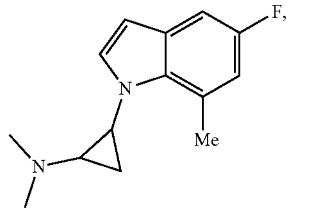
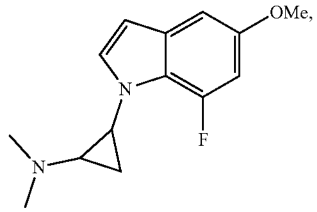
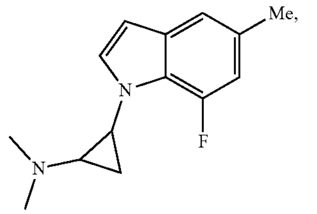
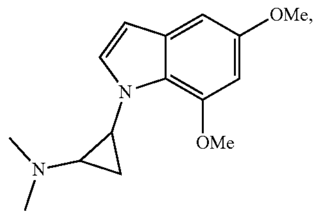
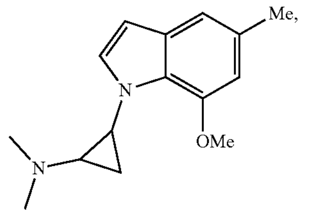
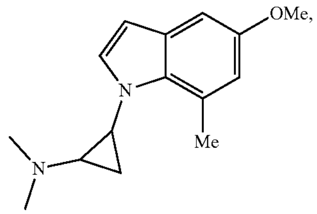
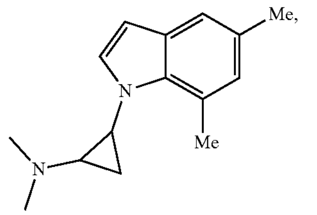
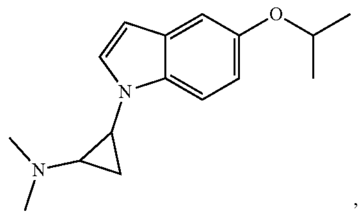

-continued
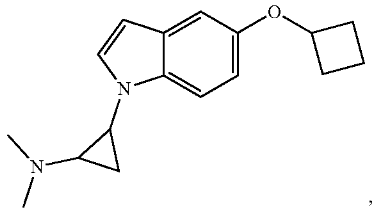
,
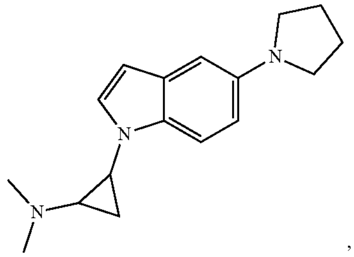
,
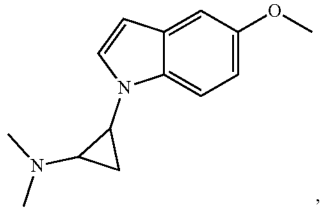
,
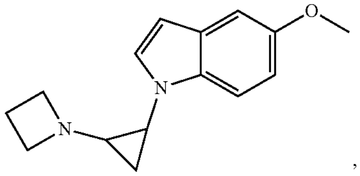
,
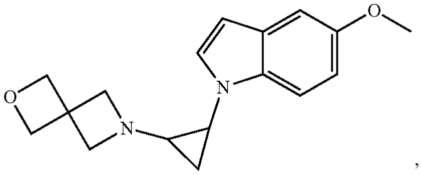
,
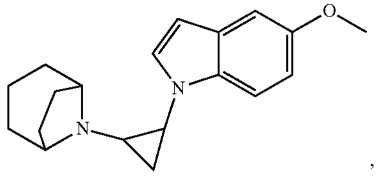
,
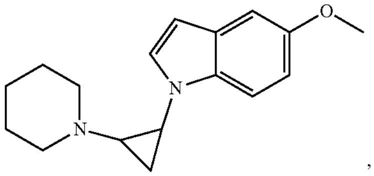
,
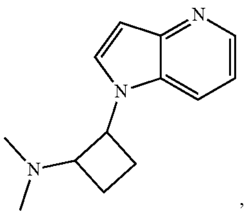
,
-continued
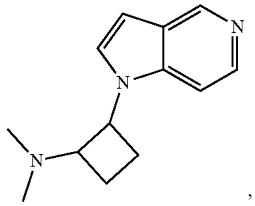
,
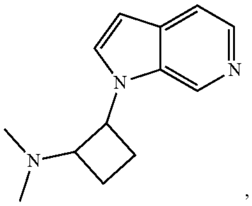
,
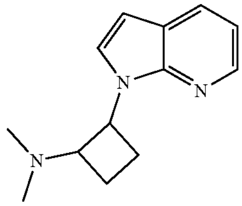
,
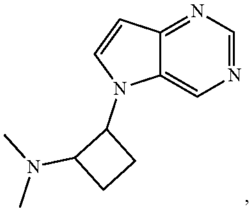
,
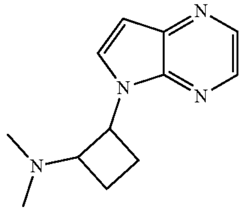
,
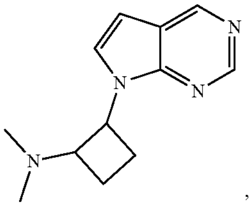
,
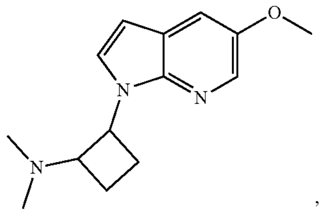
,
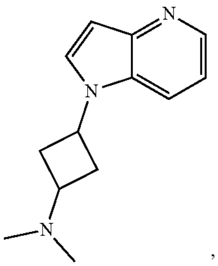
,
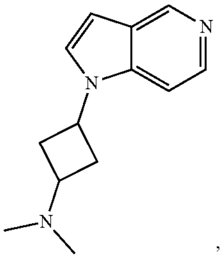
,
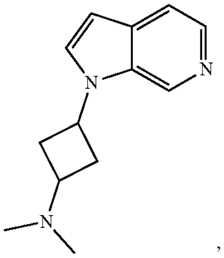
,
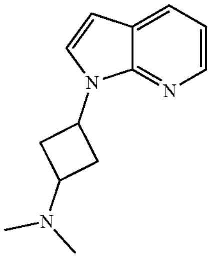
,
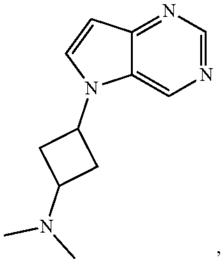
,
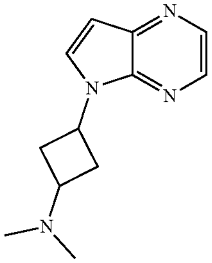
, -continued
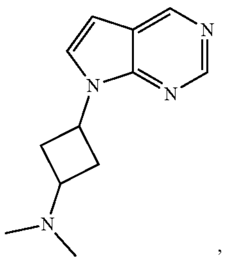
,
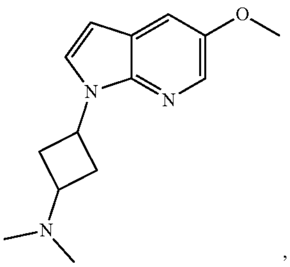
,
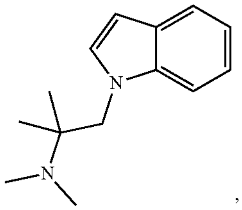
,
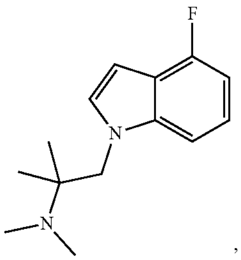
,
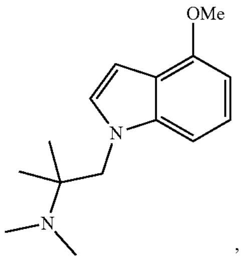
,
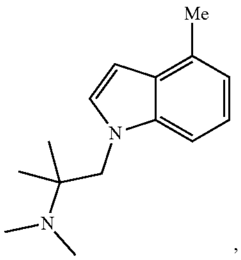
,
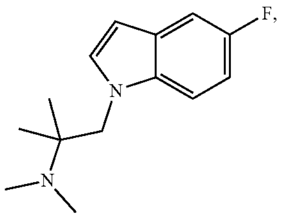
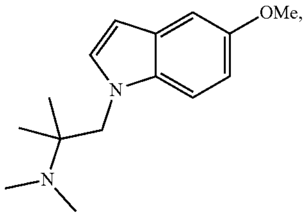
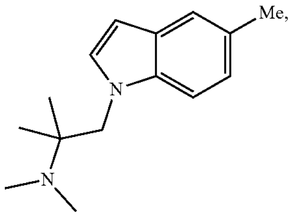
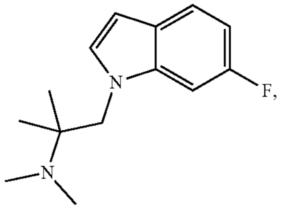
-continued
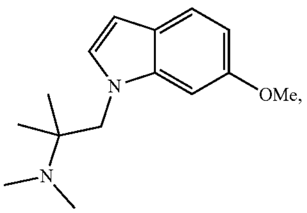
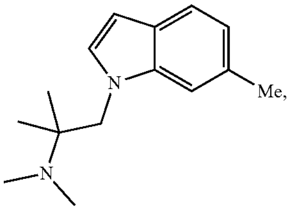
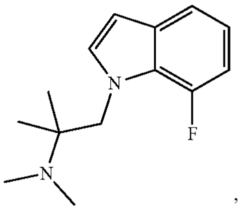
,
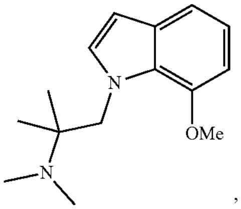
,
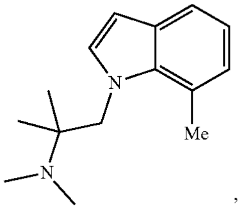
,
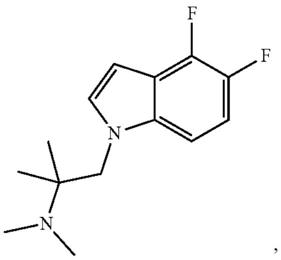
,
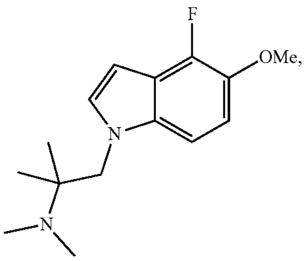
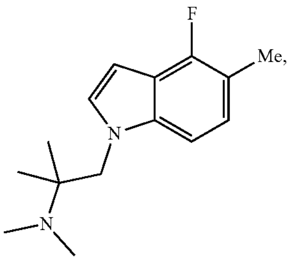

-continued
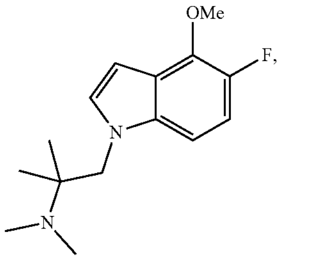
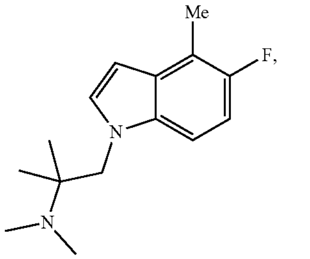
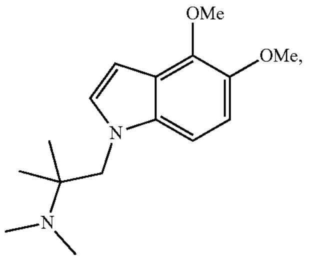
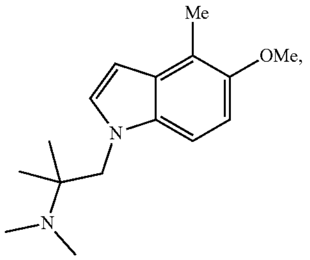
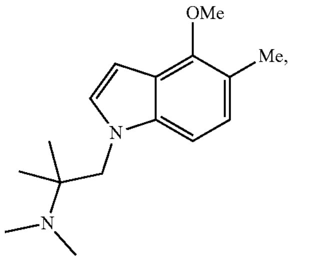
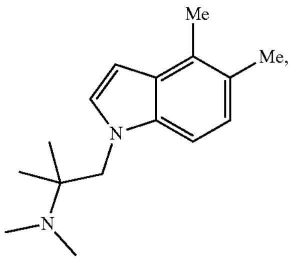
-continued
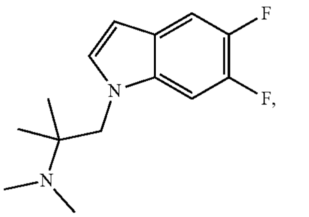
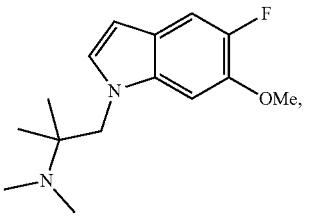
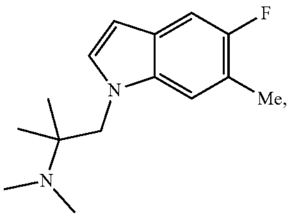
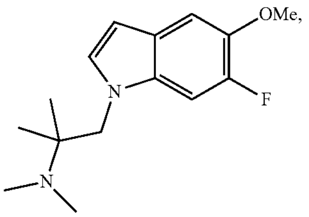
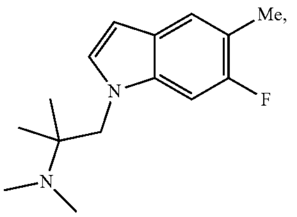
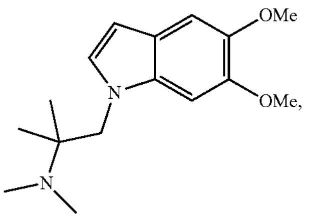
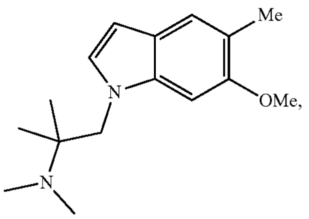

-continued
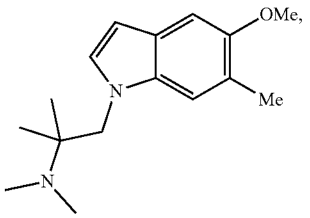
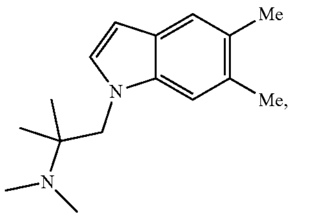
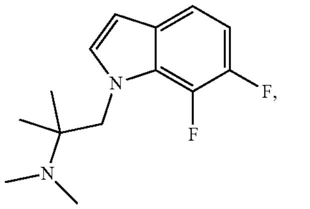
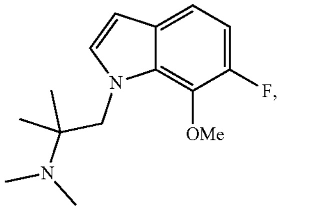
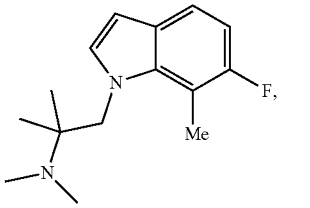
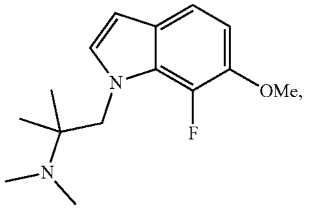
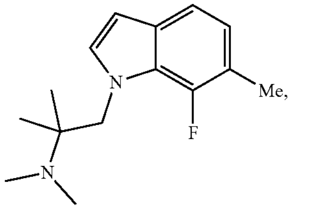
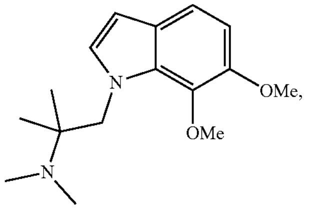
-continued
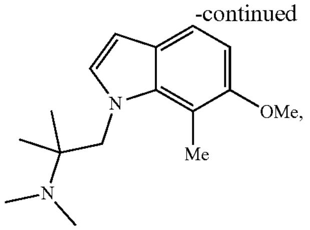
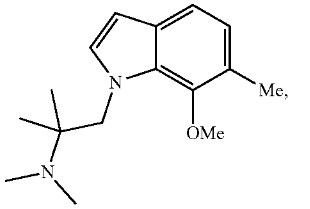
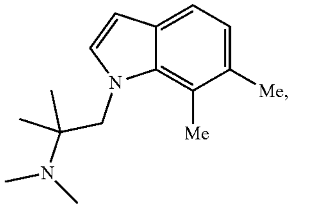
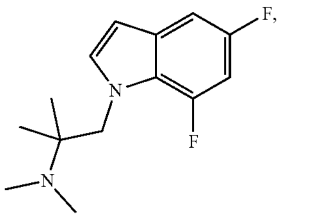
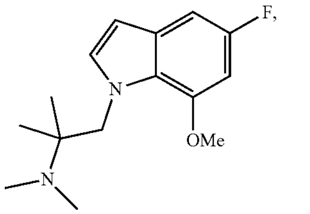
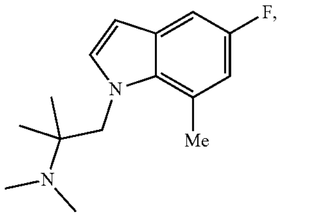
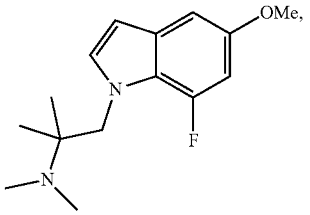
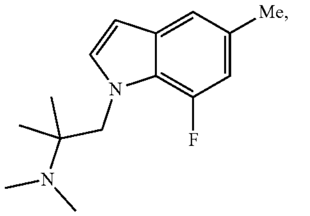

-continued
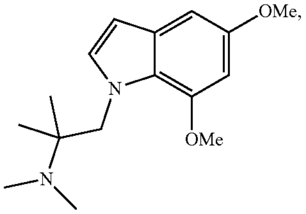
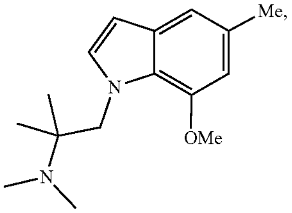
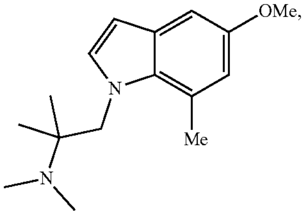
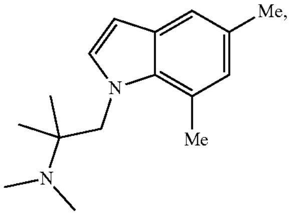
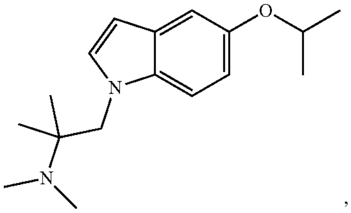
,
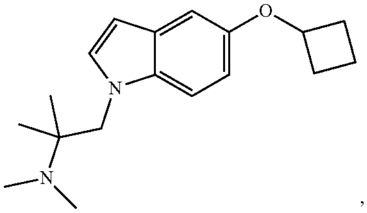
,
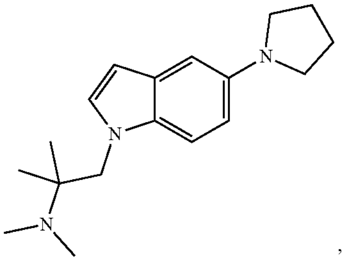
,
-continued
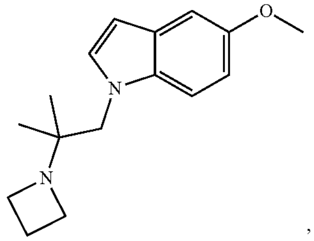
,
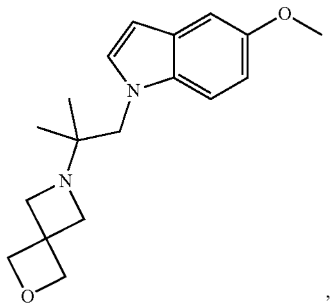
,
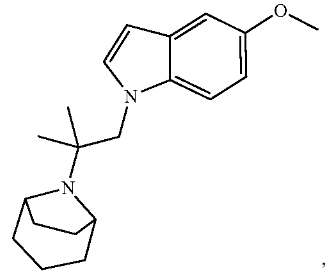
,
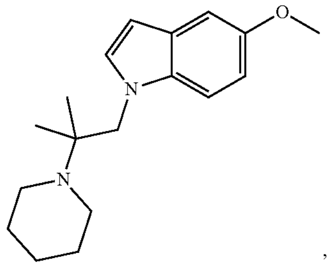
,
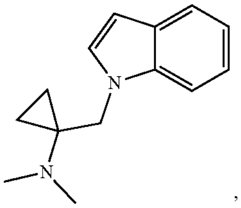
,
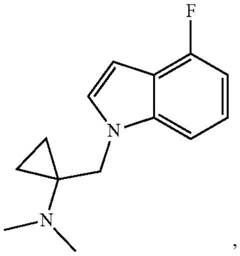
,
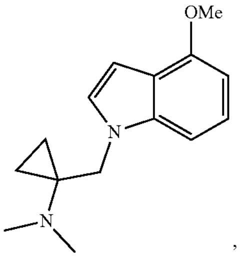
,
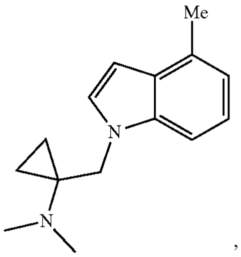
, -continued
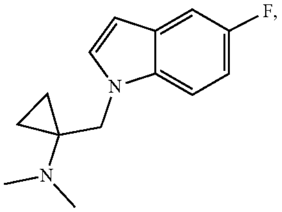
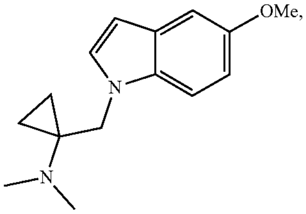
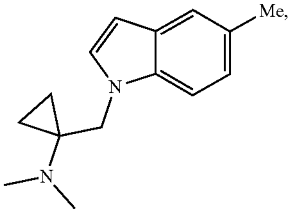
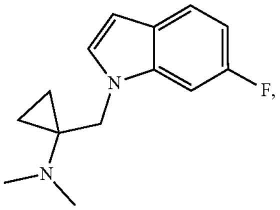
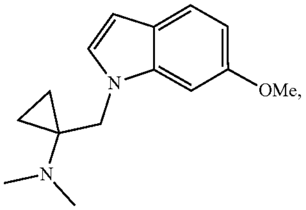
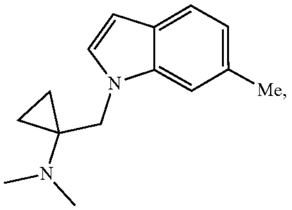
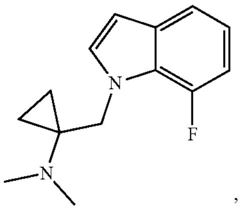
,
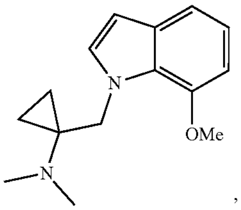
,
-continued
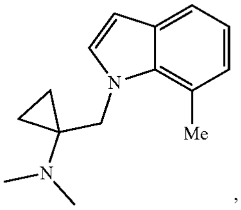
,
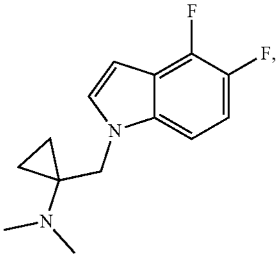
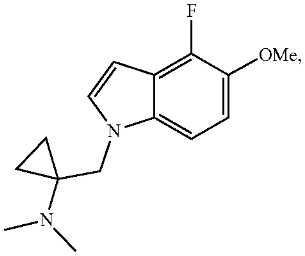
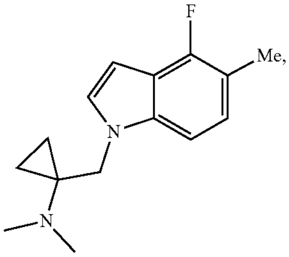
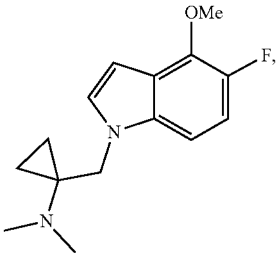
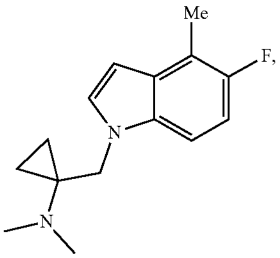
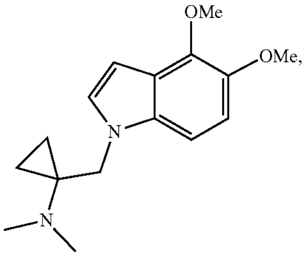

-continued
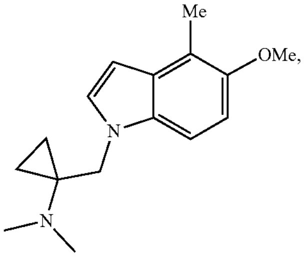
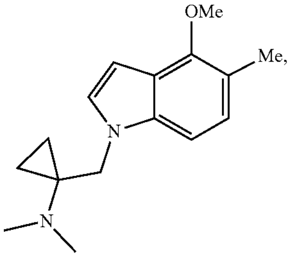
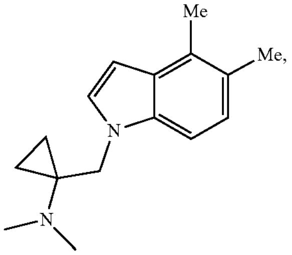
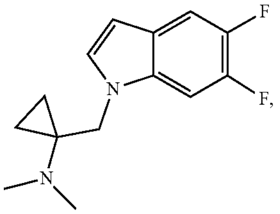
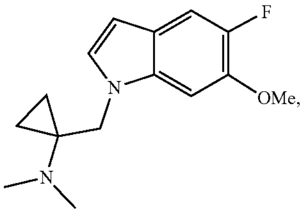
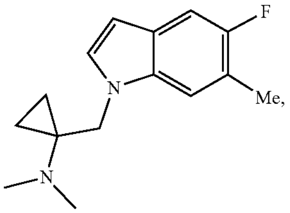
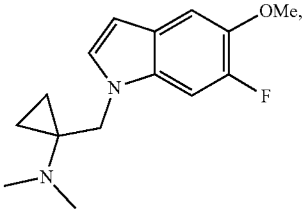
-continued
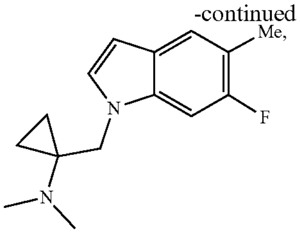
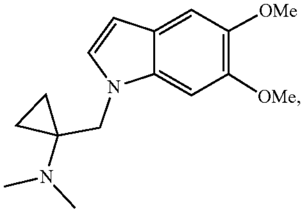
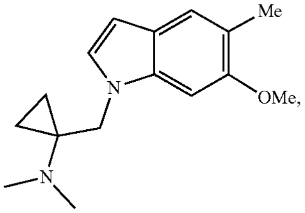
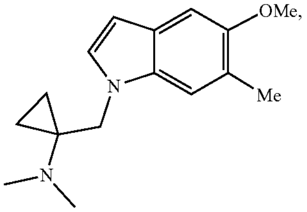
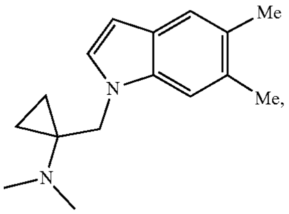
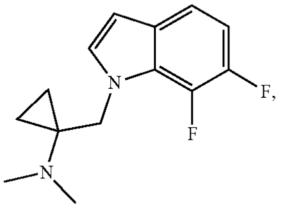
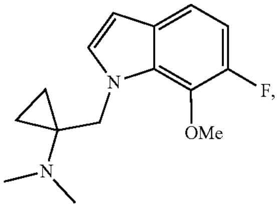
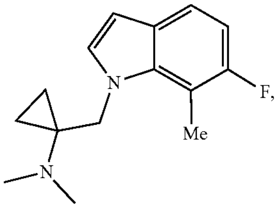

-continued
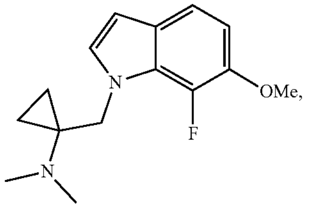
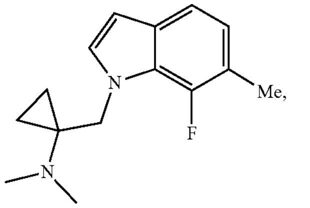
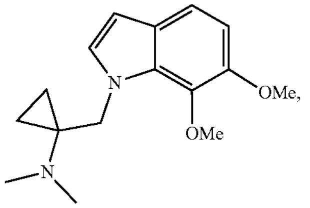
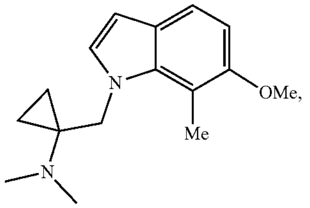
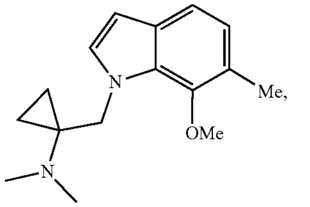
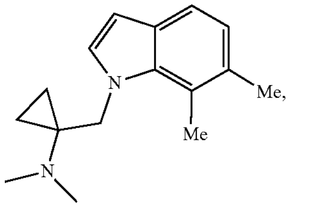
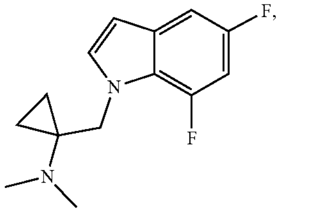
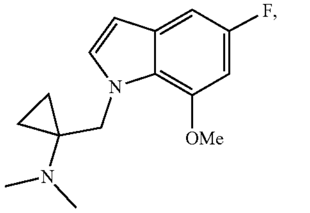
-continued
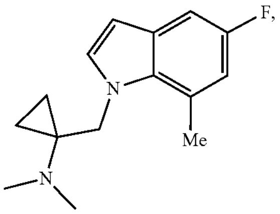
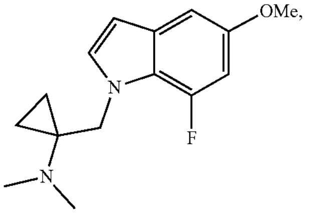
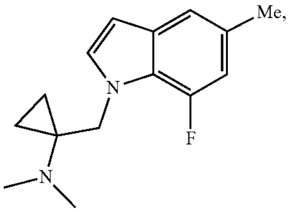
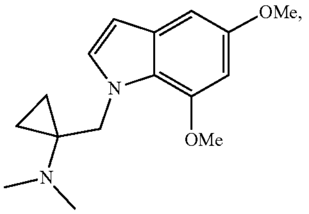
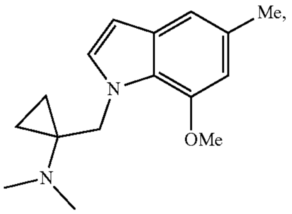
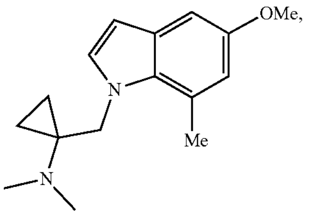
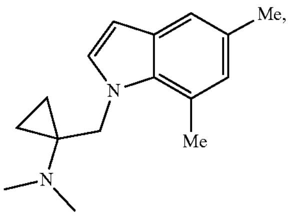
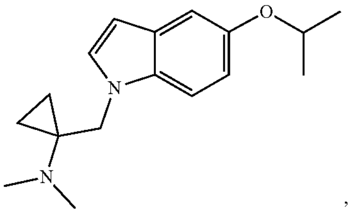
, -continued
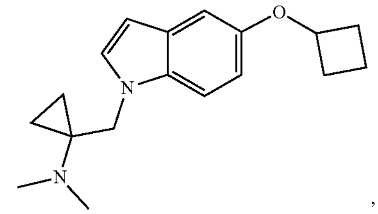
,
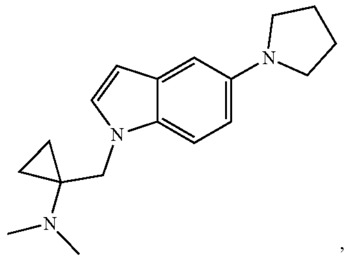
,
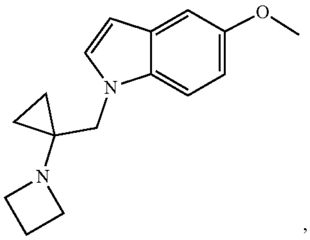
,
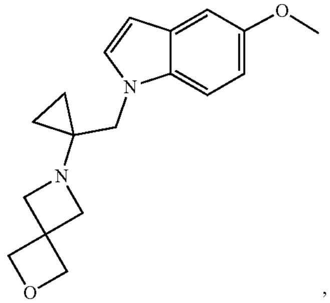
,
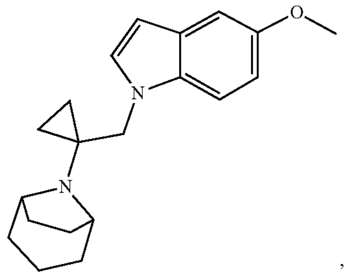
,
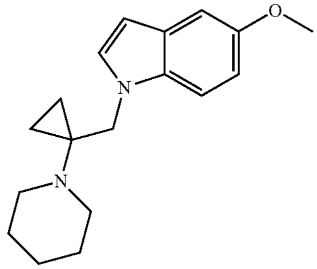
,
-continued
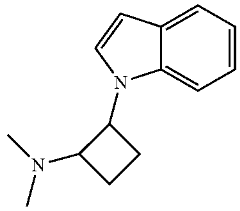
,
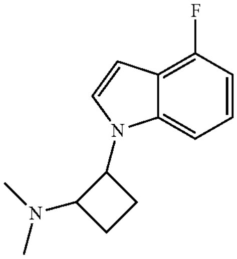
,
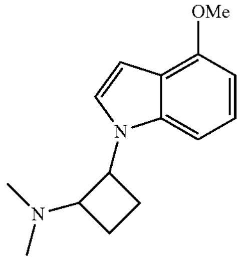
,
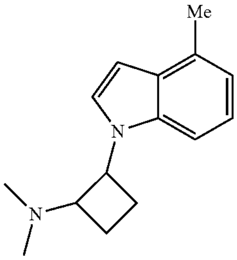
,
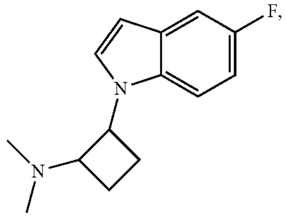
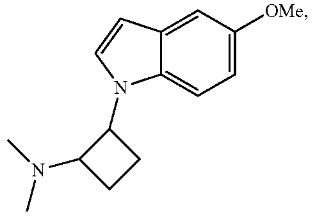
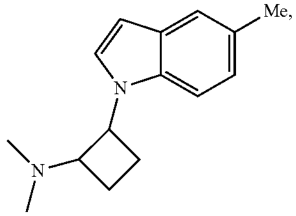
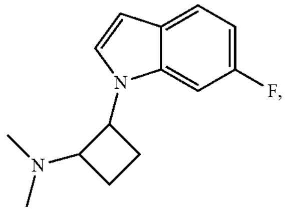
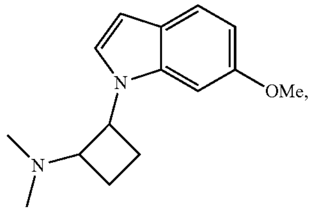

-continued
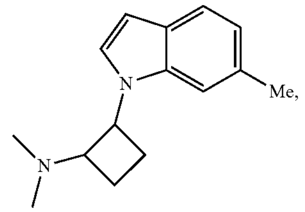
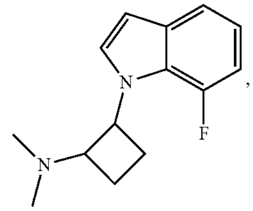
,
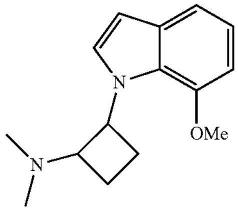
,
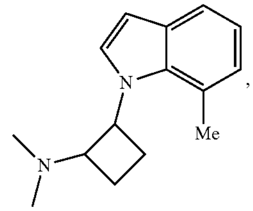
,
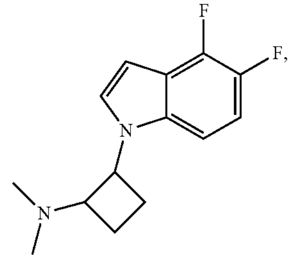
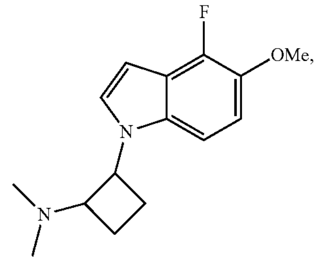
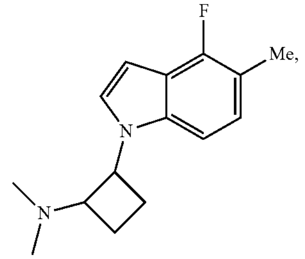
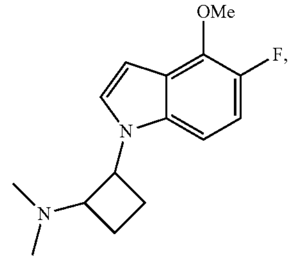
-continued
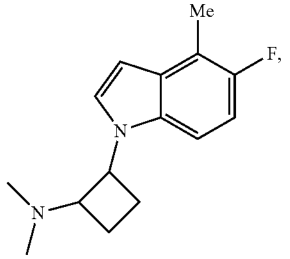
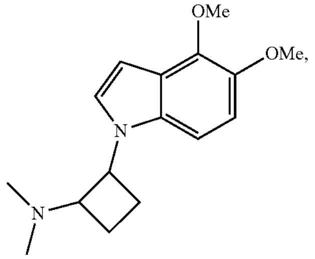
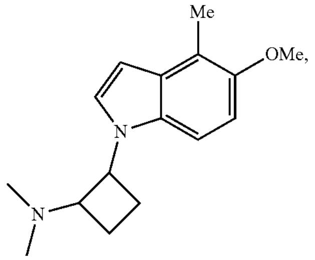
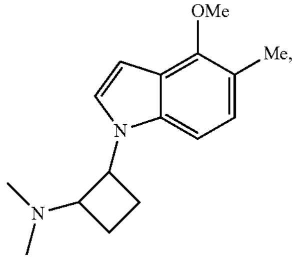
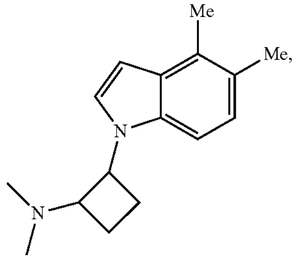
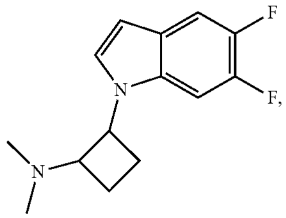
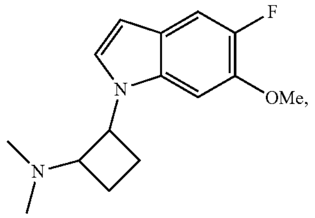

-continued
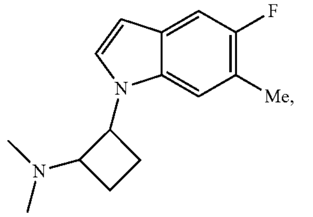
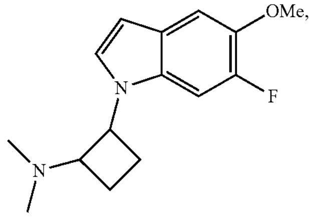
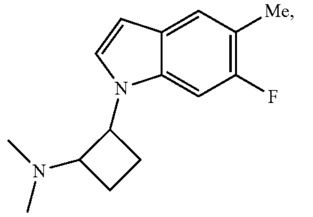
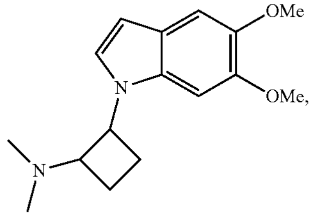
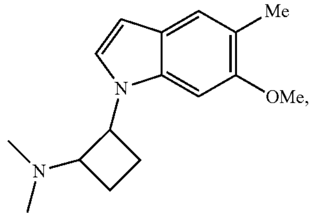
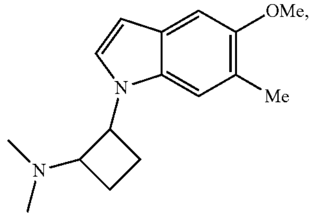
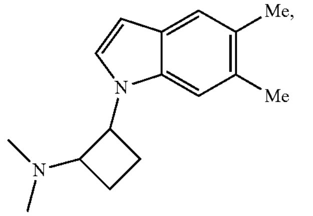
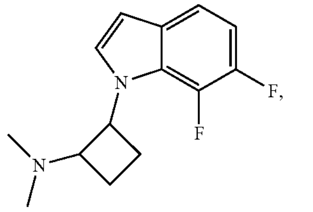
-continued
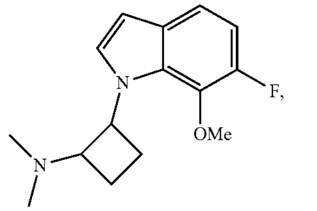
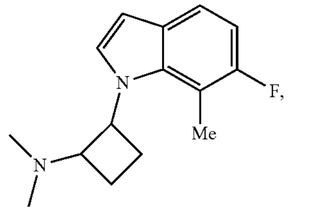
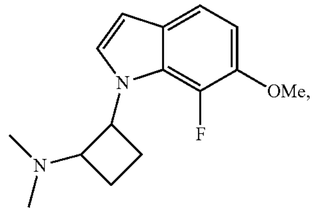
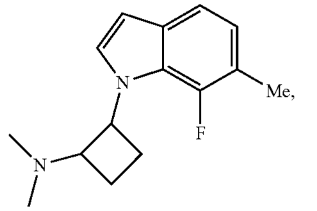
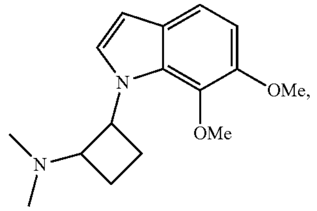
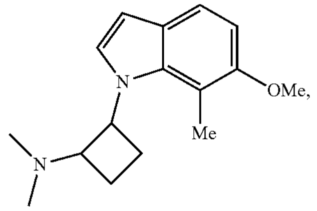
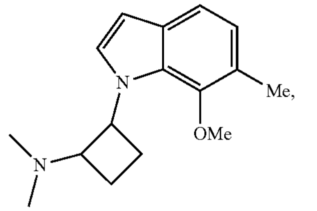
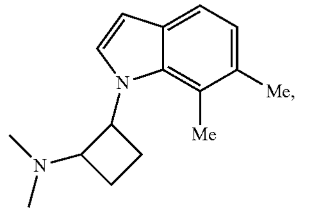

-continued
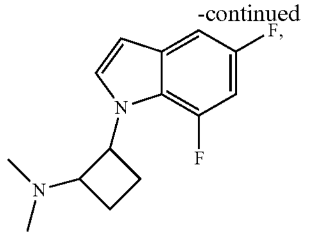
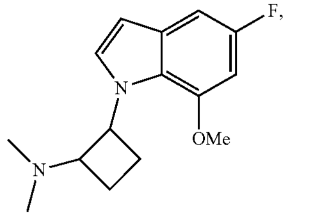
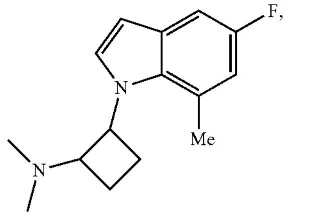
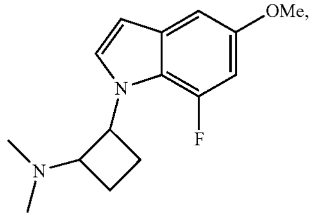
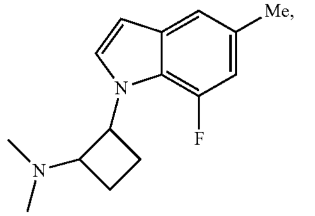
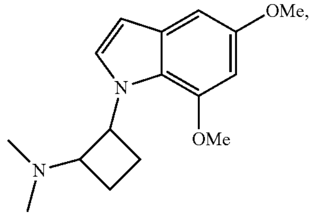
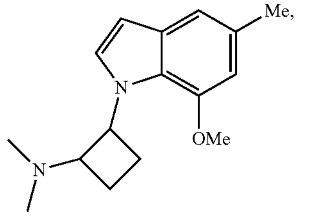
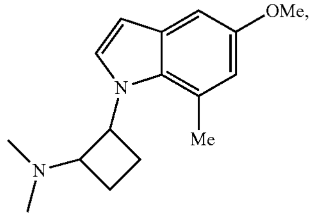
-continued
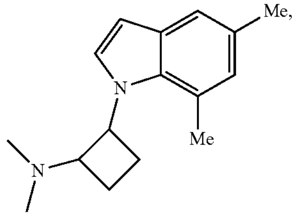
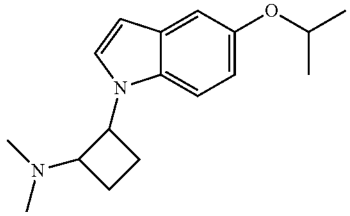
,
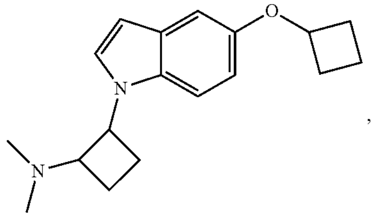
,
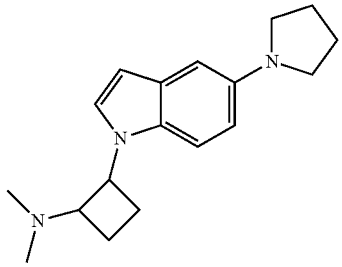
,
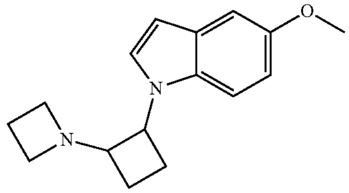
,
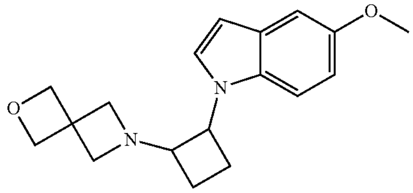
,
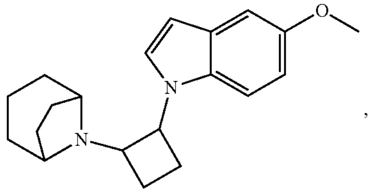
,
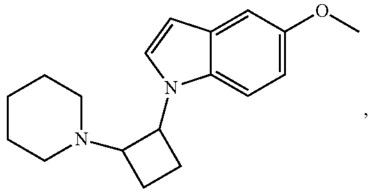
, -continued
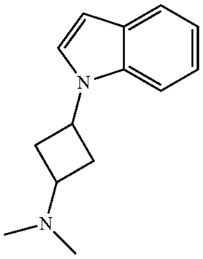,
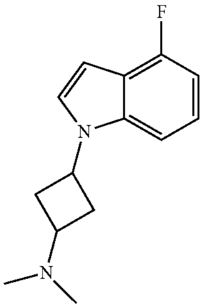,
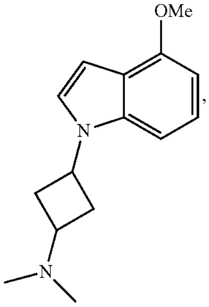,
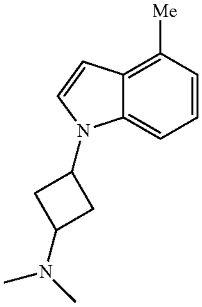,
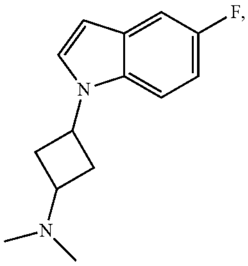,
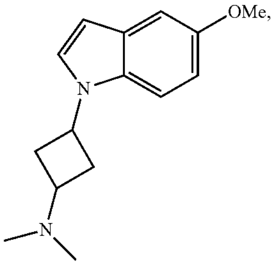,
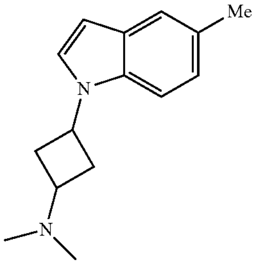,
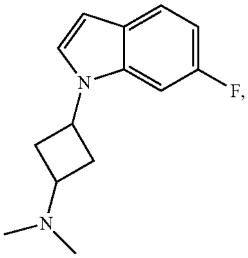,
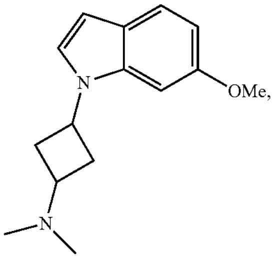,
-continued
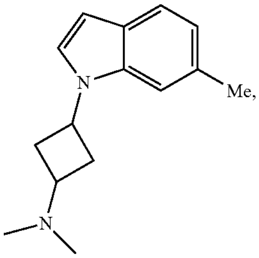,
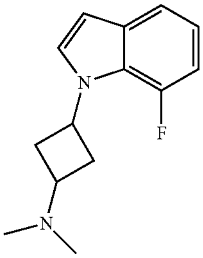,
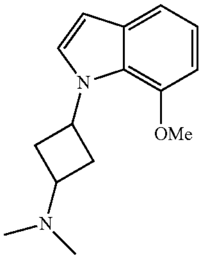,
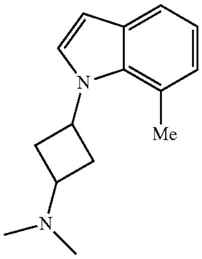,
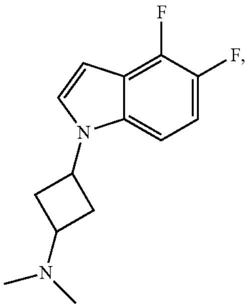,
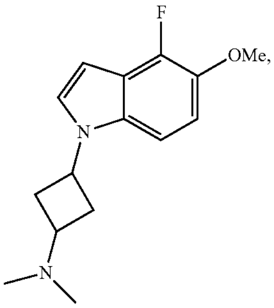,
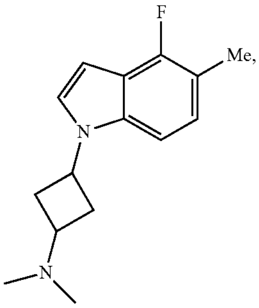,
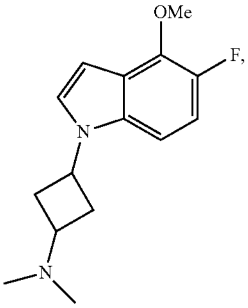, -continued
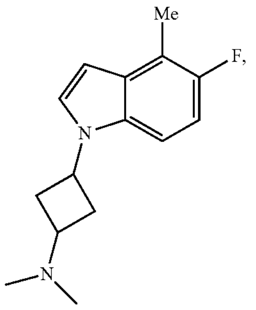
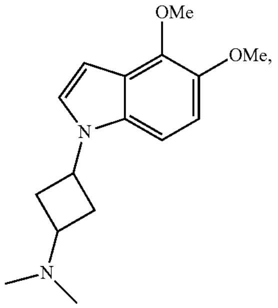
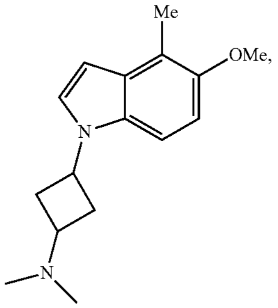
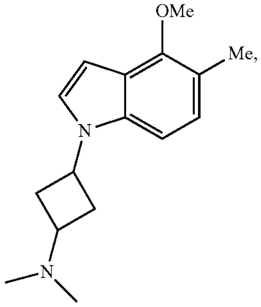
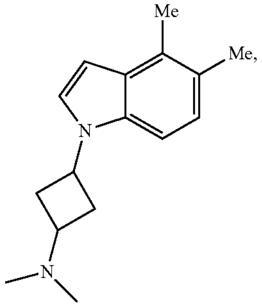
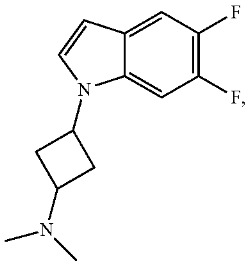
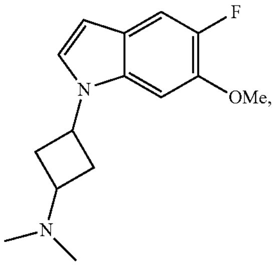
-continued
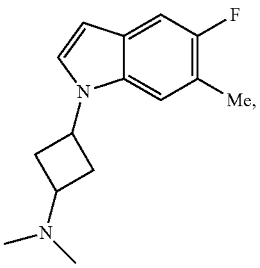
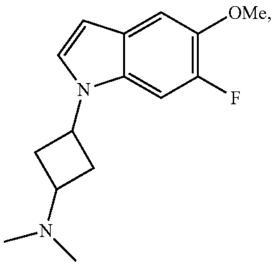
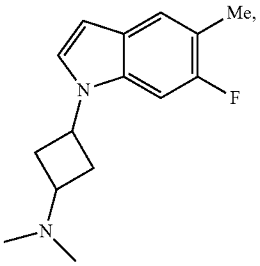
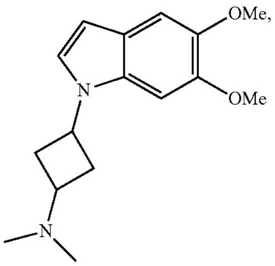
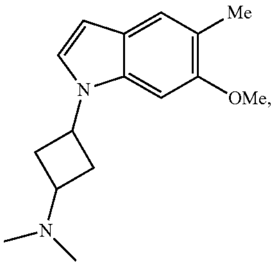
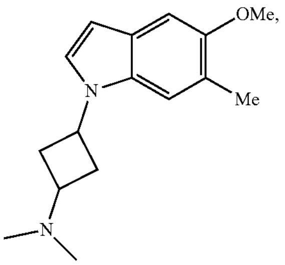

-continued
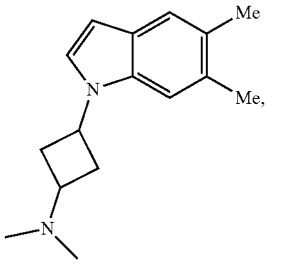
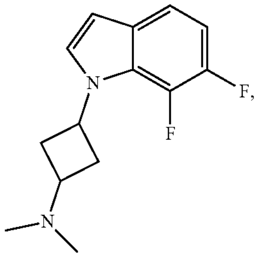
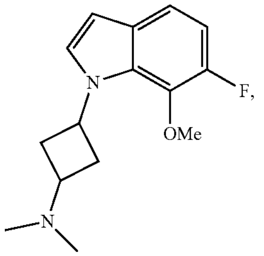
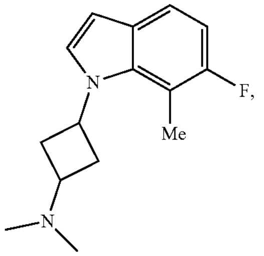
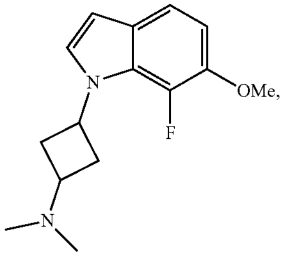
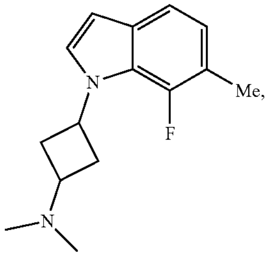
-continued
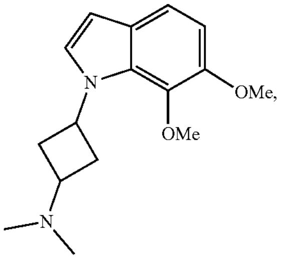
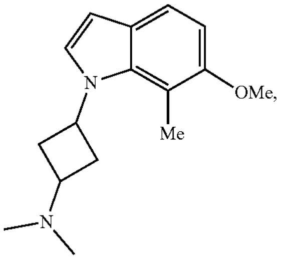
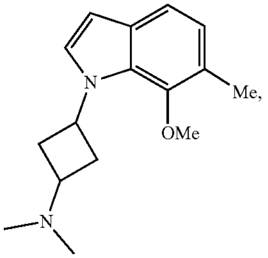
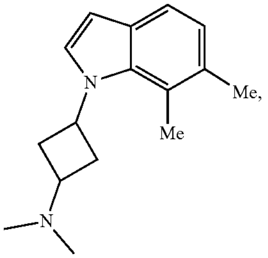
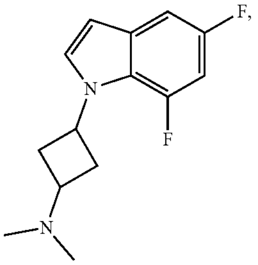
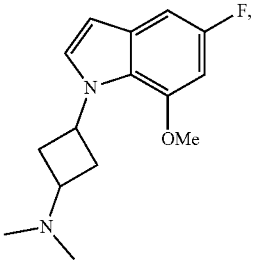

-continued
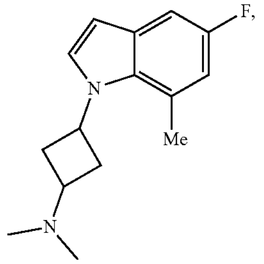
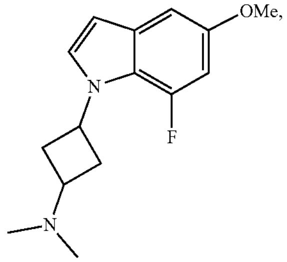
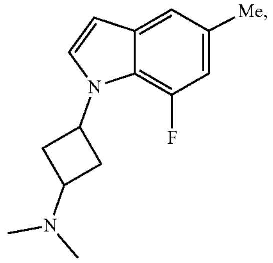
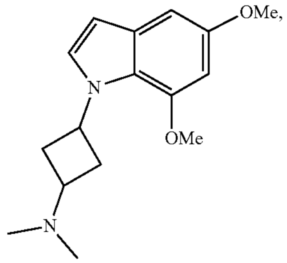
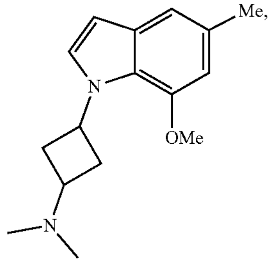
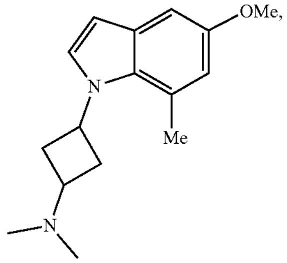
-continued
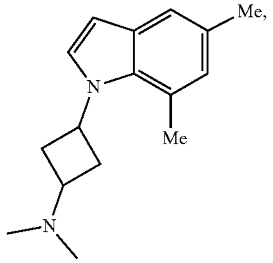
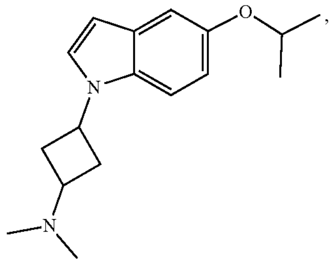
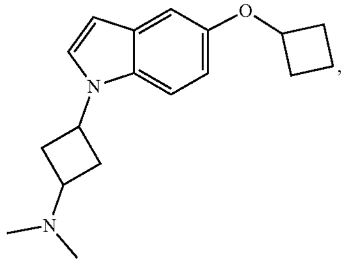
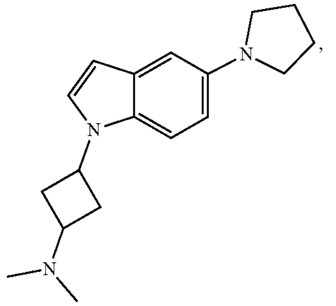
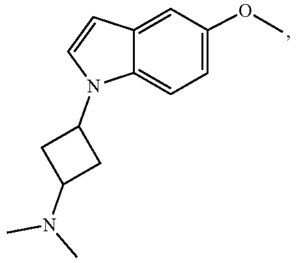
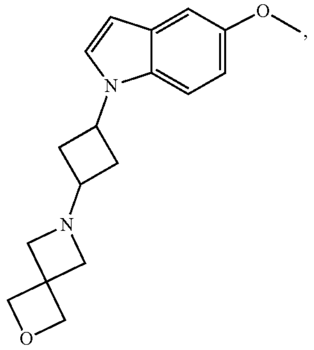

-continued
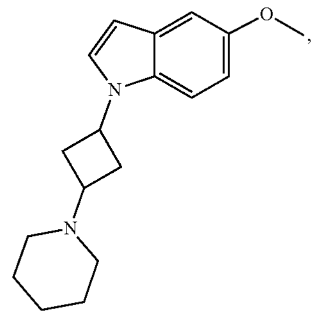
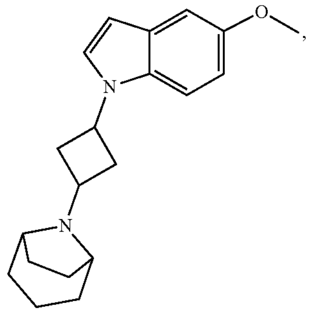
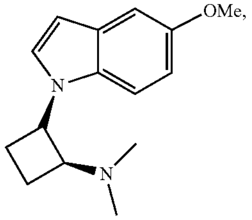
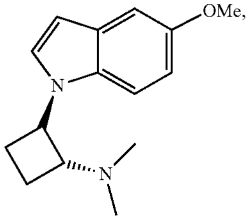
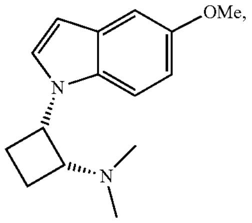
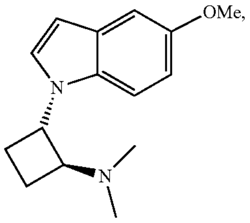
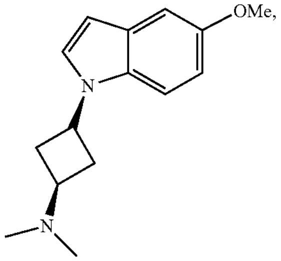
and
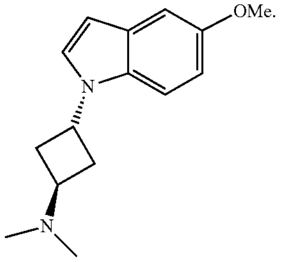
Other representative compounds of Formula (II) include, but are not limited to:
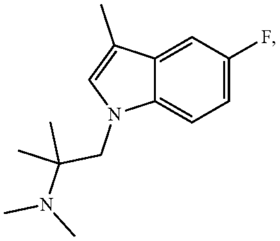
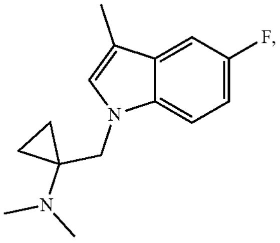
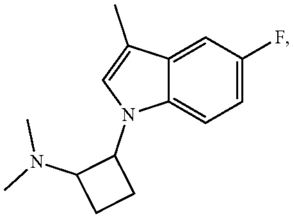
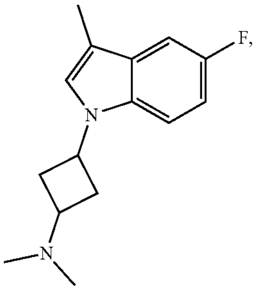
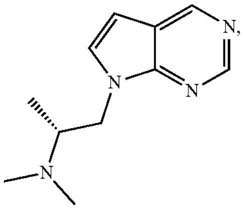
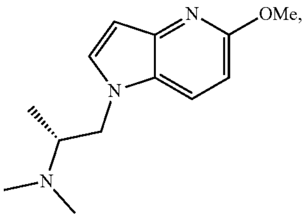
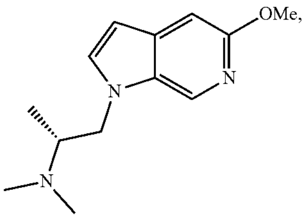

-continued
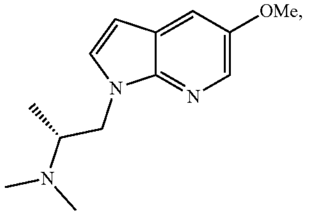
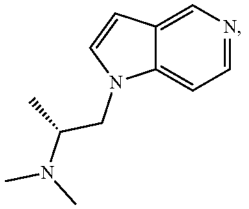
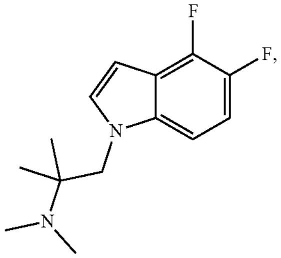
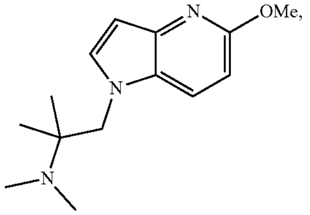
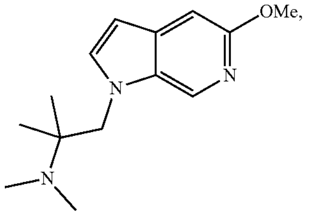
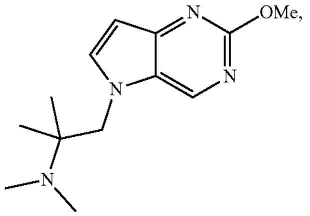
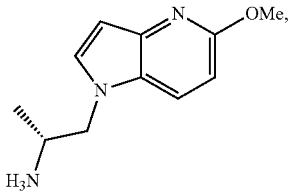
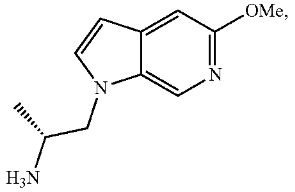
-continued
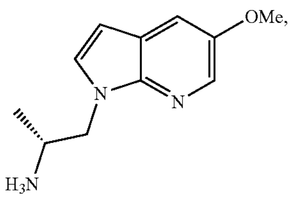
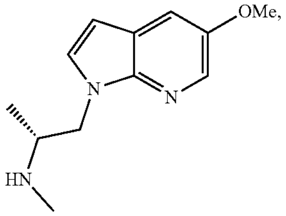
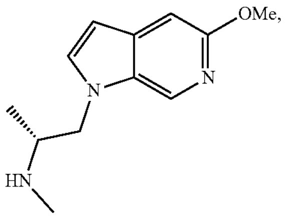
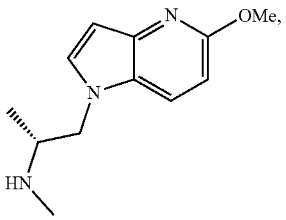
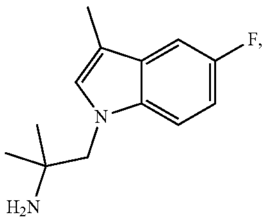
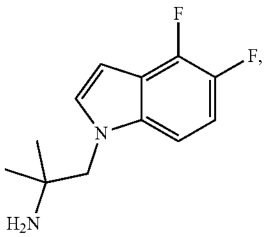
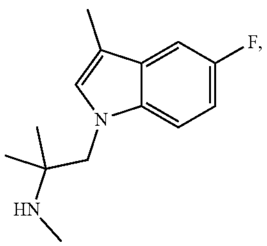

-continued
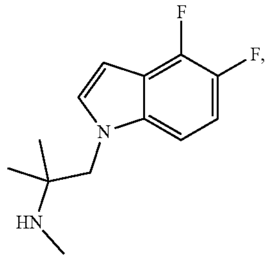
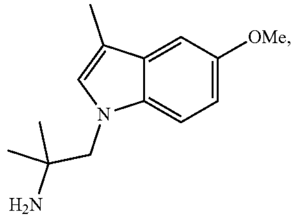
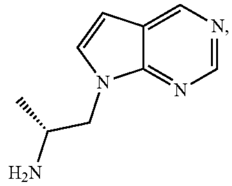
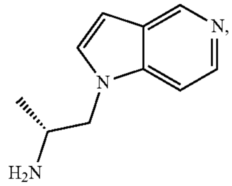
and
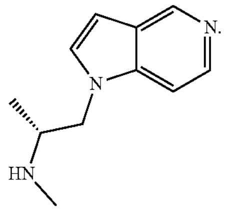
Provided in some embodiments herein is a compound, a stereoisomer thereof, or a pharmaceutically acceptable salt of the compound or the stereoisomer, having a structure provided in Table 1.
TABLE 1
| Cmpd | Structure |
| --- | --- |
| 1 | 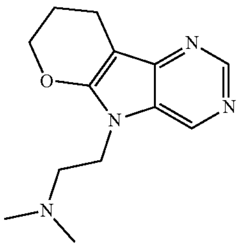 [SMILES: CN(C)CCn1c2c(c3ncncc31)CCCO2] |
TABLE 1-continued
| Cmpd | Structure |
| --- | --- |
| 2 | 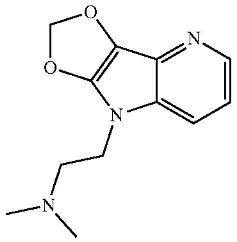 [SMILES: CN(C)CCn1c2c(c3ncccc31)OCO2] |
| 3 | 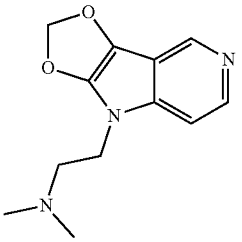 [SMILES: CN(C)CCn1c2c(c3cnccc31)OCO2] |
| 4 | 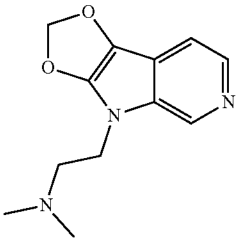 [SMILES: CN(C)CCn1c2c(c3ccncc31)OCO2] |
| 5 | 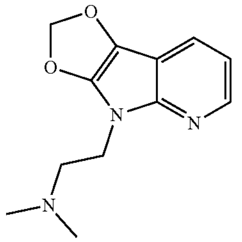 [SMILES: CN(C)CCn1c2c(c3cccnc31)OCO2] |
| 6 | 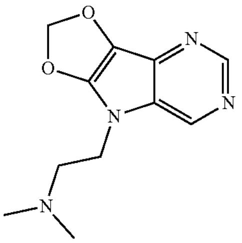 [SMILES: CN(C)CCn1c2c(c3ncncc31)OCO2] |
| 7 | 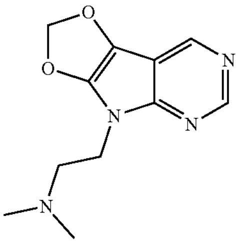 [SMILES: CN(C)CCn1c2c(c3cncnc31)OCO2] |

TABLE 1-continued
| Cmpd | Structure |
|---|---|
| 8 | 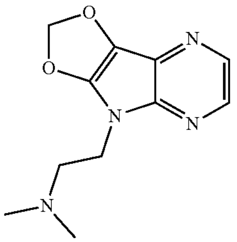 [SMILES: CN(C)CCn1c2c(c3nccnc31)OCO2] |
| 9 | 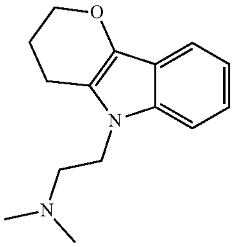 [SMILES: CN(C)CCn1c2c(c3ccccc31)OCCC2] |
| 10 | 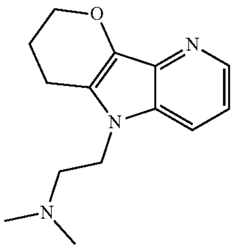 [SMILES: CN(C)CCn1c2c(c3ncccc31)OCCC2] |
| 11 | 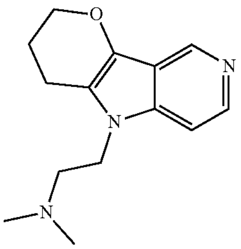 [SMILES: CN(C)CCn1c2c(c3cnccc31)OCCC2] |
| 12 | 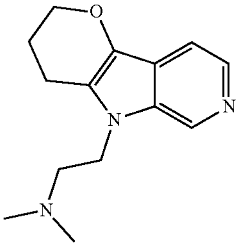 [SMILES: CN(C)CCn1c2c(c3ccncc31)OCCC2] |
| 13 | 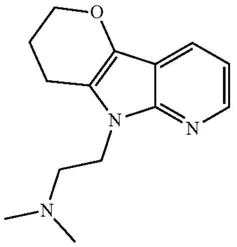 [SMILES: CN(C)CCn1c2c(c3cccnc31)OCCC2] |
TABLE 1-continued
| Cmpd | Structure |
|---|---|
| 14 | 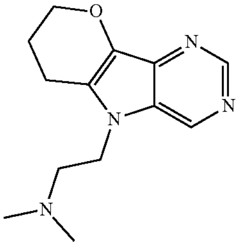 [SMILES: CN(C)CCn1c2c(c3ncncc31)OCCC2] |
| 15 | 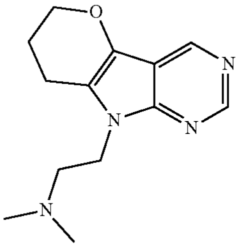 [SMILES: CN(C)CCn1c2c(c3cncnc31)OCCC2] |
| 16 | 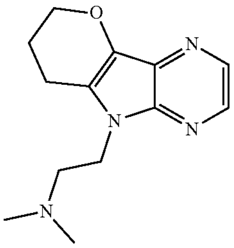 [SMILES: CN(C)CCn1c2c(c3nccnc31)OCCC2] |
| 17 | 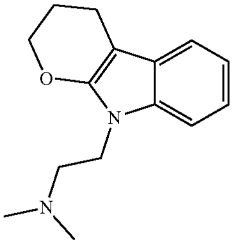 [SMILES: CN(C)CCn1c2c(c3ccccc31)CCCO2] |
| 18 | 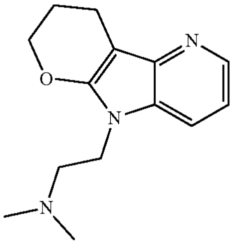 [SMILES: CN(C)CCn1c2c(c3ncccc31)CCCO2] |
| 19 | 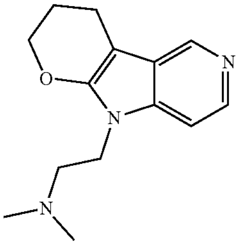 [SMILES: CN(C)CCn1c2c(c3cnccc31)CCCO2] |

TABLE 1-continued
| Cmpd | Structure |
| --- | --- |
| 20 | 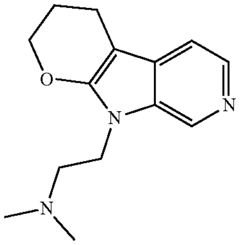 [SMILES: CN(C)CCn1c2c(c3ccncc31)CCCO2] |
| 21 | 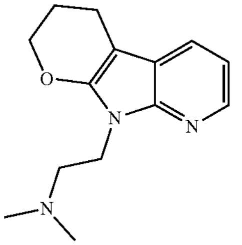 [SMILES: CN(C)CCn1c2c(c3cccnc31)CCCO2] |
| 22 | 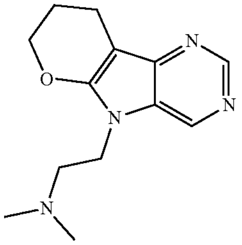 [SMILES: CN(C)CCn1c2c(c3ncncc31)CCCO2] |
| 23 | 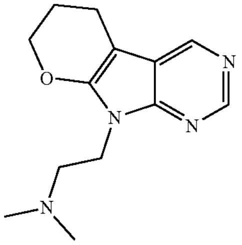 [SMILES: CN(C)CCn1c2c(c3cncnc31)CCCO2] |
| 24 | 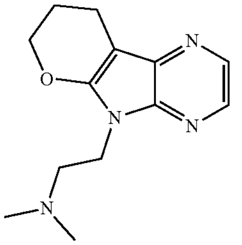 [SMILES: CN(C)CCn1c2c(c3nccnc31)CCCO2] |
| 25 | 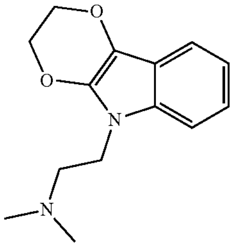 [SMILES: CN(C)CCn1c2c(c3ccccc31)OCCO2] |
TABLE 1-continued
| Cmpd | Structure |
| --- | --- |
| 26 | 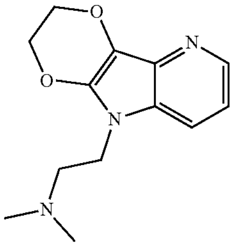 [SMILES: CN(C)CCn1c2c(c3ncccc31)OCCO2] |
| 27 | 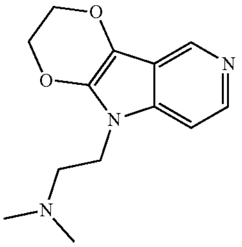 [SMILES: CN(C)CCn1c2c(c3cnccc31)OCCO2] |
| 28 | 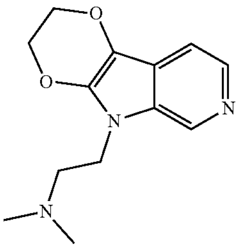 [SMILES: CN(C)CCn1c2c(c3ccncc31)OCCO2] |
| 29 | 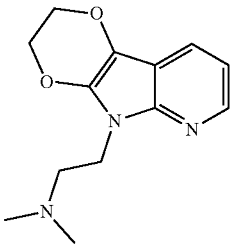 [SMILES: CN(C)CCn1c2c(c3cccnc31)OCCO2] |
| 30 | 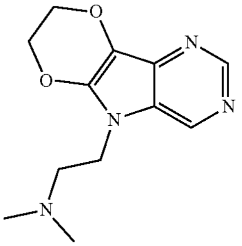 [SMILES: CN(C)CCn1c2c(c3ncncc31)OCCO2] |
| 31 | 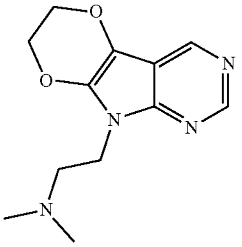 [SMILES: CN(C)CCn1c2c(c3cncnc31)OCCO2] |

TABLE 1-continued
| Cmpd | Structure |
|---|---|
| 32 | 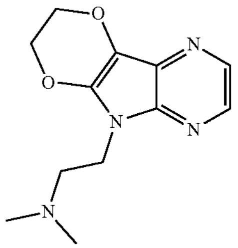 [SMILES: CN(C)CCn1c2c(c3nccnc31)OCCO2] |
| 33 | 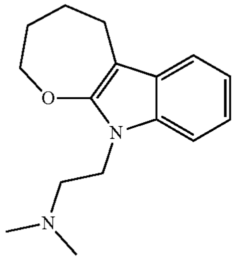 [SMILES: CN(C)CCn1c2c(c3ccccc31)CCCCO2] |
| 34 | 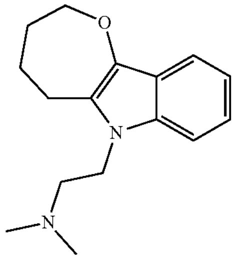 [SMILES: CN(C)CCn1c2c(c3ccccc31)OCCCC2] |
| 35 | 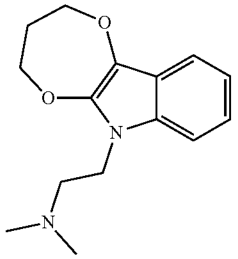 [SMILES: CN(C)CCn1c2c(c3ccccc31)OCCCO2] |
| 36 | 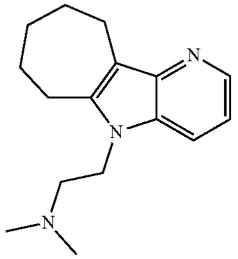 [SMILES: CN(C)CCn1c2c(c3ncccc31)CCCCC2] |
| 37 | 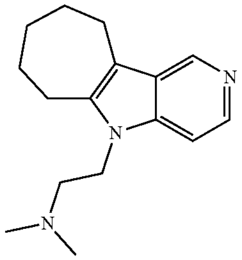 [SMILES: CN(C)CCn1c2c(c3cnccc31)CCCCC2] |
TABLE 1-continued
| Cmpd | Structure |
|---|---|
| 38 | 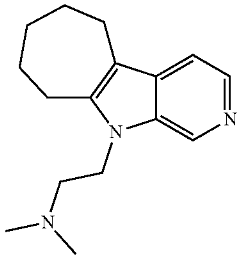 [SMILES: CN(C)CCn1c2c(c3ccncc31)CCCCC2] |
| 39 | 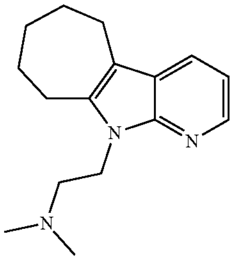 [SMILES: CN(C)CCn1c2c(c3cccnc31)CCCCC2] |
| 40 | 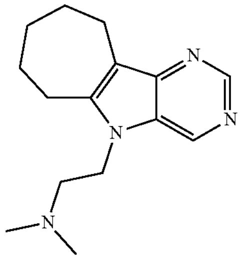 [SMILES: CN(C)CCn1c2c(c3ncncc31)CCCCC2] |
| 41 | 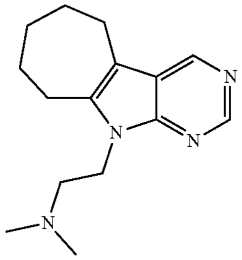 |
| 42 | 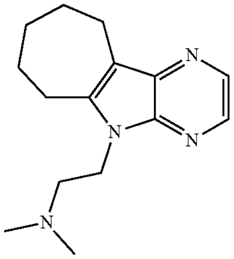 [SMILES: CN(C)CCn1c2c(c3nccnc31)CCCCC2] |
| 43 | 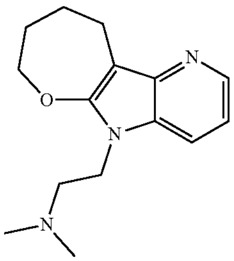 [SMILES: CN(C)CCn1c2c(c3ncccc31)CCCCO2] |

TABLE 1-continued
| Cmpd | Structure |
| --- | --- |
| 44 | 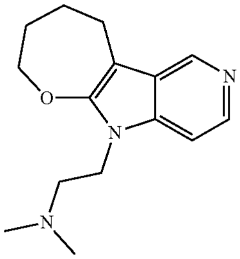 [SMILES: CN(C)CCn1c2c(c3cnccc31)CCCCO2] |
| 45 | 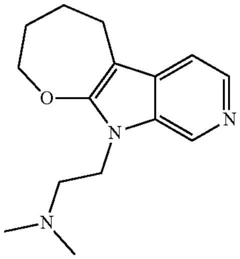 [SMILES: CN(C)CCn1c2c(c3ccncc31)CCCCO2] |
| 46 | 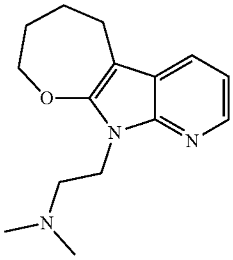 |
| 47 | 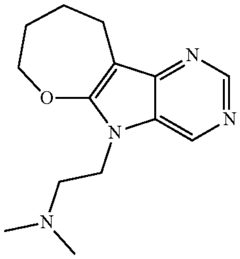 [SMILES: CN(C)CCn1c2c(c3ncncc31)CCCCO2] |
| 48 | 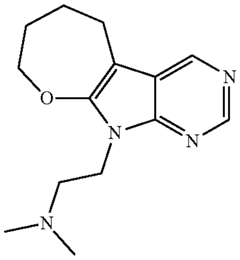 |
TABLE 1-continued
| Cmpd | Structure |
| --- | --- |
| 49 | 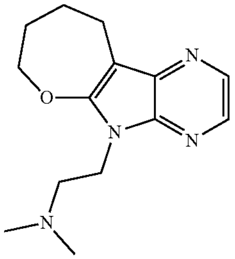 [SMILES: CN(C)CCn1c2c(c3nccnc31)CCCCO2] |
| 50 | 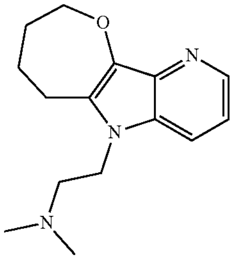 [SMILES: CN(C)CCn1c2c(c3ncccc31)OCCCC2] |
| 51 | 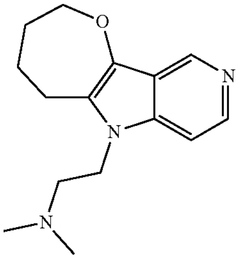 |
| 52 | 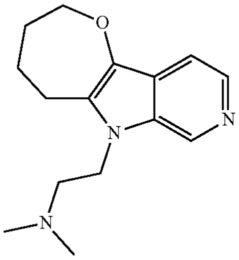 [SMILES: CN(C)CCn1c2c(c3ccncc31)OCCCC2] |
| 53 | 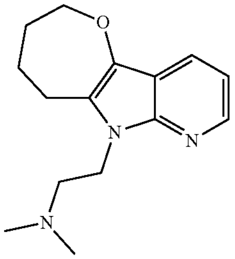 |
| 54 | 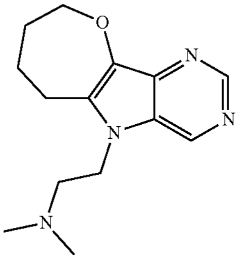 [SMILES: CN(C)CCn1c2c(c3ncncc31)OCCCC2] |

TABLE 1-continued
| Cmpd | Structure |
|---|---|
| 55 | 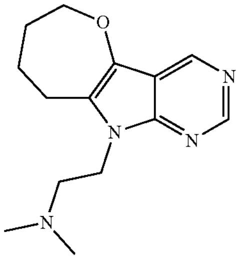 [SMILES: CN(C)CCn1c2c(c3cncnc31)OCCCC2] |
| 56 | 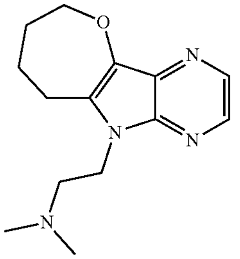 [SMILES: CN(C)CCn1c2c(c3nccnc31)OCCCC2] |
| 57 | 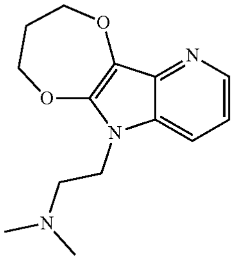 |
| 58 | 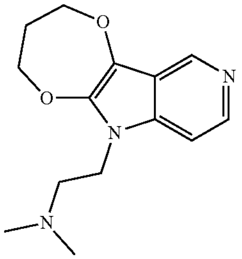 [SMILES: CN(C)CCn1c2c(c3cnccc31)OCCCO2] |
| 59 | 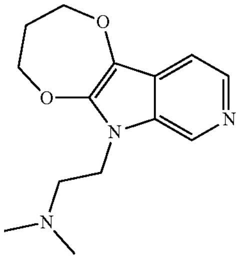 [SMILES: CN(C)CCn1c2c(c3ccncc31)OCCCO2] |
| 60 | 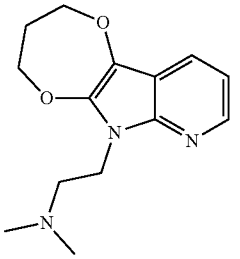 [SMILES: CN(C)CCn1c2c(c3cccnc31)OCCCO2] |
| 61 | 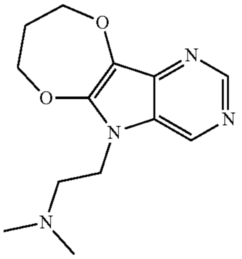 [SMILES: CN(C)CCn1c2c(c3ncncc31)OCCCO2] |
| 62 | 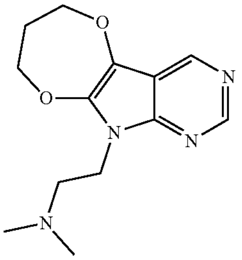 [SMILES: CN(C)CCn1c2c(c3cncnc31)OCCCO2] |
| 63 | 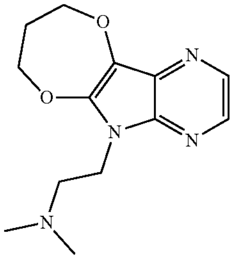 [SMILES: CN(C)CCn1c2c(c3nccnc31)OCCCO2] |
Provided in some embodiments herein is a compound, a stereoisomer thereof, or a pharmaceutically acceptable salt of the compound or the stereoisomer, having a structure provided in Table 2:
TABLE 2
| Cmpd | Structure |
|---|---|
| 64 | 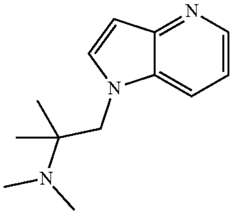 [SMILES: CN(C)C(C)(C)Cn1ccc2ncccc21] |

TABLE 2-continued
| Cmpd | Structure |
|---|---|
| 65 | 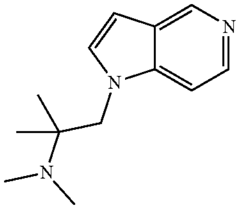 [SMILES: CN(C)C(C)(C)Cn1ccc2cnccc21] |
| 66 | 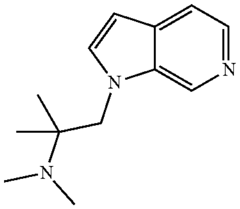 [SMILES: CN(C)C(C)(C)Cn1ccc2ccncc21] |
| 67 | 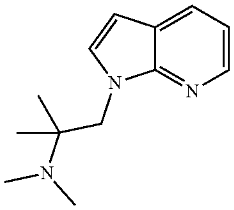 [SMILES: CN(C)C(C)(C)Cn1ccc2cccnc21] |
| 68 | 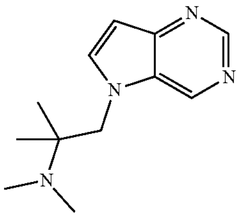 [SMILES: CN(C)C(C)(C)Cn1ccc2ncncc21] |
| 69 | 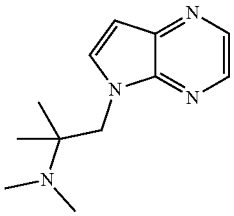 |
| 70 | 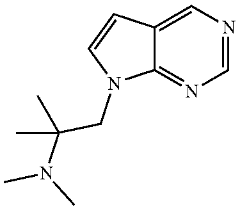 [SMILES: CN(C)C(C)(C)Cn1ccc2cncnc21] |
| 71 | 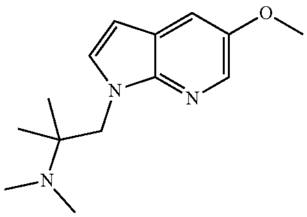 |
TABLE 2-continued
| Cmpd | Structure |
|---|---|
| 72 | 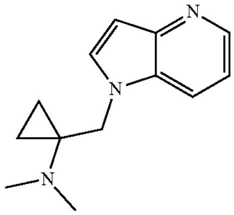 [SMILES: CN(C)C1(Cn2ccc3ncccc32)CC1] |
| 73 | 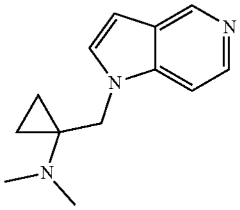 [SMILES: CN(C)C1(Cn2ccc3cnccc32)CC1] |
| 74 | 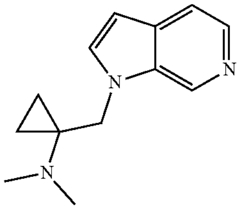 [SMILES: CN(C)C1(Cn2ccc3ccncc32)CC1] |
| 75 | 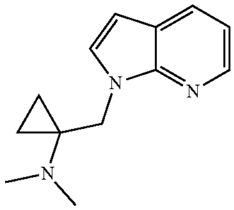 [SMILES: CN(C)C1(Cn2ccc3cccnc32)CC1] |
| 76 | 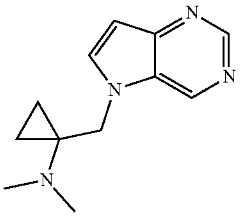 [SMILES: CN(C)C1(Cn2ccc3ncncc32)CC1] |
| 77 | 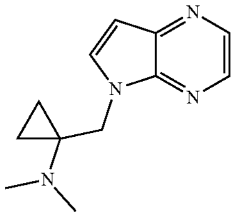 [SMILES: CN(C)C1(Cn2ccc3nccnc32)CC1] |
| 78 | 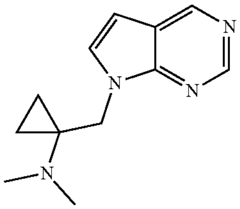 [SMILES: CN(C)C1(Cn2ccc3cncnc32)CC1] |

TABLE 2-continued
| Cmpd | Structure |
| --- | --- |
| 79 | 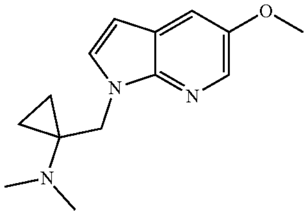 |
| 80 | 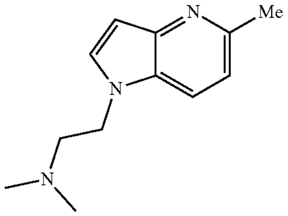 |
| 81 | 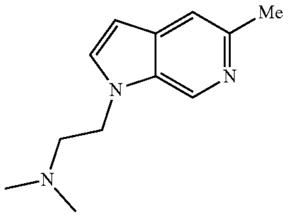 |
| 82 | 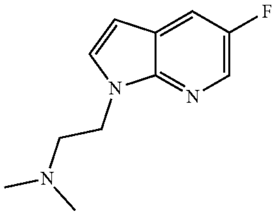 |
| 83 | 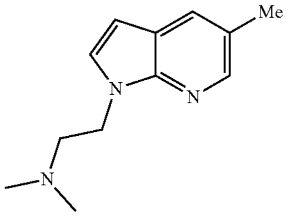 |
| 84 | 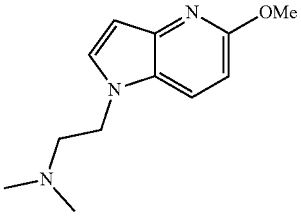 [SMILES: COc1ccc2c(ccn2CCN(C)C)n1] |
| 85 | 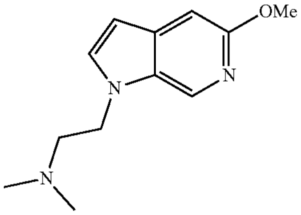 [SMILES: COc1cc2ccn(CCN(C)C)c2cn1] |
| 86 | 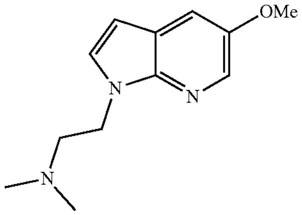 [SMILES: COc1cnc2c(ccn2CCN(C)C)c1] |
| 87 | 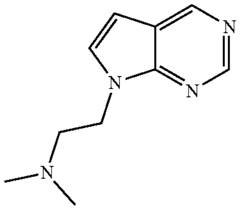 |
| 88 | 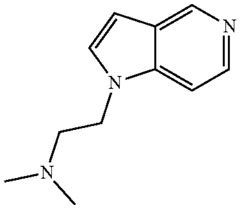 |
| 89 | 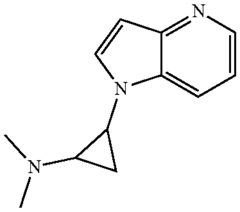 |
| 90 | 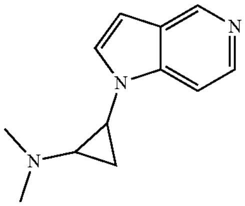 |
| 91 | 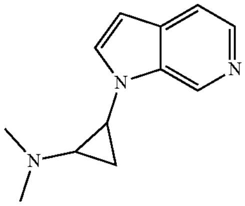 |
| 92 | 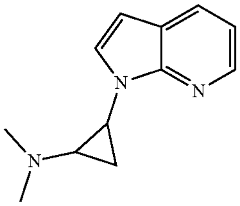 |

TABLE 2-continued
| Cmpd | Structure |
|---|---|
| 93 | 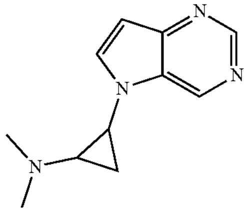 |
| 94 | 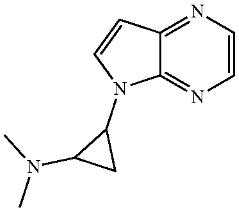 |
| 95 | 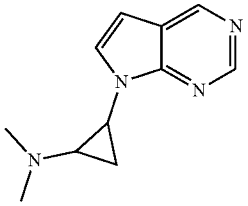 |
| 96 | 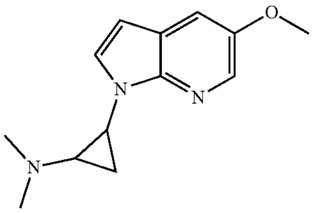 |
| 97 | 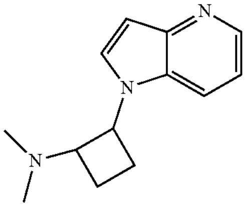 [SMILES: CN(C)C1CCC1n1ccc2ncccc21] |
| 98 | 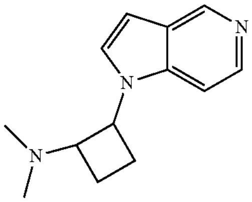 [SMILES: CN(C)C1CCC1n1ccc2cnccc21] |
| 99 | 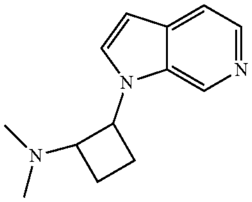 [SMILES: CN(C)C1CCC1n1ccc2ccncc21] |
TABLE 2-continued
| Cmpd | Structure |
|---|---|
| 100 | 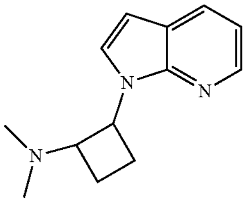 [SMILES: CN(C)C1CCC1n1ccc2cccnc21] |
| 101 | 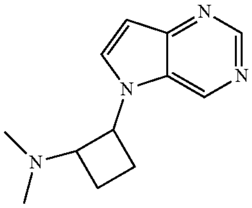 [SMILES: CN(C)C1CCC1n1ccc2ncncc21] |
| 102 | 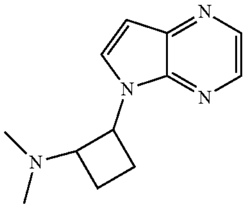 [SMILES: CN(C)C1CCC1n1ccc2nccnc21] |
| 103 | 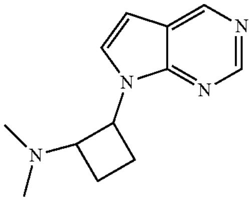 [SMILES: CN(C)C1CCC1n1ccc2cncnc21] |
| 104 | 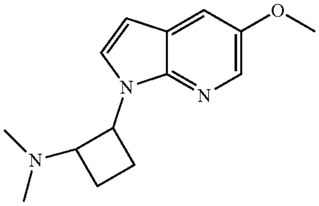 |
| 105 | 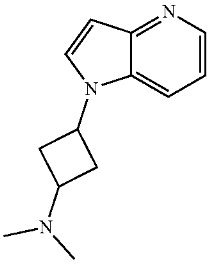 [SMILES: CN(C)C1CC(n2ccc3ncccc32)C1] |
| 106 | 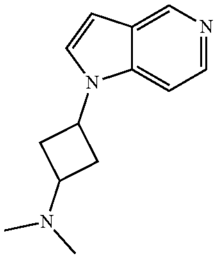 [SMILES: CN(C)C1CC(n2ccc3cnccc32)C1] |

TABLE 2-continued
| Cmpd | Structure |
|---|---|
| 107 | 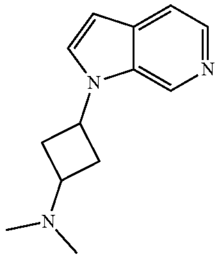 [SMILES: CN(C)C1CC(n2ccc3ccncc32)C1] |
| 108 | 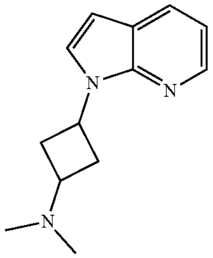 [SMILES: CN(C)C1CC(n2ccc3cccnc32)C1] |
| 109 | 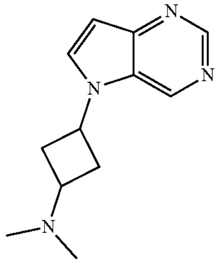 [SMILES: CN(C)C1CC(n2ccc3ncncc32)C1] |
| 110 | 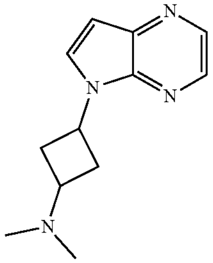 [SMILES: CN(C)C1CC(n2ccc3nccnc32)C1] |
| 111 | 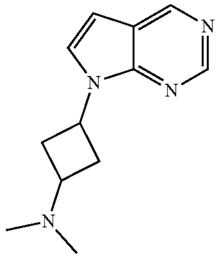 [SMILES: CN(C)C1CC(n2ccc3cncnc32)C1] |
TABLE 2-continued
| Cmpd | Structure |
|---|---|
| 112 | 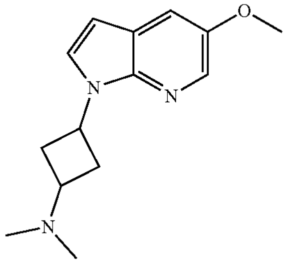 |
| 113 | 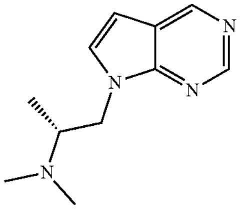 |
| 114 | 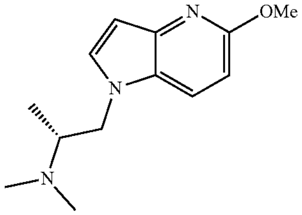 [SMILES: COc1ccc2c(ccn2C[C@@H](C)N(C)C)n1] |
| 115 | 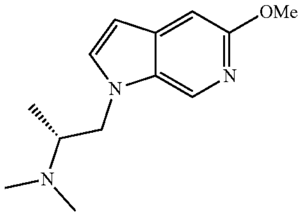 [SMILES: COc1cc2ccn(C[C@@H](C)N(C)C)c2cn1] |
| 116 | 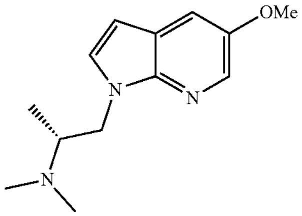 [SMILES: COc1cnc2c(ccn2C[C@@H](C)N(C)C)c1] |
| 117 | 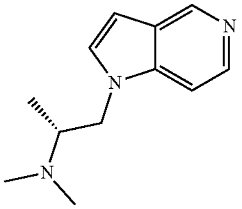 |
| 118 | 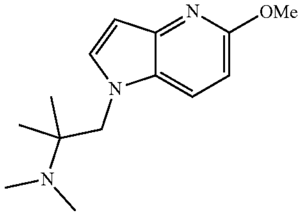 [SMILES: COc1ccc2c(ccn2CC(C)(C)N(C)C)n1] |

TABLE 2-continued
| Cmpd | Structure |
|---|---|
| 119 | 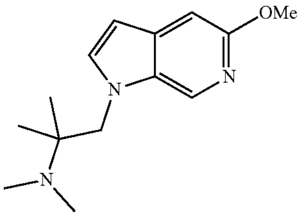 [SMILES: COc1cc2ccn(CC(C)(C)N(C)C)c2cn1] |
| 120 | 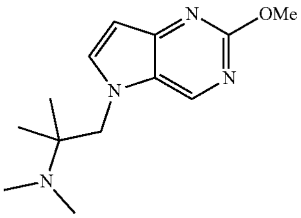 [SMILES: COc1ncc2c(ccn2CC(C)(C)N(C)C)n1] |
Provided in some embodiments herein is a compound, a stereoisomer thereof, or a pharmaceutically acceptable salt of the compound or the stereoisomer, having a structure provided in Table 3:
TABLE 3
| Cmpd | Structure |
|---|---|
| 121 | 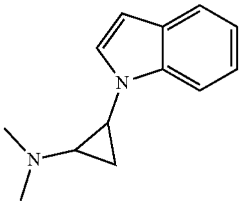 |
| 122 | 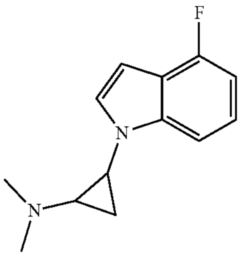 [SMILES: CN(C)C1CC1n1ccc2c(F)cccc21] |
| 123 | 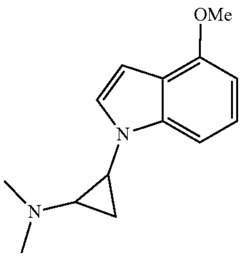 [SMILES: COc1cccc2c1ccn2C1CC1N(C)C] |
TABLE 3-continued
| Cmpd | Structure |
|---|---|
| 124 | 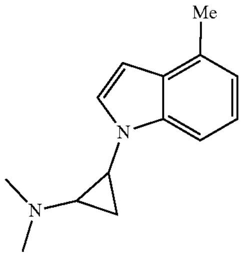 [SMILES: Cc1cccc2c1ccn2C1CC1N(C)C] |
| 125 | 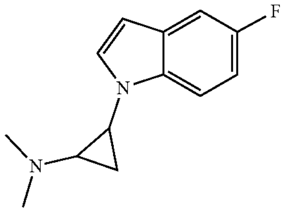 [SMILES: CN(C)C1CC1n1ccc2cc(F)ccc21] |
| 126 | 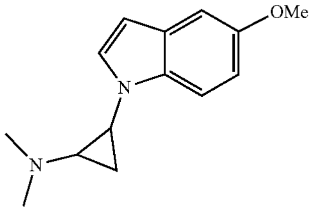 [SMILES: COc1ccc2c(ccn2C2CC2N(C)C)c1] |
| 127 | 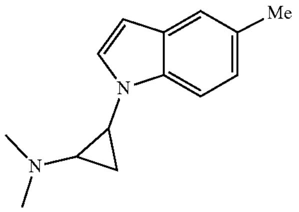 [SMILES: Cc1ccc2c(ccn2C2CC2N(C)C)c1] |
| 128 | 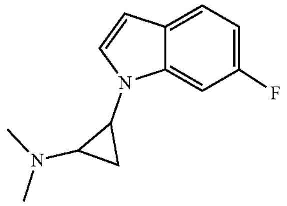 [SMILES: CN(C)C1CC1n1ccc2ccc(F)cc21] |
| 129 | 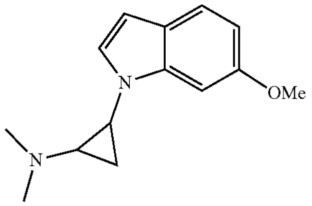 [SMILES: COc1ccc2ccn(C3CC3N(C)C)c2c1] |
| 130 | 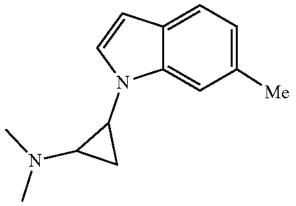 [SMILES: Cc1ccc2ccn(C3CC3N(C)C)c2c1] |

TABLE 3-continued
| Cmpd | Structure |
| --- | --- |
| 131 | 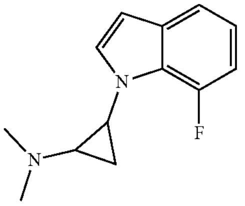 [SMILES: CN(C)C1CC1n1ccc2cccc(F)c21] |
| 132 | 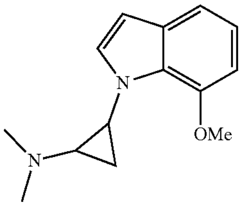 [SMILES: COc1cccc2ccn(C3CC3N(C)C)c12] |
| 133 | 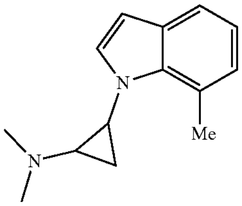 [SMILES: Cc1cccc2ccn(C3CC3N(C)C)c12] |
| 134 | 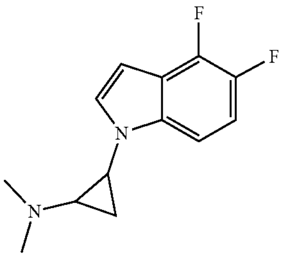 [SMILES: CN(C)C1CC1n1ccc2c(F)c(F)ccc21] |
| 135 | 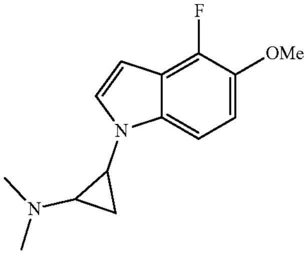 [SMILES: COc1ccc2c(ccn2C2CC2N(C)C)c1F] |
| 136 | 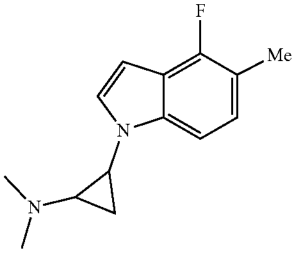 [SMILES: Cc1ccc2c(ccn2C2CC2N(C)C)c1F] |
TABLE 3-continued
| Cmpd | Structure |
| --- | --- |
| 137 | 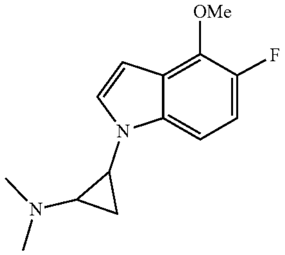 [SMILES: COc1c(F)ccc2c1ccn2C1CC1N(C)C] |
| 138 | 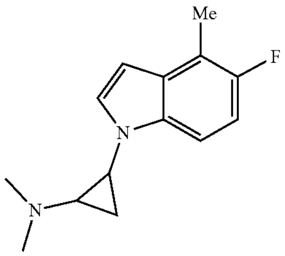 [SMILES: Cc1c(F)ccc2c1ccn2C1CC1N(C)C] |
| 139 | 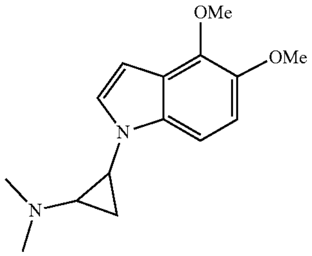 [SMILES: COc1ccc2c(ccn2C2CC2N(C)C)c1OC] |
| 140 | 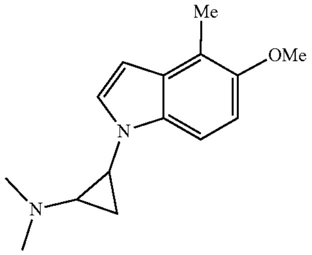 [SMILES: COc1ccc2c(ccn2C2CC2N(C)C)c1C] |
| 141 | 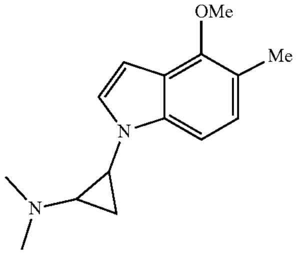 [SMILES: COc1c(C)ccc2c1ccn2C1CC1N(C)C] |
| 142 | 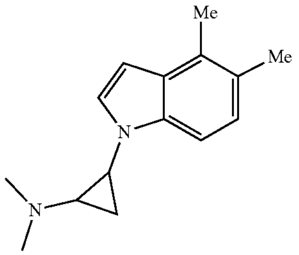 [SMILES: Cc1ccc2c(ccn2C2CC2N(C)C)c1C] |

TABLE 3-continued
| Cmpd | Structure |
|---|---|
| 143 | 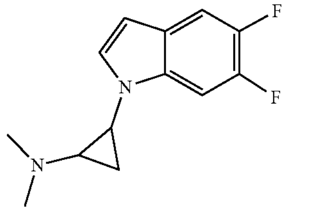 [SMILES: CN(C)C1CC1n1ccc2cc(F)c(F)cc21] |
| 144 | 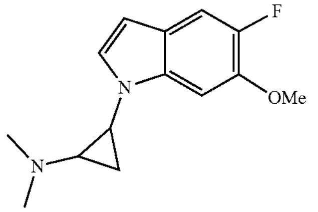 [SMILES: COc1cc2c(ccn2C2CC2N(C)C)cc1F] |
| 145 | 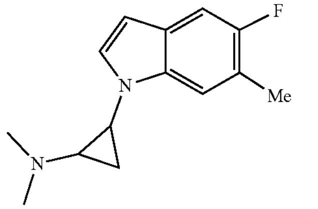 [SMILES: Cc1cc2c(ccn2C2CC2N(C)C)cc1F] |
| 146 | 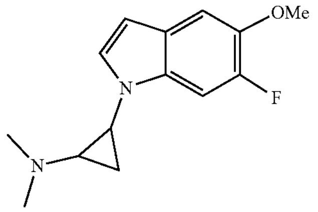 [SMILES: COc1cc2ccn(C3CC3N(C)C)c2cc1F] |
| 147 | 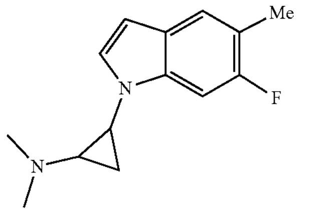 [SMILES: Cc1cc2ccn(C3CC3N(C)C)c2cc1F] |
| 148 | 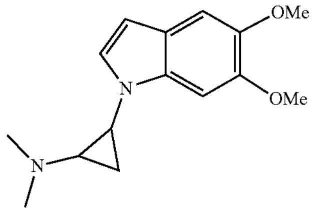 [SMILES: COc1cc2ccn(C3CC3N(C)C)c2cc1OC] |
| 149 | 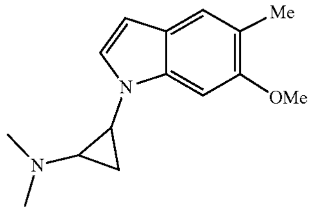 [SMILES: COc1cc2c(ccn2C2CC2N(C)C)cc1C] |
TABLE 3-continued
| Cmpd | Structure |
|---|---|
| 150 | 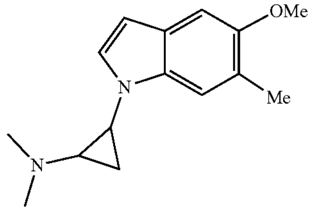 [SMILES: COc1cc2ccn(C3CC3N(C)C)c2cc1C] |
| 151 | 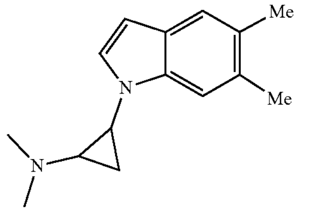 [SMILES: Cc1cc2ccn(C3CC3N(C)C)c2cc1C] |
| 152 | 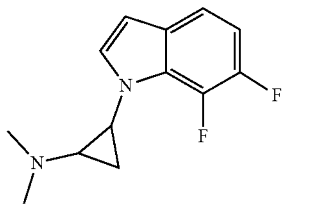 [SMILES: CN(C)C1CC1n1ccc2ccc(F)c(F)c21] |
| 153 | 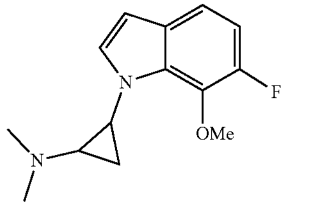 [SMILES: COc1c(F)ccc2ccn(C3CC3N(C)C)c12] |
| 154 | 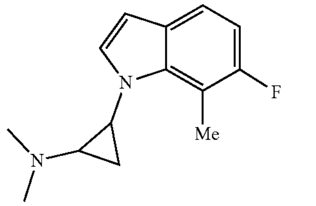 [SMILES: Cc1c(F)ccc2ccn(C3CC3N(C)C)c12] |
| 155 | 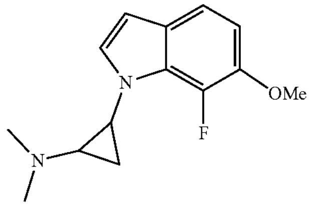 [SMILES: COc1ccc2ccn(C3CC3N(C)C)c2c1F] |
| 156 | 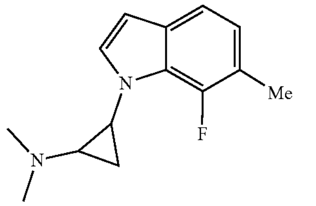 [SMILES: Cc1ccc2ccn(C3CC3N(C)C)c2c1F] |

TABLE 3-continued
| Cmpd | Structure |
| --- | --- |
| 157 | 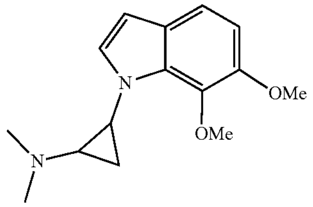 [SMILES: COc1ccc2ccn(C3CC3N(C)C)c2c1OC] |
| 158 | 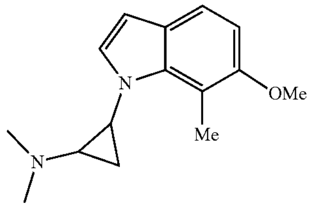 [SMILES: COc1ccc2ccn(C3CC3N(C)C)c2c1C] |
| 159 | 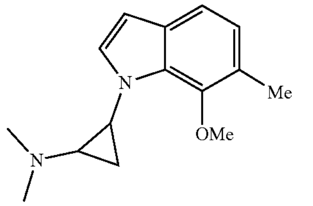 [SMILES: COc1c(C)ccc2ccn(C3CC3N(C)C)c12] |
| 160 | 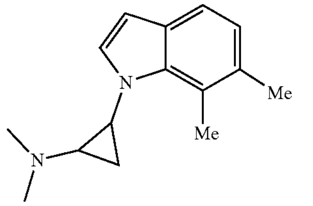 [SMILES: Cc1ccc2ccn(C3CC3N(C)C)c2c1C] |
| 161 | 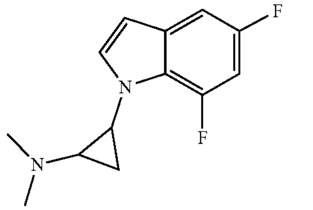 [SMILES: CN(C)C1CC1n1ccc2cc(F)cc(F)c21] |
| 162 | 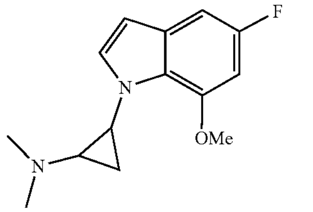 [SMILES: COc1cc(F)cc2ccn(C3CC3N(C)C)c12] |
| 163 | 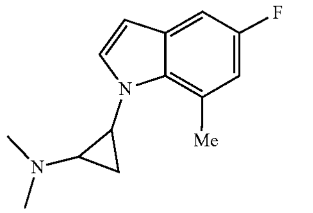 [SMILES: Cc1cc(F)cc2ccn(C3CC3N(C)C)c12] |
| 164 | 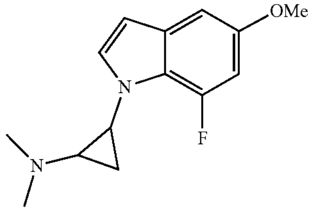 [SMILES: COc1cc(F)c2c(ccn2C2CC2N(C)C)c1] |
| 165 | 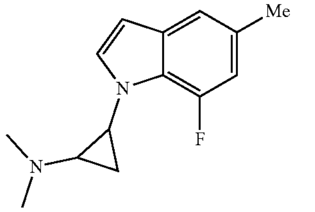 [SMILES: Cc1cc(F)c2c(ccn2C2CC2N(C)C)c1] |
| 166 | 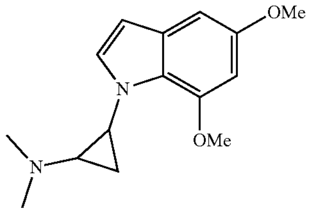 [SMILES: COc1cc(OC)c2c(ccn2C2CC2N(C)C)c1] |
| 167 | 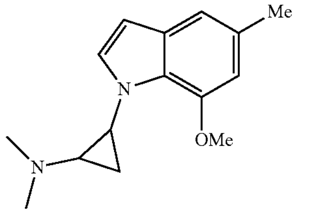 [SMILES: COc1cc(C)cc2ccn(C3CC3N(C)C)c12] |
| 168 | 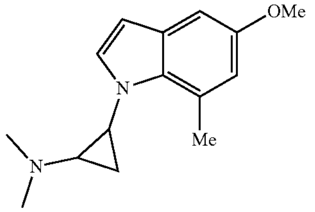 [SMILES: COc1cc(C)c2c(ccn2C2CC2N(C)C)c1] |
| 169 | 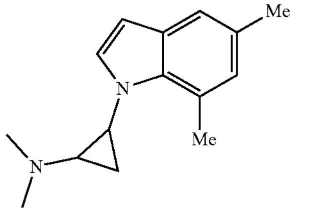 [SMILES: Cc1cc(C)c2c(ccn2C2CC2N(C)C)c1] |
| 170 | 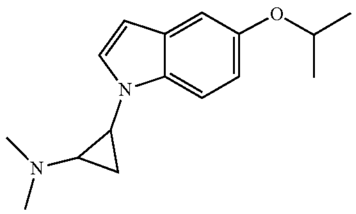 [SMILES: CC(C)Oc1ccc2c(ccn2C2CC2N(C)C)c1] |

TABLE 3-continued
| Cmpd | Structure |
|---|---|
| 171 | 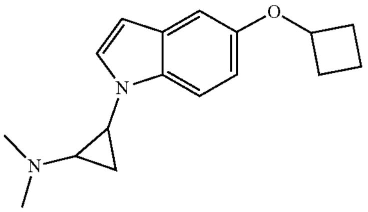 [SMILES: CN(C)C1CC1n1ccc2cc(OC3CCC3)ccc21] |
| 172 | 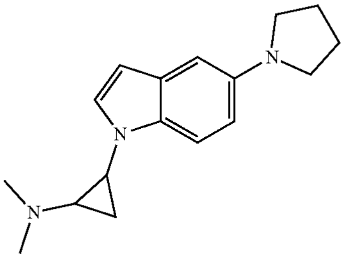 [SMILES: CN(C)C1CC1n1ccc2cc(N3CCCC3)ccc21] |
| 173 | 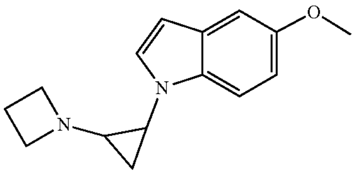 [SMILES: COc1ccc2c(ccn2C2CC2N2CCC2)c1] |
| 174 | 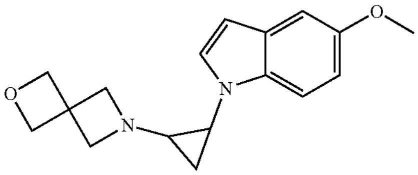 [SMILES: COc1ccc2c(ccn2C2CC2N2CC3(COC3)C2)c1] |
| 175 | 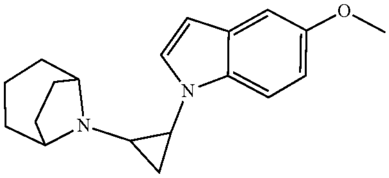 [SMILES: COc1ccc2c(ccn2C2CC2N2C3CCCC2CC3)c1] |
| 176 | 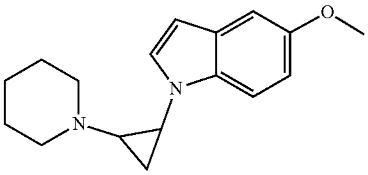 [SMILES: COc1ccc2c(ccn2C2CC2N2CCCCC2)c1] |
| 177 | 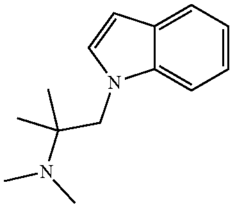 [SMILES: CN(C)C(C)(C)Cn1ccc2ccccc21] |
TABLE 3-continued
| Cmpd | Structure |
|---|---|
| 178 | 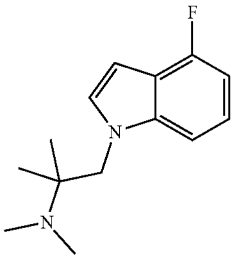 [SMILES: CN(C)C(C)(C)Cn1ccc2c(F)cccc21] |
| 179 | 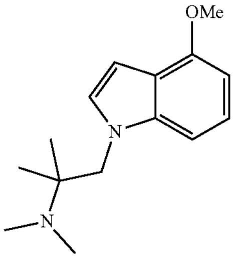 [SMILES: COc1cccc2c1ccn2CC(C)(C)N(C)C] |
| 180 | 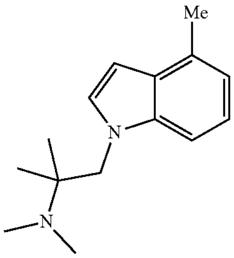 [SMILES: Cc1cccc2c1ccn2CC(C)(C)N(C)C] |
| 181 | 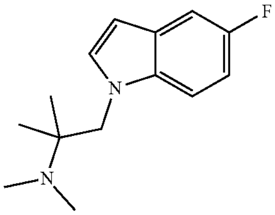 [SMILES: CN(C)C(C)(C)Cn1ccc2cc(F)ccc21] |
| 182 | 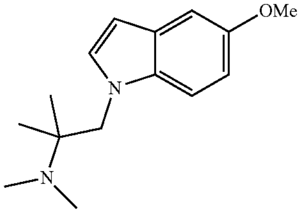 [SMILES: COc1ccc2c(ccn2CC(C)(C)N(C)C)c1] |
| 183 | 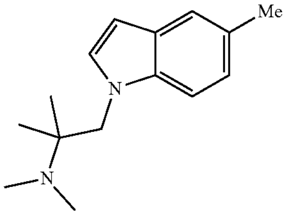 [SMILES: Cc1ccc2c(ccn2CC(C)(C)N(C)C)c1] |

TABLE 3-continued
| Cmpd | Structure |
| --- | --- |
| 184 | 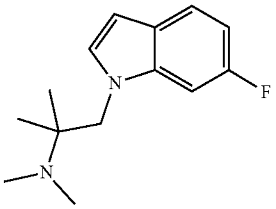 [SMILES: CN(C)C(C)(C)Cn1ccc2ccc(F)cc21] |
| 185 | 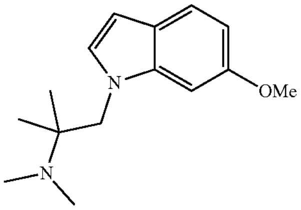 [SMILES: COc1ccc2ccn(CC(C)(C)N(C)C)c2c1] |
| 186 | 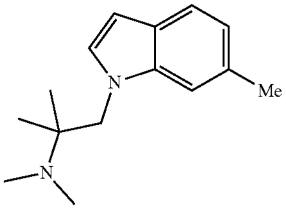 [SMILES: Cc1ccc2ccn(CC(C)(C)N(C)C)c2c1] |
| 187 | 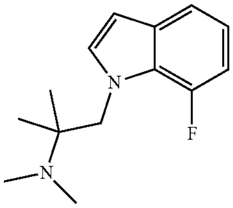 [SMILES: CN(C)C(C)(C)Cn1ccc2cccc(F)c21] |
| 188 | 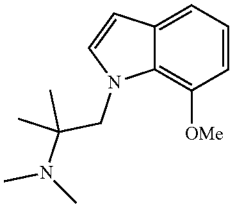 [SMILES: COc1cccc2ccn(CC(C)(C)N(C)C)c12] |
| 189 | 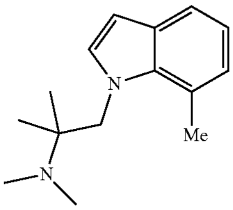 [SMILES: Cc1cccc2ccn(CC(C)(C)N(C)C)c12] |
| 190 | 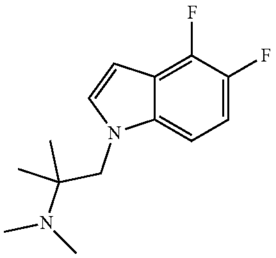 [SMILES: CN(C)C(C)(C)Cn1ccc2c(F)c(F)ccc21] |
TABLE 3-continued
| Cmpd | Structure |
| --- | --- |
| 191 | 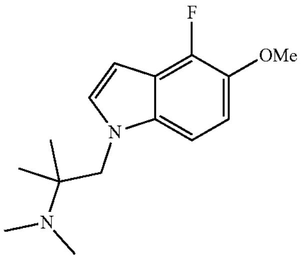 [SMILES: COc1ccc2c(ccn2CC(C)(C)N(C)C)c1F] |
| 192 | 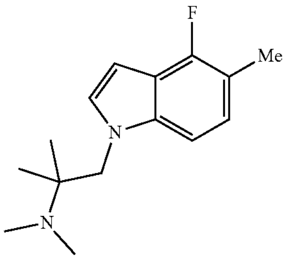 [SMILES: Cc1ccc2c(ccn2CC(C)(C)N(C)C)c1F] |
| 193 | 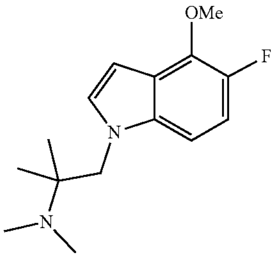 [SMILES: COc1c(F)ccc2c1ccn2CC(C)(C)N(C)C] |
| 194 | 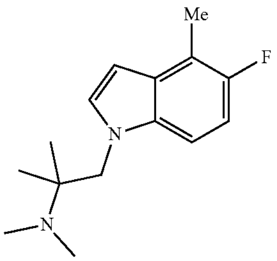 [SMILES: Cc1c(F)ccc2c1ccn2CC(C)(C)N(C)C] |
| 195 | 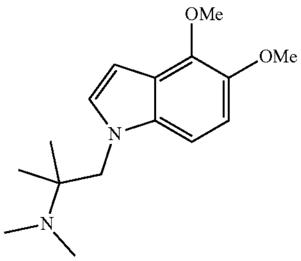 [SMILES: COc1ccc2c(ccn2CC(C)(C)N(C)C)c1OC] |
| 196 | 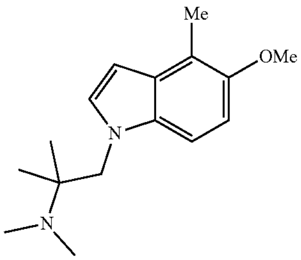 [SMILES: COc1ccc2c(ccn2CC(C)(C)N(C)C)c1C] |

TABLE 3-continued
| Cmpd | Structure |
| --- | --- |
| 197 | 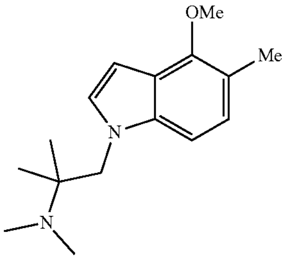 [SMILES: COc1c(C)ccc2c1ccn2CC(C)(C)N(C)C] |
| 198 | 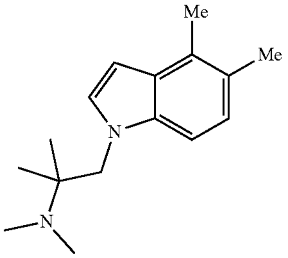 [SMILES: Cc1ccc2c(ccn2CC(C)(C)N(C)C)c1C] |
| 199 | 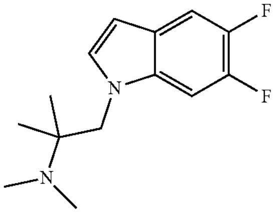 [SMILES: CN(C)C(C)(C)Cn1ccc2cc(F)c(F)cc21] |
| 200 | 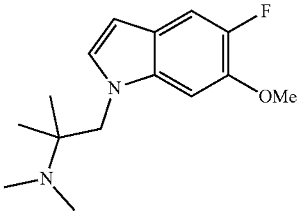 [SMILES: COc1cc2c(ccn2CC(C)(C)N(C)C)cc1F] |
| 201 | 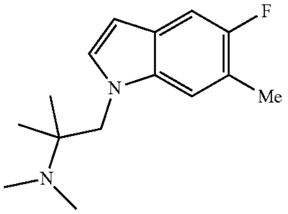 [SMILES: Cc1cc2c(ccn2CC(C)(C)N(C)C)cc1F] |
| 202 | 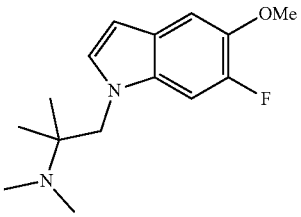 [SMILES: COc1cc2ccn(CC(C)(C)N(C)C)c2cc1F] |
| 203 | 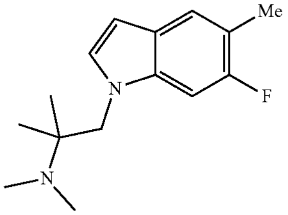 [SMILES: Cc1cc2ccn(CC(C)(C)N(C)C)c2cc1F] |
| 204 | 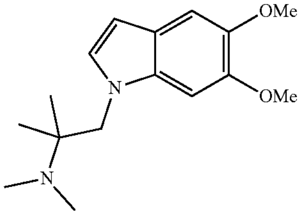 [SMILES: COc1cc2ccn(CC(C)(C)N(C)C)c2cc1OC] |
| 205 | 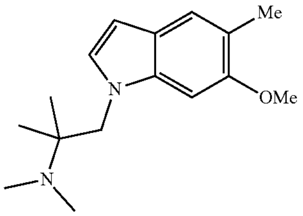 [SMILES: COc1cc2c(ccn2CC(C)(C)N(C)C)cc1C] |
| 206 | 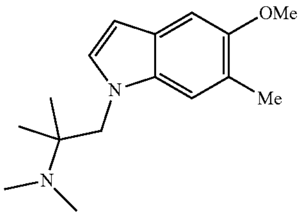 [SMILES: COc1cc2ccn(CC(C)(C)N(C)C)c2cc1C] |
| 207 | 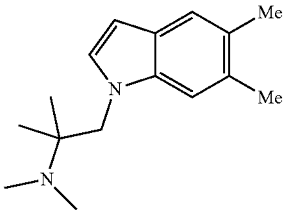 [SMILES: Cc1cc2ccn(CC(C)(C)N(C)C)c2cc1C] |
| 208 | 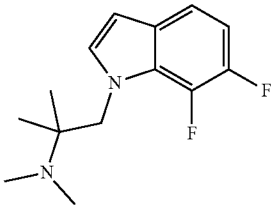 [SMILES: CN(C)C(C)(C)Cn1ccc2ccc(F)c(F)c21] |
| 209 | 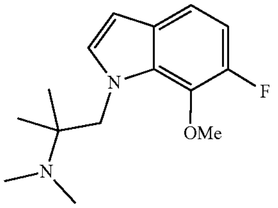 [SMILES: COc1c(F)ccc2ccn(CC(C)(C)N(C)C)c12] |

TABLE 3-continued
| Cmpd | Structure |
|---|---|
| 210 | 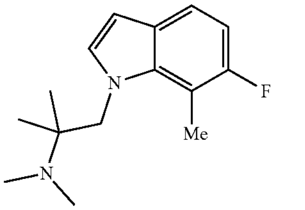 [SMILES: Cc1c(F)ccc2ccn(CC(C)(C)N(C)C)c12] |
| 211 | 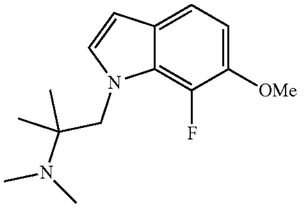 [SMILES: COc1ccc2ccn(CC(C)(C)N(C)C)c2c1F] |
| 212 | 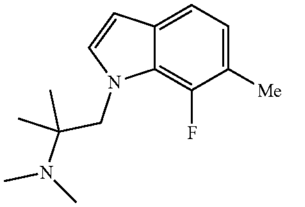 [SMILES: Cc1ccc2ccn(CC(C)(C)N(C)C)c2c1F] |
| 213 | 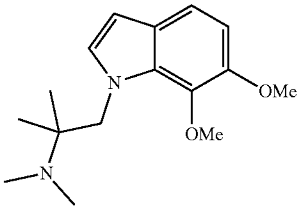 [SMILES: COc1ccc2ccn(CC(C)(C)N(C)C)c2c1OC] |
| 214 | 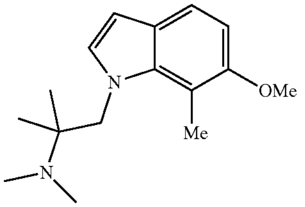 [SMILES: COc1ccc2ccn(CC(C)(C)N(C)C)c2c1C] |
| 215 | 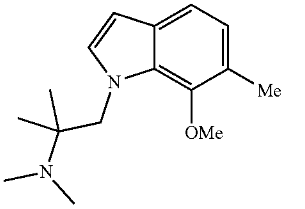 [SMILES: COc1c(C)ccc2ccn(CC(C)(C)N(C)C)c12] |
| 216 | 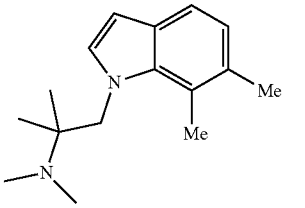 [SMILES: Cc1ccc2ccn(CC(C)(C)N(C)C)c2c1C] |
TABLE 3-continued
| Cmpd | Structure |
|---|---|
| 217 | 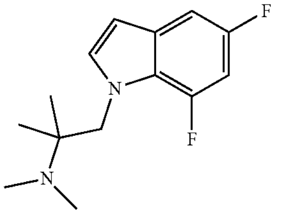 [SMILES: CN(C)C(C)(C)Cn1ccc2cc(F)cc(F)c21] |
| 218 | 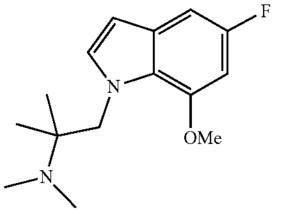 [SMILES: COc1cc(F)cc2ccn(CC(C)(C)N(C)C)c12] |
| 219 | 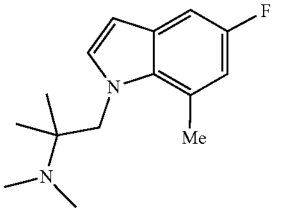 [SMILES: Cc1cc(F)cc2ccn(CC(C)(C)N(C)C)c12] |
| 220 | 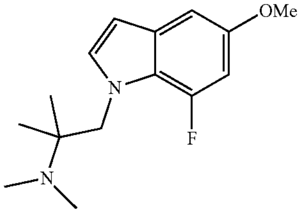 [SMILES: COc1cc(F)c2c(ccn2CC(C)(C)N(C)C)c1] |
| 221 | 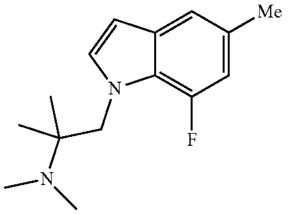 [SMILES: Cc1cc(F)c2c(ccn2CC(C)(C)N(C)C)c1] |
| 222 | 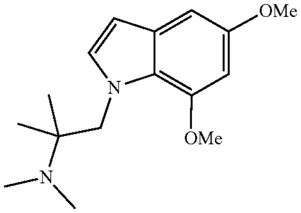 [SMILES: COc1cc(OC)c2c(ccn2CC(C)(C)N(C)C)c1] |
| 223 | 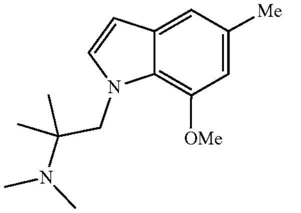 [SMILES: COc1cc(C)cc2ccn(CC(C)(C)N(C)C)c12] |

TABLE 3-continued
| Cmpd | Structure |
| --- | --- |
| 224 | 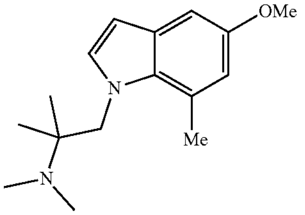 [SMILES: COc1cc(C)c2c(ccn2CC(C)(C)N(C)C)c1] |
| 225 | 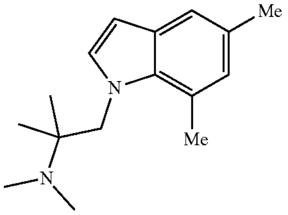 [SMILES: Cc1cc(C)c2c(ccn2CC(C)(C)N(C)C)c1] |
| 226 | 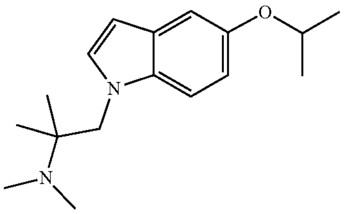 [SMILES: CC(C)Oc1ccc2c(ccn2CC(C)(C)N(C)C)c1] |
| 227 | 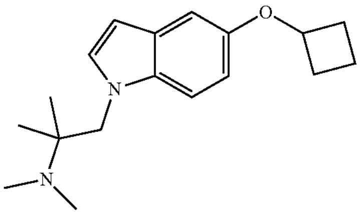 [SMILES: CN(C)C(C)(C)Cn1ccc2cc(OC3CCC3)ccc21] |
| 228 | 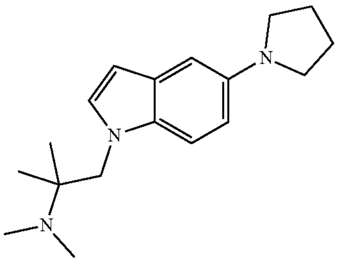 [SMILES: CN(C)C(C)(C)Cn1ccc2cc(N3CCCC3)ccc21] |
| 229 | 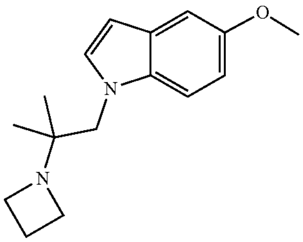 [SMILES: COc1ccc2c(ccn2CC(C)(C)N2CCC2)c1] |
TABLE 3-continued
| Cmpd | Structure |
| --- | --- |
| 230 | 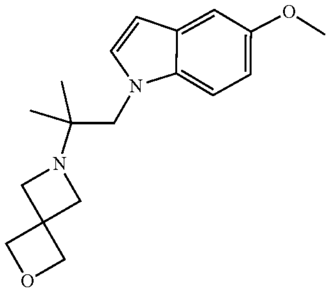 [SMILES: COc1ccc2c(ccn2CC(C)(C)N2CC3(COC3)C2)c1] |
| 231 | 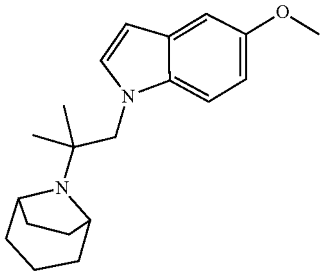 [SMILES: COc1ccc2c(ccn2CC(C)(C)N2C3CCCC2CC3)c1] |
| 232 | 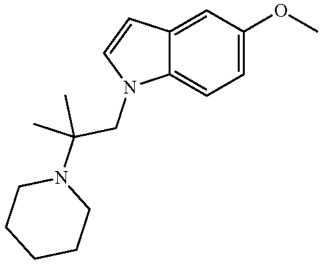 [SMILES: COc1ccc2c(ccn2CC(C)(C)N2CCCCC2)c1] |
| 233 | 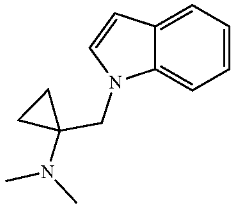 [SMILES: CN(C)C1(Cn2ccc3ccccc32)CC1] |
| 234 | 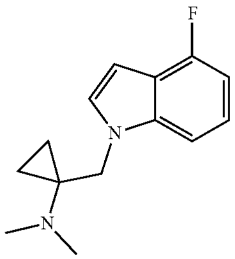 [SMILES: CN(C)C1(Cn2ccc3c(F)cccc32)CC1] |
| 235 | 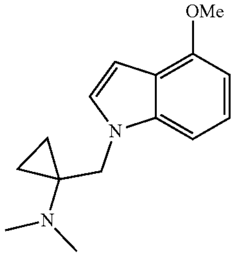 [SMILES: COc1cccc2c1ccn2CC1(N(C)C)CC1] |

TABLE 3-continued
| Cmpd | Structure |
|---|---|
| 236 | 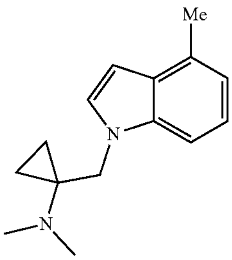 [SMILES: Cc1cccc2c1ccn2CC1(N(C)C)CC1] |
| 237 | 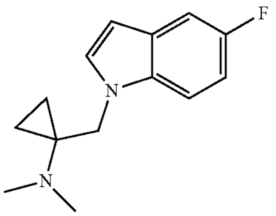 [SMILES: CN(C)C1(Cn2ccc3cc(F)ccc32)CC1] |
| 238 | 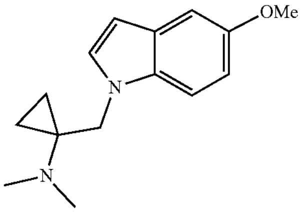 [SMILES: COc1ccc2c(ccn2CC2(N(C)C)CC2)c1] |
| 239 | 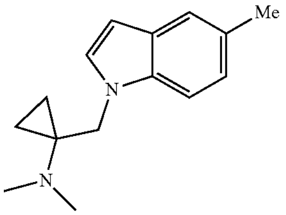 [SMILES: Cc1ccc2c(ccn2CC2(N(C)C)CC2)c1] |
| 240 | 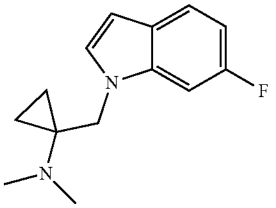 [SMILES: CN(C)C1(Cn2ccc3ccc(F)cc32)CC1] |
| 241 | 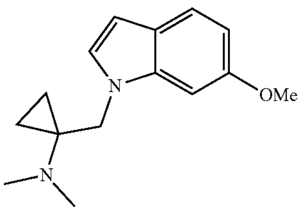 [SMILES: COc1ccc2ccn(CC3(N(C)C)CC3)c2c1] |
| 242 | 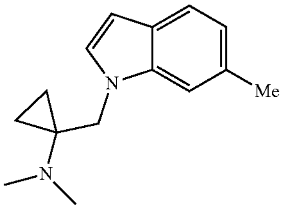 [SMILES: Cc1ccc2ccn(CC3(N(C)C)CC3)c2c1] |
TABLE 3-continued
| Cmpd | Structure |
|---|---|
| 243 | 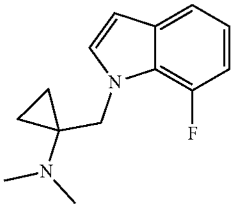 [SMILES: CN(C)C1(Cn2ccc3cccc(F)c32)CC1] |
| 244 | 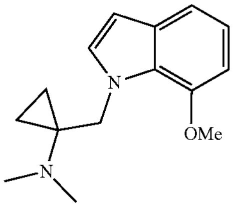 [SMILES: COc1cccc2ccn(CC3(N(C)C)CC3)c12] |
| 245 | 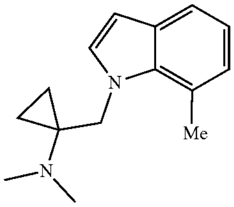 [SMILES: Cc1cccc2ccn(CC3(N(C)C)CC3)c12] |
| 246 | 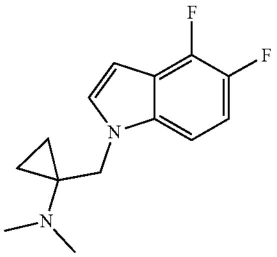 [SMILES: CN(C)C1(Cn2ccc3c(F)c(F)ccc32)CC1] |
| 247 | 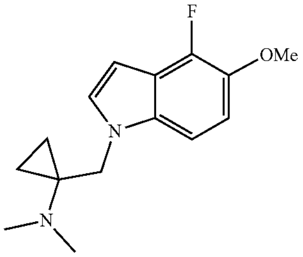 [SMILES: COc1ccc2c(ccn2CC2(N(C)C)CC2)c1F] |
| 248 | 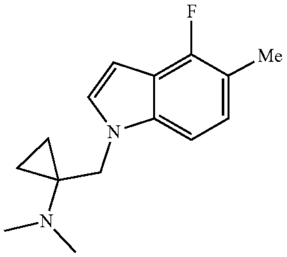 [SMILES: Cc1ccc2c(ccn2CC2(N(C)C)CC2)c1F] |

TABLE 3-continued
| Cmpd | Structure |
| --- | --- |
| 249 | 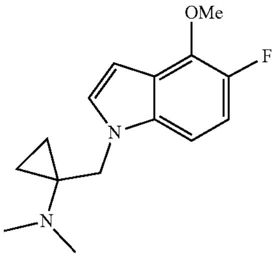 [SMILES: COc1c(F)ccc2c1ccn2CC1(N(C)C)CC1] |
| 250 | 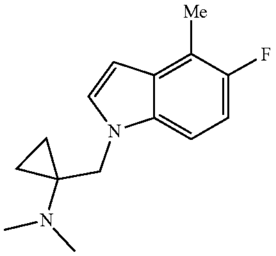 [SMILES: Cc1c(F)ccc2c1ccn2CC1(N(C)C)CC1] |
| 251 | 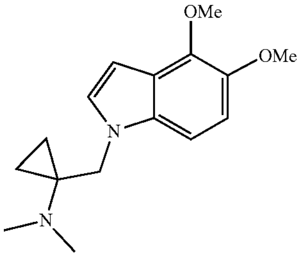 [SMILES: COc1ccc2c(ccn2CC2(N(C)C)CC2)c1OC] |
| 252 | 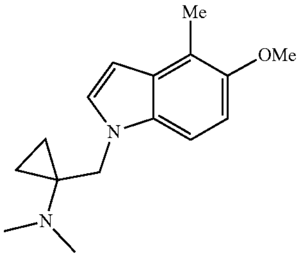 [SMILES: COc1ccc2c(ccn2CC2(N(C)C)CC2)c1C] |
| 253 | 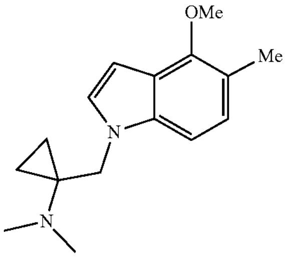 [SMILES: COc1c(C)ccc2c1ccn2CC1(N(C)C)CC1] |
| 254 | 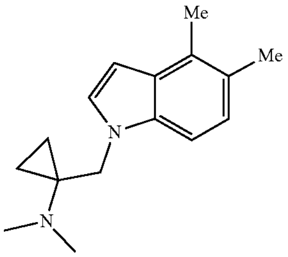 [SMILES: Cc1ccc2c(ccn2CC2(N(C)C)CC2)c1C] |
TABLE 3-continued
| Cmpd | Structure |
| --- | --- |
| 255 | 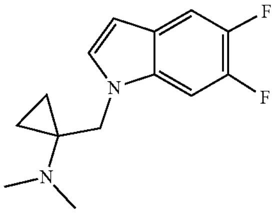 [SMILES: CN(C)C1(Cn2ccc3cc(F)c(F)cc32)CC1] |
| 256 | 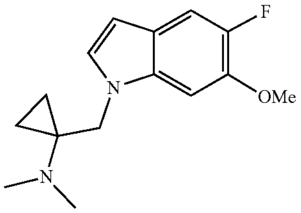 [SMILES: COc1cc2c(ccn2CC2(N(C)C)CC2)cc1F] |
| 257 | 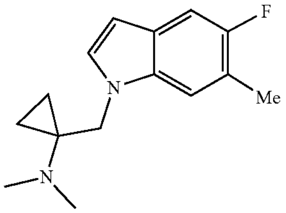 [SMILES: Cc1cc2c(ccn2CC2(N(C)C)CC2)cc1F] |
| 258 | 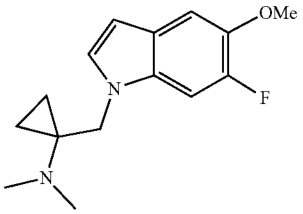 [SMILES: COc1cc2ccn(CC3(N(C)C)CC3)c2cc1F] |
| 259 | 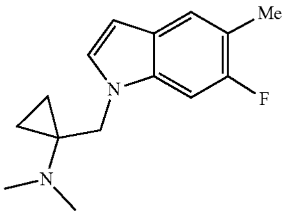 [SMILES: Cc1cc2ccn(CC3(N(C)C)CC3)c2cc1F] |
| 260 | 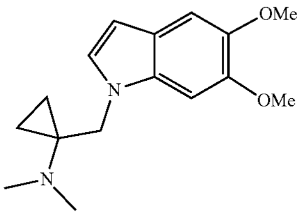 [SMILES: COc1cc2ccn(CC3(N(C)C)CC3)c2cc1OC] |
| 261 | 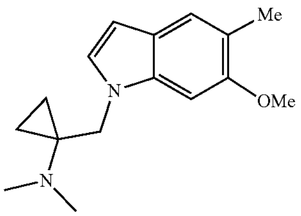 [SMILES: COc1cc2c(ccn2CC2(N(C)C)CC2)cc1C] |

TABLE 3-continued
| Cmpd | Structure |
| --- | --- |
| 262 | 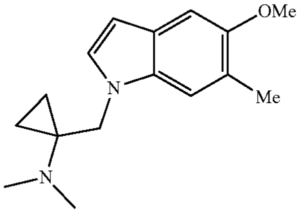 [SMILES: COc1cc2ccn(CC3(N(C)C)CC3)c2cc1C] |
| 263 | 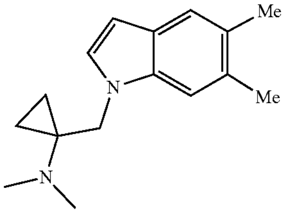 [SMILES: Cc1cc2ccn(CC3(N(C)C)CC3)c2cc1C] |
| 264 | 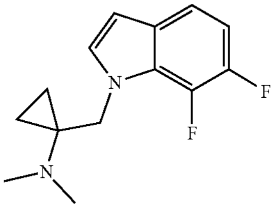 [SMILES: CN(C)C1(Cn2ccc3ccc(F)c(F)c32)CC1] |
| 265 | 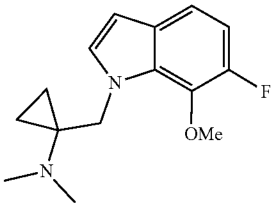 [SMILES: COc1c(F)ccc2ccn(CC3(N(C)C)CC3)c12] |
| 266 | 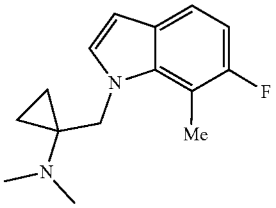 [SMILES: Cc1c(F)ccc2ccn(CC3(N(C)C)CC3)c12] |
| 267 | 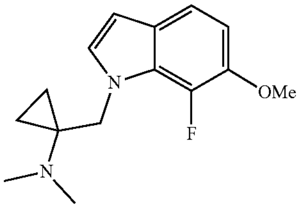 [SMILES: COc1ccc2ccn(CC3(N(C)C)CC3)c2c1F] |
| 268 | 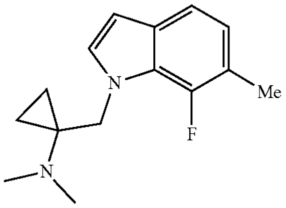 [SMILES: Cc1ccc2ccn(CC3(N(C)C)CC3)c2c1F] |
TABLE 3-continued
| Cmpd | Structure |
| --- | --- |
| 269 | 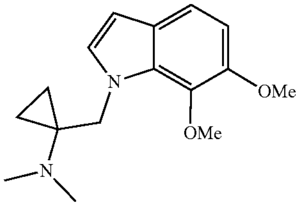 [SMILES: COc1ccc2ccn(CC3(N(C)C)CC3)c2c1OC] |
| 270 | 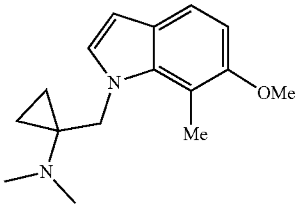 [SMILES: COc1ccc2ccn(CC3(N(C)C)CC3)c2c1C] |
| 271 | 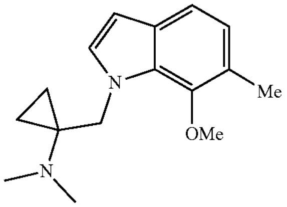 [SMILES: COc1c(C)ccc2ccn(CC3(N(C)C)CC3)c12] |
| 272 | 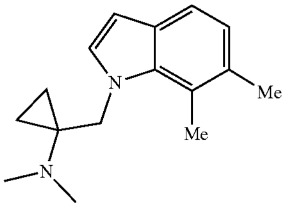 [SMILES: Cc1ccc2ccn(CC3(N(C)C)CC3)c2c1C] |
| 273 | 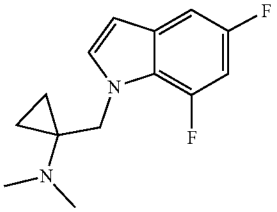 [SMILES: CN(C)C1(Cn2ccc3cc(F)cc(F)c32)CC1] |
| 274 | 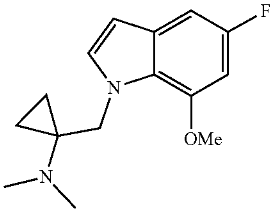 [SMILES: COc1cc(F)cc2ccn(CC3(N(C)C)CC3)c12] |
| 275 | 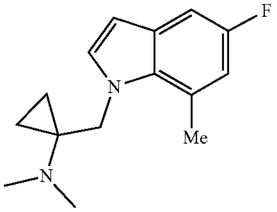 [SMILES: Cc1cc(F)cc2ccn(CC3(N(C)C)CC3)c12] |

TABLE 3-continued
| Cmpd | Structure |
|---|---|
| 276 | 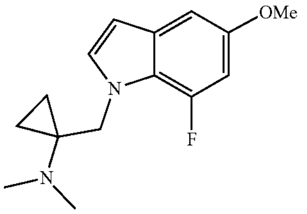 [SMILES: COc1cc(F)c2c(ccn2CC2(N(C)C)CC2)c1] |
| 277 | 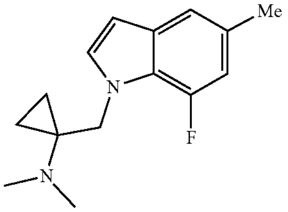 [SMILES: Cc1cc(F)c2c(ccn2CC2(N(C)C)CC2)c1] |
| 278 | 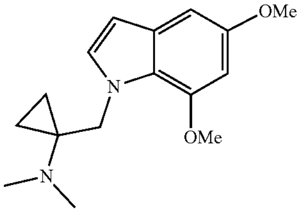 [SMILES: COc1cc(OC)c2c(ccn2CC2(N(C)C)CC2)c1] |
| 279 | 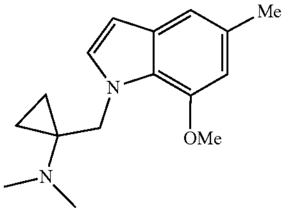 [SMILES: COc1cc(C)cc2ccn(CC3(N(C)C)CC3)c12] |
| 280 | 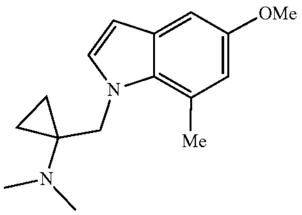 [SMILES: COc1cc(C)c2c(ccn2CC2(N(C)C)CC2)c1] |
| 281 | 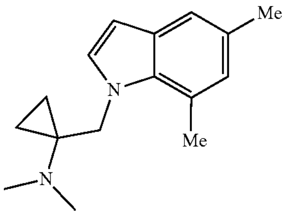 [SMILES: Cc1cc(C)c2c(ccn2CC2(N(C)C)CC2)c1] |
| 282 | 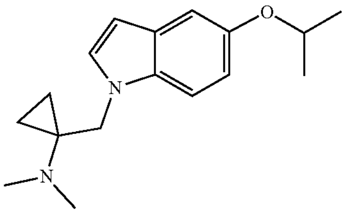 [SMILES: CC(C)Oc1ccc2c(ccn2CC2(N(C)C)CC2)c1] |
TABLE 3-continued
| Cmpd | Structure |
|---|---|
| 283 | 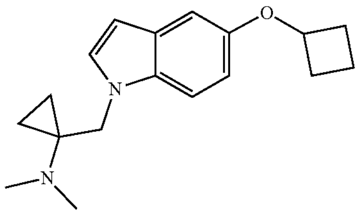 [SMILES: CN(C)C1(Cn2ccc3cc(OC4CCC4)ccc32)CC1] |
| 284 | 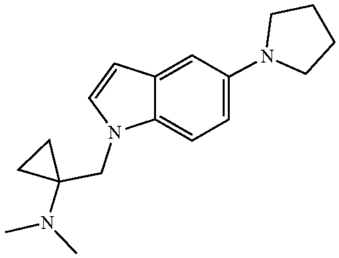 [SMILES: CN(C)C1(Cn2ccc3cc(N4CCCC4)ccc32)CC1] |
| 285 | 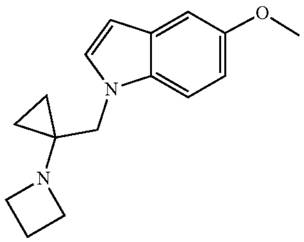 [SMILES: COc1ccc2c(ccn2CC2(N3CCC3)CC2)c1] |
| 286 | 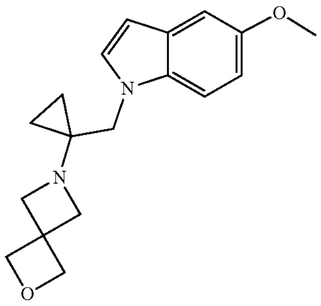 [SMILES: COc1ccc2c(ccn2CC2(N3CC4(COC4)C3)CC2)c1] |
| 287 | 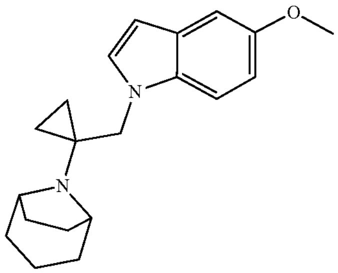 [SMILES: COc1ccc2c(ccn2CC2(N3C4CCCC3CC4)CC2)c1] |
| 288 | 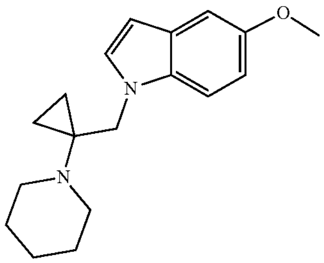 [SMILES: COc1ccc2c(ccn2CC2(N3CCCCC3)CC2)c1] |

TABLE 3-continued
| Cmpd | Structure |
|---|---|
| 289 | 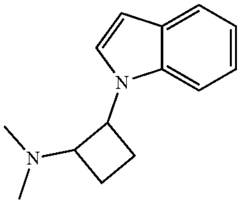 [SMILES: CN(C)C1CCC1n1ccc2ccccc21] |
| 290 | 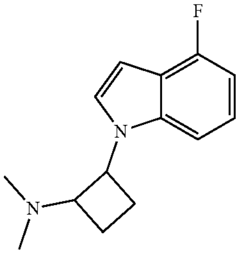 [SMILES: CN(C)C1CCC1n1ccc2c(F)cccc21] |
| 291 | 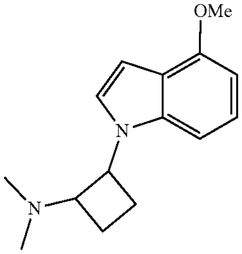 [SMILES: COc1cccc2c1ccn2C1CCC1N(C)C] |
| 292 | 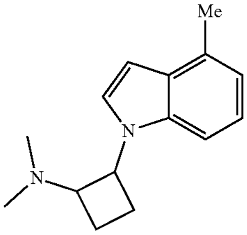 [SMILES: Cc1cccc2c1ccn2C1CCC1N(C)C] |
| 293 | 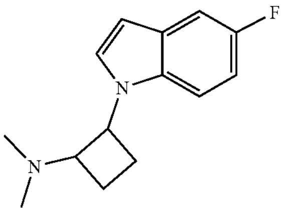 [SMILES: CN(C)C1CCC1n1ccc2cc(F)ccc21] |
| 294 | 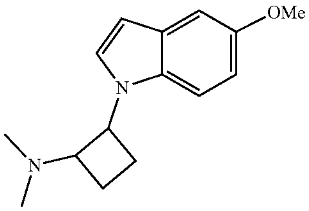 [SMILES: COc1ccc2c(ccn2C2CCC2N(C)C)c1] |
TABLE 3-continued
| Cmpd | Structure |
|---|---|
| 295 | 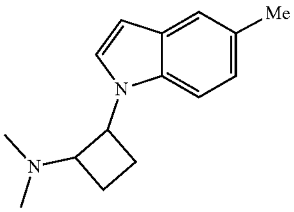 [SMILES: Cc1ccc2c(ccn2C2CCC2N(C)C)c1] |
| 296 | 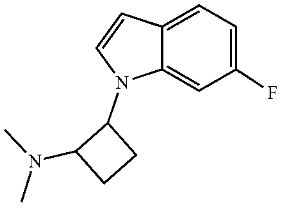 [SMILES: CN(C)C1CCC1n1ccc2ccc(F)cc21] |
| 297 | 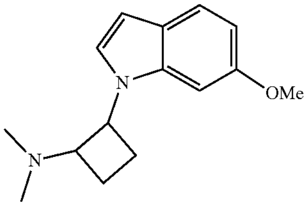 [SMILES: COc1ccc2ccn(C3CCC3N(C)C)c2c1] |
| 298 | 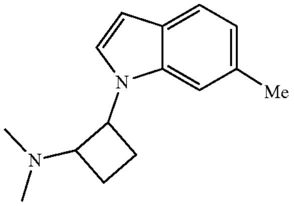 [SMILES: Cc1ccc2ccn(C3CCC3N(C)C)c2c1] |
| 299 | 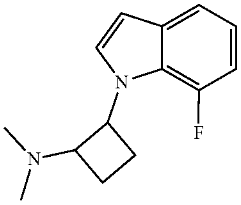 [SMILES: CN(C)C1CCC1n1ccc2cccc(F)c21] |
| 300 | 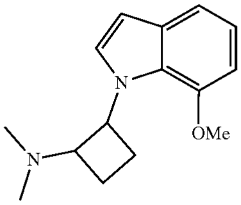 [SMILES: COc1cccc2ccn(C3CCC3N(C)C)c12] |
| 301 | 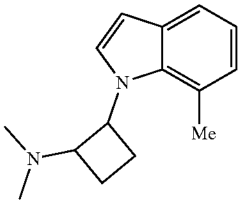 [SMILES: Cc1cccc2ccn(C3CCC3N(C)C)c12] |

TABLE 3-continued
| Cmpd | Structure |
|---|---|
| 302 | 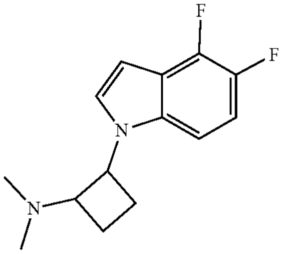 [SMILES: CN(C)C1CCC1n1ccc2c(F)c(F)ccc21] |
| 303 | 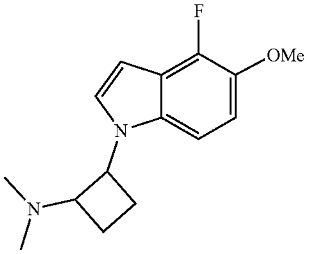 [SMILES: COc1ccc2c(ccn2C2CCC2N(C)C)c1F] |
| 304 | 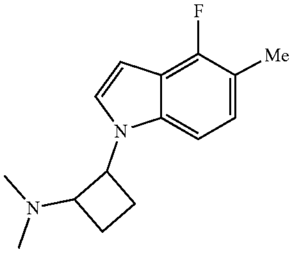 [SMILES: Cc1ccc2c(ccn2C2CCC2N(C)C)c1F] |
| 305 | 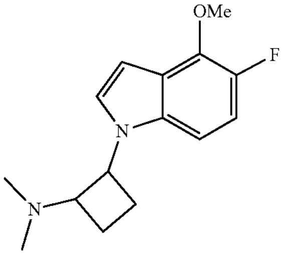 [SMILES: COc1c(F)ccc2c1ccn2C1CCC1N(C)C] |
| 306 | 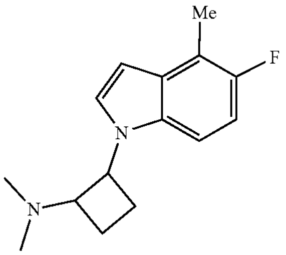 [SMILES: Cc1c(F)ccc2c1ccn2C1CCC1N(C)C] |
| 307 | 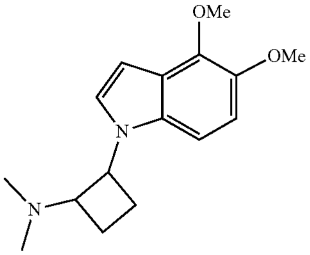 [SMILES: COc1ccc2c(ccn2C2CCC2N(C)C)c1OC] |
| 308 | 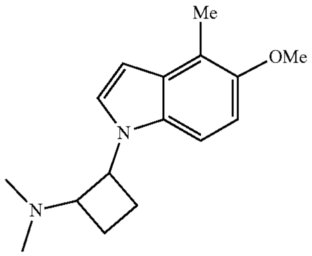 [SMILES: COc1ccc2c(ccn2C2CCC2N(C)C)c1C] |
| 309 | 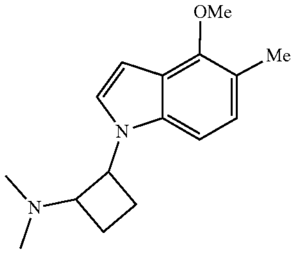 [SMILES: COc1c(C)ccc2c1ccn2C1CCC1N(C)C] |
| 310 | 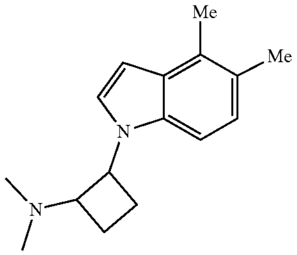 [SMILES: Cc1ccc2c(ccn2C2CCC2N(C)C)c1C] |
| 311 | 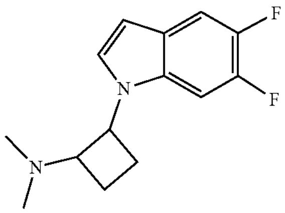 [SMILES: CN(C)C1CCC1n1ccc2cc(F)c(F)cc21] |
| 312 | 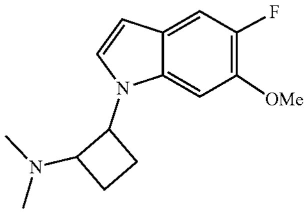 [SMILES: COc1cc2c(ccn2C2CCC2N(C)C)cc1F] |
| 313 | 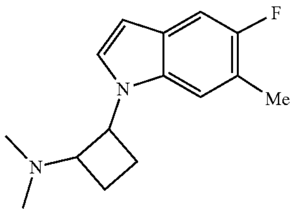 [SMILES: Cc1cc2c(ccn2C2CCC2N(C)C)cc1F] |

TABLE 3-continued
| Cmpd | Structure |
| --- | --- |
| 314 | 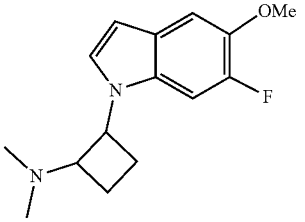 [SMILES: COc1cc2ccn(C3CCC3N(C)C)c2cc1F] |
| 315 | 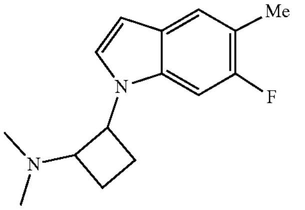 [SMILES: Cc1cc2ccn(C3CCC3N(C)C)c2cc1F] |
| 316 | 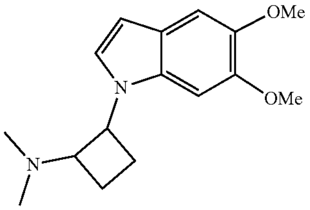 [SMILES: COc1cc2ccn(C3CCC3N(C)C)c2cc1OC] |
| 317 | 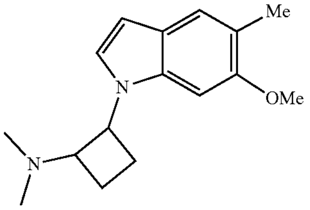 [SMILES: COc1cc2c(ccn2C2CCC2N(C)C)cc1C] |
| 318 | 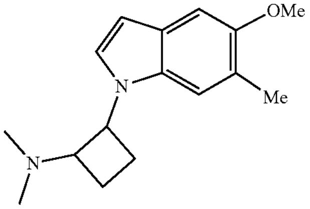 [SMILES: COc1cc2ccn(C3CCC3N(C)C)c2cc1C] |
| 319 | 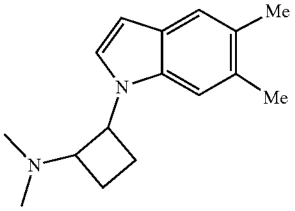 [SMILES: Cc1cc2ccn(C3CCC3N(C)C)c2cc1C] |
| 320 | 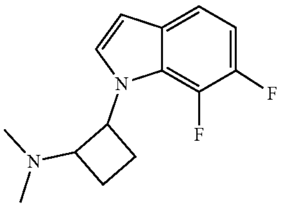 [SMILES: CN(C)C1CCC1n1ccc2ccc(F)c(F)c21] |
TABLE 3-continued
| Cmpd | Structure |
| --- | --- |
| 321 | 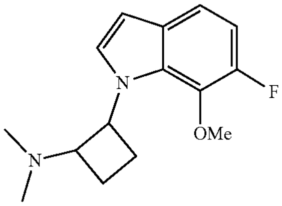 [SMILES: COc1c(F)ccc2ccn(C3CCC3N(C)C)c12] |
| 322 | 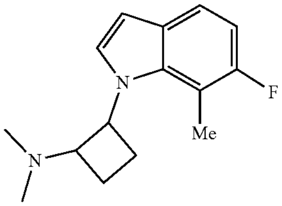 [SMILES: Cc1c(F)ccc2ccn(C3CCC3N(C)C)c12] |
| 323 | 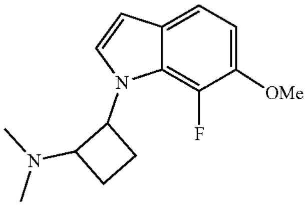 [SMILES: COc1ccc2ccn(C3CCC3N(C)C)c2c1F] |
| 324 | 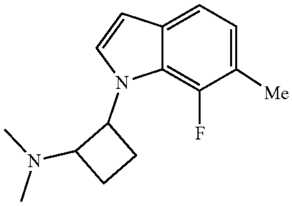 [SMILES: Cc1ccc2ccn(C3CCC3N(C)C)c2c1F] |
| 325 | 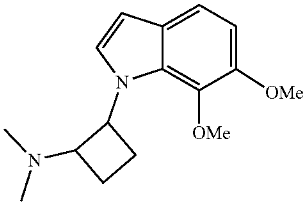 [SMILES: COc1ccc2ccn(C3CCC3N(C)C)c2c1OC] |
| 326 | 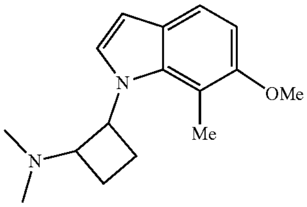 [SMILES: COc1ccc2ccn(C3CCC3N(C)C)c2c1C] |
| 327 | 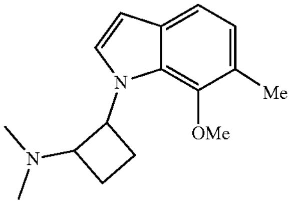 [SMILES: COc1c(C)ccc2ccn(C3CCC3N(C)C)c12] |

TABLE 3-continued
| Cmpd | Structure |
|---|---|
| 328 | 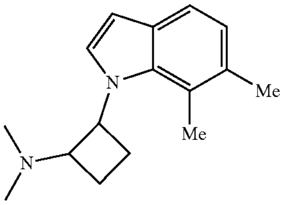 [SMILES: Cc1ccc2ccn(C3CCC3N(C)C)c2c1C] |
| 329 | 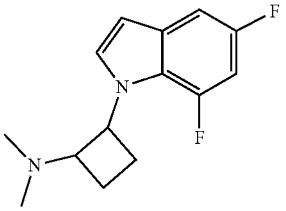 [SMILES: CN(C)C1CCC1n1ccc2cc(F)cc(F)c21] |
| 330 | 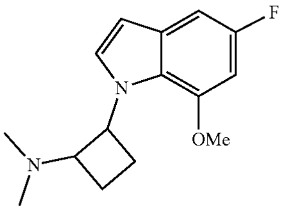 [SMILES: COc1cc(F)cc2ccn(C3CCC3N(C)C)c12] |
| 331 | 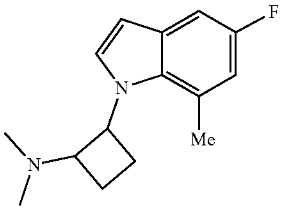 [SMILES: Cc1cc(F)cc2ccn(C3CCC3N(C)C)c12] |
| 332 | 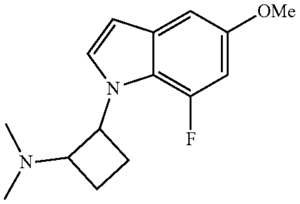 [SMILES: COc1cc(F)c2c(ccn2C2CCC2N(C)C)c1] |
| 333 | 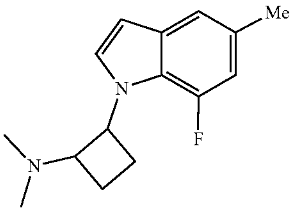 [SMILES: Cc1cc(F)c2c(ccn2C2CCC2N(C)C)c1] |
| 334 | 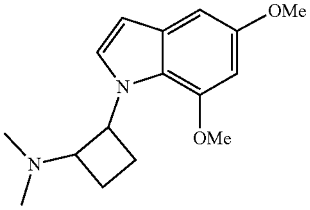 [SMILES: COc1cc(OC)c2c(ccn2C2CCC2N(C)C)c1] |
TABLE 3-continued
| Cmpd | Structure |
|---|---|
| 335 | 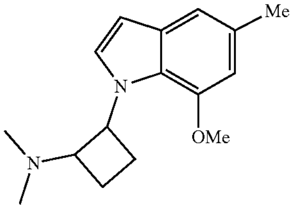 [SMILES: COc1cc(C)cc2ccn(C3CCC3N(C)C)c12] |
| 336 | 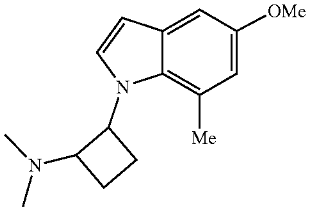 [SMILES: COc1cc(C)c2c(ccn2C2CCC2N(C)C)c1] |
| 337 | 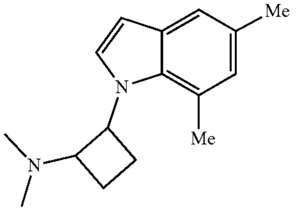 |
| 338 | 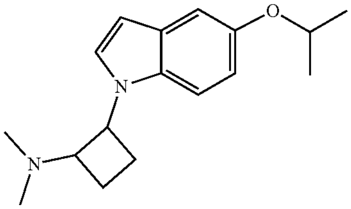 [SMILES: CC(C)Oc1ccc2c(ccn2C2CCC2N(C)C)c1] |
| 339 | 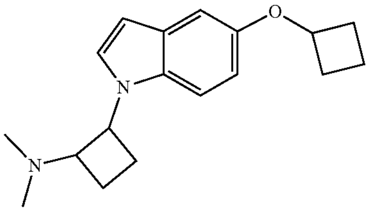 [SMILES: CN(C)C1CCC1n1ccc2cc(OC3CCC3)ccc21] |
| 340 | 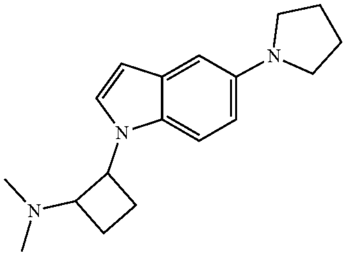 [SMILES: CN(C)C1CCC1n1ccc2cc(N3CCCC3)ccc21] |
| 341 | 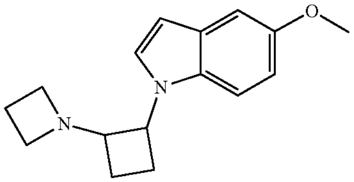 [SMILES: COc1ccc2c(ccn2C2CCC2N2CCC2)c1] |

TABLE 3-continued
| Cmpd | Structure |
| --- | --- |
| 342 | 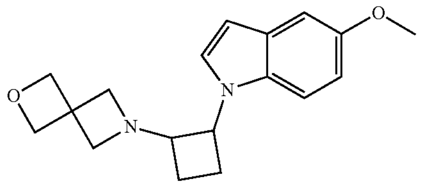 [SMILES: COc1ccc2c(ccn2C2CCC2N2CC3(COC3)C2)c1] |
| 343 | 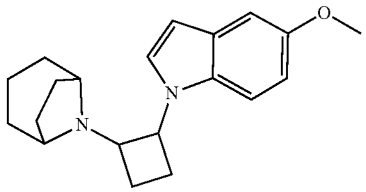 [SMILES: COc1ccc2c(ccn2C2CCC2N2C3CCCC2CC3)c1] |
| 344 | 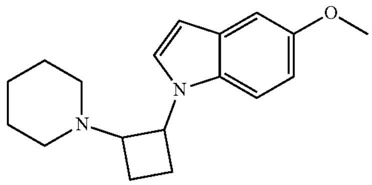 [SMILES: COc1ccc2c(ccn2C2CCC2N2CCCCC2)c1] |
| 345 | 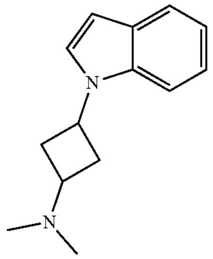 [SMILES: CN(C)C1CC(n2ccc3ccccc32)C1] |
| 346 | 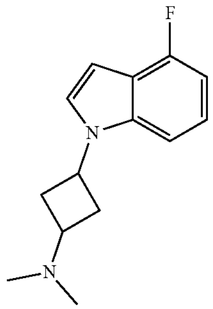 [SMILES: CN(C)C1CC(n2ccc3c(F)cccc32)C1] |
| 347 | 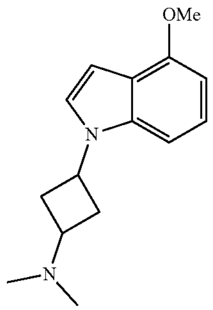 [SMILES: COc1cccc2c1ccn2C1CC(N(C)C)C1] |
TABLE 3-continued
| Cmpd | Structure |
| --- | --- |
| 348 | 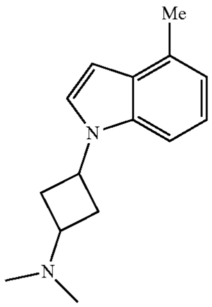 [SMILES: Cc1cccc2c1ccn2C1CC(N(C)C)C1] |
| 349 | 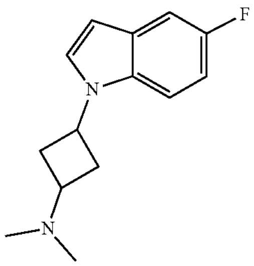 [SMILES: CN(C)C1CC(n2ccc3cc(F)ccc32)C1] |
| 350 | 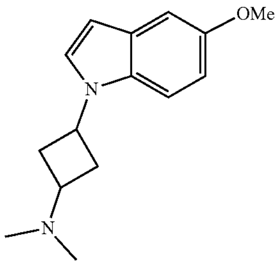 [SMILES: COc1ccc2c(ccn2C2CC(N(C)C)C2)c1] |
| 351 | 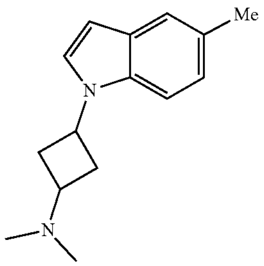 [SMILES: Cc1ccc2c(ccn2C2CC(N(C)C)C2)c1] |
| 352 | 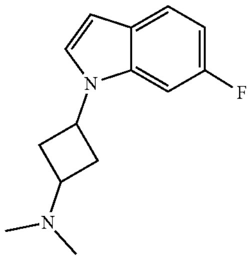 [SMILES: CN(C)C1CC(n2ccc3ccc(F)cc32)C1] |

TABLE 3-continued
| Cmpd | Structure |
| --- | --- |
| 353 | 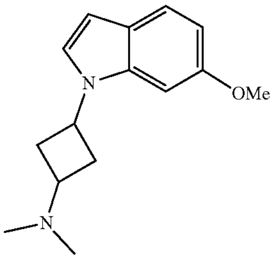 [SMILES: COc1ccc2ccn(C3CC(N(C)C)C3)c2c1] |
| 354 | 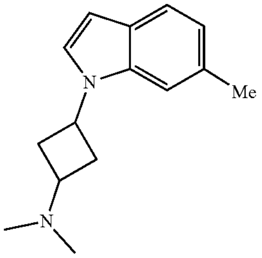 [SMILES: Cc1ccc2ccn(C3CC(N(C)C)C3)c2c1] |
| 355 | 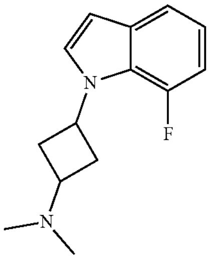 [SMILES: CN(C)C1CC(n2ccc3cccc(F)c32)C1] |
| 356 | 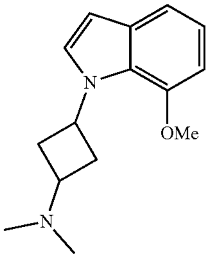 [SMILES: COc1cccc2ccn(C3CC(N(C)C)C3)c12] |
| 357 | 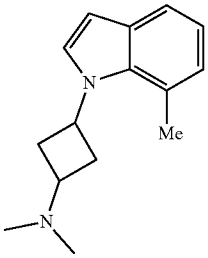 [SMILES: Cc1cccc2ccn(C3CC(N(C)C)C3)c12] |
TABLE 3-continued
| Cmpd | Structure |
| --- | --- |
| 358 | 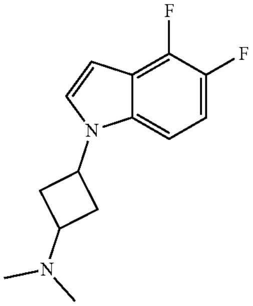 [SMILES: CN(C)C1CC(n2ccc3c(F)c(F)ccc32)C1] |
| 359 | 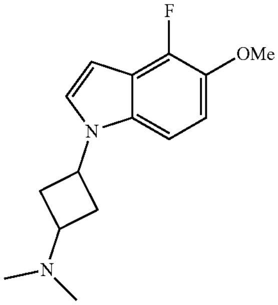 [SMILES: COc1ccc2c(ccn2C2CC(N(C)C)C2)c1F] |
| 360 | 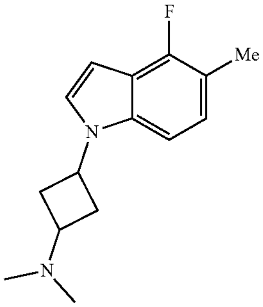 [SMILES: Cc1ccc2c(ccn2C2CC(N(C)C)C2)c1F] |
| 361 | 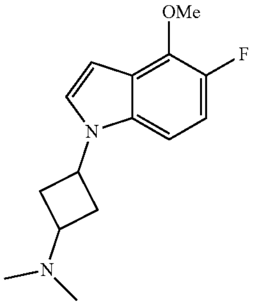 [SMILES: COc1c(F)ccc2c1ccn2C1CC(N(C)C)C1] |
| 362 | 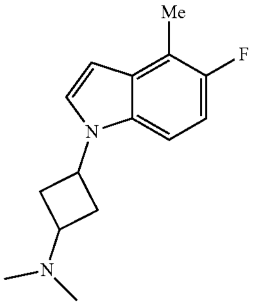 [SMILES: Cc1c(F)ccc2c1ccn2C1CC(N(C)C)C1] |

TABLE 3-continued
| Cmpd | Structure |
|---|---|
| 363 | 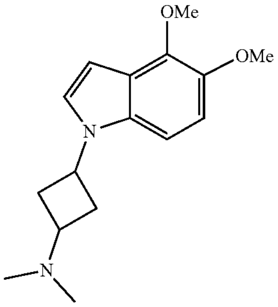 [SMILES: COc1ccc2c(ccn2C2CC(N(C)C)C2)c1OC] |
| 364 | 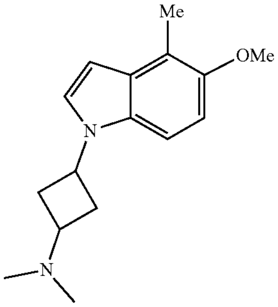 [SMILES: COc1ccc2c(ccn2C2CC(N(C)C)C2)c1C] |
| 365 | 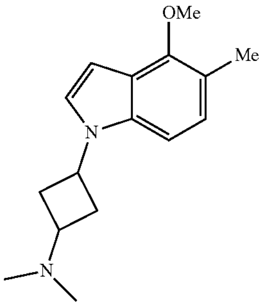 [SMILES: COc1c(C)ccc2c1ccn2C1CC(N(C)C)C1] |
| 366 | 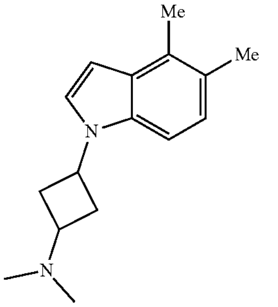 [SMILES: Cc1ccc2c(ccn2C2CC(N(C)C)C2)c1C] |
| 367 | 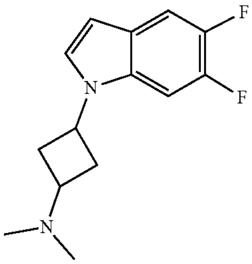 [SMILES: CN(C)C1CC(n2ccc3cc(F)c(F)cc32)C1] |
TABLE 3-continued
| Cmpd | Structure |
|---|---|
| 368 | 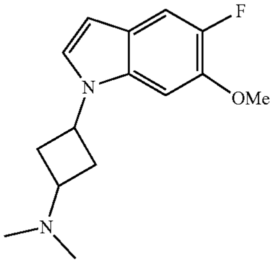 [SMILES: COc1cc2c(ccn2C2CC(N(C)C)C2)cc1F] |
| 369 | 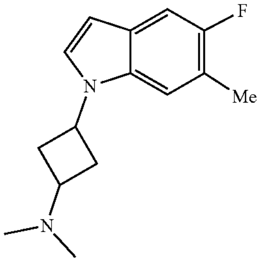 [SMILES: Cc1cc2c(ccn2C2CC(N(C)C)C2)cc1F] |
| 370 | 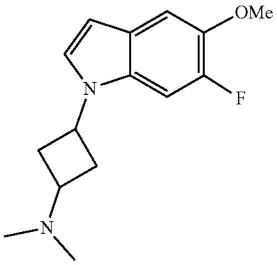 [SMILES: COc1cc2ccn(C3CC(N(C)C)C3)c2cc1F] |
| 371 | 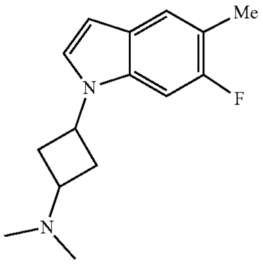 [SMILES: Cc1cc2ccn(C3CC(N(C)C)C3)c2cc1F] |
| 372 | 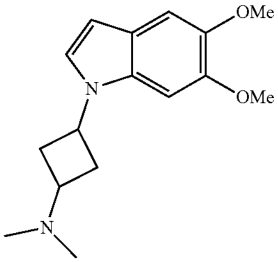 [SMILES: COc1cc2ccn(C3CC(N(C)C)C3)c2cc1OC] |

TABLE 3-continued
| Cmpd | Structure |
|---|---|
| 373 | 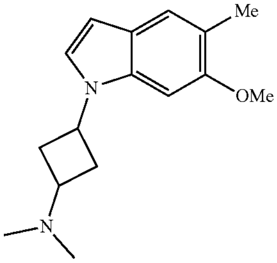 [SMILES: COc1cc2c(ccn2C2CC(N(C)C)C2)cc1C] |
| 374 | 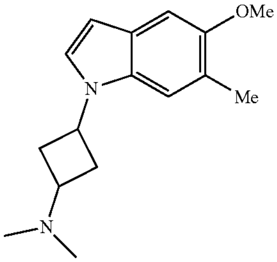 [SMILES: COc1cc2ccn(C3CC(N(C)C)C3)c2cc1C] |
| 375 | 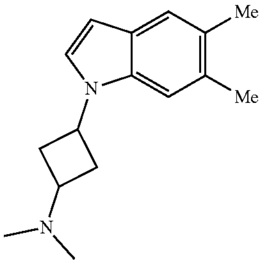 [SMILES: Cc1cc2ccn(C3CC(N(C)C)C3)c2cc1C] |
| 376 | 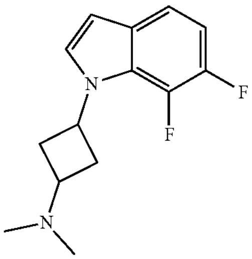 [SMILES: CN(C)C1CC(n2ccc3ccc(F)c(F)c32)C1] |
| 377 | 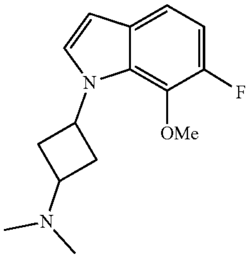 [SMILES: COc1c(F)ccc2ccn(C3CC(N(C)C)C3)c12] |
| 378 | 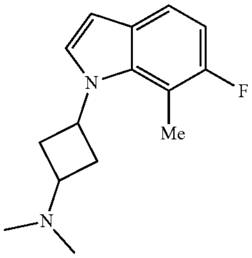 [SMILES: Cc1c(F)ccc2ccn(C3CC(N(C)C)C3)c12] |
| 379 | 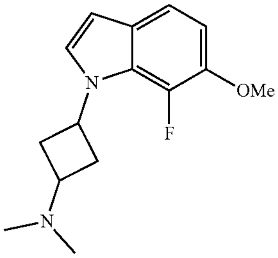 [SMILES: COc1ccc2ccn(C3CC(N(C)C)C3)c2c1F] |
| 380 | 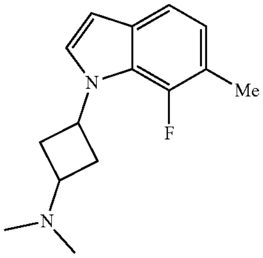 [SMILES: Cc1ccc2ccn(C3CC(N(C)C)C3)c2c1F] |
| 381 | 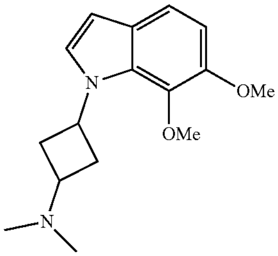 [SMILES: COc1ccc2ccn(C3CC(N(C)C)C3)c2c1OC] |
| 382 | 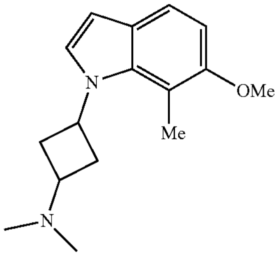 [SMILES: COc1ccc2ccn(C3CC(N(C)C)C3)c2c1C] |
| 383 | 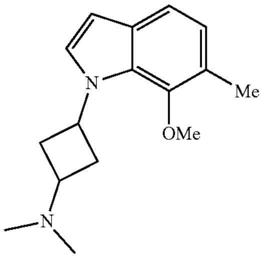 [SMILES: COc1c(C)ccc2ccn(C3CC(N(C)C)C3)c12] |
| 384 | 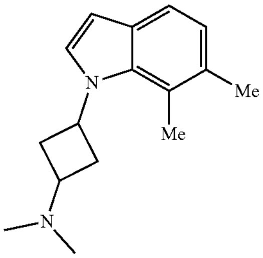 [SMILES: Cc1ccc2ccn(C3CC(N(C)C)C3)c2c1C] |

TABLE 3-continued
| Cmpd | Structure |
|---|---|
| 385 | 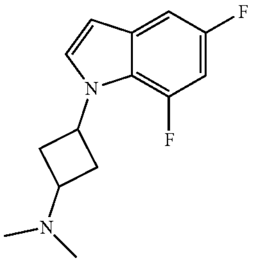 [SMILES: CN(C)C1CC(n2ccc3cc(F)cc(F)c32)C1] |
| 386 | 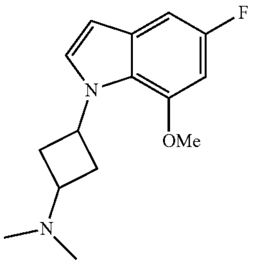 [SMILES: COc1cc(F)cc2ccn(C3CC(N(C)C)C3)c12] |
| 387 | 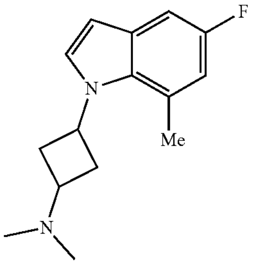 [SMILES: Cc1cc(F)cc2ccn(C3CC(N(C)C)C3)c12] |
| 388 | 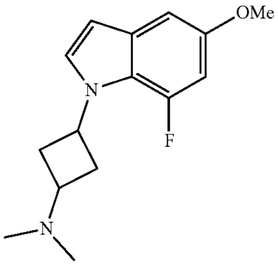 [SMILES: COc1cc(F)c2c(ccn2C2CC(N(C)C)C2)c1] |
| 389 | 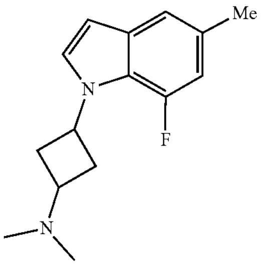 [SMILES: Cc1cc(F)c2c(ccn2C2CC(N(C)C)C2)c1] |
TABLE 3-continued
| Cmpd | Structure |
|---|---|
| 390 | 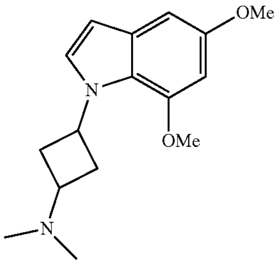 [SMILES: COc1cc(OC)c2c(ccn2C2CC(N(C)C)C2)c1] |
| 391 | 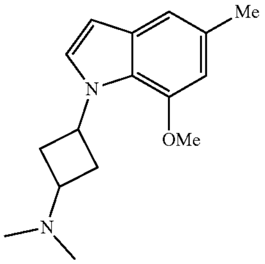 [SMILES: COc1cc(C)cc2ccn(C3CC(N(C)C)C3)c12] |
| 392 | 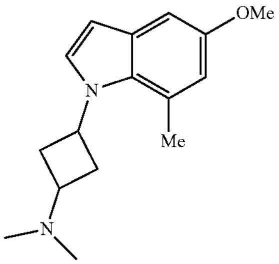 [SMILES: COc1cc(C)c2c(ccn2C2CC(N(C)C)C2)c1] |
| 393 | 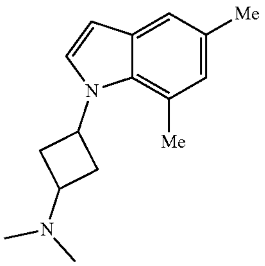 [SMILES: Cc1cc(C)c2c(ccn2C2CC(N(C)C)C2)c1] |
| 394 | 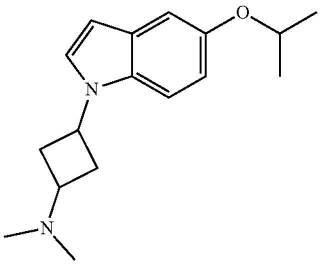 [SMILES: CC(C)Oc1ccc2c(ccn2C2CC(N(C)C)C2)c1] |

TABLE 3-continued
| Cmpd | Structure |
|---|---|
| 395 | 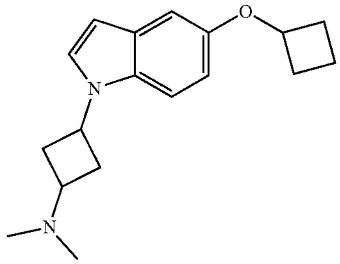 [SMILES: CN(C)C1CC(n2ccc3cc(OC4CCC4)ccc32)C1] |
| 396 | 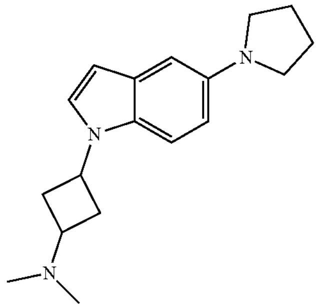 [SMILES: CN(C)C1CC(n2ccc3cc(N4CCCC4)ccc32)C1] |
| 397 | 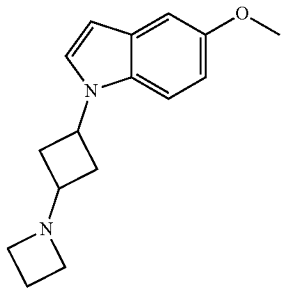 [SMILES: COc1ccc2c(ccn2C2CC(N3CCC3)C2)c1] |
| 398 | 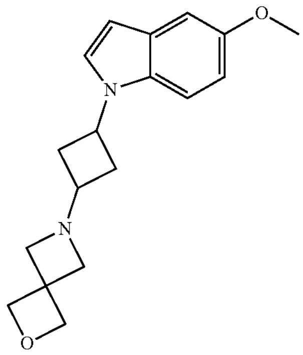 [SMILES: COc1ccc2c(ccn2C2CC(N3CC4(COC4)C3)C2)c1] |
| 399 | 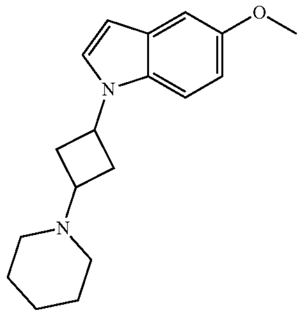 [SMILES: COc1ccc2c(ccn2C2CC(N3CCCCC3)C2)c1] |
TABLE 3-continued
| Cmpd | Structure |
|---|---|
| 400 | 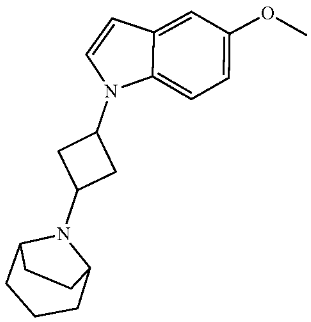 [SMILES: COc1ccc2c(ccn2C2CC(N3C4CCCC3CC4)C2)c1] |
| 401 | 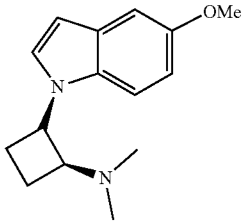 |
| 402 | 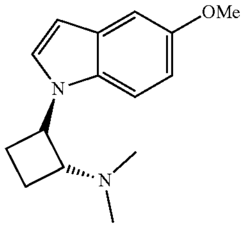 |
| 403 | 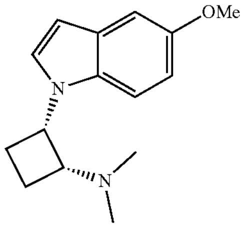 [SMILES: COc1ccc2c(ccn2[C@H]2CC[C@H]2N(C)C)c1] |
| 404 | 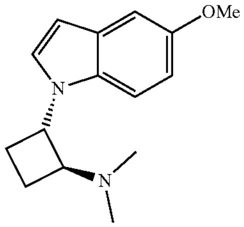 |
| 405 | 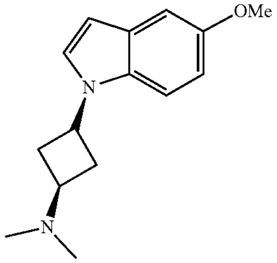 |

TABLE 3-continued
| Cmpd | Structure |
| --- | --- |
| 406 | 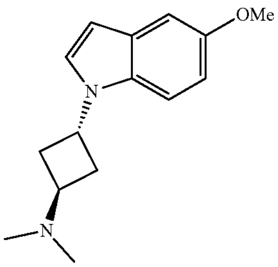 [SMILES: COc1ccc2c(ccn2[C@H]2C[C@H](N(C)C)C2)c1] |
| 407 | 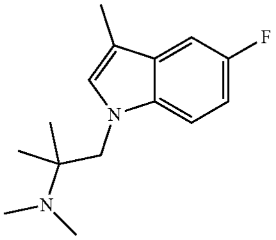 [SMILES: Cc1cn(CC(C)(C)N(C)C)c2ccc(F)cc12] |
| 408 | 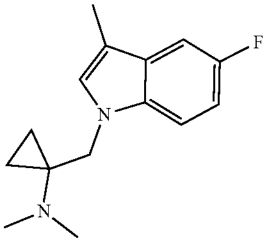 [SMILES: Cc1cn(CC2(N(C)C)CC2)c2ccc(F)cc12] |
| 409 | 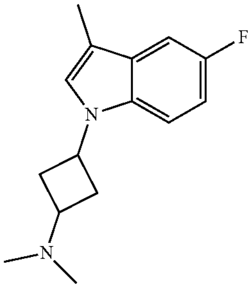 [SMILES: Cc1cn(C2CC(N(C)C)C2)c2ccc(F)cc12] |
| 410 | 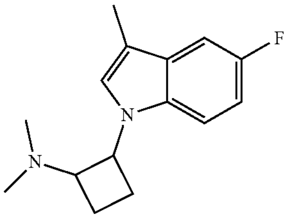 [SMILES: Cc1cn(C2CCC2N(C)C)c2ccc(F)cc12] |
Provided in some embodiments herein is a compound, a stereoisomer thereof, or a pharmaceutically acceptable salt of the compound or the stereoisomer, having a structure provided in Table 4:
TABLE 4
| Cmpd | Structure |
| --- | --- |
| 408 | 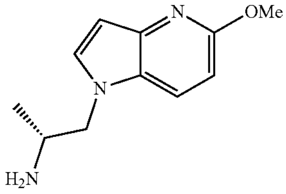 |
| 409 | 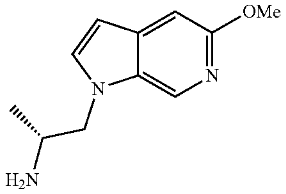 |
| 410 | 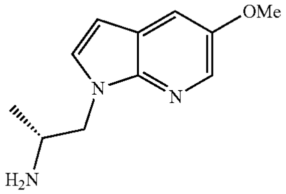 |
| 411 | 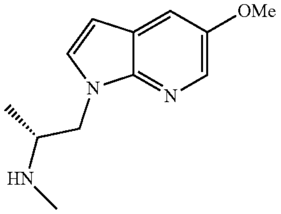 [SMILES: CN[C@H](C)Cn1ccc2cc(OC)cnc21] |
| 412 | 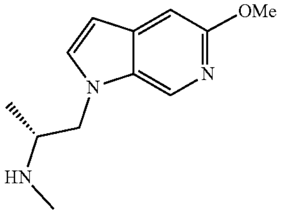 [SMILES: CN[C@H](C)Cn1ccc2cc(OC)ncc21] |
| 413 | 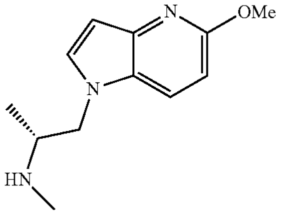 [SMILES: CN[C@H](C)Cn1ccc2nc(OC)ccc21] |
| 414 | 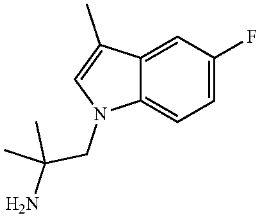 [SMILES: Cc1cn(CC(C)(C)N)c2ccc(F)cc12] |

TABLE 4-continued
| Cmpd | Structure |
|---|---|
| 415 | 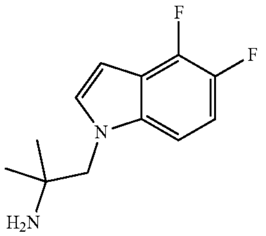 [SMILES: CC(C)(N)Cn1ccc2c(F)c(F)ccc21] |
| 416 | 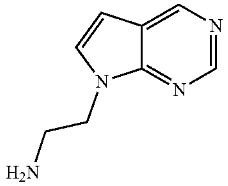 [SMILES: NCCn1ccc2cncnc21] |
| 417 | 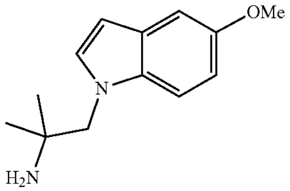 [SMILES: COc1ccc2c(ccn2CC(C)(C)N)c1] |
| 418 | 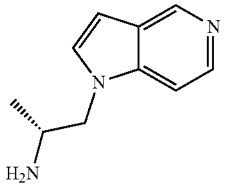 |
| 419 | 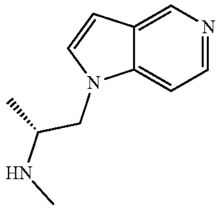 |
| 420 | 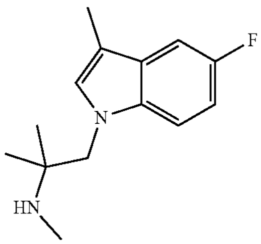 [SMILES: CNC(C)(C)Cn1cc(C)c2cc(F)ccc21] |
| 421 | 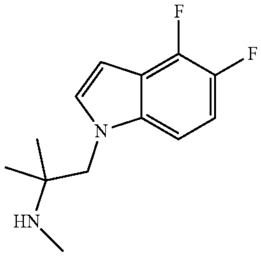 [SMILES: CNC(C)(C)Cn1ccc2c(F)c(F)ccc21] |
Representative compounds of Formula (III) include, but are not limited to:
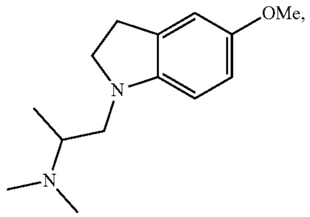
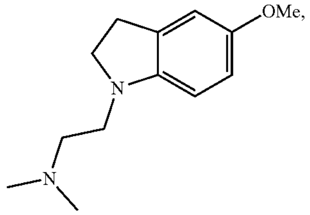
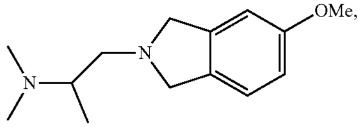
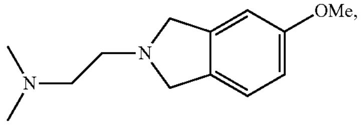
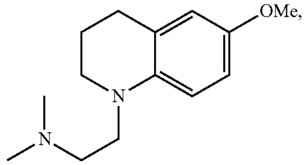
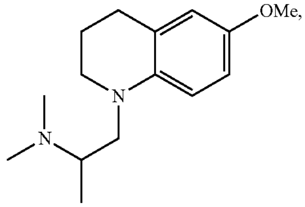
and
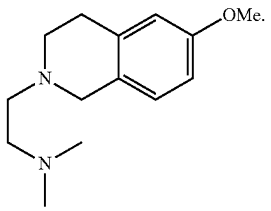
Provided in some embodiments herein is a compound, a stereoisomer thereof, or a pharmaceutically acceptable salt of the compound or the stereoisomer, having a structure provided in Table 5:

TABLE 5
| Compound | Structure |
| --- | --- |
| 422 | 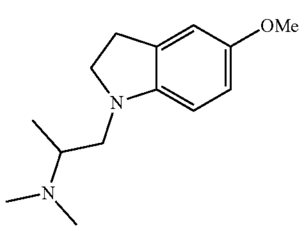 [SMILES: COc1ccc2c(c1)CCN2CC(C)N(C)C] |
| 423 | 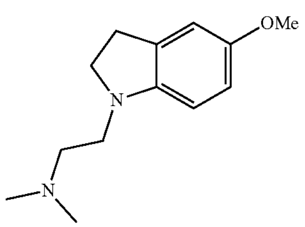 [SMILES: COc1ccc2c(c1)CCN2CCN(C)C] |
| 424 | 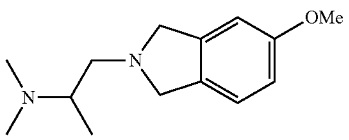 [SMILES: COc1ccc2c(c1)CN(CC(C)N(C)C)C2] |
| 425 | 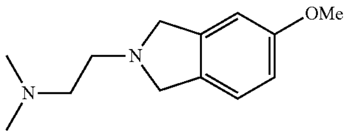 [SMILES: COc1ccc2c(c1)CN(CCN(C)C)C2] |
| 426 | 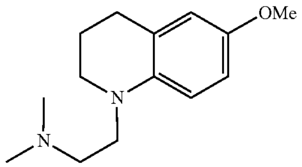 [SMILES: COc1ccc2c(c1)CCCN2CCN(C)C] |
| 427 | 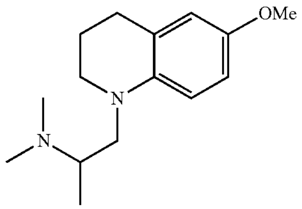 [SMILES: COc1ccc2c(c1)CCCN2CC(C)N(C)C] |
| 428 | 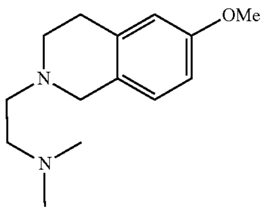 [SMILES: COc1ccc2c(c1)CCN(CCN(C)C)C2] |
Representative compounds of Formula (V) include, but are not limited to:
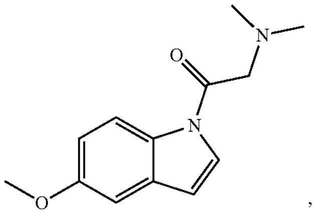
,
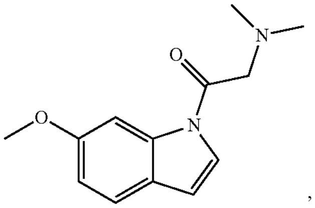
,
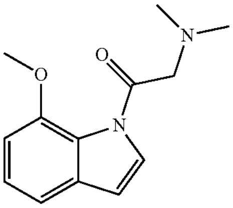
,
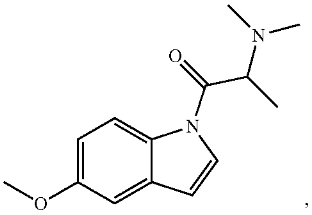
,
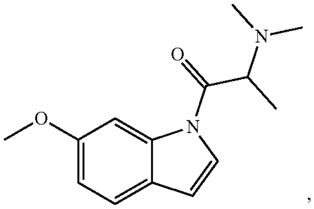
,
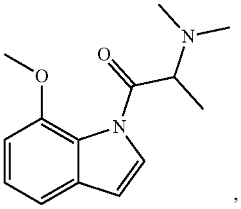
,
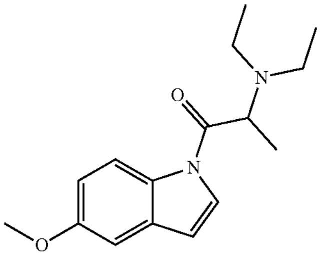
,
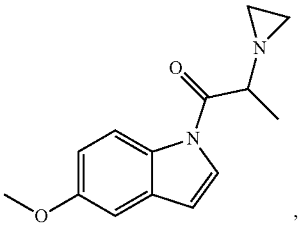
,
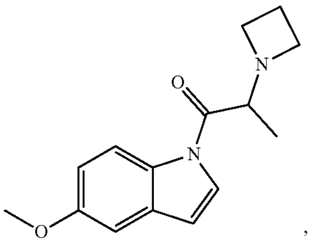
, -continued
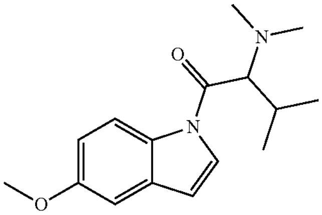,
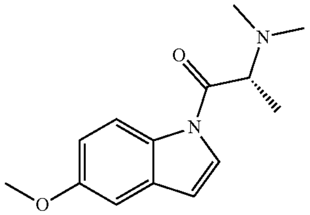,
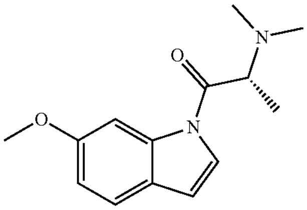, 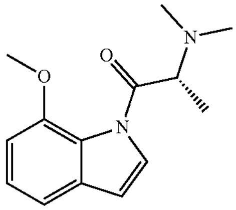,
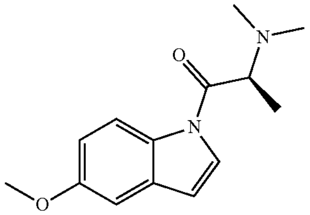,
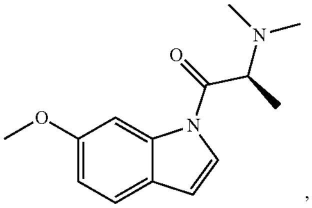, 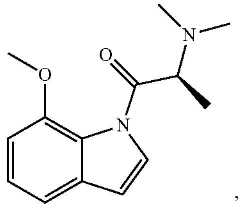,
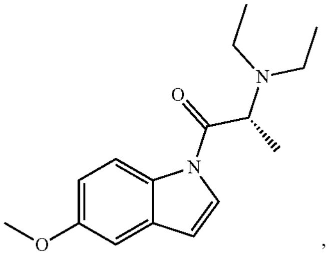,
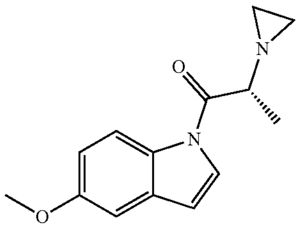,
-continued
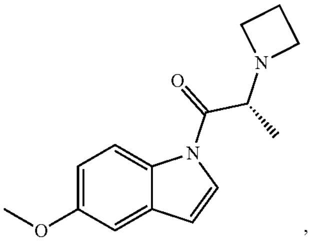,
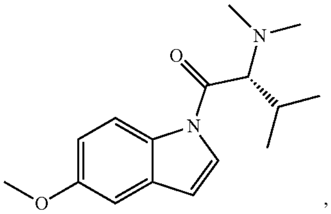,
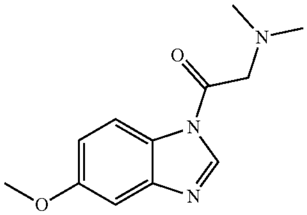,
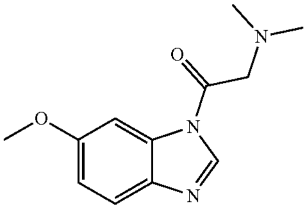, 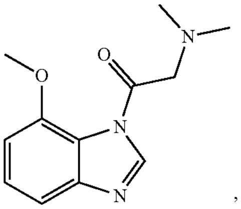,
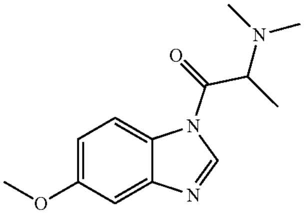,
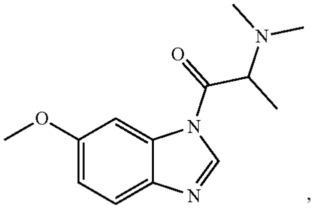, 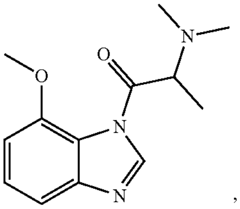,
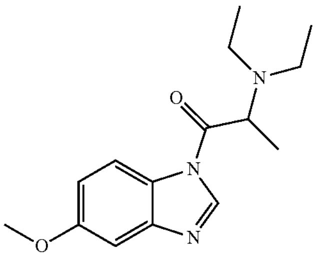, -continued
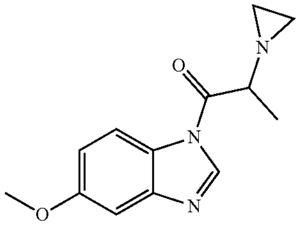,
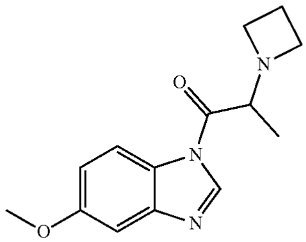,
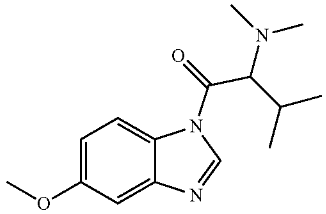,
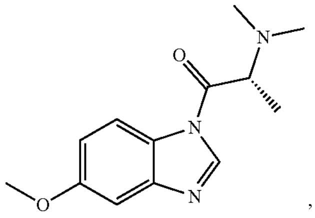,
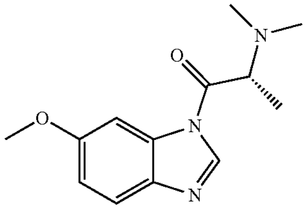, 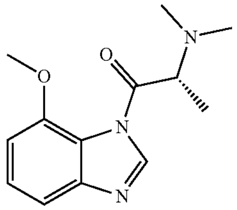,
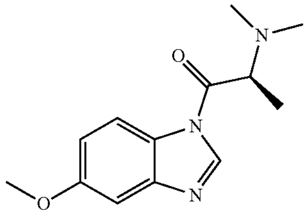,
-continued
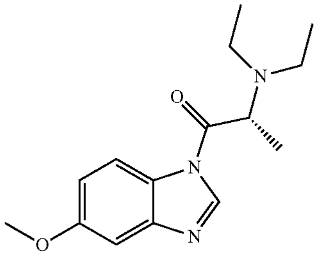,
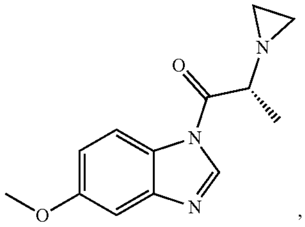,
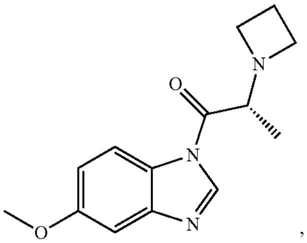,
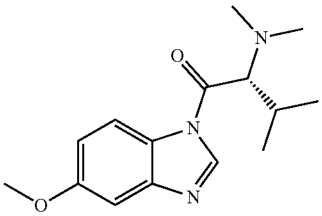,
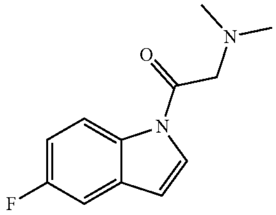,
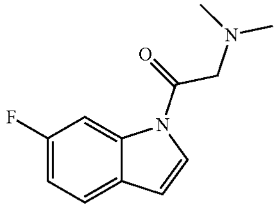,
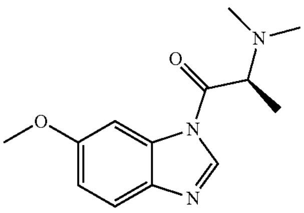, 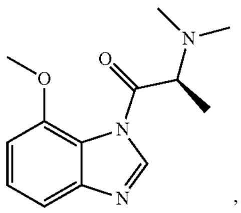, 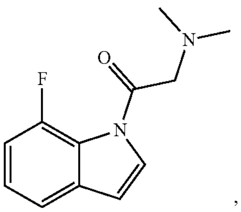, 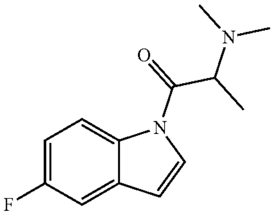, -continued
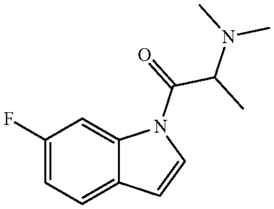
,
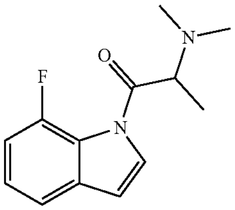
,
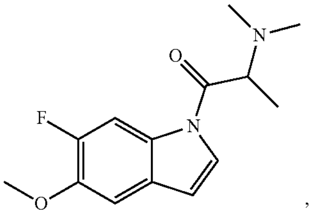
,
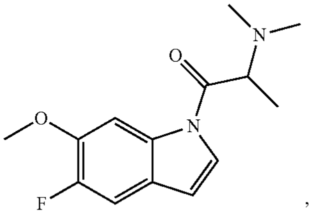
,
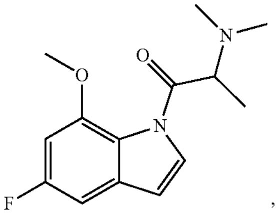
,
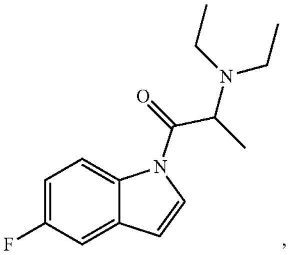
,
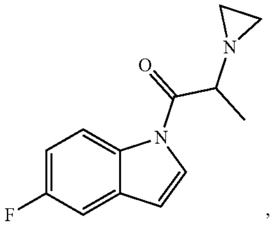
,
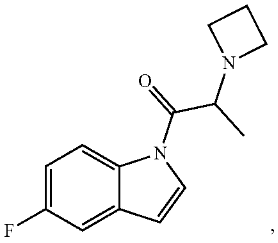
,
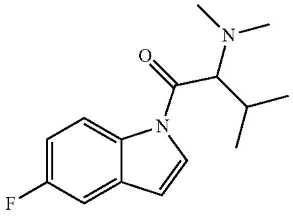
,
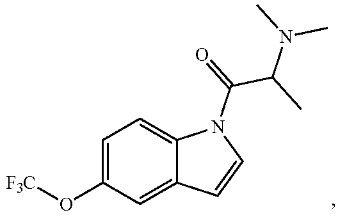
,
-continued
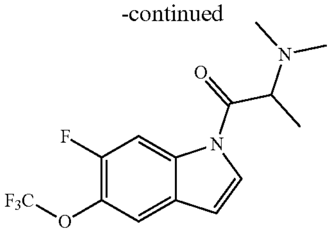
,
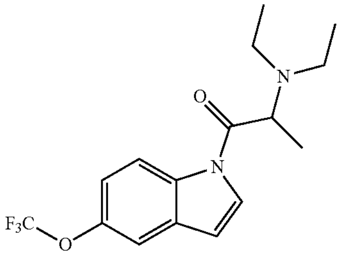
,
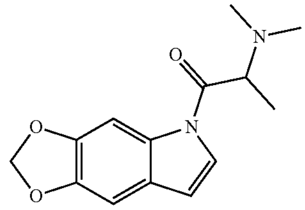
,
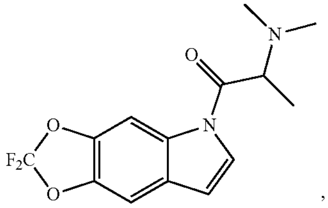
,
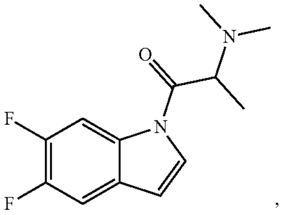
,
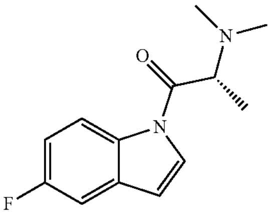
,
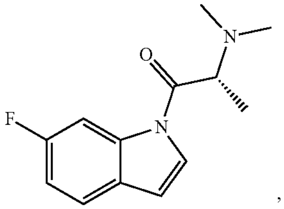
,
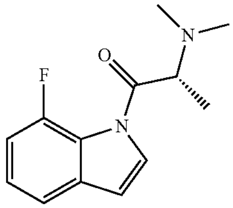
,
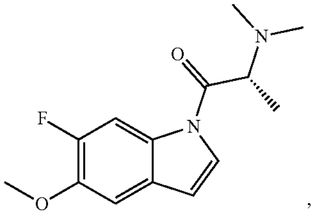
,
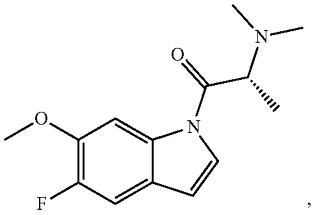
, -continued
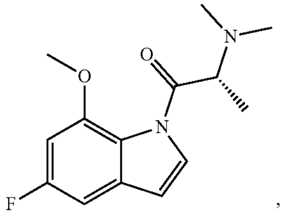
,
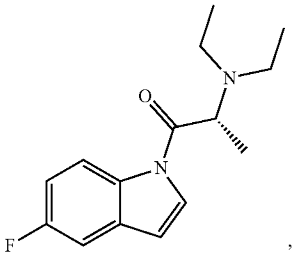
,
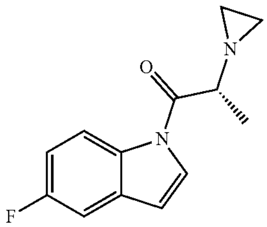
,
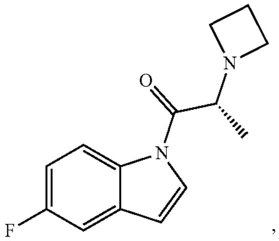
,
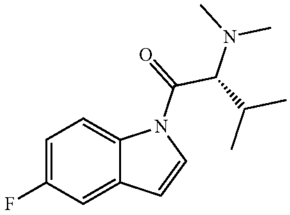
,
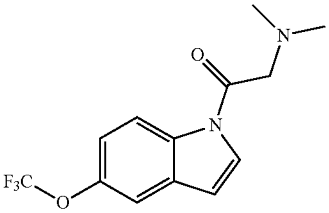
,
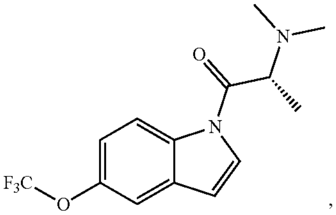
,
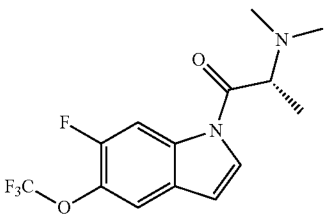
,
-continued
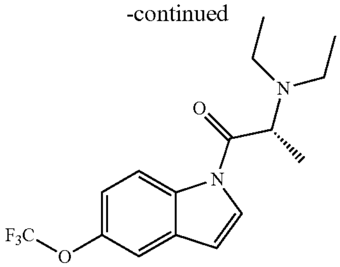
,
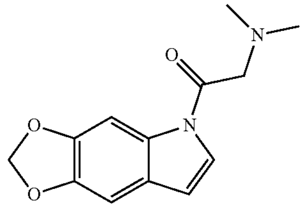
,
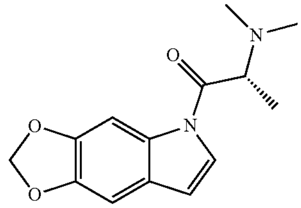
,
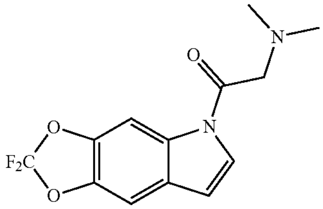
,
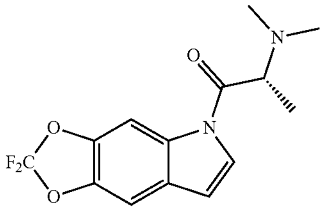
,
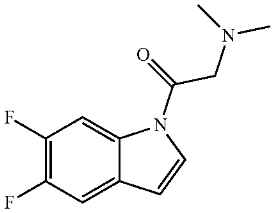
,
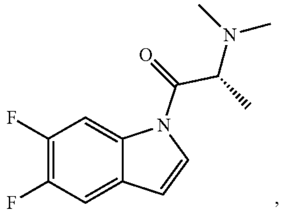
,
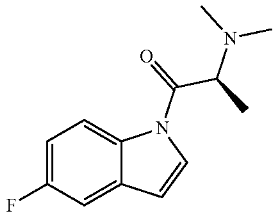
,
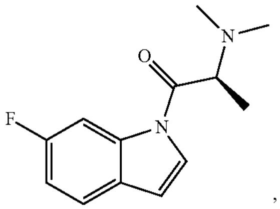
,
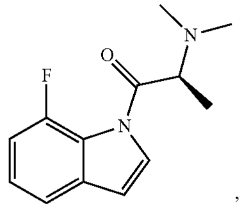
,
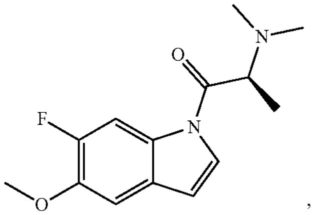
, -continued
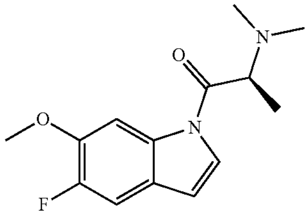
,
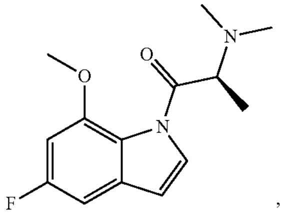
,
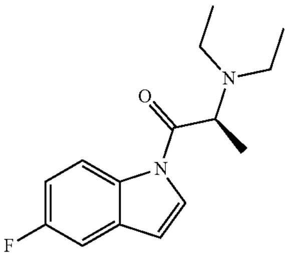
,
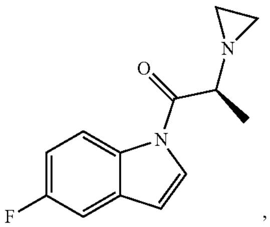
,
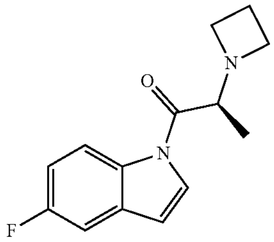
,
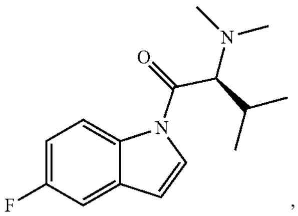
,
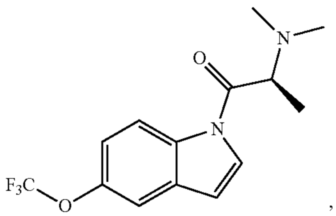
,
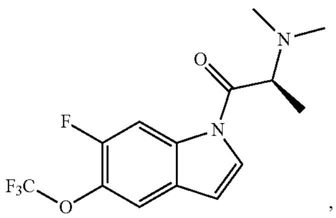
,
-continued
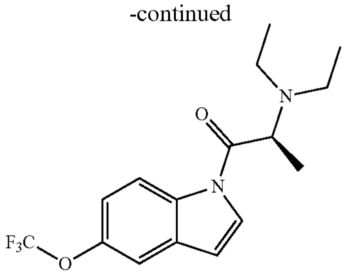
,
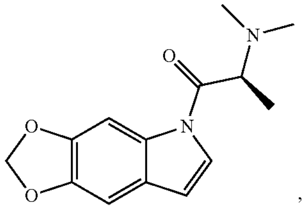
,
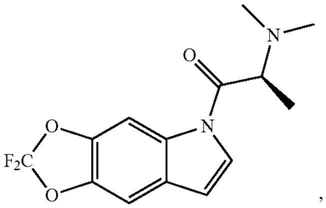
,
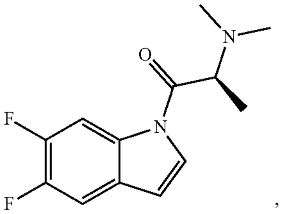
,
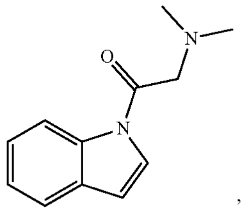
,
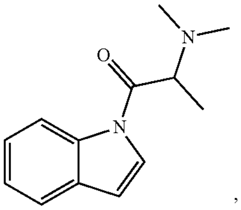
,
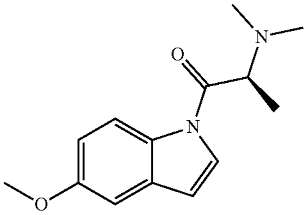
,
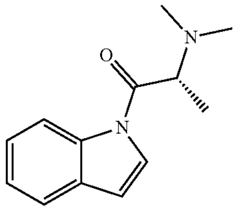
,
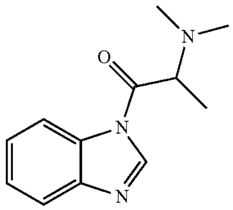
,
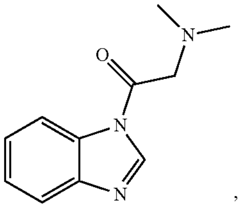
,
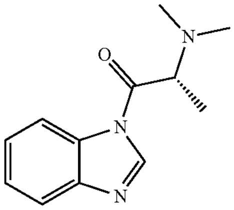
,
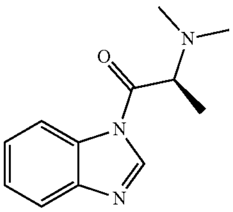
, and -continued
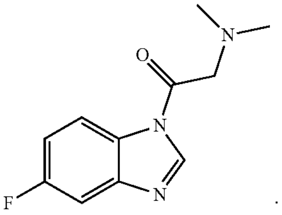
Provided in some embodiments herein is a compound, a stereoisomer thereof, or a pharmaceutically acceptable salt of the compound or the stereoisomer, having a structure provided in Table 6:
TABLE 6
| Cmp | Structure |
|---|---|
| 429 | 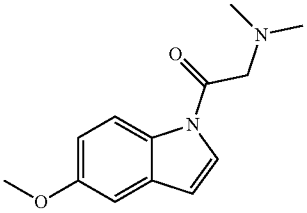 |
| 430 | 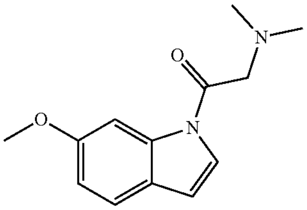 |
| 431 | 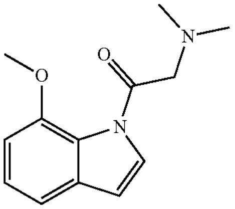 |
| 432 | 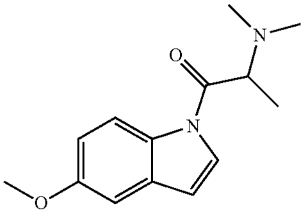 |
| 433 | 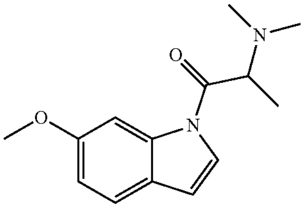 |
TABLE 6-continued
| Cmp | Structure |
|---|---|
| 434 | 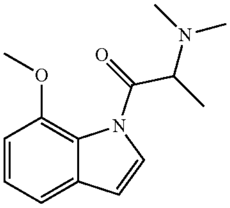 |
| 435 | 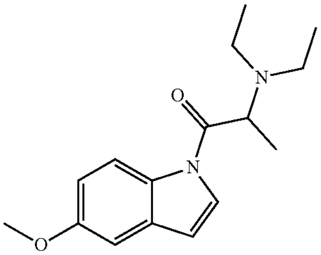 [SMILES: CCN(CC)C(C)C(=O)n1ccc2cc(OC)ccc21] |
| 436 | 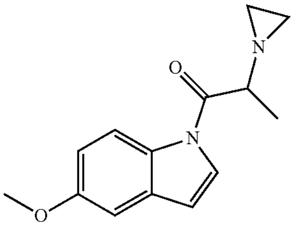 [SMILES: COc1ccc2c(ccn2C(=O)C(C)N2CC2)c1] |
| 437 | 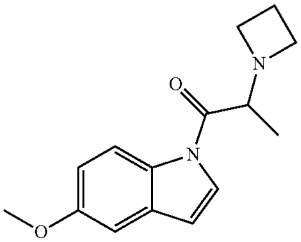 [SMILES: COc1ccc2c(ccn2C(=O)C(C)N2CCC2)c1] |
| 438 | 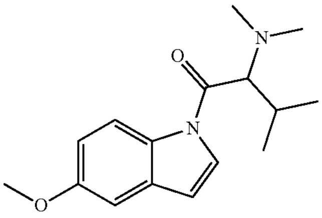 [SMILES: COc1ccc2c(ccn2C(=O)C(C(C)C)N(C)C)c1] |
| 439 | 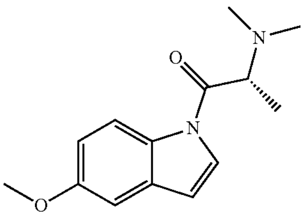 |

TABLE 6-continued
| Cmp | Structure |
|---|---|
| 440 | 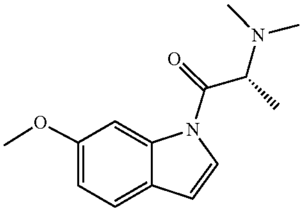 |
| 441 | 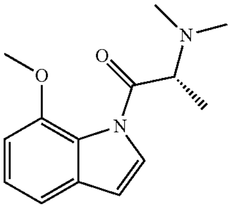 |
| 442 | 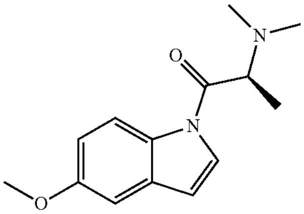 |
| 443 | 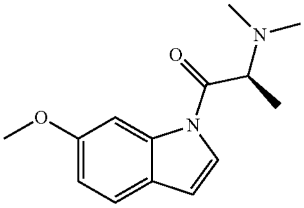 |
| 444 | 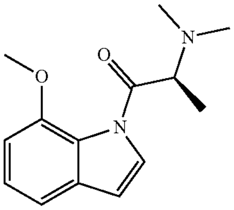 |
| 445 | 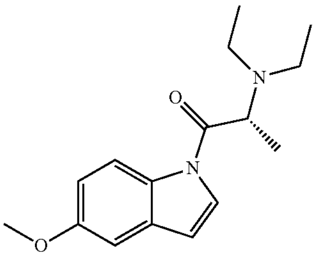 [SMILES: CCN(CC)[C@H](C)C(=O)n1ccc2cc(OC)ccc21] |
| 446 | 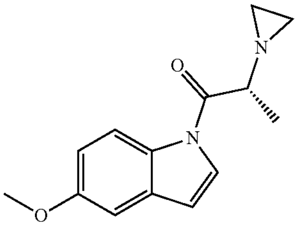 [SMILES: COc1ccc2c(ccn2C(=O)[C@@H](C)N2CC2)c1] |
| 447 | 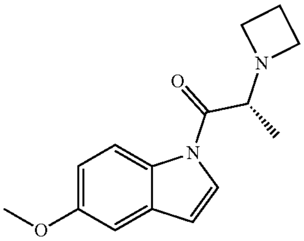 [SMILES: COc1ccc2c(ccn2C(=O)[C@@H](C)N2CCC2)c1] |
| 448 | 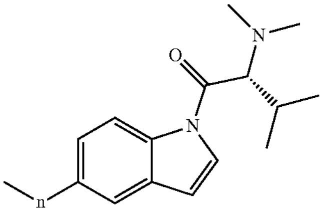 |
| 449 | 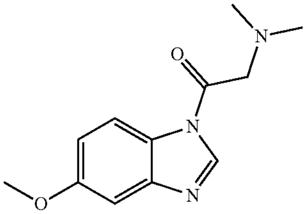 |
| 450 | 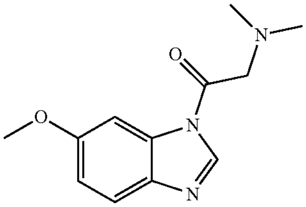 |
| 451 | 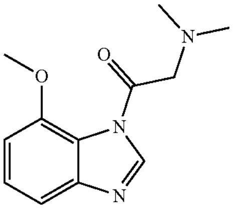 |
| 452 | 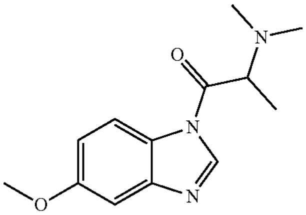 |
| 453 | 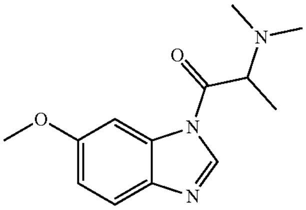 |

TABLE 6-continued
| Cmp | Structure |
|---|---|
| 454 | 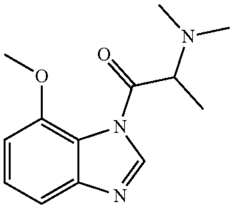 |
| 455 | 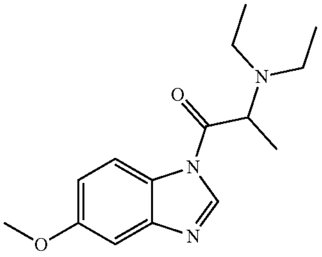 [SMILES: CCN(CC)C(C)C(=O)n1cnc2cc(OC)ccc21] |
| 456 | 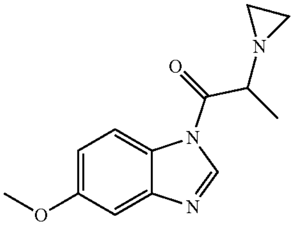 |
| 457 | 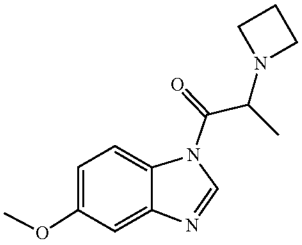 |
| 458 | 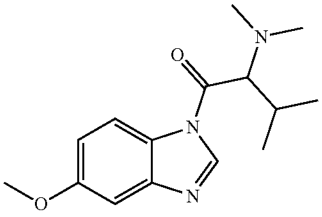 |
| 459 | 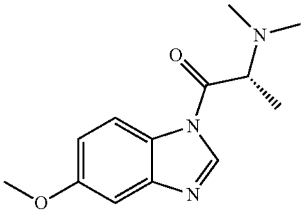 |
TABLE 6-continued
| Cmp | Structure |
|---|---|
| 460 | 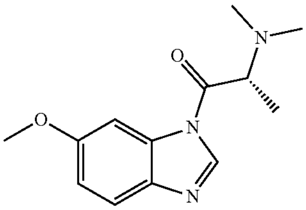 |
| 461 | 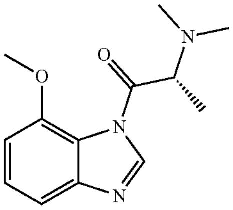 |
| 462 | 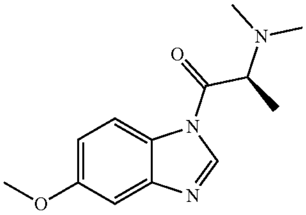 |
| 463 | 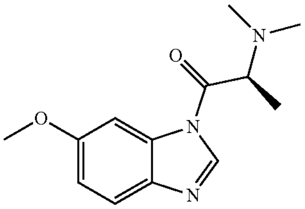 |
| 464 | 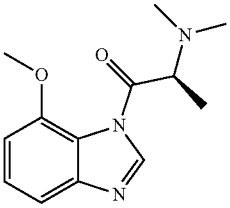 |
| 465 | 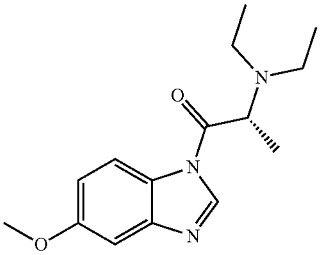 [SMILES: CCN(CC)[C@H](C)C(=O)n1cnc2cc(OC)ccc21] |
| 466 | 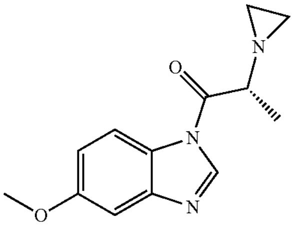 [SMILES: COc1ccc2c(c1)ncn2C(=O)[C@@H](C)N1CC1] |

TABLE 6-continued
| Cmp | Structure |
|---|---|
| 467 | 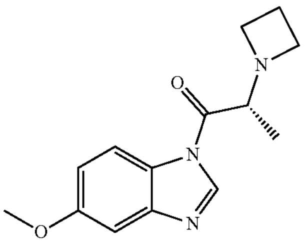 [SMILES: COc1ccc2c(c1)ncn2C(=O)[C@@H](C)N1CCC1] |
| 468 | 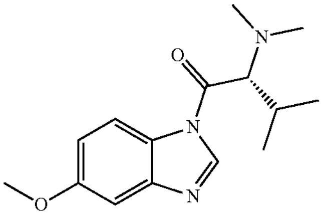 [SMILES: COc1ccc2c(c1)ncn2C(=O)[C@@H](C(C)C)N(C)C] |
| 469 | 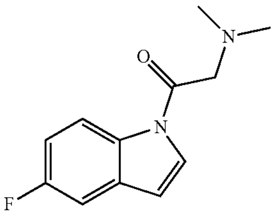 [SMILES: CN(C)CC(=O)n1ccc2cc(F)ccc21] |
| 470 | 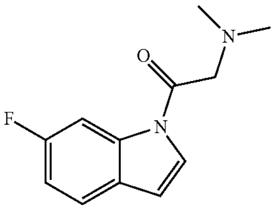 [SMILES: CN(C)CC(=O)n1ccc2ccc(F)cc21] |
| 471 | 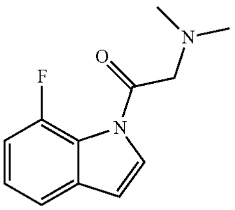 [SMILES: CN(C)CC(=O)n1ccc2cccc(F)c21] |
| 472 | 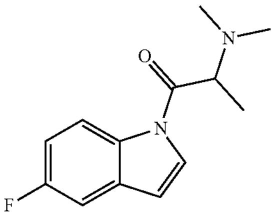 [SMILES: CC(C(=O)n1ccc2cc(F)ccc21)N(C)C] |
| 473 | 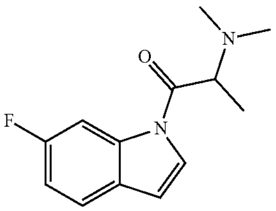 [SMILES: CC(C(=O)n1ccc2ccc(F)cc21)N(C)C] |
TABLE 6-continued
| Cmp | Structure |
|---|---|
| 474 | 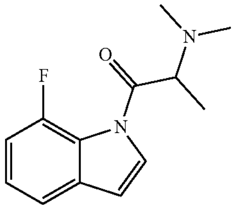 [SMILES: CC(C(=O)n1ccc2cccc(F)c21)N(C)C] |
| 475 | 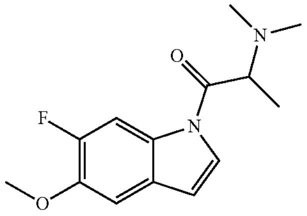 |
| 476 | 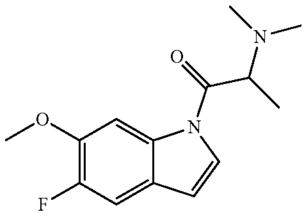 |
| 477 | 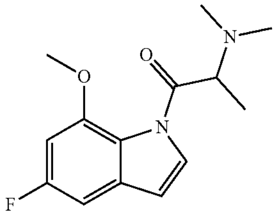 [SMILES: COc1cc(F)cc2ccn(C(=O)C(C)N(C)C)c12] |
| 478 | 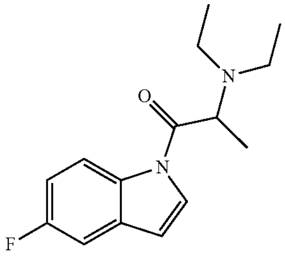 [SMILES: CCN(CC)C(C)C(=O)n1ccc2cc(F)ccc21] |
| 479 | 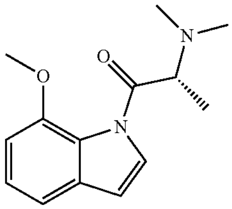 |

TABLE 6-continued
| Cmp | Structure |
|---|---|
| 480 | 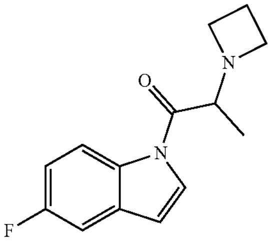 [SMILES: CC(C(=O)n1ccc2cc(F)ccc21)N1CCC1] |
| 481 | 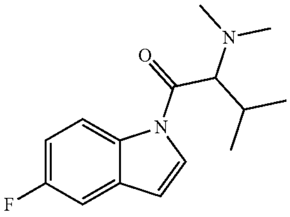 |
| 482 | 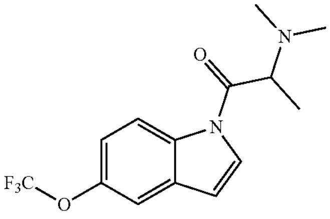 [SMILES: CC(C(=O)n1ccc2cc(OC(F)(F)F)ccc21)N(C)C] |
| 483 | 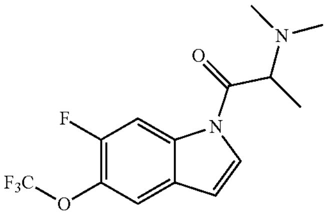 [SMILES: CC(C(=O)n1ccc2cc(OC(F)(F)F)c(F)cc21)N(C)C] |
| 484 | 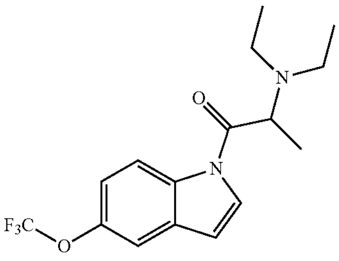 [SMILES: CCN(CC)C(C)C(=O)n1ccc2cc(OC(F)(F)F)ccc21] |
| 485 | 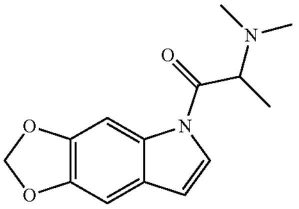 [SMILES: CC(C(=O)n1ccc2cc3c(cc21)OCO3)N(C)C] |
TABLE 6-continued
| Cmp | Structure |
|---|---|
| 486 | 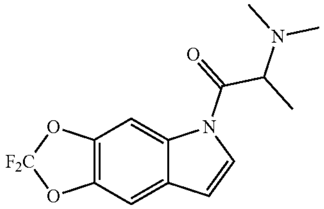 [SMILES: CC(C(=O)n1ccc2cc3c(cc21)OC(F)(F)O3)N(C)C] |
| 487 | 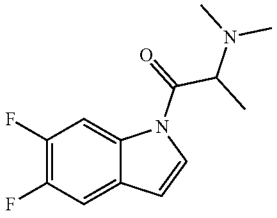 [SMILES: CC(C(=O)n1ccc2cc(F)c(F)cc21)N(C)C] |
| 488 | 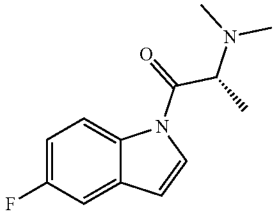 [SMILES: C[C@H](C(=O)n1ccc2cc(F)ccc21)N(C)C] |
| 489 | 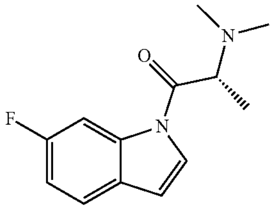 [SMILES: C[C@H](C(=O)n1ccc2ccc(F)cc21)N(C)C] |
| 490 | 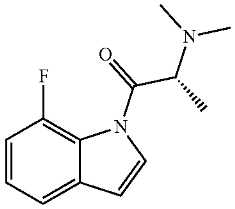 [SMILES: C[C@H](C(=O)n1ccc2cccc(F)c21)N(C)C] |
| 491 | 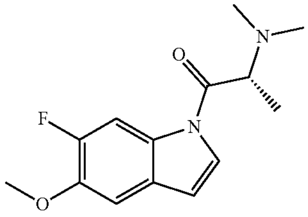 |
| 492 | 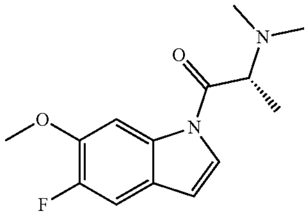 |

TABLE 6-continued
| Cmp | Structure |
| --- | --- |
| 493 | 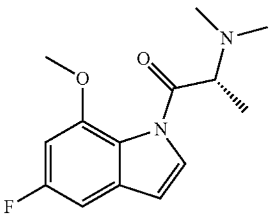 [SMILES: COc1cc(F)cc2ccn(C(=O)[C@@H](C)N(C)C)c12] |
| 494 | 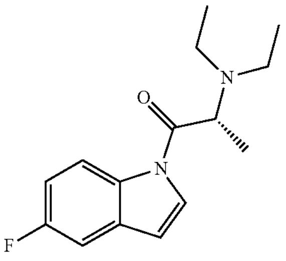 [SMILES: CCN(CC)[C@H](C)C(=O)n1ccc2cc(F)ccc21] |
| 495 | 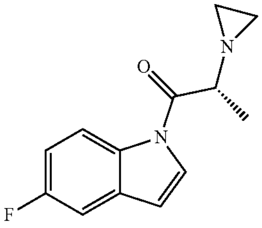 [SMILES: C[C@H](C(=O)n1ccc2cc(F)ccc21)N1CC1] |
| 496 | 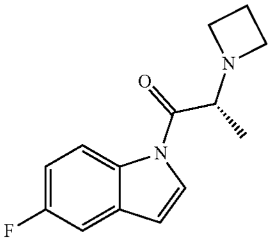 [SMILES: C[C@H](C(=O)n1ccc2cc(F)ccc21)N1CCC1] |
| 497 | 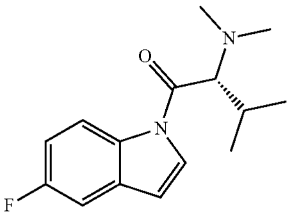 [SMILES: CC(C)[C@H](C(=O)n1ccc2cc(F)ccc21)N(C)C] |
| 498 | 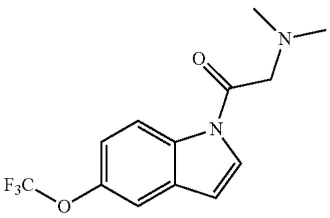 [SMILES: CN(C)CC(=O)n1ccc2cc(OC(F)(F)F)ccc21] |
TABLE 6-continued
| Cmp | Structure |
| --- | --- |
| 499 | 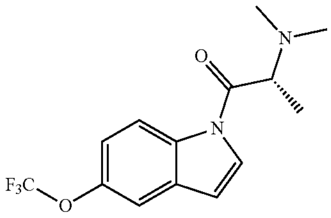 [SMILES: C[C@H](C(=O)n1ccc2cc(OC(F)(F)F)ccc21)N(C)C] |
| 500 | 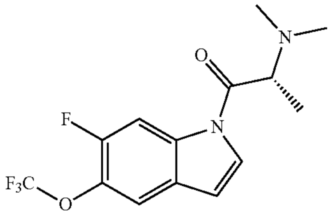 [SMILES: C[C@H](C(=O)n1ccc2cc(OC(F)(F)F)c(F)cc21)N(C)C] |
| 501 | 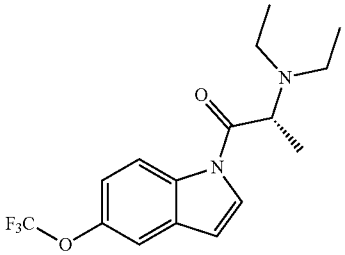 [SMILES: CCN(CC)[C@H](C)C(=O)n1ccc2cc(OC(F)(F)F)ccc21] |
| 502 | 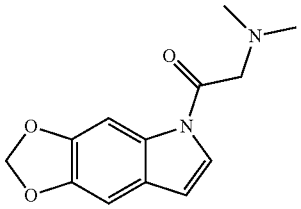 [SMILES: CN(C)CC(=O)n1ccc2cc3c(cc21)OCO3] |
| 503 | 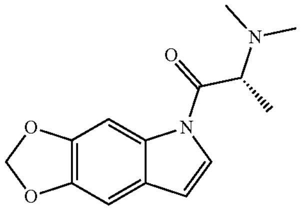 [SMILES: C[C@H](C(=O)n1ccc2cc3c(cc21)OCO3)N(C)C] |
| 504 | 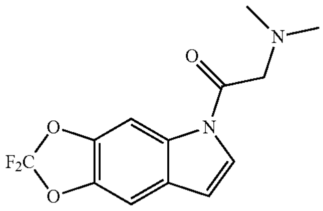 [SMILES: CN(C)CC(=O)n1ccc2cc3c(cc21)OC(F)(F)O3] |
| 505 | 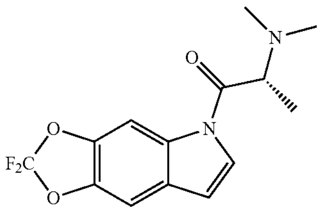 [SMILES: C[C@H](C(=O)n1ccc2cc3c(cc21)OC(F)(F)O3)N(C)C] |

TABLE 6-continued
| Cmp | Structure |
|---|---|
| 506 | 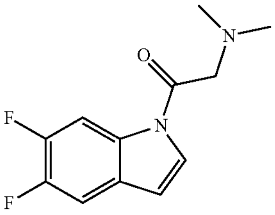 [SMILES: CN(C)CC(=O)n1ccc2cc(F)c(F)cc21] |
| 507 | 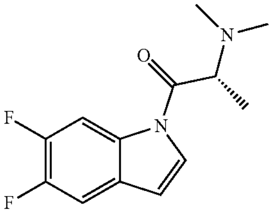 [SMILES: C[C@H](C(=O)n1ccc2cc(F)c(F)cc21)N(C)C] |
| 508 | 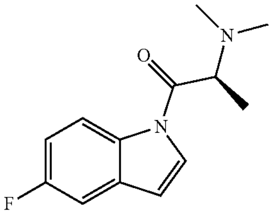 [SMILES: C[C@@H](C(=O)n1ccc2cc(F)ccc21)N(C)C] |
| 509 | 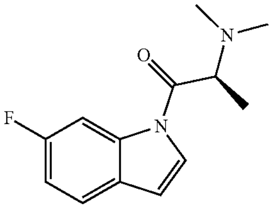 [SMILES: C[C@@H](C(=O)n1ccc2ccc(F)cc21)N(C)C] |
| 510 | 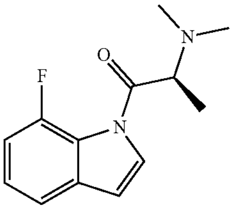 [SMILES: C[C@@H](C(=O)n1ccc2cccc(F)c21)N(C)C] |
| 511 | 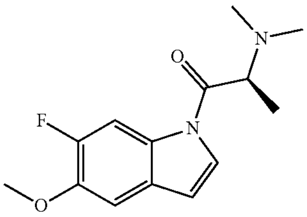 |
| 512 | 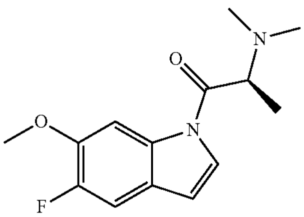 |
TABLE 6-continued
| Cmp | Structure |
|---|---|
| 513 | 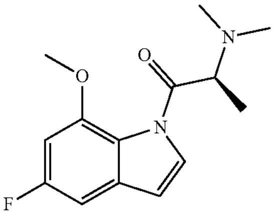 [SMILES: COc1cc(F)cc2ccn(C(=O)[C@H](C)N(C)C)c12] |
| 514 | 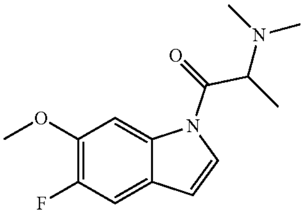 |
| 515 | 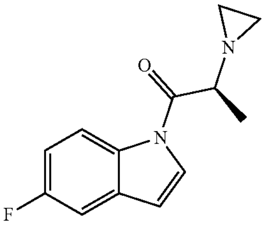 |
| 516 | 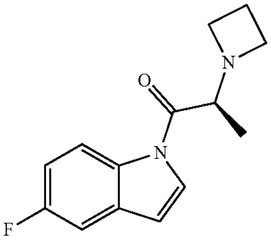 [SMILES: C[C@@H](C(=O)n1ccc2cc(F)ccc21)N1CCC1] |
| 517 | 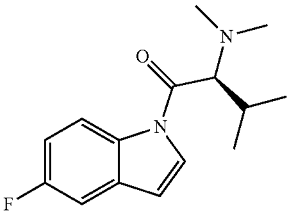 [SMILES: CC(C)[C@@H](C(=O)n1ccc2cc(F)ccc21)N(C)C] |
| 518 | 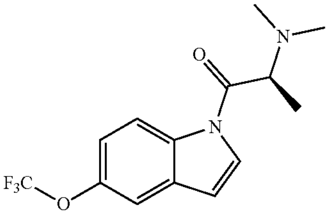 [SMILES: C[C@@H](C(=O)n1ccc2cc(OC(F)(F)F)ccc21)N(C)C] |
| 519 | 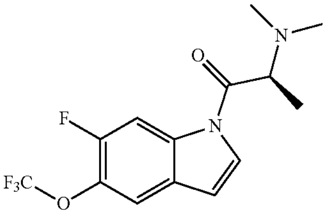 [SMILES: C[C@@H](C(=O)n1ccc2cc(OC(F)(F)F)c(F)cc21)N(C)C] |

TABLE 6-continued

| Cmp | Structure |
|---|---|
| 520 | 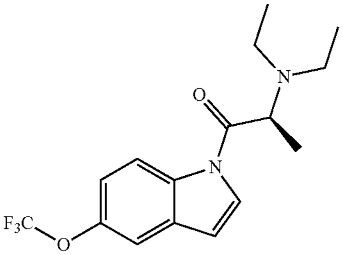 [SMILES: CCN(CC)[C@@H](C)C(=O)n1ccc2cc(OC(F)(F)F)ccc21] |
| 521 | 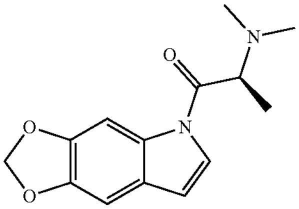 [SMILES: C[C@@H](C(=O)n1ccc2cc3c(cc21)OCO3)N(C)C] |
| 522 | 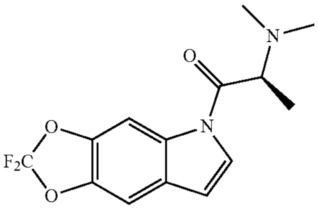 [SMILES: C[C@@H](C(=O)n1ccc2cc3c(cc21)OC(F)(F)O3)N(C)C] |
| 523 | 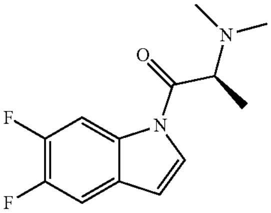 [SMILES: C[C@@H](C(=O)n1ccc2cc(F)c(F)cc21)N(C)C] |
| 524 | 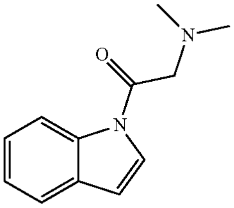 |
| 525 | 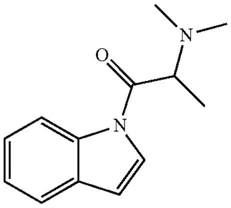 [SMILES: CC(C(=O)n1ccc2ccccc21)N(C)C] |
| 526 | 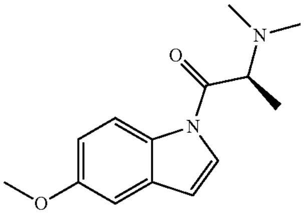 |
| 527 | 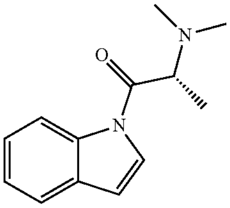 [SMILES: C[C@H](C(=O)n1ccc2ccccc21)N(C)C] |
| 528 | 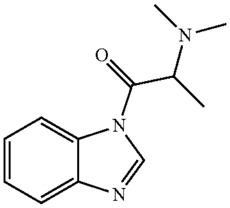 [SMILES: CC(C(=O)n1cnc2ccccc21)N(C)C] |
| 529 | 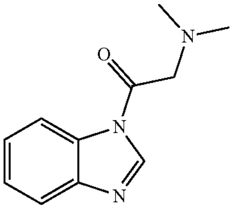 |
| 530 | 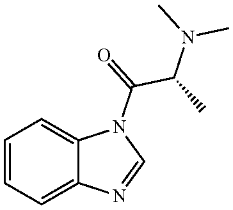 [SMILES: C[C@H](C(=O)n1cnc2ccccc21)N(C)C] |
| 531 | 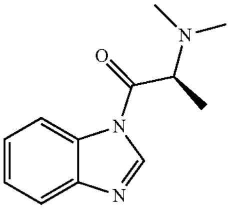 [SMILES: C[C@@H](C(=O)n1cnc2ccccc21)N(C)C] |
| 532 | 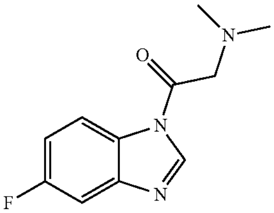 |

Any combination of the groups described above for the various variables is contemplated herein. Throughout the specification, groups and substituents thereof are chosen by one skilled in the field to provide stable moieties and compounds.

Further Forms of Compounds

In one aspect, compounds described herein are in the form of pharmaceutically acceptable salts. In some embodiments, any compound provided herein is a pharmaceutically acceptable salt, such as, for example, any salt described herein (such as, e.g., a fumarate salt of the compound provided herein or maleate salt of the compound provided herein). In some embodiments, any compound provided herein is a fumarate salt of the compound provided herein. In some embodiments, any compound provided herein is a maleate salt of the compound provided herein.

As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, pharmaceutically acceptable salts are obtained by reacting a compound represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, the compound represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) (i.e. free base form) is basic and is reacted with maleic acid.

In some embodiments, the compound represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) (i.e. free base form) is basic and is reacted with fumaric acid.

In some embodiments, pharmaceutically acceptable salts are obtained by reacting a compound represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) with a base. In some embodiments, the compound represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) is acidic and is reacted with a base. In such situations, an acidic proton of the compound represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds having the structure of Formula (II), Formula (III), Formula (IV), or Formula (V), as well as active metabolites of these compounds having the same type of activity.

In some embodiments, sites on the organic radicals (e.g. alkyl groups, aromatic rings) of compounds of Formula (II), Formula (III), Formula (IV), or Formula (V) are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}S$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogens of the compounds of Formula (II), Formula (III), Formula (IV), or Formula (V) are replaced with deuterium.

In some embodiments, the compounds represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) possess one or more stereocenters and each stereocenter exists independently in either the R or S configuration. In some embodiments, the compound represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) exists in the R configuration. In some embodiments, the compound represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V C)), Table 1, Table 2, Table 3, Table 4, Table 5, or Table 6) exists in the S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

In some embodiments, a composition provided herein comprises a racemic mixture of a compound represented by a structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6). In some embodiments, a compound provided herein is a racemate of a compound represented by a structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6).

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. In some instances, a prodrug is an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, N-alkyloxyacyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (II), Formula (III), Formula (IV), or Formula (V) as set forth herein are included within the scope of the claims.

In some embodiments, any one of the hydroxyl group(s), amino group(s) and/or carboxylic acid group(s) are functionalized in a suitable manner to provide a prodrug moiety. In some embodiments, the prodrug moiety is as described above.

In additional or further embodiments, the compounds described herein are metabolized upon administration to an organism in need to produce a metabolite that is then used to produce a desired effect, including a desired therapeutic effect.

In some instances, a metabolite of a compound disclosed herein is a derivative of that compound that is formed when the compound is metabolized. In some instances, an active metabolite of a compound provided herein is a biologically active derivative of the compound provided herein that is formed when the compound is metabolized. In some instances, metabolism is the sum of the processes (including, but not limited to, hydrolysis reactions and reactions catalyzed by enzymes) by which a particular substance is changed by an organism. In some instances, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. In some instances, a metabolite of a compound disclosed herein is optionally identified either by administration of compounds to a host and analysis of tissue samples from the host, or by incubation of compounds with hepatic cells in vitro and analysis of the resulting compounds.

Synthesis of Compounds

Compounds of Formula (II), Formula (III), Formula (IV), or Formula (V) described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, $6^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are synthesized as outlined in the Examples.

Pharmaceutical Compositions

In some embodiments, the compound provided herein is a pharmaceutically acceptable salt, such as, for example, any salt described herein (e.g., a fumarate salt of the compound provided herein or maleate salt of the compound provided herein). In some embodiments, provided herein is a pharmaceutical composition comprising a compound provided herein (e.g., a compound having a structure represented by Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6), and a pharmaceutically acceptable salt or solvate thereof. In some embodiments, the pharmaceutical composition further comprises at least one pharmaceutically acceptable excipient.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be affected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

It should be understood that in addition to the ingredients particularly mentioned above, the compounds and compositions described herein may include other agents conventional in the art having regard to the type of formulation in question, for example those suitable for oral administration may include flavoring agents.

Methods of Treatment, Dosing and Treatment Regimens

The compounds disclosed herein, or pharmaceutically acceptable salts, solvates, or stereoisomers thereof, are useful for promoting neuronal growth and/or improving neuronal structure.

Provided herein are non-hallucinogenic psychoplastogens that useful for treating one or more diseases or disorders associated with loss of synaptic connectivity and/or plasticity.

In some embodiments, provided herein is a method of promoting neural plasticity (e.g., cortical structural plasticity) in an individual by administering a compound described herein (e.g., a compound represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) to the individual. In some embodiments, provided herein are methods of modulating 5-$HT_{2A}$ in an individual by administering a compound described herein (e.g., a compound represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) to the individual. In some embodiments, provided herein are methods of agonizing 5-$HT_{2A}$ in an individual by administering a compound described herein (e.g., a compound represented by the structure of Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6) to the individual. In some embodiments, the individual has or is diagnosed with a brain disorder or other conditions described herein.

In some embodiments, provided herein is a method of promoting neuronal growth in an individual in need thereof, comprising administering to the individual in need thereof a therapeutically effective amount of a compound or pharmaceutical composition provided herein (e.g., a compound having a structure represented by Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6).

In some embodiments, provided herein is a method of improving neuronal structure in an individual in need thereof, comprising administering to the individual in need thereof a therapeutically effective amount of a compound or pharmaceutical composition provided herein (e.g., a compound having a structure represented by Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6).

In some embodiments, provided herein is a method of modulating the activity of 5-hydroxytryptamine receptor 2A (5-$HT_{2A}$) receptor in an individual in need thereof, comprising administering to the individual in need thereof a therapeutically effective amount of a compound or pharmaceutical composition provided herein (e.g., a compound having a structure represented by Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V C)), Table 1, Table 2, Table 3, Table 4, Table 5, or Table 6).

In some embodiments, provided herein is a method of treating a disease or disorder in an individual in need thereof that is mediated by the action of 5-hydroxytryptamine (5-HT) at 5-hydroxytryptamine receptor 2A (5-$HT_{2A}$), comprising administering to the individual in need thereof a therapeutically effective amount of a compound or pharmaceutical composition provided herein (e.g., a compound having a structure represented by Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6).

In some embodiments, provided herein is a method of treating a disease or disorder in an individual in need thereof that is mediated by the loss of synaptic connectivity, plasticity, or a combination thereof, comprising administering to the individual in need thereof a therapeutically effective amount of a compound or pharmaceutical composition provided herein (e.g., a compound having a structure represented by Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6).

In some embodiments, provided herein is a method of treating a neurological disease or disorder in an individual in need thereof, comprising administering to the individual in need thereof a therapeutically effective amount of a compound or pharmaceutical composition provided herein (e.g., a compound having a structure represented by Formula (II) (e.g., Formula (II), Formula (IIA'), Formula (IIA), Formula (IIB), Formula (IIC), Formula (IID'), Formula (IID), Formula (IIE), Formula (IIF'), Formula (IIF), Formula (VI), and Formula (VI')), Formula (III), Formula (III'), Formula (III-1), Formula (III-1'), Formula (IV'), Formula (IV), Formula (V'), Formula (V) (e.g., Formula (V-A), Formula (V-B), or Formula (V-C)), Table 1, Table 2, Table 3, Table 4, Table 5, or Table 6).

In some embodiments, an individual administered a compound provided herein has a hallucinogenic event. In some embodiments, an individual administered a compound provided herein does not have a hallucinogenic event. In some embodiments, an individual administered a compound provided herein has a hallucinogenic event after the compound provided herein reaches a particular maximum concentration ($C_{max}$) in the individual. In some embodiments, the particular maximum concentration ($C_{max}$) in the individual is the hallucinogenic threshold of the compound provided herein. In some embodiments, a compound provided herein is administered to an individual in need thereof below the hallucinogenic threshold of the compound provided herein.

In some embodiments, described herein are methods for treating a disease or disorder in an individual in need thereof, wherein the disease or disorder is a neurological diseases and disorder.

In some embodiments, a compound of the present invention is used to treat neurological diseases. In some embodiments, a compound provided herein has, for example, anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder). In some embodiments, the neurological disease is a migraine or cluster headache. In some embodiments, the neurological disease is a neurodegenerative disorder, Alzheimer's disease, or Parkinson's disease. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some instances, a compound disclosed herein, or pharmaceutically acceptable salts, solvates, or stereoisomers thereof, is useful for the modulation of a 5-hydroxytryptamine (5-HT) receptor. In some embodiments, the 5-HT receptor modulated by the compounds and methods is 5-hydroxytryptamine receptor 2A (5-$HT_{2A}$).

Provided in some instances herein are modulators of 5-hydroxytryptamine receptor 2A (5-$HT_{2A}$) that are useful for treating one or more diseases or disorders associated with 5-$HT_{2A}$ activity.

In some embodiments, a compound described herein, or a pharmaceutically acceptable salt thereof, is used in the preparation of medicaments for the treatment of diseases or conditions in a mammal that would benefit from inhibition or reduction of 5-$HT_{2A}$ activity.

In some embodiments, a compound described herein, or a pharmaceutically acceptable salt thereof, is used in the preparation of medicaments for the treatment of diseases or conditions in a mammal that would benefit from promoting neuronal growth and/or improving neuronal structure.

Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a mammal already suffering from a disease or condition, in an amount sufficient to cure or at least partially arrest at least one of the symptoms of the disease or condition. Amounts effective for this use depend on the severity and course of the disease or condition, previous therapy, the mammal's health status, weight, and response to the drugs, and the judgment of a healthcare practitioner. Therapeutically effective amounts are optionally determined by methods including, but not limited to, a dose escalation and/or dose ranging clinical trial.

In prophylactic applications, compositions containing the compounds described herein are administered to a mammal susceptible to or otherwise at risk of a particular disease, disorder or condition. Such an amount is defined to be a "prophylactically effective amount or dose." In this use, the precise amounts also depend on the mammal's state of health, weight, and the like. When used in mammals, effective amounts for this use will depend on the severity and course of the disease, disorder or condition, previous therapy, the mammal's health status and response to the drugs, and the judgment of a healthcare professional. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the mammal's condition does not improve, upon the discretion of a healthcare professional the administration of the compounds are administered chronically, that is, for an extended period of time, including throughout the duration of the mammal's life in order to ameliorate or otherwise control or limit the symptoms of the mammal's disease or condition.

In certain embodiments wherein a mammal's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the mammal requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the disease(s) for which relief is sought, is modified in accordance with a variety of factors (e.g. the disease or disorder from which the subject suffers; the age, weight, sex, diet, and medical condition of the subject). Thus, in some instances, the dosage regimen actually employed varies and, in some embodiments, deviates from the dosage regimens set forth herein.

EXAMPLES

The following examples are provided for illustrative purposes only and not to limit the scope of the claims provided herein.

General

All reagents were obtained commercially and used without purification unless otherwise noted. DMSO was purified by passage under 12 psi $N_2$ through activated alumina columns. Reactions were performed using glassware that was flame-dried under reduced pressure (~1 Torr). Compounds purified by chromatography were adsorbed to the silica gel before loading. Thin layer chromatography was performed on Millipore silica gel 60 $F_{254}$ Silica Gel plates. Visualization of the developed chromatogram was accomplished by fluorescence quenching or by staining with ninhydrin or aqueous ceric ammonium molybdate (CAM).

Nuclear magnetic resonance (NMR) spectra were acquired on either a Bruker 400 operating at 400 and 100 MHz, a Varian 600 operating at 600 and 150 MHz, or a Bruker 800 operating at 800 and 200 MHz for $^{1}H$ and $^{13}C$, respectively, and are referenced internally according to residual solvent signals. Data for $^{1}H$ NMR are recorded as follows: chemical shift (S, ppm), multiplicity (s, singlet; d, doublet; t, triplet; q, quartet; m, multiplet), integration, coupling constant (Hz). Data for $^{13}C$ NMR are reported in terms of chemical shift (S, ppm). Infrared spectra were recorded using a Thermo Nicolet iS 10 FT-IR spectrometer with a Smart iTX Accessory (diamond ATR) and are reported in frequency of absorption (v, $cm^{1}$). Liquid chromatography-mass spectrometry (LC-MS) was performed using a Waters LC-MS with an ACQUITY Arc QDa detector.

Chemistry

Procedure A

In some embodiments, intermediates used in the preparation of compounds described herein are prepared as outlined in Scheme 1.

Scheme 1

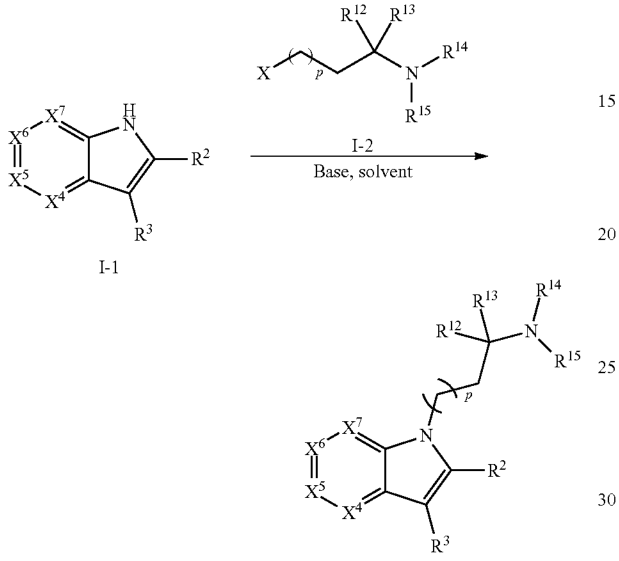

I-1

I-3

In Scheme 1, $X^4$-$X^7$, p, $R^2$, $R^3$, $R^{12}$, $R^{13}$, $R^{14}$ and $R^{15}$ are as described herein. In some embodiments, X is halo or a sulfone. In some embodiments, halo is iodo, bromo, or chloro. In some embodiments, halo is chloro. In some embodiments, the sulfone is a tosylate, a nosylate, a brosylate, or a mesylate. In some embodiments, X is chloro.

In some embodiments, indole I-1 is reacted with I-2 under suitable condensation reaction conditions, optionally, followed by suitable salt formation conditions to provide I-3. In some embodiments, suitable condensation reaction conditions include an appropriate base, an appropriate additive, an appropriate solvent, for an appropriate time at an appropriate temperature. In some embodiments, the appropriate base is a hydroxide base, a carbonate base, or a bicarbonate base. In some embodiments, the appropriate base is a hydroxide base or a hydride base. In some embodiments, the appropriate hydroxide base is sodium hydroxide or potassium hydroxide. In some embodiments, the appropriate hydroxide base is potassium hydroxide. In some embodiments, the appropriate hydride base is sodium hydride. In some embodiments, the appropriate additive is a salt. In some embodiments, the salt is potassium iodide, sodium iodide, or lithium iodide. In some embodiments, the appropriate salt is potassium iodide. In some embodiments, the appropriate solvent is a polar aprotic solvent. In some embodiments, the polar aprotic solvent is dichloromethane (DCM), tetrahydrofuran (THF), ethyl acetate (EtOAc), acetone, dimethylformamide (DMF), or acetonitrile (MeCN). In some embodiments, the polar aprotic solvent is DMSO, DMF, MeCN, or acetone. In some embodiments, the polar aprotic solvent is DMSO. In some embodiments, the appropriate time and appropriate temperature are overnight and about 25° C.

In some embodiments, the appropriate salt formation conditions include an appropriate acid in an appropriate solvent at an appropriate temperature for an appropriate time. In some embodiments, the appropriate acid is a carboxylic acid. In some embodiments, the carboxylic acid is fumaric acid. In some embodiments, the appropriate solvent is acetone. In some embodiments, the appropriate time and temperature are 5 minutes to 1 hour and 55° C.

For example, to a solution of respective indole or related heterocycle in DMSO (0.4 M) was added 2-chloro-N,N-dimethylethylamine hydrochloride (1.1 equiv), potassium iodide (1.1 equiv), and potassium hydroxide pellets (5.0 equiv). The reaction was stirred at room temperature for 24 h before being diluted with 1.0 M NaOH(aq). The aqueous phase was extracted three times with DCM. The organic extracts were combined, dried over $Na_2SO_4$, filtered, and concentrated under reduced pressure to yield an oil. The unpurified oil was dissolved in a minimal amount of acetone and added dropwise to a boiling solution of fumaric acid (1.0 equiv) in acetone. In most cases, a precipitate formed immediately, which was stored at −20° C. overnight. The resulting crystals were filtered and washed with several portions of ice-cold acetone to yield the desired product. In cases where the desired product did not readily crystalize as the fumarate salt, the oil was subjected to column chromatography (9:1 $CH_2Cl_2$:MeOH:1% $NH_4OH$(aq)) unless noted otherwise.

Procedure B

In some embodiments, intermediates used in the preparation of compounds described herein are prepared as outlined in Scheme 2A.

Scheme 2A

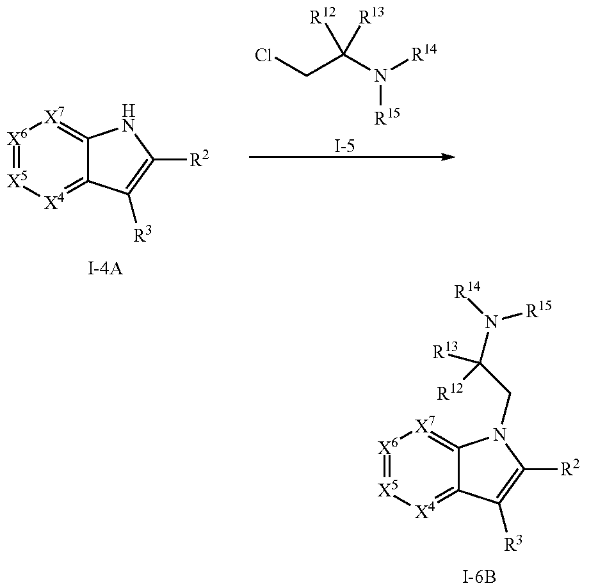

I-4A

I-6B

In Scheme 2A, $X^4$—$X^7$, $R^2$, $R^3$, $R^{12}$, $R^{13}$, $R^{14}$ and $R^{15}$ are as described herein.

In some embodiments, intermediates used in the preparation of compounds described herein are prepared as outlined in Scheme 2B.

Scheme 2B

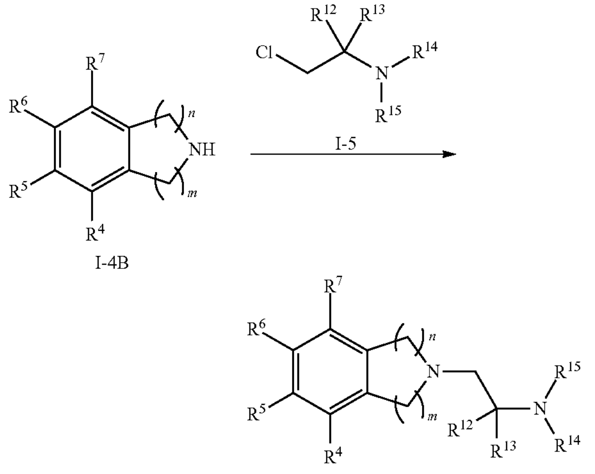

I-4B

I-6B

In Scheme 2B, $R^4$-$R^7$, n, m, $R^{12}$, $R^{13}$, $R^{14}$ and $R^{15}$ are as described herein.

General procedure-1 (B1): To a stirred solution of I-4A or I-4B (1.0 eq) in DMF (10 vol) was added NaH (60% in mineral oil, 1.2 eq) at 0° C. The reaction mixture was stirred for 20 min at 0° C. To the resultant reaction mixture were added reagent I-5 (1.0 eq) followed by NaI (Cat.). The reaction was slowly warmed to room temperature and stirred for 16 h. The progress of the reaction was monitored by TLC.

General procedure-2 (B2): To a stirred solution of I-4A or I-4B (1.0 eq) in DMF (10 vol) was added NaH (60% in mineral oil, 1.2 eq) at 0° C. The reaction mixture was stirred for 20 min at 0° C. To the resultant reaction mixture were added reagent I-5 (1.0 eq) followed by NaI (Cat.). The reaction mixture was slowly warmed to room temperature and stirred at 60 to 65° C. for 16 h. The progress of the reaction was monitored by TLC.

General procedure-3 (B3): To a stirred solution of I-4A or I-4B (1.0 eq) in DMF (10 vol) were added $K_2CO_3$ (3.0 eq) followed by reagent I-5 (2.0 eq) and NaI (1.0 eq) at room temperature and then the contents were heated at 70° C. for 16 h. The progress of the reaction was monitored by TLC.

General Work up/purification procedure-B1: The reaction was diluted and quenched with ice cold water. A 2N HCl solution was added until the pH of the solution was 2. The resultant aqueous layer was washed with EtOAc until the unreacted starting material was totally removed (TLC). The aqueous layer was then basified with aq. $NaHCO_3$ solution and extracted with EtOAc. The combined organic layer was washed with water, followed by brine solution and then dried over anhydrous $Na_2SO_4$ and concentrated to get the expected product which was sufficiently pure (>95% LC-MS and HPLC purity).

General Work up/purification procedure-B2: The Reaction mixture was quenched with ice cold water and extracted with ethyl acetate. The combined organic layer was washed with ice cold water followed by brine wash. The organic layer was separated, dried over $Na_2SO_4$ and concentrated under reduced pressure to get crude material which was purified by combi-flash chromatography using either EtOAc/Heptane or $CH_2Cl_2$/MeOH gradients based on the polarity of the compounds. The pure fractions were evaporated and dried to get the compounds with >95% LC-MS and HPLC purity.

Preparation of 1-chloro-N,N,2-trimethylpropan-2-amine (I-13)

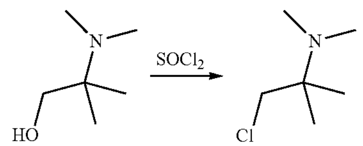

I-12 I-13

To a solution of intermediate I-12 (1.0 eq.) in $CHCl_3$ (10 vol) was added $SOCl_2$ (5 vol) at 0° C. and the reaction mixture was stirred under reflux for 12 hours. The crude reaction mixture was cooled to room temperature, dried by evaporation in vacuo and then by azeotropic co-evaporation with toluene (2×). The crude intermediate I-13 was used directly in the N-alkylation step without further purification.

Preparation of 1-(chloromethyl)-N,N-dimethylcyclopropan-1-amine (I-14)

I-14

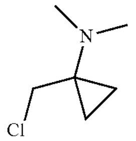

Intermediate I-14 was prepared as described for intermediate I-13 but using (1-(dimethylamino)cyclopropyl)methanol as the starting material.

Preparation of 7-fluoro-5-methoxy-1H-indole (I-15)

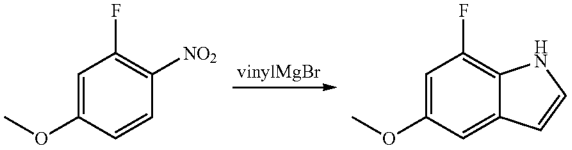

I-15

To a solution of 2-fluoro-4-methoxy-1-nitrobenzene (5 g, 29.2 mmol, 1.0 eq.) in THF (50 mL) was added vinyl magnesium bromide (1.0M in THF, 117 mL, 117 mmol, 4.0 eq.) at −40° C., the reaction mixture was allowed to warm slowly to room temperature and stirred for additional 2 hours. Saturated aq. $NH_4Cl$ solution (150 mL) was added carefully and extracted with ethyl acetate (2×150 mL). The combined organic layers were washed with ice cold water and aqueous solution of NaCl, the combined organic layers were dried over anhydrous $Na_2SO_4$, solids were removed by filtration and the filtrate was concentrated in vacuo to provide crude reaction product that was purified by silica-gel chromatography (5% EtOAc in hexane) to provide intermediate I-15. Yield: 190 mg, 4%, pale brown syrup; m/z=166.1 $[M+H]^+$; $^1H$ NMR (400 MHz, DMSO-d6) δ=11.37 (br s, 1H), 7.34 (t, J=2.8 Hz, 1H), 6.88 (d, J=1.8 Hz, 1H), 6.60 (dd, J=12.8, 2.0 Hz, 1H), 6.46-6.37 (m, 1H), 3.77-3.73 (m, 3H).

Preparation of 1-(2-chloro-5H-pyrrolo[3,2-d]pyrimidin-5-yl)-N,N,2-trimethylpropan-2-amine (I-16)

I-16

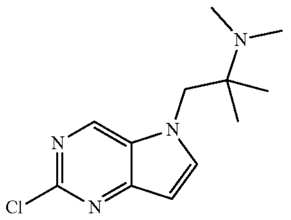

Intermediate I-16 was prepared as described for 1-(5-methoxy-1H-indol-1-yl)-N,N,2-trimethylpropan-2-amine but using 2-chloro-5H-pyrrolo[3,2-d]pyrimidine as the starting material. Yield: 200 mg, 49%, pale yellow semi solid; m/z=253.1 $[M+H]^+$; $^1H$ NMR (400 MHz, DMSO-d6) S=9.04 (d, J=0.8 Hz, 1H), 7.89 (d, J=3.1 Hz, 1H), 6.60-6.56 (m, 1H), 4.25 (s, 2H), 2.23 (s, 6H), 0.89 (s, 6H).

Preparation of 5-methoxy-1-tosyl-1H-indole (I-17)

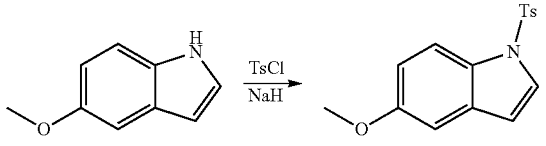

I-17

To a solution of 5-methoxyindole (1 g, 6.80 mmol, 1.0 eq.) in DMF (10 mL) was added NaH (60% in mineral oil, 408 mg, 10.18 mmol, 1.5 eq.) at 0° C. and the reaction mixture was stirred for 20 min. To the reaction mixture was added tosyl chloride (1.94 g, 4.69 mmol, 1.0 eq.) and the reaction mixture was allowed to warm slowly to room temperature and stirred for additional 16 hours. The reaction mixture was diluted with ice cold water, extracted with ethyl acetate (2×10 mL), the combined organic layers were washed with ice cold water and aqueous solution of NaCl, dried over anhydrous $Na_2SO_4$, solids were removed by filtration and the filtrate was concentrated in vacuo to provide the crude intermediate I-17. Yield: 2.1 g, off-white solid that was used in the next step without further purification. m/z=302.0 $[M+H]^+$; 1H NMR (CDCl3, 500 MHz) d=7.88 (d, J=8.79 Hz, 1H), 7.74 (br d, J=7.69 Hz, 2H), 7.52 (d, J=3.84 Hz, 1H), 7.21 (br d, J=8.24 Hz, 2H), 6.97 (s, 1H), 6.91-6.94 (m, 1H), 6.59 (d, J=3.29 Hz, 1H), 3.81 (s, 3H), 2.34 (s, 3H).

Preparation of (1s,3s)-3-(dimethylamino)cyclobutyl 4-methylbenzenesulfonate (I-18)

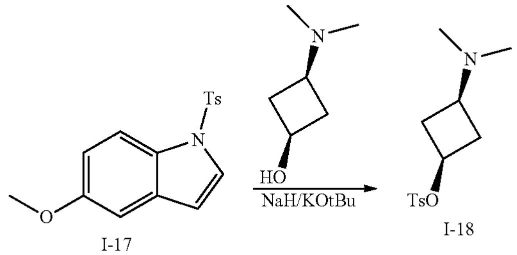

I-17 I-18

To a solution of (1s,3s)-3-(dimethylamino)cyclobutan-1-ol (194 mg, 1.69 mmol, 1.0 eq.) in THE (5 mL) were added activated 4 Å molecular sieves powder (500 mg) followed by KOtBu (380 mg, 3.39 mmol, 2.0 eq.) at room temperature and the reaction mixture was stirred for 1 hour. To the reaction mixture was added intermediate I-17 (510 mg, 1.69 mmol, 1.0 eq.) at room temperature and the reaction mixture was stirred for additional 16 hours. The reaction mixture was diluted with water and extracted with ethyl acetate (2×10 mL). The combined organic layers were washed with ice cold water and aqueous solution of NaCl, dried over anhydrous $Na_2SO_4$, solids were removed by filtration and the filtrate was concentrated in vacuo to provide the crude reaction product that was purified by silica-gel chromatography to afford intermediate I-18. Yield: 280 mg, m/z=270.1. $[M+H]^+$.

Preparation of tert-butyl (R)-2-methylaziridine-1-carboxylate (I-19)

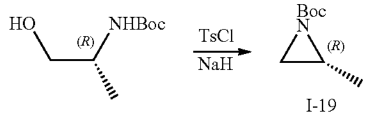

I-19

To a solution of tert-butyl (R)-(1-hydroxypropan-2-yl) carbamate (20 g, 114.28 mmol, 1.0 eq.) in dry diethylether (200 mL) was added tosyl chloride (26.15 g, 137.14 mmol, 1.2 eq.) followed by powdered KOH (25.6 g, 457.14 mmol, 4.0 eq.) at room temperature under an argon atmosphere and the reaction mixture was stirred under reflux for 4 hours. The reaction mixture was allowed to cool to room temperature and poured into ice cold water (200 mL). The ether layer was washed with brine solution (100 mL), the separated organic layer was dried over anhydrous $Na_2SO_4$, solids were removed by filtration and the filtrate was concentrated in vacuo to provide the crude reaction product that was purified by silica-gel chromatography (2% EtOAc/hexane) to afford intermediate I-19. Yield: 10 g, 55%, pale brown liquid). $^1H$ NMR (CDCl3, 400 MHz) δ=2.44 (dt, J=5.6, 3.9 Hz, 1H), 2.24 (d, J=5.9 Hz, 1H), 1.88 (d, J=3.8 Hz, 1H), 1.46 (s, 9H), 1.27 (d, J=5.5 Hz, 3H).

Preparation of tert-butyl (R)-(1-(7H-pyrrolo[2,3-d]pyrimidin-7-yl)propan-2-yl)carbamate (I 20)

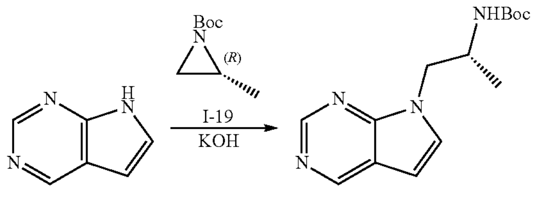

I-20

To a solution of 7H-pyrrolo[2,3-d]pyrimidine (200 mg, 1.68 mmol, 1.0 eq.) in DMSO (2 mL) in a sealed tube was added intermediate I-19 (316 mg, 2.01 mmol, 1.2 eq.) followed by powdered KOH (18.8 mg, 0.33 mmol, 0.2 eq.) at room temperature under an argon atmosphere and the reaction mixture was stirred at 40° C. for 16 hours. The reaction mixture was allowed to cool to room temperature, diluted with water (10 mL) and extracted with ethyl acetate (2×10 mL). The combined organic layers were washed with a brine solution (10 mL), dried over anhydrous $Na_2SO_4$, solids were removed by filtration and the filtrate was concentrated in vacuo to provide the crude reaction product that was purified by silica-gel chromatography (2% MeOH/$CH_2Cl_2$) to afford intermediate I-20. Yield: 160 mg, 34%, pale brown solid; m/z=277.2 $[M+H]^+$; $^1H$ NMR (DMSO-d6, 400 MHz) δ=8.96 (s, 1H), 8.77 (s, 1H), 7.52 (br d, J=3.1 Hz, 1H), 6.86 (br d, J=8.3 Hz, 1H), 6.59 (d, J=3.5 Hz, 1H), 4.30 (br dd, J=5.2, 13.6 Hz, 1H), 4.11 (br s, 1H), 3.94 (br d, J=6.4 Hz, 1H), 1.29-1.13 (m, 9H), 1.13-0.93 (m, 3H).

Preparation of tert-butyl (R)-(1-(5-methoxy-1H-pyrrolo[3,2-b]pyridin-1-yl)propan-2-yl)carbamate (I-21)

I-21

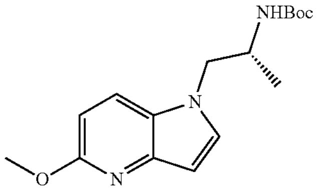

Intermediate I-21 was prepared as described for intermediate I-20 but using 5-methoxy-1H-pyrrolo[3,2-b]pyridine as the starting material. Yield: 900 mg, 43%, pale brown solid; m/z=306.2 $[M+H]^+$; $^1H$ NMR (400 MHz, DMSO-d6) δ=7.84 (d, J=8.8 Hz, 1H), 7.42 (d, J=2.8 Hz, 1H), 6.87 (br d, J=7.9 Hz, 1H), 6.58 (d, J=8.7 Hz, 1H), 6.36 (d, J=2.9 Hz, 1H), 4.07 (br d, J=6.4 Hz, 2H), 3.84-3.72 (m, 4H), 1.45-1.15 (m, 8H), 1.01 (br d, J=6.7 Hz, 3H).

Preparation of tert-butyl (R)-(1-(5-methoxy-1H-pyrrolo[2,3-c]pyridin-1-yl)propan-2-yl)carbamate (I-22)

I-22

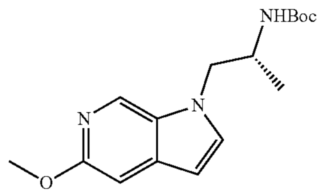

Intermediate I-22 was prepared as described for intermediate I-20 but using 5-methoxy-1H-pyrrolo[2,3-c]pyridine as the starting material. Yield: 200 mg, 48%, pale brown solid; m/z=306.2 $[M+H]^+$; $^1H$ NMR (DMSO-d6, 400 MHz) δ=8.48 (s, 1H), 7.46 (br s, 1H), 6.90 (br d, J=7.3 Hz, 1H), 6.82 (s, 1H), 6.31 (d, J=2.7 Hz, 1H), 4.19-4.06 (m, 2H), 3.82 (s, 4H), 1.34-1.18 (m, 9H), 1.04 (br d, J=6.5 Hz, 3H).

Preparation of tert-butyl (R)-(1-(5-methoxy-1H-pyrrolo[2,3-b]pyridin-1-yl)propan-2-yl)carbamate (I-23)

I-23

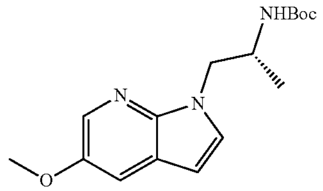

Intermediate I-23 was prepared as described for intermediate I-20 but using 5-methoxy-1H-pyrrolo[2,3-b]pyridine as the starting material. Yield: 1.5 g, 72%, pale brown semi-solid; m/z=306.1 $[M+H]^+$; $^1H$ NMR (400 MHz, DMSO-d6) δ=7.98 (d, J=2.7 Hz, 1H), 7.53 (d, J=2.7 Hz, 1H), 7.40 (br d, J=3.1 Hz, 1H), 6.89 (br d, J=8.3 Hz, 1H), 6.35 (d, J=3.4 Hz, 1H), 4.24 (dd, J=13.6, 5.9 Hz, 1H), 4.13-4.00 (m, 1H), 3.97-3.85 (m, 1H), 3.83-3.77 (m, 3H), 1.30 (s, 7H), 1.10-0.93 (m, 4H).

Preparation of tert-butyl (R)-(1-(1H-pyrrolo[3,2-c]pyridin-1-yl)propan-2-yl)carbamate (I-24)

I-24

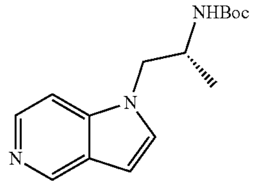

Intermediate I-24 was prepared as described for intermediate I-20 but using 1H-pyrrolo[3,2-c]pyridine as the starting material. Yield: 1.5 g, 64%, pale brown semi solid; m/z=276.1 $[M+H]^+$; $^1H$ NMR (400 MHz, DMSO-d6)

δ=8.78 (s, 1H), 8.21-8.14 (m, 1H), 7.50 (d, J=5.7 Hz, 1H), 7.43-7.34 (m, 1H), 6.95-6.81 (m, 1H), 6.59-6.53 (m, 1H), 4.24-4.05 (m, 2H), 3.83 (quind, J=13.4, 6.8 Hz, 1H), 1.25 (s, 8H), 1.04 (br d, J=6.6 Hz, 3H).

Preparation of 2,2-dimethyl-1-tosylaziridine (I-25)

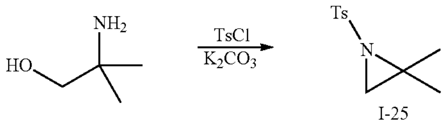

I-25

To a solution of 2-amino-2-methylpropan-1-ol (4 g, 44.9 mmol, 1.0 eq.) in $CH_2Cl_2$ (80 mL) was added $K_2CO_3$ (18.5 g, 134.8 mmol, 3.0 eq.) and the reaction mixture was stirred for 20 minutes. To the reaction mixture was added tosyl chloride (25.69 g, 134.8 mmol, 1.0 eq.) at 0° C., the reaction mixture was allowed to warm slowly to room temperature and stirred for 16 hours. The reaction mixture was washed with a saturated aqueous solution of $NaHCO_3$ and extracted with ethyl acetate (2×100 mL). The combined organic layers were washed with ice cold water and aqueous solution of NaCl, dried over anhydrous $Na_2SO_4$, solids were removed by filtration and the filtrate was concentrated in vacuo to provide the crude reaction product that was purified by silica-gel chromatography (2% MeOH in $CH_2Cl_2$) to afford intermediate I-25. Yield: 3.5 g, 35%, off-white solid; m/z=226.1 $[M+H]^+$; $^1$H NMR (400 MHz, DMSO-d6) δ=7.78-7.75 (m, 1H), 7.75-7.73 (m, 1H), 7.43 (d, J=8.0 Hz, 2H), 2.46 (s, 2H), 2.40 (s, 3H), 1.45-1.43 (m, 6H).

Preparation of N-(1-(5-fluoro-3-methyl-1H-indol-1-yl)-2-methylpropan-2-yl)-4-methylbenzenesulfonamide (I-26)

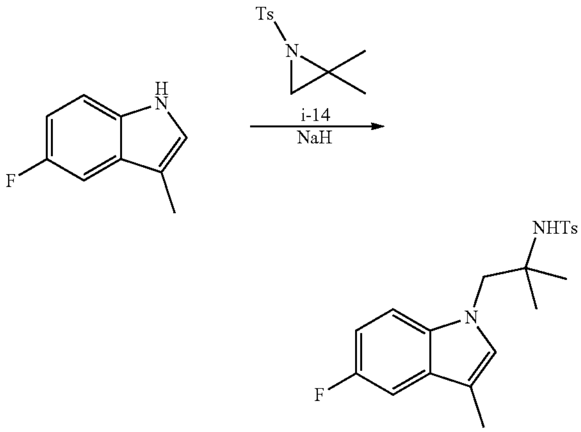

I-26

To a solution of 5-fluoro-3-methyl-1H-indole (300 mg, 2.01 mmol, 1.0 eq.) in DMF (3 mL) was added NaH (60% in mineral oil, 120 mg, 3.02 mmol, 1.5 eq.) at 0° C. and the reaction mixture was stirred for 20 minutes. To the reaction mixture was added intermediate I-14 (906 mg, 4.02 mmol, 2.0 eq.), the reaction mixture was allowed to warm slowly to room temperature and stirred for 16 hours. The reaction mixture was diluted with ice cold water and extracted with ethyl acetate (2×5 mL). The combined organic layers were washed with ice cold water and aqueous solution of NaCl, dried over anhydrous $Na_2SO_4$, solids were removed by filtration and the filtrate was concentrated in vacuo to provide the crude reaction product that was purified by silica-gel chromatography (2% MeOH in $CH_2Cl_2$) to afford intermediate I-26. Yield: 400 mg, 53%, off-white solid; m/z=373.1 $[M-H]^+$; $^1$H NMR (400 MHz, DMSO-d6) δ=7.70-7.60 (m, 3H), 7.50 (dd, J=8.9, 4.4 Hz, 1H), 7.32 (d, J=8.0 Hz, 2H), 7.27-7.17 (m, 2H), 6.94 (dt, J=9, 2, 2.5 Hz, 1H), 4.15 (s, 2H), 2.38-2.33 (m, 3H), 2.26-2.16 (m, 3H), 1.07-0.91 (m, 6H).

Preparation of N-(1-(4,5-difluoro-1H-indol-1-yl)-2-methylpropan-2-yl)-4-methylbenzenesulfonamide (I-27)

I-27

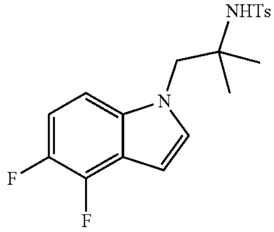

Intermediate I-27 was prepared as described for intermediate I-26 but using 4,5-di-fluoro-1H-indole as the starting material. Yield: 400 mg, 57%, off-white solid; m/z=377.0 $[M-H]^+$; $^1$H NMR (400 MHz, DMSO-d6) δ=7.78-7.73 (m, 1H), 7.69 (s, 1H), 7.66-7.61 (m, 2H), 7.53-7.49 (m, 1H), 7.47-7.40 (m, 2H), 7.34-7.29 (m, 2H), 7.16 (td, J=11.1, 8.4 Hz, 1H), 6.60 (d, J=3.0 Hz, 1H), 4.25 (s, 2H), 2.45-2.37 (m, 1H), 2.37-2.32 (m, 3H), 1.44 (s, 2H), 1.01 (s, 6H).

Preparation N-(1-(5-methoxy-1H-indol-1-yl)-2-methylpropan-2-yl)-4-methylbenzenesulfonamide (I-28)

I-28

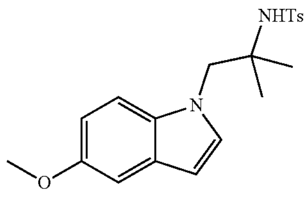

Intermediate I-28 was prepared as described for intermediate I-26 but using 5-methoxy-1H-indole as the starting material. Yield: 500 mg, 65%, off-white solid; m/z=373.0 $[M+H]^+$; $^1$H NMR (400 MHz, DMSO-d6) δ=7.78-7.73 (m, 1H), 7.66 (d, J=8.4 Hz, 3H), 7.47-7.38 (m, 2H), 7.38-7.28 (m, 3H), 7.03 (d, J=2.4 Hz, 1H), 6.75 (dd, J=8.9, 2.4 Hz, 1H), 6.37 (d, J=2.9 Hz, 1H), 4.18 (s, 2H), 3.75 (s, 3H), 2.47-2.40 (m, 2H), 2.36 (s, 3H), 1.47-1.41 (m, 2H), 1.00 (s, 6H).

Example 1. 1-(5-methoxy-1H-indol-1-yl)-N,N,2-trimethylpropan-2-amine

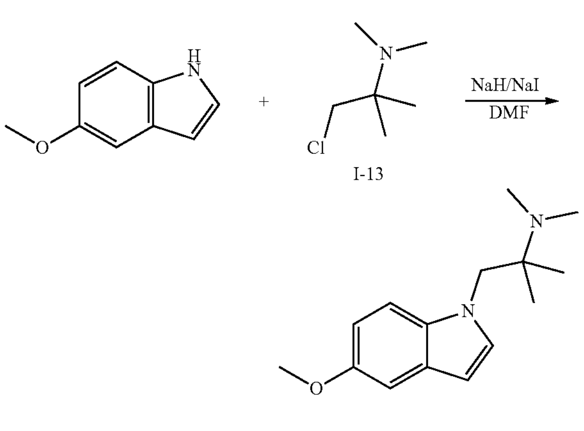

I-13

To a solution of 5-methoxy-indole (1.2 g, 8.16 mmol, 1.0 eq.) in DMF (12 mL) was added NaH (60% in mineral oil, 488 mg, 12.2 mmol, 1.5 eq.) at 0° C. and the reaction mixture was stirred for 20 minutes. Intermediate I-13 (1.1 g, 8.16 mmol, 1.0 eq.) was added followed by a catalytic amount of NaI, the reaction mixture was allowed to warm slowly to room temperature and then stirred at 65-70° C. for additional 16 hours. The crude reaction mixture was allowed to cool to room temperature, diluted with ice cold water and extracted with ethyl acetate (2×20 mL). The combined organic layers were washed with ice cold water and aqueous solution of NaCl. The combined organic layers were dried over anhydrous $Na_2SO_4$, solids were removed by filtration and the filtrate was concentrated in vacuo to provide a crude reaction product that was purified by silica-gel chromatography (2% MeOH in $CH_2Cl_2$) to afford 1-(5-methoxy-1H-indol-1-yl)-N,N,2-trimethylpropan-2-amine. Yield: 200 mg, 20%, brown liquid; LC-MS: 97.7%, m/z=247.1 $[M+H]^+$; H NMR (DMSO-d6, 400 MHz) δ=7.39 (d, J=8.93 Hz, 1H), 7.27 (d, J=3.06 Hz, 1H), 7.01 (d, J=2.45 Hz, 1H), 6.73 (dd, J=2.45, 8.93 Hz, 1H), 6.31 (dd, J=0.61, 3.06 Hz, 1H), 4.06 (s, 2H), 3.74 (s, 3H), 2.25 (s, 6H), 0.90 (s, 6H).

Example 2. 1-((5-methoxy-1H-indol-1-yl)methyl)-N,N-dimethylcyclopropan-1-amine

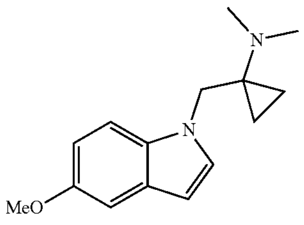 [SMILES: COc1ccc2c(ccn2CC2(N(C)C)CC2)c1]

1-((5-methoxy-1H-indol-1-yl)methyl)-N,N-dimethylcyclopropan-1-amine was prepared as described for 1-(5-methoxy-1H-indol-1-yl)-N,N,2-trimethylpropan-2-amine but using intermediate I-14 as the starting material. Yield: 65 mg, 13%, brown liquid; LC-MS: 99.8%, m/z=245.2 $[M+H]^+$; $^1H$ NMR (DMSO-d6, 400 MHz) d=7.32-7.41 (m, 2H), 7.02 (d, J=2.32 Hz, 1H), 6.78 (dd, J=2.38, 8.86 Hz, 1H), 6.34 (d, J=2.93 Hz, 1H), 4.24 (s, 2H), 3.74 (s, 3H), 2.14 (s, 6H), 0.54 (s, 4H).

Example 3. 2-(5-methoxy-1H-pyrrolo[3,2-b]pyridin-1-yl)-N,N-dimethylethan-1-amine

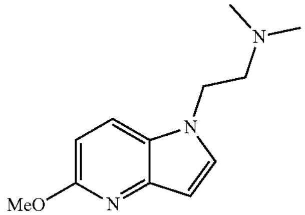 [SMILES: COc1ccc2c(ccn2CCN(C)C)n1]

2-(5-methoxy-1H-pyrrolo[3,2-b]pyridin-1-yl)-N,N-dimethylethan-1-amine was prepared as described for 1-(5-methoxy-1H-indol-1-yl)-N,N,2-trimethylpropan-2-amine but using 2-chloro-N,N-dimethylethan-1-aminium chloride as the starting material. Yield: 280 mg, 38%, brown liquid; LC-MS: 99.4%, m/z=220.2 $[M+H]^+$; $^1H$ NMR (DMSO-$d_6$, 400 MHz): δ 7.83-7.86 (m, 1H), 7.51 (d, J=3.06 Hz, 1H), 6.56 (d, J=8.68 Hz, 1H), 6.36 (dd, J=0.73, 3.06 Hz, 1H), 4.22 (t, J=6.54 Hz, 2H), 3.84 (s, 3H), 2.57 (t, J=6.54 Hz, 2H), 2.16 (s, 6H).

Example 4. 2-(5-methoxy-1H-pyrrolo[2,3-c]pyridin-1-yl)-N,N-dimethylethan-1-amine

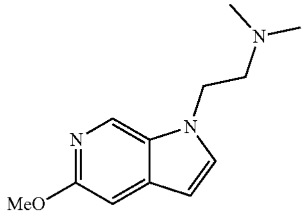 [SMILES: COc1cc2ccn(CCN(C)C)c2cn1]

2-(5-methoxy-1H-pyrrolo[2,3-c]pyridin-1-yl)-N,N-dimethylethan-1-amine was prepared as described for 1-(5-methoxy-1H-indol-1-yl)-N,N,2-trimethylpropan-2-amine but using 5-methoxy-1H-pyrrolo[2,3-c]pyridine and 2-chloro-N,N-dimethylethan-1-aminium chloride as the starting materials. Yield: 500 mg, 45%, brown liquid; LC-MS: 98.8%, m/z=220.2 $[M+H]^+$; $^1H$ NMR (DMSO-$d_6$, 400 MHz): δ 8.46 (s, 1H), 7.56 (d, J=3.06 Hz, 1H), 6.83 (d, J=0.98 Hz, 1H), 6.31 (dd, J=0.67, 3.00 Hz, 1H), 4.25-4.29 (m, 2H), 3.83 (s, 3H), 2.61 (t, J=6.42 Hz, 2H), 2.17 (s, 6H).

Example 5. 2-(5-methoxy-1H-pyrrolo[2,3-b]pyridin-1-yl)-N,N-dimethylethan-1-amine

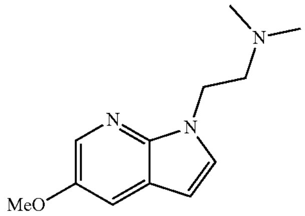 [SMILES: COc1cnc2c(ccn2CCN(C)C)c1]

2-(5-methoxy-1H-pyrrolo[2,3-b]pyridin-1-yl)-N,N-dimethylethan-1-amine was prepared as described for 1-(5-methoxy-1H-indol-1-yl)-N,N,2-trimethylpropan-2-amine but using 5-methoxy-1H-pyrrolo[2,3-b]pyridine and 2-chloro-N,N-dimethylethan-1-aminium chloride as the starting materials. Yield: 150 mg, 14%, colour-less liquid; LC-MS: 98.0%, m/z=220.2 $[M+H]^+$; $^1H$ NMR (DMSO-$d_6$, 400 MHz): δ 7.99 (d, J=2.69 Hz, 1H), 7.52 (dd, J=3.06, 6.72 Hz, 2H), 6.35 (d, J=3.42 Hz, 1H), 4.29 (t, J=6.60 Hz, 2H), 3.81 (s, 3H), 2.63 (t, J=6.60 Hz, 2H), 2.17 (s, 6H).

Example 6. N,N-dimethyl-2-(7H-pyrrolo[2,3-d]pyrimidin-7-yl)ethan-1-amine

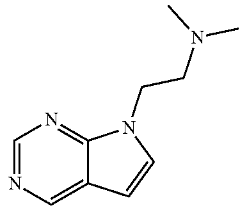

N,N-dimethyl-2-(7H-pyrrolo[2,3-d]pyrimidin-7-yl) ethan-1-amine was prepared as described for 1-(5-methoxy-1H-indol-1-yl)-N,N,2-trimethylpropan-2-amine but using 7H-pyrrolo[2,3-d]pyrimidine and 2-chloro-N,N-dimethyl-ethan-1-aminium chloride as the starting materials. Yield: 40 mg, 4%, colorless liquid; LC-MS: 98.0%, m/z=191.2 $[M+H]^+$; $^1H$ NMR (DMSO-d6, 400 MHz) δ=8.97 (s, 1H), 8.77 (s, 1H), 7.66 (d, J=3.55 Hz, 1H), 6.60 (d, J=3.55 Hz, 1H), 4.34 (t, J=6.42 Hz, 2H), 2.66 (t, J=6.42 Hz, 2H), 2.17 (s, 6H).

Example 7. N,N-dimethyl-2-(1H-pyrrolo[3,2-c]pyridin-1-yl)ethan-1-amine

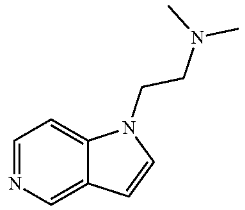

S N,N-dimethyl-2-(1H-pyrrolo[3,2-c]pyridin-1-yl)ethan-1-amine was prepared as described for 1-(5-methoxy-1H-indol-1-yl)-N,N,2-trimethylpropan-2-amine but using 1H-pyrrolo[3,2-c]pyridine and 2-chloro-N,N-dimethyl-ethan-1-aminium chloride as the starting materials. Yield: 120 mg, 10%, colour-less liquid; LC-MS: 99.2%, m/z=190.2 $[M+H]^+$; $^1H$ NMR (DMSO-$d_6$, 400 MHz): δ 8.80 (s, 1H), 8.18 (d, J=5.75 Hz, 1H), 7.48-7.53 (m, 2H), 6.56-6.60 (m, 1H), 4.26-4.30 (m, 2H), 2.62 (t, J=6.48 Hz, 2H), 2.18 (s, 6H).

Example 8. 2-(5-methoxyindolin-1-yl)-N,N-dimethylethan-1-amine

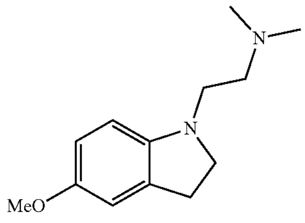 [SMILES: COc1ccc2c(c1)CCN2CCN(C)C]

2-(5-methoxyindolin-1-yl)-N,N-dimethylethan-1-amine was prepared as described for 1-(5-methoxy-1H-indol-1-yl)-N,N,2-trimethylpropan-2-amine but using 5-methoxyindoline and 2-chloro-N,N-dimethylethan-1-aminium chloride as the starting materials. Yield: 400 mg, 40%, colour-less liquid; LC-MS: 99.8%, m/z=221.2 $[M+H]^+$; $^1H$ NMR (DMSO-$d_6$, 400 MHz): δ 6.67-6.71 (m, 1H), 6.57 (dd, J=2.57, 8.44 Hz, 1H), 6.42 (d, J=8.44 Hz, 1H), 3.64 (s, 3H), 3.24 (t, J=8.19 Hz, 2H), 3.00-3.05 (m, 2H), 2.78-2.84 (m, 2H), 2.43 (t, J=7.09 Hz, 2H), 2.19 (s, 6H).

Example 9. 2-(6-methoxy-3,4-dihydroquinolin-1(2H)-yl)-N,N-dimethylethan-1-amine

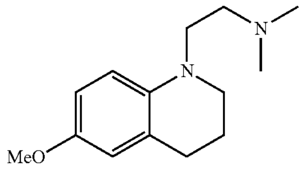 [SMILES: COc1ccc2c(c1)CCCN2CCN(C)C]

Method 1: Synthesized according to Procedure B. Yield: 15% (brown semi-solid). LC-MS: 99.2%, m/z=235.1 $[M+H]^+$; $^1H$ NMR (DMSO-$d_6$, 400 MHz): δ 6.57-6.61 (m, 1H), 6.47-6.52 (m, 2H), 3.62 (s, 3H), 3.24-3.28 (m, 2H), 3.16-3.20 (m, 2H), 2.62-2.66 (m, 2H), 2.35-2.41 (m, 2H), 2.18-2.20 (m, 6H), 1.78-1.84 (m, 2H).

Method 2: To a solution of 6-methoxy-1,2,3,4-tetrahydroquinoline, 750 mg, 4.59 mmol, 1.0 eq,) in DMF (7.5 mL) was added $K_2CO_3$ (1.9 g, 13.78 mmol, 3.0 eq.) followed by 2-chloro-N,N-dimethylethan-1-aminium chloride (1.32 g, 9.18 mmol, 2.0 eq.) and NaI (688 mg, 4.59 mmol, 1.0 eq.) at room temperature and the reaction mixture was stirred at 70° C. for 16 hours. The reaction mixture was allowed to cool to room temperature, diluted with ice cold water and extracted with ethyl acetate (2×15 mL). The combined organic layers were washed with ice cold water and aqueous solution of NaCl, dried over anhydrous $Na_2SO_4$, solids were removed by filtration and the filtrate was concentrated in vacuo to provide the crude reaction product that was purified by silica-gel chromatography (2% MeOH in $CH_2Cl_2$) to afford 2-(6-methoxy-3,4-dihydroquinolin-1(2H)-yl)-N,N-dimethylethan-1-amine Yield: 90 mg, 9%, brown semi solid; m/z=235.1 $[M+H]^+$; $^1H$ NMR (DMSO-d6, 400 MHz) δ=6.57-6.61 (m, 1H), 6.47-6.52 (m, 2H), 3.62 (s, 3H), 3.24-3.28 (m, 2H), 3.16-3.20 (m, 2H), 2.62-2.66 (m, 2H), 2.35-2.41 (m, 2H), 2.18-2.20 (m, 6H), 1.78-1.84 (m, 2H).

Example 10. 2-(5-methoxyisoindolin-2-yl)-N,N-dimethylethan-1-amine

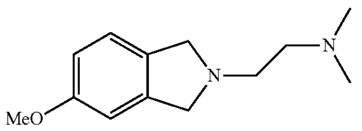 [SMILES: COc1ccc2c(c1)CN(CCN(C)C)C2]

2-(5-methoxyisoindolin-2-yl)-N,N-dimethylethan-1-amine was prepared as described for 2-(6-methoxy-3,4-dihydroquinolin-1(2H)-yl)-N,N-dimethylethan-1-amine but using 5-methoxyisoindoline and 2-chloro-N,N-dimethylethan-1-aminium chloride as the starting materials. Yield: 34 mg, 4%, brown semi solid; m/z=265.1 $[M+H]^+$; $^1H$ NMR (400 MHz, DMSO-d6) δ=7.23 (dd, J=8.1, 5.6 Hz, 1H), 6.95-6.89 (m, 1H), 6.86 (dd, J=8.3, 2.2 Hz, 1H), 4.63-4.50 (m, 4H), 4.16 (t, J=5.7 Hz, 2H), 3.77-3.70 (m, 3H), 2.63-2.53 (m, 2H), 2.29-2.20 (m, 6H).

Example 11. 2-(6-methoxy-3,4-dihydroisoguinolin-2(1H)-yl)-N,N-dimethylethan-1-amine

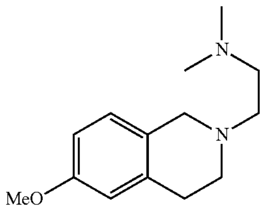 [SMILES: COc1ccc2c(c1)CCN(CCN(C)C)C2]

2-(6-methoxy-3,4-dihydroisoquinolin-2(1H)-yl)-N,N-dimethylethan-1-amine was prepared as described for 2-(6-methoxy-3,4-dihydroquinolin-1(2H)-yl)-N,N-dimethylethan-1-amine but using 6-methoxy-1,2,3,4-tetrahydroisoquinoline and 2-chloro-N,N-dimethylethan-1-aminium chloride as the starting materials. Yield: 65 mg, 6.5%, colorless semi solid; m/z=235.2 $[M+H]^+$; $^1H$ NMR (DMSO-d6, 400 MHz) δ=6.94 (d, J=8.44 Hz, 1H), 6.63-6.70 (m, 2H), 3.70 (s, 3H), 3.50 (s, 2H), 2.74-2.79 (m, 2H), 2.63-2.69 (m, 2H), 2.56 (br s, 4H), 2.25 (s, 6H).

Preparation of 1-(4,5-difluoro-1H-indol-1-yl)-N,N,2-trimethylpropan-2-amine (Example 12)

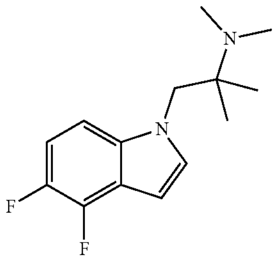 [SMILES: CN(C)C(C)(C)Cn1ccc2c(F)c(F)ccc21]

1-(4,5-difluoro-1H-indol-1-yl)-N,N,2-trimethylpropan-2-amine was prepared as described for 1-(5-methoxy-1H-indol-1-yl)-N,N,2-trimethylpropan-2-amine but using 4,5-difluoro-1H-indole as the starting material. Yield: 62 mg, 37%, pale yellow semi solid; m/z=253.1 $[M+H]^+$; $^1H$ NMR (400 MHz, DMSO-d6) δ=7.45-7.42 (m, 1H), 7.39 (dd, J=9.1, 3.4 Hz, 1H), 7.16-7.07 (m, 1H), 6.56-6.51 (m, 1H), 4.13 (s, 2H), 2.24 (s, 6H), 0.90 (s, 6H).

To a stirred solution of 1-(4,5-difluoro-1H-indol-1-yl)-N,N,2-trimethylpropan-2-amine (60 mg, 0.24 mmol, 1.0 eq) in MTBE (lml) was added maleic acid (29 mg, 0.21 mmol, 1.0 eq) and the reaction mixture was stirred at room temperature for 3 hours. Volatiles were removed in vacuo; the solid residue was washed with ether and dried in vacuo to afford the maleate salt of 1-(4,5-difluoro-1H-indol-1-yl)-N,N,2-trimethylpropan-2-amine. Yield: 40 mg, 45% as an off-white solid. $^1H$ NMR (400 MHz, DMSO-d6) δ=7.52 (d, J=3.3 Hz, 1H), 7.42 (dd, J=9.0, 3.3 Hz, 1H), 7.25 (td, J=11.0, 8.4 Hz, 1H), 6.68 (d, J=3.0 Hz, 1H), 6.05 (s, 2H), 4.51 (s, 2H), 2.87 (s, 6H), 1.23 (s, 6H).

Preparation of 1-(5-fluoro-3-methyl-1H-indol-1-yl)-N,N,2-trimethylpropan-2-amine (Example 13)

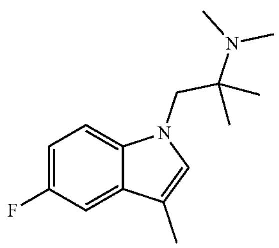 [SMILES: Cc1cn(CC(C)(C)N(C)C)c2ccc(F)cc12]

1-(5-fluoro-3-methyl-1H-indol-1-yl)-N,N,2-trimethylpropan-2-amine was prepared as described for 1-(5-methoxy-1H-indol-1-yl)-N,N,2-trimethylpropan-2-amine but using 5-fluoro-3-methyl-1H-indole as the starting material. Yield: 70 mg, 42%, pale yellow semi solid). m/z=249.2 $[M+H]^+$; $^1H$ NMR (400 MHz, $CDCl_3$) δ=7.21-7.14 (m, 2H), 6.97 (s, 1H), 6.91 (dt, J=9.1, 2.5 Hz, 1H), 4.05-3.98 (m, 2H), 2.39-2.35 (m, 6H), 2.27 (d, J=0.9 Hz, 3H), 1.02 (s, 6H).

The maleate salt of 1-(5-fluoro-3-methyl-1H-indol-1-yl)-N,N,2-trimethylpropan-2-amine was prepared as described for 1-(4,5-difluoro-1H-indol-1-yl)-N,N,2-trimethylpropan-2-amine. Yield: 60 mg as a white solid. $^1H$ NMR (400 MHz, DMSO-d6) δ=10.04-8.98 (m, 1H), 7.51 (dd, J=0.0. 4.3 Hz, 1H), 7.28 (dd, J=9.7, 2.4 Hz, 1H), 7.23 (s, 1H), 7.03 (br d, J=2.4 Hz, 1H), 6.03 (s, 2H), 4.40 (s, 2H), 2.85 (br s, 6H), 2.23 (s, 3H), 1.23 (s, 6H).

Preparation of 1-(5-fluoro-1H-indol-1-yl)-N,N,2-trimethylpropan-2-amine (Example 14)

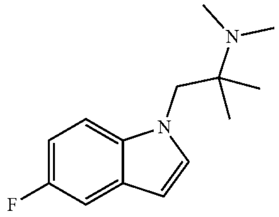 [SMILES: CN(C)C(C)(C)Cn1ccc2cc(F)ccc21]

1-(5-fluoro-1H-indol-1-yl)-N,N,2-trimethylpropan-2-amine was prepared as described for 1-(5-methoxy-1H-indol-1-yl)-N,N,2-trimethylpropan-2-amine but using 5-fluoro-1H-indole as the starting material. Yield: 350 mg, 40%, pale brown semi solid; m/z=235.1 $[M+H]^+$; $^1H$ NMR (400 MHz, DMSO-d6) δ=7.52 (dd, J=9.0, 4.5 Hz, 1H), 7.39 (d, J=3.1 Hz, 1H), 7.26 (dd, J=9.9, 2.6 Hz, 1H), 6.93 (dt, J=9.2, 2.6 Hz, 1H), 6.40 (d, J=2.6 Hz, 1H), 4.18-4.04 (m, 2H), 2.31-2.17 (m, 6H), 0.90 (s, 6H).

The maleate salt of 1-(5-fluoro-1H-indol-1-yl)-N,N,2-trimethylpropan-2-amine was prepared as described for 1-(4,5-difluoro-1H-indol-1-yl)-N,N,2-trimethylpropan-2-amine. Yield: 350 mg as an off-white solid. $^1H$ NMR (400 MHz, DMSO-d6) δ=10.28-9.13 (m, 1H), 7.57 (dd, J=9.0, 4.4 Hz, 1H), 7.46 (d, J=3.3 Hz, 1H), 7.34 (dd, J=9.8, 2.5 Hz, 1H), 7.05 (dt, J=9.2, 2.6 Hz, 1H), 6.53 (d, J=2.9 Hz, 1H), 6.04 (s, 2H), 4.48 (s, 2H), 2.86 (s, 6H), 1.22 (s, 6H).

Preparation of 1-(4-fluoro-5-methoxy-1H-indol-1-yl)-N,N,2-trimethylpropan-2-amine (Example 15)

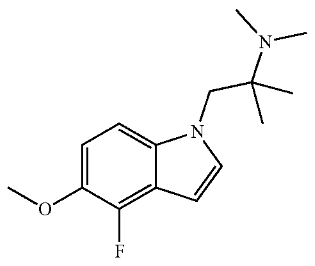

1-(4-fluoro-5-methoxy-1H-indol-1-yl)-N,N,2-trimethylpropan-2-amine was prepared as described for 1-(5-methoxy-1H-indol-1-yl)-N,N,2-trimethylpropan-2-amine but using 4-fluoro-5-methoxy-1H-indole as the starting material. Yield: 42 mg, 33%, pale yellow semi solid; m/z=265.1 $[M+H]^+$; $^1H$ NMR (400 MHz, DMSO-d6) δ=7.33 (d, J=3.3 Hz, 1H), 7.31-7.26 (m, 1H), 6.99 (t, J=8.6 Hz, 1H), 6.42-6.39 (m, 1H), 4.08 (s, 2H), 3.82 (s, 3H), 2.26-2.22 (m, 6H), 0.90 (s, 6H)

The maleate salt of 1-(4-fluoro-5-methoxy-1H-indol-1-yl)-N,N,2-trimethylpropan-2-amine was prepared as described for 1-(4,5-difluoro-1H-indol-1-yl)-N,N,2-trimethylpropan-2-amine. Yield: 28 mg as an off-white solid; $^1H$ NMR (400 MHz, DMSO-d6) δ=9.90-9.28 (m, 1H), 7.40 (d, J=3.3 Hz, 1H), 7.33 (d, J=8.9 Hz, 1H), 7.11 (s, 1H), 6.55 (d, J=3.0 Hz, 1H), 6.05 (s, 2H), 4.46 (s, 2H), 3.88-3.81 (m, 3H), 2.87 (s, 6H), 1.23 (s, 6H).

Preparation of 1-(6-fluoro-5-methoxy-1H-indol-1-yl)-N,N,2-trimethylpropan-2-amine (Example 16)

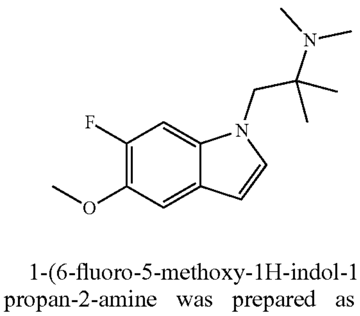

1-(6-fluoro-5-methoxy-1H-indol-1-yl)-N,N,2-trimethylpropan-2-amine was prepared as described for 1-(5-methoxy-1H-indol-1-yl)-N,N,2-trimethylpropan-2-amine but using 6-fluoro-5-methoxy-1H-indole as the starting material. Yield: 130 mg, 54%, pale yellow semi solid; m/z=265.1 $[M+H]^+$; $^1H$ NMR (400 MHz, DMSO-d6) δ=7.44 (d, J=12.5 Hz, 1H), 7.27 (d, J=3.1 Hz, 1H), 7.18 (d, J=8.6 Hz, 1H), 6.34 (dd, J=3.1, 0.6 Hz, 1H), 4.04 (s, 2H), 3.81 (s, 3H), 2.27-2.22 (m, 6H), 1.09-1.09 (m, 1H), 0.90 (s, 6H).

The maleate salt of 1-(6-fluoro-5-methoxy-1H-indol-1-yl)-N,N,2-trimethylpropan-2-amine was prepared as described for 1-(4,5-difluoro-1H-indol-1-yl)-N,N,2-trimethylpropan-2-amine. Yield: 125 mg as an off-white gummy. $^1H$ NMR (400 MHz, DMSO-d6) δ=9.82-9.21 (m, 1H), 7.52 (d, J=12.3 Hz, 1H), 7.33 (d, J=3.1 Hz, 1H), 7.26 (d, J=8.5 Hz, 1H), 6.48 (d, J=3.0 Hz, 1H), 6.04 (s, 2H), 4.41 (s, 2H), 3.83 (s, 3H), 2.90-2.81 (m, 6H), 1.22 (s, 6H).

Preparation of 1-(7-fluoro-5-methoxy-1H-indol-1-yl)-N,N,2-trimethylpropan-2-amine (Example 17)

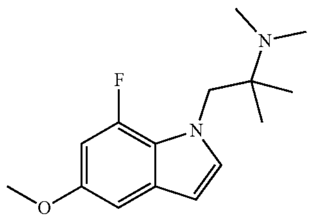

1-(7-fluoro-5-methoxy-1H-indol-1-yl)-N,N,2-trimethylpropan-2-amine was prepared as described for 1-(5-methoxy-1H-indol-1-yl)-N,N,2-trimethylpropan-2-amine but using intermediate I-13 and intermediate I-15 as the starting materials. Yield: 140 mg, 46%, pale yellow semi solid; m/z=265.2 $[M+H]^+$; $^1H$ NMR (400 MHz, DMSO-d6) δ=7.27 (d, J=3.1 Hz, 1H), 6.87 (d, J=2.2 Hz, 1H), 6.63-6.57 (m, 1H), 6.39 (t, J=2.6 Hz, 1H), 4.19 (s, 2H), 3.76-3.74 (m, 3H), 2.24 (s, 6H), 0.87 (s, 6H).

The maleate salt of 1-(7-fluoro-5-methoxy-1H-indol-1-yl)-N,N,2-trimethylpropan-2-amine was prepared as described for 1-(4,5-difluoro-1H-indol-1-yl)-N,N,2-trimethylpropan-2-amine. Yield: 140 mg as a pale brown solid. $^1H$ NMR (400 MHz, DMSO-d6) δ=9.96-9.38 (m, 1H), 7.39-7.34 (m, 1H), 6.93 (d, J=2.1 Hz, 1H), 6.73-6.66 (m, 1H), 6.51 (t, J=2.5 Hz, 1H), 6.03 (s, 2H), 4.58-4.46 (m, 2H), 3.76 (s, 3H), 2.84 (br d, J=0.7 Hz, 5H), 1.28-1.14 (m, 6H).

Preparation of 1-(4-fluoro-1H-indol-1-yl)-N,N,2-trimethylpropan-2-amine (Example 18)

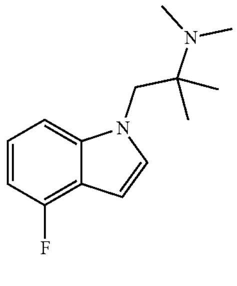 [SMILES: CN(C)C(C)(C)Cn1ccc2c(F)cccc21]

1-(4-fluoro-1H-indol-1-yl)-N,N,2-trimethylpropan-2-amine was prepared as described for 1-(5-methoxy-1H-indol-1-yl)-N,N,2-trimethylpropan-2-amine but using 4-fluoro-1H-indole as the starting material. Yield: 55 mg, 31%, colour-less semi solid; m/z=235.1 $[M+H]^+$; $^1H$ NMR (400 MHz, DMSO-d6) δ=7.40-7.34 (m, 2H), 7.07 (br d, J=5.5 Hz, 1H), 6.76 (dd, J=10.6, 7.7 Hz, 1H), 6.48 (d, J=2.9 Hz, 1H), 4.14 (s, 2H), 2.26 (s, 6H), 0.91 (s, 6H).

The maleate salt of 1-(4-fluoro-1H-indol-1-yl)-N,N,2-trimethylpropan-2-amine was prepared as described for 1-(4,5-difluoro-1H-indol-1-yl)-N,N,2-trimethylpropan-2-amine. Yield: 40 mg as an off-white solid. $^1H$ NMR (400 MHz, DMSO-d6) δ=9.82-9.40 (m, 1H), 7.45-7.41 (m, 2H), 7.22-7.13 (m, 1H), 6.85 (dd, J=10.1, 8.0 Hz, 1H), 6.65-6.57 (m, 1H), 6.02 (s, 2H), 4.61-4.38 (m, 2H), 3.01-2.78 (m, 6H), 1.30-1.16 (m, 6H).

Preparation of 1-(6-fluoro-1H-indol-1-yl)-N,N,2-trimethylpropan-2-amine (Example 19)

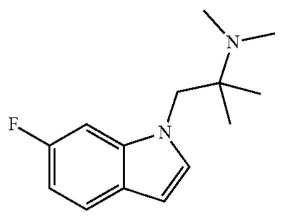 [SMILES: CN(C)C(C)(C)Cn1ccc2ccc(F)cc21]

1-(6-fluoro-1H-indol-1-yl)-N,N,2-trimethylpropan-2-amine was prepared as described for 1-(5-methoxy-1H-indol-1-yl)-N,N,2-trimethylpropan-2-amine but using 6-fluoro-1H-indole as the starting material. Yield: 240 mg, 69%, colour-less semi solid; m/z=235.1 $[M+H]^+$; $^1H$ NMR (400 MHz, DMSO-d6) δ=7.55-7.43 (m, 1H), 7.43-7.35 (m, 1H), 7.32 (d, J=3.1 Hz, 1H), 6.88-6.78 (m, 1H), 6.46-6.37 (m, 1H), 4.08 (s, 2H), 2.25 (s, 6H), 0.96-0.87 (m, 6H).

The maleate salt of 1-(6-fluoro-1H-indol-1-yl)-N,N,2-trimethylpropan-2-amine was prepared as described for 1-(4,5-difluoro-1H-indol-1-yl)-N,N,2-trimethylpropan-2-amine. Yield: 260 mg as an off-white solid. $^1H$ NMR (400 MHz, DMSO-d6) δ=9.99-9.28 (m, 1H), 7.57 (dd, J=8.6, 5.6 Hz, 1H), 7.46 (dd, J=10.6, 1.9 Hz, 1H), 7.38 (d, J=3.3 Hz, 1H), 6.96-6.88 (m, 1H), 6.56 (d, J=3.1 Hz, 1H), 6.03 (s, 2H), 4.44 (s, 2H), 2.86 (br s, 6H), 1.23 (s, 6H).

Preparation of 1-(7-fluoro-1H-indol-1-yl)-N,N,2-trimethylpropan-2-amine (Example 20)

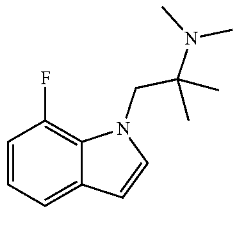 [SMILES: CN(C)C(C)(C)Cn1ccc2cccc(F)c21]

1-(7-fluoro-1H-indol-1-yl)-N,N,2-trimethylpropan-2-amine was prepared as described for 1-(5-methoxy-1H-indol-1-yl)-N,N,2-trimethylpropan-2-amine but using 7-fluoro-1H-indole as the starting material. Yield: 70 mg, 21%, colour-less semi solid; m/z=235.1 $[M+H]^+$; $^1H$ NMR (400 MHz, DMSO-d6) δ=7.37-7.30 (m, 2H), 6.98-6.86 (m, 2H), 6.53-6.47 (m, 1H), 4.26 (s, 2H), 2.27-2.22 (m, 6H), 0.91-0.87 (m, 6H).

The maleate salt of 1-(7-fluoro-1H-indol-1-yl)-N,N,2-trimethylpropan-2-amine was prepared as described for 1-(4,5-difluoro-1H-indol-1-yl)-N,N,2-trimethylpropan-2-amine. Yield: 35 mg as an off-white solid. $^1H$ NMR (400 MHz, DMSO-d6) δ=9.93-9.53 (m, 1H), 7.43-7.39 (m, 2H), 7.05-6.96 (m, 2H), 6.64-6.59 (m, 1H), 6.04-6.02 (m, 2H), 4.67-4.54 (m, 2H), 2.96-2.82 (m, 6H), 1.23 (br s, 6H).

Preparation of 1-(5-methoxy-1H-pyrrolo[3,2-b]pyridin-1-yl)-N,N,2-trimethylpropan-2-amine (Example 21)

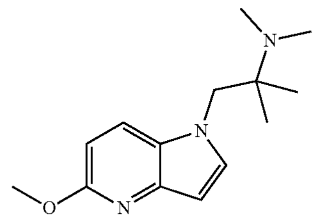

1-(5-methoxy-1H-pyrrolo[3,2-b]pyridin-1-yl)-N,N,2-trimethylpropan-2-amine was prepared as described for 1-(5-methoxy-1H-indol-1-yl)-N,N,2-trimethylpropan-2-amine but using 5-methoxy-1H-pyrrolo[3,2-b]pyridine as the starting material. Yield: 131 mg, 26%, colour-less semi solid; m/z=248.1 $[M+H]^+$; $^1H$ NMR (400 MHz, DMSO-d6) δ=7.90-7.85 (m, 1H), 7.44 (d, J=3.1 Hz, 1H), 6.54 (d, J=8.9 Hz, 1H), 6.39-6.35 (m, 1H), 4.13-4.07 (m, 2H), 3.84 (s, 3H), 2.24 (s, 6H), 0.89 (s, 6H).

The maleate salt of 1-(5-methoxy-1H-pyrrolo[3,2-b]pyridin-1-yl)-N,N,2-trimethylpropan-2-amine was prepared as described for 1-(4,5-difluoro-1H-indol-1-yl)-N,N,2-trimethylpropan-2-amine. Yield: 78 mg as an off-white solid. $^1H$ NMR (400 MHz, DMSO-d6) δ=9.85-9.34 (m, 1H), 7.92 (d, J=8.9 Hz, 1H), 7.53 (d, J=3.1 Hz, 1H), 6.65 (d, J=8.9 Hz, 1H), 6.50 (d, J=3.0 Hz, 1H), 6.03 (s, 2H), 4.45 (br s, 2H), 3.85 (s, 3H), 3.00-2.73 (m, 6H), 1.20 (br s, 6H).

Preparation of 1-(5-methoxy-1H-pyrrolo[2,3-c]pyridin-1-yl)-N,N,2-trimethylpropan-2-amine (Example 22)

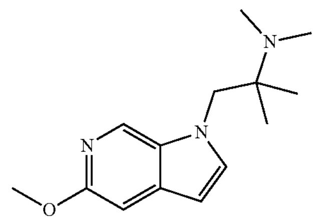

1-(5-methoxy-1H-pyrrolo[2,3-c]pyridin-1-yl)-N,N,2-trirmethylpropan-2-amine was prepared as described for 1-(5-methoxy-1H-indol-1-yl)-N,N,2-trimethylpropan-2-amine but using 5-methoxy-1H-pyrrolo[2,3-c]pyridine as the starting material. Yield: 70 mg, 41%, pale brown semi solid; m/z=248.2 $[M+H]^+$; $^1H$ NMR (400 MHz, DMSO-d6)

δ=8.49 (s, 1H), 7.48 (d, J=3.0 Hz, 1H), 6.81 (s, 1H), 6.32 (d, J=2.8 Hz, 1H), 4.15 (br s, 2H), 3.82 (s, 3H), 2.33-2.15 (m, 6H), 0.92 (br s, 6H).

The maleate salt of 1-(5-methoxy-1H-pyrrolo[2,3-c]pyridin-1-yl)-N,N,2-trimethylpropan-2-amine was prepared as described for 1-(4,5-difluoro-1H-indol-1-yl)-N,N,2-trimethylpropan-2-amine. Yield: 16 mg as a pale orange solid. $^1$H NMR (400 MHz, DMSO-d6) δ=9.80-9.36 (m, 1H), 8.57-8.53 (m, 1H), 7.60-7.55 (m, 1H), 6.89 (s, 1H), 6.50-6.45 (m, 1H), 6.13 (s, 4H), 4.52 (s, 2H), 3.86-3.82 (m, 3H), 2.89 (s, 6H), 1.27 (s, 6H).

Preparation of 1-(2-methoxy-5H-pyrrolo[3,2-d]pyrimidin-5-yl)-N,N,2-trimethylpropan-2-amine (Example 23)

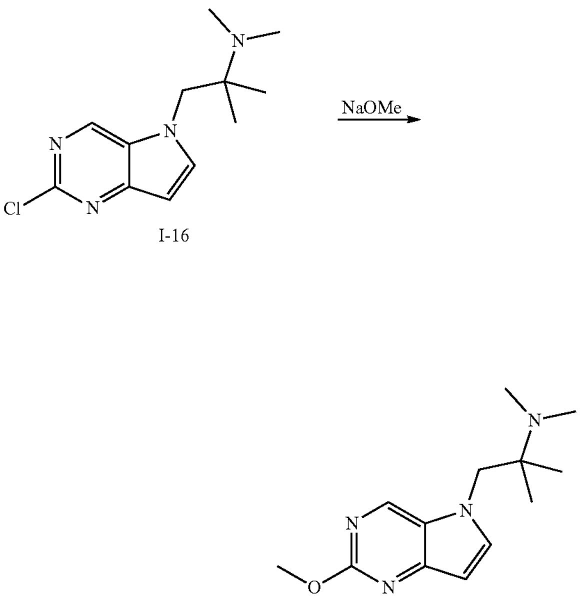

I-16

To a solution of intermediate I-16 (200 mg, 0.79 mmol, 1.0 eq.) in MeOH (2 mL) was added NaOMe (30% solution in MeOH, 0.42 mL, 2.38 mmol, 3.0 eq.) at 0° C., the reaction was allowed to warm slowly to room temperature and stirred at 65° C. for 12 hours. The reaction mixture was allowed to room temperature, diluted with ice cold water, extracted with ethyl acetate (2×5 mL). The combined organic layers were washed with ice cold water and aqueous solution of NaCl, dried over anhydrous $Na_2SO_4$, solids were removed by filtration and the filtrate was concentrated in vacuo to provide the crude reaction product that was purified by silica-gel chromatography (2% MeOH in $CH_2Cl_2$) to afford 1-(2-methoxy-5H-pyrrolo[3,2-d]pyrimidin-5-yl)-N,N,2-trimethylpropan-2-amine (120 mg, 61%, colour-less semi solid). m/z=249.2 $[M+H]^+$.

The maleate salt of 1-(2-methoxy-5H-pyrrolo[3,2-d]pyrimidin-5-yl)-N,N,2-trimethylpropan-2-amine was prepared as described for 1-(4,5-difluoro-1H-indol-1-yl)-N,N,2-trimethylpropan-2-amine. Yield: 100 mg as a white solid. $^1$H NMR (400 MHz, DMSO-d6) δ=8.93 (s, 1H), 7.84 (d, J=3.0 Hz, 1H), 6.54 (d, J=2.9 Hz, 1H), 6.09 (s, 2H), 4.57 (s, 2H), 3.90 (s, 3H), 2.88 (s, 6H), 1.26 (s, 6H).

Preparation of (1s,3s)-3-(5-methoxy-1H-indol-1-yl)-N,N-dimethylcyclobutan-1-amine (Example 24)

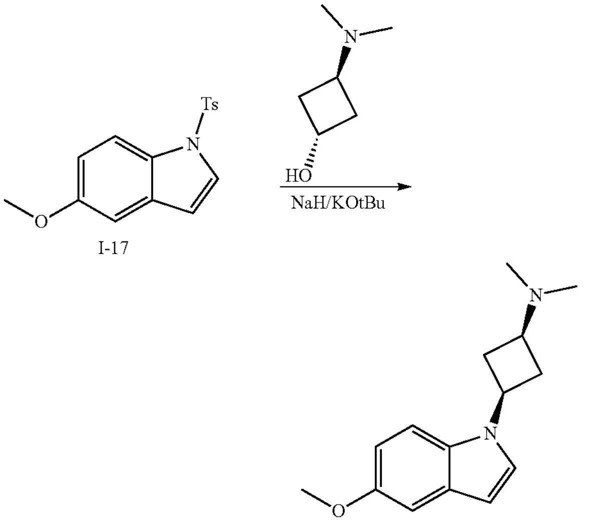

I-17

To a solution of (1r,3r)-3-(dimethylamino)cyclobutan-1-ol (152 mg, 1.32 mmol, 1.0 eq.) in THE (4 mL) were added activated 4 Å molecular sieves powder (400 mg) followed by KOtBu (297 mg, 2.65 mmol, 2.0 eq.) at room temperature and the reaction mixture was stirred for 1 hour. To the reaction mixture was added intermediate I-17 (400 mg, 1.32 mmol, 1.0 eq.) was added at room temperature and the reaction mixture was stirred for 16 hours. The reaction mixture was diluted with water and extracted with ethyl acetate (2×10 mL). The combined organic layers were washed with ice cold water, aqueous solution of NaCl, the combined organic layers were dried over anhydrous $Na_2SO_4$, solids were removed by filtration and the filtrate was concentrated in vacuo to provide crude reaction product that was purified by silica-gel chromatography (5% MeOH in $CH_2Cl_2$) to afford a mixture that was further purified by preparative HPLC to afford (1s,3s)-3-(5-methoxy-1H-indol-1-yl)-N,N-dimethylcyclobutan-1-amine. Yield: 18 mg, 2.2%, pale brown syrup; m/z=245.1 $[M+H]^+$; $^1$H NMR (DMSO-d6, 400 MHz) d=7.42 (d, J=3.06 Hz, 1H), 7.38 (d, J=8.80 Hz, 1H), 7.03 (d, J=2.20 Hz, 1H), 6.73-6.78 (m, 1H), 6.36 (d, J=3.06 Hz, 1H), 4.55-4.65 (m, 1H), 3.74 (s, 3H), 2.60-2.71 (m, 3H), 2.08-2.18 (m, 8H).

Preparation of (1r,3r)-3-(5-methoxy-1H-indol-1-yl)-N,N-dimethylcyclobutan-1-amine (Example 25)

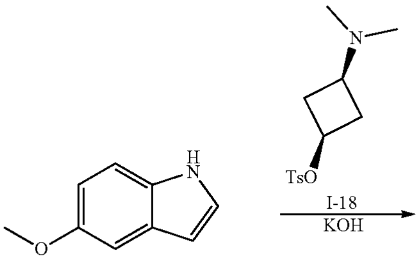

-continued

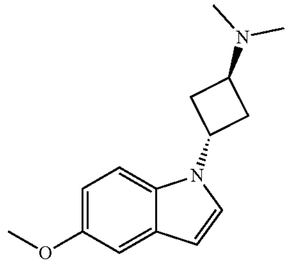

36

To a solution of 5-methoxyindole (76 mg, 0.5 mmol, 1.0 eq.) in DMSO (10 mL) was added KOH (58 mg, 1.03 mmol, 2.0 eq.) followed by intermediate I-18 (280 mg, 1.03 mmol, 2.0 eq.) at room temperature and the reaction mixture was stirred for 24 hours. The reaction mixture was diluted with water and extracted with ethyl acetate (2×10 mL). The combined organic layers were washed with ice cold water and aqueous solution of NaCl, dried over anhydrous $Na_2SO_4$, solids were removed by filtration and the filtrate was concentrated in vacuo to provide the crude reaction product that was purified by preparative HPLC to afford 140 mg of (1r,3r)-3-(5-methoxy-1H-indol-1-yl)-N,N-dimethyl-cyclobutan-1-amine. Yield: 25 mg, 19%, pale brown semi solid; m/z=245.2 $[M+H]^+$; $^1H$ NMR ($CD_3OD$, 400 MHz) d=7.42 (d, J=3.2 Hz, 1H), 7.22 (d, J=8.8 Hz, 1H), 7.06 (d, J=2.3 Hz, 1H), 6.79 (dd, J=8.9, 2.4 Hz, 1H), 6.42 (d, J=3.1 Hz, 1H), 5.04-4.91 (m, 1H), 3.80 (s, 3H), 3.28-3.21 (m, 1H), 2.71-2.58 (m, 4H), 2.39 (s, 6H).

Preparation of (R)-1-(7H-pyrrolo[2,3-d]pyrimidin-7-yl)propan-2-amine (Example 26)

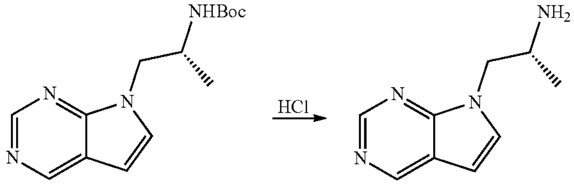

I-20

To a stirred solution of intermediate I-20 (500 mg, 1.81 mmol, 1.0 eq.) in $CH_2Cl_2$ (5 mL) was added HCl (2M in diethyl ether, 3.6 mL, 7.25 mmol, 4.0 eq.) at 0° C., the reaction mixture was allowed to warm to room temperature and stirred for 16 hours. Volatiles were removed in vacuo and residual solvents were removed by azeotropic distillation with toluene (2×5 mL) to afford (R)-1-(7H-pyrrolo[2,3-d]pyrimidin-7-yl)propan-2-amine as an HCl salt. Yield: 400 mg, 78%, pale brown solid; m/z=177.2 $[M+H]^+$; $^1H$ NMR (DMSO-d6, 400 MHz) δ=9.40 (s, 1H), 9.20 (s, 1H), 8.42 (br s, 3H), 8.09 (d, J=3.7 Hz, 1H), 7.03 (d, J=3.7 Hz, 1H), 4.66-4.49 (m, 3H), 4.27-3.00 (m, 8H), 1.23 (d, J=6.6 Hz, 3H).

Preparation of (R)—N,N-dimethyl-1-(7H-pyrrolo[2,3-d]pyrimidin-7-yl)propan-2-amine (Example 27)

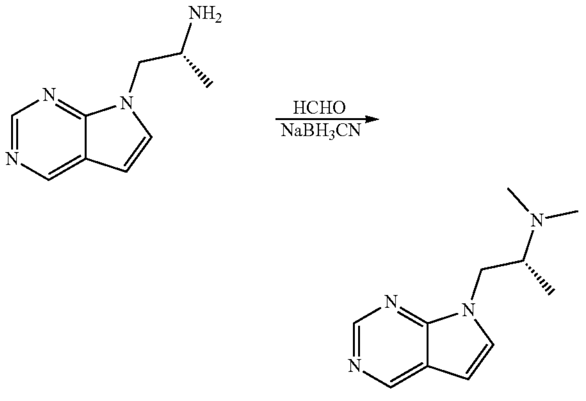

To a stirred solution of (R)-1-(7H-pyrrolo[2,3-d]pyrimidin-7-yl)propan-2-amine (230 mg, 1.3 mmol, 1.0 eq.) in a mixture of MeOH (1.2 mL) and THE (1.2 mL) was added a solution of formaldehyde (37% in water, 0.63 mL, 7.83 mmol, 6.0 eq.) at room temperature and the reaction mixture was stirred for 30 minutes. The reaction mixture was allowed to cool to 0° C. and $NaCNBH_3$ (328 mg, 5.22 mmol, 4.0 eq.) was added portion-wise. The reaction mixture was allowed to warm to room temperature and stirred for additional 16 hours. Volatiles were removed in vacuo, the crude reaction residue was diluted with water and extracted with ethyl acetate (2×10 mL). The combined organic layers were washed with an aqueous solution of NaCl, dried over anhydrous $Na_2SO_4$ and concentrated in vacuo. The crude reaction residue was purified by silica-gel chromatography (2% MeOH in $CH_2Cl_2$) followed by preparative HPLC to afford (R)—N,N-dimethyl-1-(7H-pyrrolo[2,3-d]pyrimidin-7-yl)propan-2-amine. Yield: 50 mg, 18%, off-white solid; m/z=205.2 $[M+H]^+$; $^1H$ NMR (DMSO-d6, 400 MHz) δ=8.97 (s, 1H), 8.77 (s, 1H), 7.62 (d, J=3.5 Hz, 1H), 6.60 (d, J=3.5 Hz, 1H), 4.31 (dd, J=8.0, 13.9 Hz, 1H), 4.12 (dd, J=6.5, 13.9 Hz, 1H), 3.12 (td, J=6.6, 8.0 Hz, 1H), 2.16 (s, 6H), 0.85 (d, J=6.6 Hz, 3H).

The maleate salt of (R)—N,N-dimethyl-1-(7H-pyrrolo[2,3-d]pyrimidin-7-yl)propan-2-amine was prepared as described for 1-(4,5-difluoro-1H-indol-1-yl)-N,N,2-trimethylpropan-2-amine. Yield: 50 mg as an off-white solid. $^1H$ NMR (DMSO-d6, 400 MHz) δ=9.97-9.29 (m, 1H), 9.05 (s, 1H), 8.84 (s, 1H), 7.69 (d, J=3.5 Hz, 1H), 6.73 (d, J=3.6 Hz, 1H), 6.05 (s, 2H), 4.67 (dd, J=6.6, 14.5 Hz, 1H), 4.44 (dd, J=7.1, 14.6 Hz, 1H), 4.01-3.85 (m, 1H), 2.83-2.77 (m, 6H), 1.18 (d, J=6.8 Hz, 3H).

Preparation of (R)-1-(5-methoxy-1H-pyrrolo[3,2-b]pyridin-1-yl)propan-2-amine (Example 28)

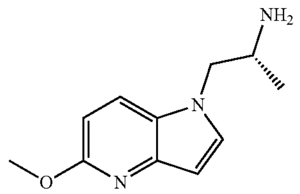

(R)-1-(5-methoxy-1H-pyrrolo[3,2-b]pyridin-1-yl)propan-2-amine was prepared as described for (R)-1-(7H-pyrrolo[2,3-d]pyrimidin-7-yl)propan-2-amine but using intermediate I-21 as the starting material. The crude HCl salt residue was diluted with $CH_2Cl_2$ (2 mL) and basified with an aqueous solution of $NaHCO_3$ (1M) and extracted with $CH_2Cl_2$ (2×5 mL). The combined organic layers were washed with a brine solution (5 mL), dried over anhydrous $Na_2SO_4$, solids were removed by filtration and the filtrate was concentrated in vacuo to provide the crude reaction product that was purified by silica-gel chromatography (0.5% $NH_4OH$ in 5% $MeOH/CH_2Cl_2$) to afford (R)-1-(5-methoxy-1H-pyrrolo[3,2-b]pyridin-1-yl)propan-2-amine. Yield: 250 mg, 74%, yellow gummy syrup; m/z=206.2 $[M+H]^+$; $^1H$ NMR (400 MHz, DMSO-d6) δ=7.87 (d, J=8.8 Hz, 1H), 7.48 (d, J=3.1 Hz, 1H), 6.56 (d, J=8.8 Hz, 1H), 6.38 (d, J=3.1 Hz, 1H), 3.96 (d, J=6.5 Hz, 2H), 3.84 (s, 3H), 3.14 (q, J=6.4 Hz, 1H), 1.42 (br s, 3H), 0.91 (d, J=6.4 Hz, 3H).

The maleate salt of (R)-1-(5-methoxy-1H-pyrrolo[3,2-b]pyridin-1-yl)propan-2-amine was prepared as described for 1-(4,5-difluoro-1H-indol-1-yl)-N,N,2-trimethylpropan-2-amine. Yield: 50 mg as an off-white solid. $^1H$ NMR (400 MHz, DMSO-d6) δ=7.97-7.80 (m, 4H), 7.51 (d, J=3.3 Hz, 1H), 6.65 (d, J=8.8 Hz, 1H), 6.48 (d, J=3.0 Hz, 1H), 6.02 (s, 2H), 4.27 (dd, J=14.1, 6.6 Hz, 2H), 3.85 (s, 3H), 3.62 (br d, J=6.6 Hz, 1H), 1.20-1.12 (m, 3H).

Preparation of (R)-1-(5-methoxy-1H-pyrrolo[3,2-b]pyridin-1-yl)-N-methylpropan-2-amine (Example 29)

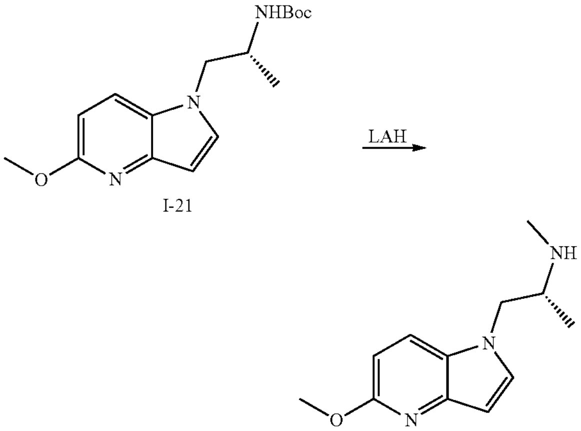

To a stirred solution of intermediate I-21 (400 mg, 1.31 mmol, 1.0 eq.) in THF (4 mL) was added LAH (2.0M in THF, 1.96 mL, 3.93 mmol, 3.0 eq.) at 0° C., the reaction mixture was allowed to warm to room temperature and stirred at 60° C. for 4 hours. The reaction mixture was allowed to cool to room temperature and a saturated aqueous solution of $NH_4Cl$ (10 mL) was added. The crude reaction mixture was extracted with ethyl acetate (2×10 mL), the combined organic layers were washed with a brine solution (5 mL), dried over anhydrous $Na_2SO_4$, the solids were removed by filtration and the filtrate was concentrated in vacuo to provide the crude reaction product that was purified by silica-gel chromatography (2% $MeOH/CH_2Cl_2$) to afford (R)-1-(5-methoxy-1H-pyrrolo[3,2-b]pyridin-1-yl)-N-methylpropan-2-amine. Yield: 100 mg, 34%, pale brown gummy syrup; m/z=220.2 $[M+H]^+$; $^1H$ NMR (400 MHz, DMSO-d6) δ=7.84 (d, J=8.8 Hz, 1H), 7.47 (d, J=3.1 Hz, 1H), 6.56 (d, J=8.8 Hz, 1H), 6.37 (d, J=3.1 Hz, 1H), 4.13-4.06 (m, 1H), 3.96 (dd, J=14.0, 6.4 Hz, 1H), 3.84 (s, 3H), 2.89-2.79 (m, 1H), 2.24 (s, 3H), 0.86 (d, J=6.4 Hz, 3H).

The maleate salt of (R)-1-(5-methoxy-1H-pyrrolo[3,2-b]pyridin-1-yl)-N-methylpropan-2-amine was prepared as described for 1-(4,5-difluoro-1H-indol-1-yl)-N,N,2-trimethylpropan-2-amine. Yield: 100 mg as a brown semi-solid. $^1H$ NMR (400 MHz, DMSO-d6) δ=8.49 (br s, 2H), 7.91 (d, J=8.9 Hz, 1H), 7.54 (d, J=3.1 Hz, 1H), 6.65 (d, J=8.8 Hz, 1H), 6.49 (d, J=2.9 Hz, 1H), 6.06 (s, 2H), 4.46 (dd, J=14.7, 5.9 Hz, 1H), 4.26 (dd, J=14.7, 7.3 Hz, 1H), 3.88-3.83 (m, 3H), 3.67-3.58 (m, 1H), 2.58 (s, 3H), 1.12 (d, J=6.6 Hz, 3H).

Preparation of (R)-1-(5-methoxy-1H-pyrrolo[3,2-b]pyridin-1-yl)-N,N-dimethylpropan-2-amine (Example 30)

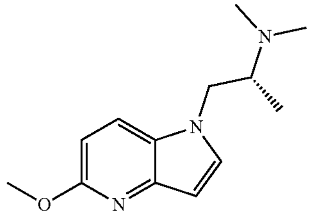

(R)-1-(5-methoxy-1H-pyrrolo[3,2-b]pyridin-1-yl)-N,N-dimethylpropan-2-amine was prepared as described for (R)—N,N-dimethyl-1-(7H-pyrrolo[2,3-d]pyrimidin-7-yl)propan-2-amine but using (R)-1-(5-methoxy-1H-pyrrolo[3,2-b]pyridin-1-yl)propan-2-amine as the starting material. Yield: 115 mg, 52%, off-white solid; m/z=234.2 $[M+H]^+$; $^1H$ NMR (400 MHz, DMSO-d6) δ=7.87-7.82 (m, 1H), 7.49 (d, J=3.1 Hz, 1H), 6.55 (d, J=8.8 Hz, 1H), 6.36 (d, J=2.6 Hz, 1H), 4.19 (dd, J=14.2, 7.2 Hz, 1H), 4.00 (dd, J=14.2, 7.1 Hz, 1H), 3.83 (s, 3H), 3.01-2.91 (m, 1H), 2.22-2.14 (m, 6H), 0.79 (d, J=6.6 Hz, 3H).

The maleate salt of (R)-1-(5-methoxy-1H-pyrrolo[3,2-b]pyridin-1-yl)-N,N-dimethylpropan-2-amine was prepared as described for 1-(4,5-difluoro-1H-indol-1-yl)-N,N,2-trimethylpropan-2-amine. Yield: 120 mg as a pale-yellow gummy. $^1H$ NMR (400 MHz, DMSO-d6) δ=10.06-9.12 (m, 1H), 7.97 (d, J=8.8 Hz, 1H), 7.56 (d, J=3.2 Hz, 2H), 6.65 (d, J=8.8 Hz, 1H), 6.49 (d, J=3.1 Hz, 1H), 6.06 (s, 2H), 4.55 (dd, J=14.4, 5.3 Hz, 1H), 4.34 (dd, J=14.4, 9.0 Hz, 1H), 3.88-3.77 (m, 4H), 2.93-2.68 (m, 6H), 1.07 (d, J=6.7 Hz, 3H).

Preparation of (R)-1-(5-methoxy-1H-pyrrolo[2,3-c]pyridin-1-yl)propan-2-amine (Example 31)

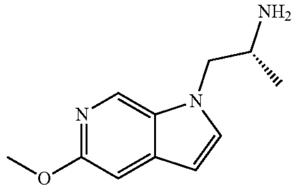

(R)-1-(5-methoxy-1H-pyrrolo[2,3-c]pyridin-1-yl)propan-2-amine was prepared as described for (R)-1-(5-methoxy-1H-pyrrolo[3,2-b]pyridin-1-yl)propan-2-amine but using intermediate I-22 as the starting material. Yield: 60 mg, 90%, colour-less syrup; m/z=206.1 $[M+H]^+$; $^1$H NMR (DMSO-d6, 400 MHz) δ=8.49-8.46 (m, 1H), 7.55-7.50 (m, 1H), 6.85-6.82 (m, 1H), 6.34-6.30 (m, 1H), 4.04-3.98 (m, 2H), 3.84-3.81 (m, 3H), 3.23-3.16 (m, 1H), 1.59-1.48 (m, 2H), 0.95-0.91 (m, 3H).

The maleate salt of (R)-1-(5-methoxy-1H-pyrrolo[2,3-c]pyridin-1-yl)propan-2-amine was prepared as described for 1-(4,5-difluoro-1H-indol-1-yl)-N,N,2-trimethylpropan-2-amine. Yield: 70 mg as an off-white solid. $^1$H NMR (DMSO-d6, 400 MHz) δ=8.50 (s, 1H), 7.90 (br s, 3H), 7.55 (d, J=3.1 Hz, 1H), 6.89 (s, 1H), 6.43 (d, J=2.9 Hz, 1H), 6.03 (s, 2H), 4.39-4.25 (m, 2H), 3.84 (s, 3H), 3.73-3.65 (m, 1H), 1.17 (d, J=6.6 Hz, 3H).

Preparation of (R)-1-(5-methoxy-1H-pyrrolo[2,3-c]pyridin-1-yl)-N-methylpropan-2-amine Example 32

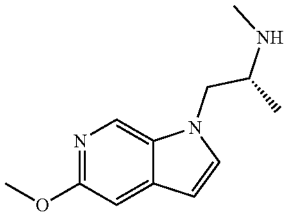 [SMILES: CN[C@H](C)Cn1ccc2cc(OC)ncc21]

(R)-1-(5-methoxy-1H-pyrrolo[2,3-c]pyridin-1-yl)-N-methylpropan-2-amine was prepared as described for (R)-1-(5-methoxy-1H-pyrrolo[3,2-b]pyridin-1-yl)-N-methylpropan-2-amine but using intermediate I-22 as the starting material. Yield: 100 mg, 27%, pale brown syrup; m/z=220.2 $[M+H]^+$; $^1$H NMR (DMSO-d6, 400 MHz) S=8.46 (s, 1H), 7.52 (d, J=3.1 Hz, 1H), 6.83 (d, J=0.9 Hz, 1H), 6.32 (d, J=2.9 Hz, 1H), 4.15 (dd, J=14.1, 6.1 Hz, 1H), 4.09-3.96 (m, 1H), 3.82 (s, 3H), 2.90 (q, J=6.2 Hz, 1H), 2.26-2.25 (m, 3H), 1.87-1.60 (m, 1H), 0.91-0.87 (m, 3H).

The maleate salt of (R)-1-(5-methoxy-1H-pyrrolo[2,3-c]pyridin-1-yl)-N-methylpropan-2-amine was prepared as described for 1-(4,5-difluoro-1H-indol-1-yl)-N,N,2-trimethylpropan-2-amine. Yield: 100 mg as a pale brown solid. $^1$H NMR (DMSO-d6, 400 MHz) δ=8.53-8.51 (m, 1H), 7.58 (d, J=3.1 Hz, 1H), 6.91-6.84 (m, 1H), 6.42 (d, J=2.8 Hz, 1H), 6.01 (s, 2H), 4.49 (dd, J=14.6, 5.9 Hz, 1H), 4.28 (dd, J=14.7, 7.3 Hz, 1H), 3.84 (s, 3H), 3.67-3.63 (m, 1H), 2.58 (s, 3H), 1.14-1.10 (m, 3H).

Preparation of (R)-1-(5-methoxy-1H-pyrrolo[2,3-c]pyridin-1-yl)-N,N-dimethylpropan-2-amine (Example 33)

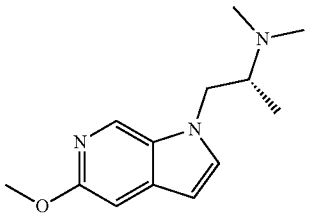

(R)-1-(5-methoxy-1H-pyrrolo[2,3-c]pyridin-1-yl)-N,N-dimethylpropan-2-amine was prepared as described for (R)—N,N-dimethyl-1-(7H-pyrrolo[2,3-d]pyrimidin-7-yl)propan-2-amine but using (R)-1-(5-methoxy-1H-pyrrolo[2,3-c]pyridin-1-yl)propan-2-amine as the starting material. Yield: 200 mg, 65%, pale brown solid; m/z=234.2 $[M+H]^+$; $^1$H NMR (DMSO-d6, 400 MHz) δ=8.45 (s, 1H), 7.53 (d, J=2.9 Hz, 1H), 6.82 (d, J=0.9 Hz, 1H), 6.31 (d, J=2.4 Hz, 1H), 4.29-4.19 (m, 1H), 4.08-3.98 (m, 1H), 3.82 (s, 3H), 3.07-2.96 (m, 1H), 2.20-2.18 (m, 6H), 0.83 (d, J=6.6 Hz, 3H).

The maleate salt of (R)-1-(5-methoxy-1H-pyrrolo[2,3-c]pyridin-1-yl)-N,N-dimethylpropan-2-amine was prepared as described for 1-(4,5-difluoro-1H-indol-1-yl)-N,N,2-trimethylpropan-2-amine. Yield: 180 mg as a pale brown solid. $^1$H NMR (DMSO-d6, 400 MHz) δ=9.90-9.17 (m, 1H), 8.57 (s, 1H), 7.60 (d, J=3.0 Hz, 1H), 6.91-6.88 (m, 1H), 6.43 (d, J=3.0 Hz, 1H), 6.07 (s, 2H), 4.64-4.57 (m, 1H), 4.42-4.34 (m, 1H), 3.94-3.83 (m, 4H), 2.84-2.80 (m, 6H), 1.10 (d, J=6.8 Hz, 3H).

Preparation of (R)-1-(5-methoxy-1H-pyrrolo[2,3-b]pyridin-1-yl)propan-2-amine (Example 34)

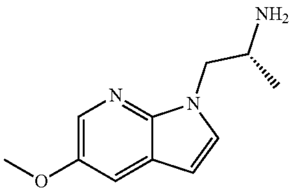

(R)-1-(5-methoxy-1H-pyrrolo[2,3-b]pyridin-1-yl)propan-2-amine was prepared as described for (R)-1-(5-methoxy-1H-pyrrolo[3,2-b]pyridin-1-yl)propan-2-amine but using intermediate I-23 as the starting material. Yield: 300 mg, 89%, off-white solid; m/z=206.1 $[M+H]^+$; $^1$H NMR (400 MHz, DMSO-d6) δ=7.98 (d, J=2.7 Hz, 1H), 7.54 (d, J=2.7 Hz, 1H), 7.49 (d, J=3.4 Hz, 1H), 6.36 (d, J=3.4 Hz, 1H), 4.03 (dd, J=6.5, 4.0 Hz, 2H), 3.81 (s, 3H), 3.23 (d, J=6.5 Hz, 1H), 1.60-1.45 (m, 2H), 0.90 (d, J=6.5 Hz, 3H).

The maleate salt of (R)-1-(5-methoxy-1H-pyrrolo[2,3-b]pyridin-1-yl)propan-2-amine was prepared as described for 1-(4,5-difluoro-1H-indol-1-yl)-N,N,2-trimethylpropan-2-amine. Yield: 45 mg as an off-white solid. $^1$H NMR (400 MHz, METHANOL-d4) δ=8.03 (d, J=2.6 Hz, 1H), 7.59 (d, J=2.7 Hz, 1H), 7.36 (d, J=3.5 Hz, 1H), 6.49 (d, J=3.4 Hz, 1H), 6.24 (s, 2H), 4.50-4.36 (m, 2H), 3.91-3.82 (m, 4H), 1.41-1.25 (m, 3H).

Preparation of (R)-1-(5-methoxy-1H-pyrrolo[2,3-b]pyridin-1-yl)-N-methylpropan-2-amine (Example 35)

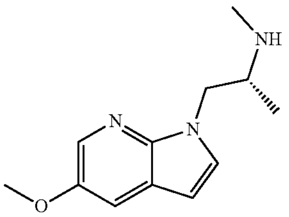 [SMILES: CN[C@H](C)Cn1ccc2cc(OC)cnc21]

(R)-1-(5-methoxy-1H-pyrrolo[2,3-b]pyridin-1-yl)-N-methylpropan-2-amine was prepared as described for (R)-1-(5-methoxy-1H-pyrrolo[3,2-b]pyridin-1-yl)-N-methyl-propan-2-amine but using intermediate I-23 as the starting material. Yield: 80 mg, 55%, colorless syrup; m/z=220.0 $[M+H]^+$; $^1$H NMR (400 MHz, DMSO-d6) δ=7.99 (d, J=2.7 Hz, 1H), 7.54 (d, J=2.7 Hz, 1H), 7.48 (d, J=3.3 Hz, 1H), 6.36 (d, J=3.3 Hz, 1H), 4.21 (dd, J=13.6, 6.1 Hz, 1H), 4.04 (dd, J=13.7, 6.5 Hz, 1H), 3.81 (s, 3H), 3.00-2.94 (m, 1H), 2.28 (s, 3H), 0.87 (d, J=6.4 Hz, 3H).

The maleate salt of (R)-1-(5-methoxy-1H-pyrrolo[2,3-b]pyridin-1-yl)-N-methylpropan-2-amine was prepared as described for 1-(4,5-difluoro-1H-indol-1-yl)-N,N,2-trimethylpropan-2-amine. Yield: 80 mg as an off-white solid. $^1$H NMR (400 MHz, DMSO-d6) δ=10.01-9.39 (m, 1H), 7.50 (d, J=8.9 Hz, 1H), 7.05 (d, J=2.4 Hz, 1H), 6.90-6.85 (m, 1H), 6.57 (s, 1H), 6.03 (s, 2H), 4.60-4.45 (m, 1H), 4.42-4.27 (m, 1H), 3.82-3.67 (m, 4H), 3.29-3.19 (m, 3H), 1.11-1.04 (m, 3H).

Preparation of (R)-1-(5-methoxy-1H-pyrrolo[2,3-b]pyridin-1-yl)-N,N-dimethylpropan-2-amine (Example 36)

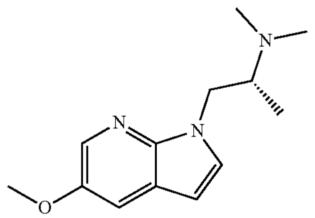

(R)-1-(5-methoxy-1H-pyrrolo[2,3-b]pyridin-1-yl)-N,N-dimethylpropan-2-amine was prepared as described for (R)—N,N-dimethyl-1-(7H-pyrrolo[2,3-d]pyrimidin-7-yl)propan-2-amine but using (R)-1-(5-methoxy-1H-pyrrolo[2,3-b]pyridin-1-yl)propan-2-amine as the starting material. Yield: 160 mg, 50%, off-white solid; m/z=234.1 $[M+H]^+$; $^1$H NMR (400 MHz, DMSO-d6) δ=8.04-7.93 (m, 1H), 7.57-7.44 (m, 2H), 6.35 (d, J=3.4 Hz, 1H), 4.25 (dd, J=13.9, 7.4 Hz, 1H), 4.08 (dd, J=13.9, 7.0 Hz, 1H), 3.81 (s, 3H), 3.10 (br d, J=6.8 Hz, 1H), 2.18 (s, 6H), 0.81 (d, J=6.6 Hz, 4H).

The maleate salt of (R)-1-(5-methoxy-1H-pyrrolo[2,3-b]pyridin-1-yl)-N,N-dimethylpropan-2-amine was prepared as described for 1-(4,5-difluoro-1H-indol-1-yl)-N,N,2-trimethylpropan-2-amine. Yield: 40 mg as is pale brown solid. $^1$H NMR (400 MHz, DMSO-d6) δ=9.88-9.24 (m, 1H), 8.04 (d, J=2.8 Hz, 1H), 7.62 (d, J=2.8 Hz, 1H), 7.56 (d, J=3.5 Hz, 1H), 6.48 (d, J=3.4 Hz, 1H), 6.02 (s, 2H), 4.61 (dd, J=14.4, 6.4 Hz, 1H), 4.37 (dd, J=14.5, 7.3 Hz, 1H), 3.91 (br d, J=5.5 Hz, 1H), 3.83 (s, 3H), 2.78 (br s, 6H), 1.15 (d, J=6.8 Hz, 3H).

Preparation of (R)-1-(1H-pyrrolo[3,2-c]pyridin-1-yl)propan-2-amine (Example 37)

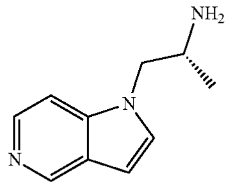

(R)-1-(1H-pyrrolo[3,2-c]pyridin-1-yl)propan-2-amine was prepared as described for (R)-1-(5-methoxy-1H-pyrrolo[3,2-b]pyridin-1-yl)propan-2-amine but using intermediate I-24 as the starting material. Yield: 390 mg, 87%, off-white solid; m/z=176.1 $[M+H]^+$; $^1$H NMR (400 MHz, DMSO-d6) δ=15.11-14.88 (m, 1H), 9.32-9.20 (m, 1H), 8.51 (d, J=6.7 Hz, 2H), 8.17 (br d, J=6.8 Hz, 1H), 7.89 (d, J=3.2 Hz, 1H), 7.09-7.00 (m, 1H), 6.96-6.86 (m, 1H), 4.47-4.37 (m, 1H), 4.30-4.15 (m, 1H), 3.96-3.84 (m, 1H), 1.19-1.07 (m, 11H), 1.00-0.84 (m, 1H).

The maleate salt of (R)-1-(1H-pyrrolo[3,2-c]pyridin-1-yl)propan-2-amine was prepared as described for 1-(4,5-difluoro-1H-indol-1-yl)-N,N,2-trimethylpropan-2-amine. Yield: 80 mg as a brown gummy solid. $^1$H NMR (400 MHz, DMSO-d6) δ=9.08 (s, 1H), 8.41 (d, J=6.4 Hz, 1H), 8.14-7.83 (m, 3H), 7.72 (d, J=3.2 Hz, 1H), 6.91 (d, J=3.2 Hz, 1H), 6.03 (s, 3H), 4.51-4.34 (m, 2H), 3.74-3.67 (m, 1H), 1.19 (d, J=6.6 Hz, 3H).

Preparation of (R)—N-methyl-1-(1H-pyrrolo[3,2-c]pyridin-1-yl)propan-2-amine (Example 38)

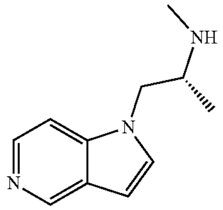

(R)—N-methyl-1-(1H-pyrrolo[3,2-c]pyridin-1-yl)propan-2-amine was prepared as described for (R)-1-(5-methoxy-1H-pyrrolo[3,2-b]pyridin-1-yl)-N-methylpropan-2-amine but using intermediate I-24 as the starting material. Yield: 25 mg, 18%, pale green semi solid; m/z=190.2 $[M+H]^+$; $^1$H NMR (400 MHz, DMSO-d6) δ=8.81-8.77 (m, 1H), 8.20-8.14 (m, 1H), 7.53-7.41 (m, 2H), 6.61-6.55 (m, 1H), 4.20-4.11 (m, 1H), 4.06-3.97 (m, 1H), 2.94-2.83 (m, 1H), 2.28-2.22 (m, 3H), 2.21-2.13 (m, 1H), 1.52-1.48 (m, 1H), 0.91-0.85 (m, 3H).

The maleate salt of (R)—N-methyl-1-(1H-pyrrolo[3,2-c]pyridin-1-yl)propan-2-amine was prepared as described for 1-(4,5-difluoro-1H-indol-1-yl)-N,N,2-trimethylpropan-2-amine. Yield: 20 mg as an off-white solid. $^1$H NMR (400 MHz, DMSO-d6) δ=9.17 (s, 1H), 8.50-8.45 (m, 1H), 7.99 (d, J=6.3 Hz, 1H), 7.82 (d, J=3.3 Hz, 1H), 7.01 (d, J=3.3 Hz, 1H), 6.04 (s, 2H), 4.61 (br d, J=6.3 Hz, 1H), 4.46 (dd, J=7.0, 14.8 Hz, 1H), 3.75-3.69 (m, 1H), 2.61 (s, 3H), 1.16 (d, J=6.6 Hz, 3H).

Preparation of (R)—N,N-dimethyl-1-(1H-pyrrolo[3,2-c]pyridin-1-yl)propan-2-amine (Example 39)

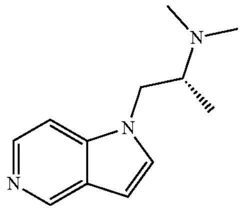

(R)—N,N-dimethyl-1-(1H-pyrrolo[3,2-c]pyridin-1-yl)propan-2-amine was prepared as described for (R)—N,N-dimethyl-1-(7H-pyrrolo[2,3-d]pyrimidin-7-yl)propan-2-amine but using (R)-1-(1H-pyrrolo[3,2-c]pyridin-1-yl)propan-2-amine as the starting material. Yield: 105 mg, 60%, pale green semi solid). m/z=204.2 $[M+H]^+$.

The maleate salt of (R)—N,N-dimethyl-1-(1H-pyrrolo[3,2-c]pyridin-1-yl)propan-2-amine was prepared as described for 1-(4,5-difluoro-1H-indol-1-yl)-N,N,2-trimethylpropan-2-amine. Yield: 35 mg as a pale brown solid. $^1$H NMR (400 MHz, DMSO-d6) δ=9.20 (s, 1H), 8.49 (d, J=6.5 Hz, 1H), 8.12 (d, J=6.5 Hz, 1H), 7.88 (d, J=3.4 Hz, 1H), 7.04 (d, J=3.1 Hz, 1H), 6.06 (s, 2H), 4.66 (br dd, J=14.4, 5.9 Hz, 1H), 4.55-4.48 (m, 1H), 3.77 (br d, J=1.3 Hz, 1H), 2.74-2.66 (m, 6H), 1.07 (d, J=6.6 Hz, 3H).

Preparation of 1-(5-fluoro-3-methyl-1H-indol-1-yl)-2-methylpropan-2-amine (Example 40)

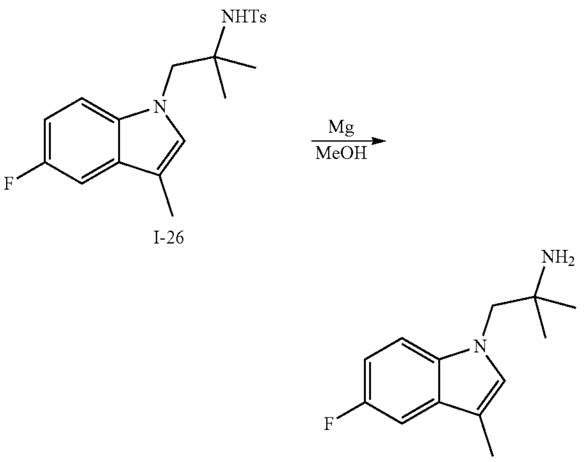

I-26

To a solution of intermediate I-26 (400 mg, 1.06 mmol, 1.0 eq.) in MeOH (8 mL) was added Mg (102 mg, 4.27 mmol, 4.0 eq.) and the reaction mixture was stirred at 70° C. for 12 hours. The reaction mixture was allowed to cool to room temperature, a saturated aqueous solution of $NH_4Cl$ was added and volatiles were removed in vacuo. The crude reaction residue was diluted with water and extracted with ethyl acetate (2×10 mL). The combined organic layers were washed with aqueous solution of NaCl. The separated organic layers were dried over anhydrous $Na_2SO_4$, solids were removed by filtration and the filtrate was concentrated in vacuo to provide the crude reaction product that was purified by silica-gel chromatography (2% MeOH in $CH_2Cl_2$) to afford 1-(5-fluoro-3-methyl-1H-indol-1-yl)-2-methylpropan-2-amine. Yield: 75 mg, 31%, off-white solid; m/z=221.1 $[M+H]^+$; $^1$H NMR (400 MHz, DMSO-d6) δ=7.48 (dd, J=8.9, 4.4 Hz, 1H), 7.23-7.17 (m, 2H), 6.92 (d, J=2.5 Hz, 1H), 3.94 (s, 2H), 2.24-2.20 (m, 3H), 1.95-1.62 (m, 2H), 1.00 (s, 6H).

The maleate salt of 1-(5-fluoro-3-methyl-1H-indol-1-yl)-2-methylpropan-2-amine was prepared as described for 1-(4,5-difluoro-1H-indol-1-yl)-N,N,2-trimethylpropan-2-amine. Yield: 80 mg as a white solid. $^1$H NMR (400 MHz, DMSO-d6) δ=7.95 (br s, 3H), 7.52 (dd, J=9.0, 4.3 Hz, 1H), 7.29 (dd, J=9.7, 2.5 Hz, 1H), 7.19 (s, 1H), 7.06-7.00 (m, 1H), 6.02 (s, 2H), 4.24 (s, 2H), 2.24 (s, 3H), 1.34-1.24 (m, 6H).

Preparation of 1-(4,5-difluoro-1H-indol-1-yl)-2-methylpropan-2-amine (Example 41)

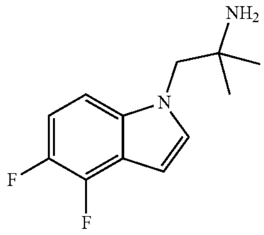 [SMILES: CC(C)(N)Cn1ccc2c(F)c(F)ccc21]

1-(4,5-difluoro-1H-indol-1-yl)-2-methylpropan-2-amine was prepared as described for 1-(5-fluoro-3-methyl-1H-indol-1-yl)-2-methylpropan-2-amine but using Intermediate I-27 as the starting material. Yield: 30 mg, 12%, pale yellow semi solid; m/z=225.1 $[M+H]^+$; $^1$H NMR (400 MHz, DMSO-d6) δ=7.53-7.48 (m, 1H), 7.45 (dd, J=9.0, 3.4 Hz, 1H), 7.22-7.12 (m, 1H), 6.61 (d, J=3.1 Hz, 1H), 5.34-4.57 (m, 2H), 4.18 (s, 2H), 1.12 (s, 7H).

The maleate salt of 1-(4,5-difluoro-1H-indol-1-yl)-2-methylpropan-2-amine was prepared as described for 1-(4,5-difluoro-1H-indol-1-yl)-N,N,2-trimethylpropan-2-amine. Yield: 20 mg as an off-white solid. $^1$H NMR (400 MHz, DMSO-d6) δ=8.22-7.96 (m, 3H), 7.53-7.44 (m, 2H), 7.29-7.19 (m, 1H), 6.69 (d, J=3.0 Hz, 1H), 6.02 (s, 1H), 4.37 (s, 2H), 1.29 (s, 6H).

Preparation of 1-(5-methoxy-1H-indol-1-yl)-2-methylpropan-2-amine (Example 42)

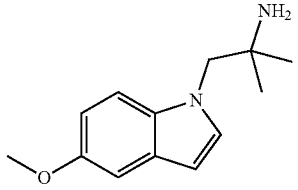 [SMILES: COc1ccc2c(ccn2CC(C)(C)N)c1]

1-(5-methoxy-1H-indol-1-yl)-2-methylpropan-2-amine was prepared as described for 1-(5-fluoro-3-methyl-1H-indol-1-yl)-2-methylpropan-2-amine but using Intermediate I-17 as the starting material. Yield: 50 mg, 17%, off-white solid; m/z=219.1 $[M+H]^+$; $^1$H NMR (400 MHz, DMSO-d6) δ=7.50-7.36 (m, 1H), 7.29 (d, J=3.0 Hz, 1H), 7.02 (d, J=2.4 Hz, 1H), 6.74 (dd, J=8.9, 2.3 Hz, 1H), 6.34 (d, J=2.9 Hz, 1H), 3.99 (s, 2H), 3.74 (s, 3H), 1.02 (s, 7H).

The maleate salt of 1-(5-methoxy-1H-indol-1-yl)-2-methylpropan-2-amine was prepared as described for 1-(4,5-difluoro-1H-indol-1-yl)-N,N,2-trimethylpropan-2-amine. Yield: 40 mg as an off-white solid. 1H NMR (400 MHz, DMSO-d6) δ=8.01-7.88 (m, 3H), 7.48-7.43 (m, 1H), 7.30-7.26 (m, 1H), 7.08 (d, J=2.4 Hz, 1H), 6.85-6.80 (m, 1H), 6.46 (d, J=3.1 Hz, 1H), 6.02-6.00 (m, 2H), 4.26 (s, 3H), 3.76 (s, 4H), 1.32-1.22 (m, 6H).

Preparation of 2-(dimethylamino)-1-(5-fluoro-1H-indol-1-yl)ethan-1-one (Example 43)

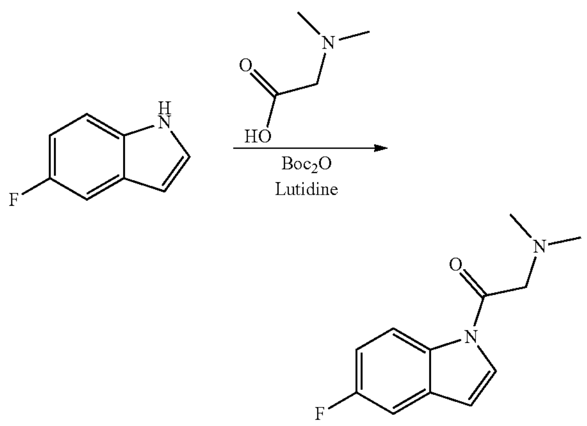

To a stirred solution of 5-fluoro indole (1.0 g, 7.04 mmol, 1.0 eq.) in acetonitrile (10 mL) was added Boc$_2$O (1.6 g, 7.04 mmol, 1.0 eq.), 2,6-lutidine (39 mg, 0.37 mmol, 0.05 eq.) followed by DMAP (18 mg, 0.148 mmol, 0.02 eq.) at 0° C. and the reaction mixture was stirred for 5 minutes. To the reaction mixture was added dimethyl glycine (381 mg, 3.703 mmol, 0.5 eq.), the reaction mixture was allowed to warm slowly to room temperature and stirred for additional 48 hours. The reaction mixture was diluted with ice-cold water (15 mL) and extracted with ethyl acetate (2×15 mL). The combined organic layers were washed with a brine solution (10 mL), dried over anhydrous Na$_2$SO$_4$, solids were removed by filtration and the filtrate was concentrated in vacuo to provide the crude reaction product that was purified by silica-gel chromatography (35% EtOAc/hexane) to afford 2-(dimethylamino)-1-(5-fluoro-1H-indol-1-yl)ethan-1-one. Yield: 600 mg, 36%, brown liquid; m/z=221.1 [M+H]$^+$; $^1$H NMR (DMSO-d6, 400 MHz): δ 8.33 (dd, J=9.0, 4.9 Hz, 1H), 7.99 (d, J=3.8 Hz, 1H), 7.42 (dd, J=9.2, 2.6 Hz, 1H), 7.16 (dt, J=9.2, 2.6 Hz, 1H), 6.72 (d, J=3.7 Hz, 1H), 3.76 (s, 2H), 2.32 (s, 6H).

Preparation of 2-(dimethylamino)-1-(1H-indol-1-yl) ethan-1-one (Example 44)

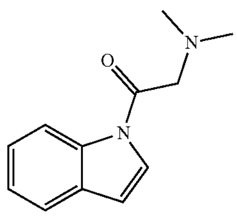

2-(dimethylamino)-1-(1H-indol-1-yl)ethan-1-one was prepared as described for 2-(dimethylamino)-1-(5-fluoro-1H-indol-1-yl)ethan-1-one but using Indole as the starting material. Yield: 600 mg, 40%, brown liquid; m/z=203.1 [M+H]$^+$; $^1$H NMR (DMSO-d6, 400 MHz): δ 8.36-8.32 (m, 1H), 7.91 (d, J=3.8 Hz, 1H), 7.63-7.60 (m, 1H), 7.34-7.24 (m, 2H), 6.73-6.71 (m, 1H), 3.76 (s, 2H), 2.33 (s, 6H).

Preparation of 2-(dimethylamino)-1-(5-methoxy-1H-indol-1-yl)ethan-1-one (Example 45)

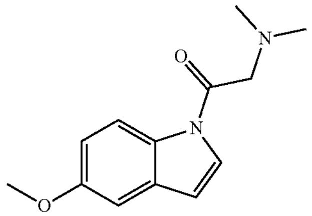

2-(dimethylamino)-1-(5-methoxy-1H-indol-1-yl)ethan-1-one was prepared as described for 2-(dimethylamino)-1-(5-fluoro-1H-indol-1-yl)ethan-1-one but using 5-methoxy indole as the starting material. Yield: 600 mg, 36%, brown liquid; m/z=233.1 [M+H]$^+$; $^1$H NMR (DMSO-d6, 400 MHz): δ 8.21 (d, J=9.0 Hz, 1H), 7.87 (d, J=3.8 Hz, 1H), 7.13 (d, J=2.4 Hz, 1H), 6.92 (dd, J=9.0, 2.5 Hz, 1H), 6.64 (d, J=3.8 Hz, 1H), 3.79 (s, 3H), 3.72 (s, 2H), 2.31 (s, 6H).

Preparation of (R)-2-(dimethylamino)-1-(1H-indol-1-yl)propan-1-one (Example 46)

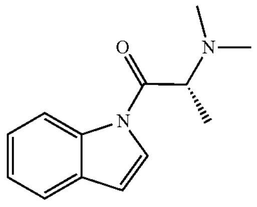 [SMILES: C[C@H](C(=O)n1ccc2ccccc21)N(C)C]

(R)-2-(dimethylamino)-1-(1H-indol-1-yl)propan-1-one was prepared as described for 2-(dimethylamino)-1-(5-fluoro-1H-indol-1-yl)ethan-1-one but using dimethyl-D-alanine as the starting material. Yield: 50 mg, 22%, brown liquid; m/z=217.2 [M+H]$^+$; $^1$H NMR (400 MHz, DMSO-d6) δ=8.37 (d, J=8.0 Hz, 1H), 7.99 (d, J=3.8 Hz, 1H), 7.61 (d, J=7.4 Hz, 1H), 7.36-7.21 (m, 2H), 6.71 (d, J=3.6 Hz, 1H), 4.28 (q, J=6.5 Hz, 1H), 2.26 (s, 6H), 1.22 (d, J=6.6 Hz, 3H).

The maleate salt of (R)-2-(dimethylamino)-1-(1H-indol-1-yl)propan-1-one was prepared as described for 1-(4,5-difluoro-1H-indol-1-yl)-N,N,2-trimethylpropan-2-amine. Yield: 50 mg as a white solid. $^1$H NMR (400 MHz, CD$_3$OD) δ=8.43 (d, J=8.1 Hz, 1H), 7.73 (d, J=3.9 Hz, 1H), 7.63 (d, J=7.1 Hz, 1H), 7.42-7.31 (m, 2H), 6.86 (d, J=3.7 Hz, 1H), 6.26 (s, 2H), 4.98 (q, J=6.9 Hz, 1H), 2.99 (s, 6H), 1.72 (d, J=7.0 Hz, 3H).

Preparation of (R)-2-(dimethylamino)-1-(5-methoxy-1H-indol-1-yl)propan-1-one (Example 47)

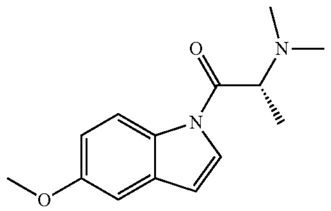

(R)-2-(dimethylamino)-1-(5-methoxy-1H-indol-1-yl)propan-1-one was prepared as described for (R)-2-(dimethylamino)-1-(5-methoxy-1H-indol-1-yl)propan-1-one but using 5-methoxy-1H-indole and dimethyl-D-alanine as the starting materials. Yield: 100 mg, 27%, brown gummy liquid; m/z=247.2 $[M+H]^+$; $^1H$ NMR (400 MHz, DMSO-d6) δ=8.24 (d, J=9.0 Hz, 1H), 7.96 (d, J=3.8 Hz, 1H), 7.13 (d, J=2.5 Hz, 1H), 6.91 (dd, J=2.6, 8.9 Hz, 1H), 6.63 (d, J=3.6 Hz, 1H), 4.29-4.20 (m, 1H), 3.79 (s, 3H), 2.25 (s, 6H), 1.21 (d, J=6.6 Hz, 3H)

The maleate salt of (R)-2-(dimethylamino)-1-(5-methoxy-1H-indol-1-yl)propan-1-one was prepared as described for 1-(4,5-difluoro-1H-indol-1-yl)-N,N,2-trimethylpropan-2-amine. Yield: 80 mg as a white solid. $^1H$ NMR (400 MHz, $CD_3OD$) δ=8.31 (d, J=9.0 Hz, 1H), 7.69 (d, J=3.8 Hz, 1H), 7.15 (d, J=2.5 Hz, 1H), 6.98 (dd, J=9.0, 2.5 Hz, 1H), 6.79 (d, J=3.9 Hz, 1H), 6.25 (s, 2H), 4.95 (q, J=7.1 Hz, 1H), 3.85 (s, 3H), 2.98 (s, 6H), 1.71 (d, J=7.0 Hz, 3H).

Preparation of (R)-2-(dimethylamino)-1-(5-fluoro-1H-indol-1-yl)propan-1-one (Example 48)

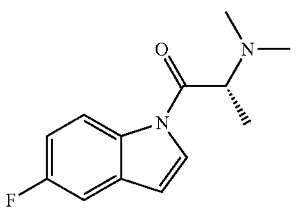 [SMILES: C[C@H](C(=O)n1ccc2cc(F)ccc21)N(C)C]

(R)-2-(dimethylamino)-1-(5-fluoro-1H-indol-1-yl)propan-1-one was prepared as described for (R)-2-(dimethylamino)-1-(5-methoxy-1H-indol-1-yl)propan-1-one but using 5-fluoro-1H-indole and dimethyl-D-alanine as the starting materials. Yield: 30 mg, 14%, brown gummy liquid). m/z=235.2 $[M+H]^+$.

The maleate salt of (R)-2-(dimethylamino)-1-(5-fluoro-1H-indol-1-yl)propan-1-one was prepared as described for 1-(4,5-difluoro-1H-indol-1-yl)-N,N,2-trimethylpropan-2-amine. Yield: 20 mg as an off-white solid. $^1H$ NMR (400 MHz, DMSO-d6) δ=10.62-9.56 (m, 1H), 8.40-8.32 (m, 1H), 8.05-7.99 (m, 1H), 7.52-7.44 (m, 1H), 7.28-7.18 (m, 1H), 6.90-6.81 (m, 1H), 6.11 (s, 2H), 5.31-4.50 (m, 1H), 2.87-2.70 (m, 3H), 1.71-1.35 (m, 3H).

Procedure C

In some embodiments, intermediates used in the preparation of compounds described herein are prepared as outlined in Scheme 3.

Scheme 3

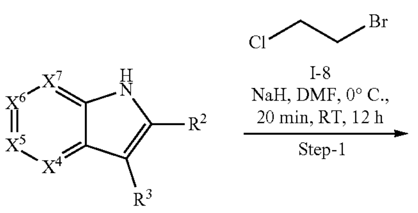

I-7

-continued

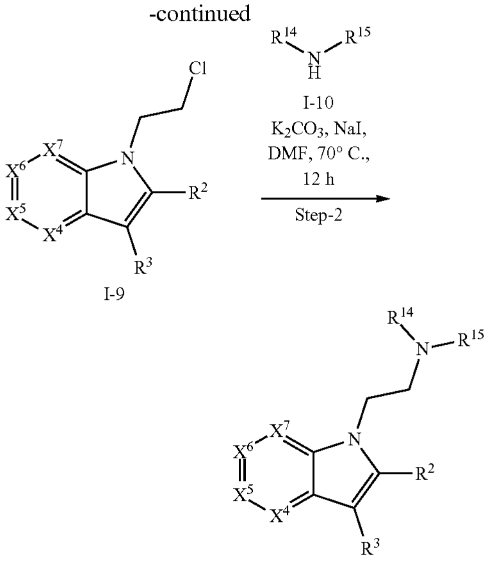

I-9

I-11

In Scheme 3, $X^4$—$X^7$, $R^2$, $R^3$, $R^{12}$, $R^{13}$, $R^{14}$, and $R^{15}$ are as described herein.

General Synthetic Procedures

Step-C1: To a stirred solution of I-7 (1.0 eq) in DMF (10 vol) was added NaH (60% in mineral oil, 1.2 eq) at 0° C. and the reaction mixture was stirred for 20 min. Reagent I-8 (1.0 eq) was added to the reaction that was then slowly warmed to room temperature and stirred for 16 h. The progress of the reaction was monitored by TLC. TLC indicated a non-polar spot with respect to I-7.

Work up after step-C1: The reaction mixture was quenched with ice cold water and extracted with ethyl acetate. The combined organic layer was washed with ice cold water followed by brine wash. The organic layer was separated, dried over $Na_2SO_4$ and concentrated under reduced pressure to get crude material which was purified by combi-flash chromatography using EtOAc/Heptane and then the cleaner fractions are evaporated to obtain I-9.

Step-C2: To a stirred solution of I-9 (1.0 eq) in DMF (10 vol) were added $K_2CO_3$ (3 eq) followed by reagent I-10 (1.2 eq) and NaI (1 eq) at room temperature and then the reaction mixture was heated at 70° C. for 16 h. The progress of the reaction was monitored by TLC. TLC indicated a polar spot with respect to I-9.

Work up after Step-C2: The reaction mixture was quenched with ice cold water and extracted with ethyl acetate. The combined organic layer was washed with ice cold water followed by brine wash. The organic layer was separated, dried over $Na_2SO_4$ and concentrated under reduced pressure to get crude material which was purified by combi-flash chromatography using $CH_2Cl_2$/MeOH based and then cleaner fractions (by TLC) were evaporated and dried to obtain the target compound with >95% LC-MS and HPLC purity.

Pharmaceutical Compositions

Example A-1: Parenteral Pharmaceutical Composition

To prepare a parenteral pharmaceutical composition suitable for administration by injection (subcutaneous, intravenous), 1-1000 mg of a water-soluble salt of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection.

Example A-2: Oral Solution

To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound described herein, or a pharmaceutically acceptable salt thereof, 20-50% by weight of microcrystalline cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 1-1000 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 1-1000 mg of a compound described herein, or a pharmaceutically acceptable salt thereof, is placed into Size 4 capsule, or size 1 capsule (hypromellose or hard gelatin) and the capsule is closed.

Biological Examples

Hallucinogenic Potential. Hallucinogenic compound 5-MeO-DMT produces a robust, dose-dependent head-twitch response (HTR) in mice. However, the isosteric compound 6-MeO-DMT is significantly less potent. As expected based on drug-discrimination data, 6-MeO-DMT does not produce a HTR. Finally, potent plasticity-promoting compounds do not produce a HTR, demonstrating that hallucinogenic potential and psychoplastogenicity can be decoupled.

Hallucinogens (e.g., LSD and 5-MeO-DMT) activate a $5HT_{2A}$ sensor assay in agonist mode, but their non-hallucinogenic congeners (lisuride (LIS) and 6-MeO-DMT) do not. Moreover, compounds, such as, for example, 5-MeO-DMT, LSD, DMT, DOI, which are hallucinogenic in animals (e.g., humans), activate the $5HT_{2A}$ sensor assay in agonist mode, whereas compounds, such as, for example, 6-MeO-DMT, LIS, 6-F-DET, L-MDMA, R-MDMA, Ketanserin, BOL148, which are non-hallucinogenic in animals (e.g., humans), do not activate the $5HT_{2A}$ sensor assay in agonist mode. In some embodiments, hallucinogenic potential of a compound provided herein is determined in vitro. In some embodiments, hallucinogenic potential of a compound provided herein is determined using a $5HT_{2A}$ sensor assay. In some embodiments, the $5HT_{2A}$ sensor assay is in an agonist mode or an antagonist mode. In some embodiments, the $5HT_{2A}$ sensor assay is in an agonist mode. In some embodiments, a compound provided herein does not activate the sensor in agonist mode and has non-hallucinogenic potential. In some embodiments, a compound of provided herein does not activate the sensor in agonist mode and is a non-hallucinogenic compound.

In some embodiments, the hallucinogenic potential of the compound provided herein are assessed in a $5HT_{2A}$ sensor assay in an agonist mode. In some embodiments, the hallucinogenic potential of the compounds assessed in agonist mode is shown in Table 7.

TABLE 7

| | $5HT_{2A}$ Agonist mean @ 100 μM (%) | $5HT_{2A}$ Agonist mean @ 10 μM (%) | $5HT_{2A}$ Agonist mean @ 100 nM (%) |
|---|---|---|---|
| Example 3 | not tested | B | B |
| Example 4 | A | B | B |
| Example 5 | B | B | B |
| Example 6 | B | B | B |
| Example 8 | B | B | B |

Table legend:
A: activates $5HT_{2A}$ sensor assay in agonist mode;
B: does not activate $5HT_{2A}$ sensor assay in agonist mode. The percent is relative to the positive control (5-HT at 100 uM for agonist mode). A compound that produces > 15% response is considered to activate the sensor in agonist mode.

Furthermore, non-hallucinogenic compounds (e.g., lisuride and 6-MeO-DMT) compete off 5-HT when the $5HT_{2A}$ sensor assay is run in antagonist mode. Additionally, compounds, such as, for example, 6-F-DET, Ketanserin, BOL148, which are non-hallucinogenic in animals (e.g., humans), compete with 5HT binding to $5HT_{2A}$ in the antagonist mode sensor assay. In some embodiments, a compound provided herein prevents binding of 5-HT to $5HT_{2A}$. In some embodiments, the $5HT_{2A}$ sensor assay is in an antagonist mode. In some embodiments, a compound provided herein prevents binding of 5-HT to $5HT_{2A}$ and has non-hallucinogenic potential. In some embodiments, a compound provided herein prevents binding of 5-HT to $5HT_{2A}$ and is non-hallucinogenic. In some embodiments, a compound provided herein prevents binding of 5-HT to $5HT_{2A}$ in antagonist mode has non-hallucinogenic potential. In some embodiments, a compound provided herein that prevents binding of 5-HT in antagonist mode is a non-hallucinogenic compound. In some embodiments, a compound provided herein that inhibits the response of the sensor assay in antagonist mode has non-hallucinogenic potential. In some embodiments, a compound provided herein that inhibits the response of the sensor assay in antagonist mode is a non-hallucinogenic compound.

In some embodiments, the results for the agonist mode sensor assay suggests a compound provided herein is a non-hallucinogenic ligand of the $5\text{-}HT_{2A}$ receptor. In some embodiments, the results for the antagonist mode sensor assay suggests a compound provided herein is a non-hallucinogenic ligand of the $5\text{-}HT_{2A}$ receptor. In some embodiments, the results for the agonist mode and antagonist mode sensor assay together suggest a compound provided herein is a non-hallucinogenic ligand of the $5\text{-}HT_{2A}$ receptor.

In some embodiments, the hallucinogenic potential of the compounds are assessed in a $5HT_{2A}$ sensor assay in an antagonist mode. In some embodiments, the hallucinogenic potential of the compounds assessed in antagonist mode is shown in Table 8.

TABLE 8

| | $5HT_{2A}$ Agonist mean @ 100 μM (%) | $5HT_{2A}$ Agonist mean @ 10 μM (%) | $5HT_{2A}$ Agonist mean @ 100 nM (%) |
|---|---|---|---|
| Example 3 | not tested | C | C |
| Example 4 | A | C | C |
| Example 5 | A | C | C |
| Example 6 | A | C | C |
| Example 8 | C | C | C |

Table legend:
A: inhibits 5HT response by > 100%;
B: inhibits 5HT response by 75% to 100%;
C: inhibits 5HT response by < 75%. the percent is relative to the positive control (5-HT at 100 nM for antagonist mode).

Calcium Flux Assay. The Calcium No Wash$^{PLUS}$ assay monitors the activation of a GPCR (e.g., $5HT_{2A}$) via Gq secondary messenger signaling in a live cell, non-imaging assay format. Calcium mobilization in PathHunter® cell lines or other cell lines stably expressing Gq-coupled GPCRs (e.g., $5HT_2$A) is monitored using a calcium-sensitive dye that is loaded into cells. GPCR (e.g., $5HT_{2A}$) activation by a compound results in the release of calcium from intracellular stores and an increase in dye fluorescence that is measured in real-time. In some embodiments, the ability of a compound provided herein to modulate $5\text{-}HT_{2A}$ function is determined using a calcium flux assay. In some embodiments, a compound provided herein activates a calcium flux assay. In some embodiments, the activation of a calcium flux assay indicates that a compound provided herein modulates $5\text{-}HT_{2A}$ function.

In some embodiments, the ability of the compounds provided herein to modulate $5\text{-}HT_2$A function is assessed using a calcium flux assay. In some embodiments, the ability of the compounds of the present invention to modulate $5\text{-}HT_{2A}$ function is assessed from the results of the calcium flux assay (Table 9).

TABLE 9

| | $EC_{50}$ (μM) |
|---|---|
| Example 3 | A |
| Example 4 | A |
| Example 5 | A |
| Example 6 | A |
| Example 7 | A |
| Example 8 | A |

Table legend:
A: > 110 μM;
B: < 10 μM

Forced Swim Test. As increased cortical structural plasticity in the anterior parts of the brain mediates the sustained (>24 h) antidepressant-like effects of ketamine and play a role in the therapeutic effects of $5\text{-}HT_{2A}$ agonists, the impact of compounds on forced swim test (FST) behavior is used evaluate therapeutic potential of compounds provided herein. First, a pretest is used to induce a depressive phenotype. Compounds are administered 24 h after the pre-test, and the FST is performed 24 h and 7 d post drug administration.

Neurite outgrowth assay. Changes in the pattern of neurite outgrowth have been implicated in neurodegenerative disorders as well as traumatic injuries. The discovery of new compounds that can positively affect neuritogenesis are important for developing new therapeutics for neurological diseases. Measurement of neurite outgrowth of rat cortical neurons using an automated image-based assay is used to determine the neuroplastic effects of the compounds provided herein. In some embodiments, a compound provided herein increases the pattern of neurite outgrowth. In some embodiments, a compound provided herein increases neurite average length compared to a control. In some embodiments, a compound provided herein increases neurite branch points compared to a control. In some embodiments, a compound provided herein increases neurite average length and neurite branch points compared to a control.

In some embodiments, the plastogenic potential of compounds provided herein is assessed by measuring the changes in neurite development. In some embodiments, the plastogenic potential (as measured by Neurite Outgrowth Procedure A) of the compounds is shown in Table 10.

TABLE 10

| | Neurite Average Length @ 10 μM | Neurite Branch Points: @ 10 μM |
|---|---|---|
| Example 3 | B | A |
| Example 4 | B | B |
| Example 5 | B | C |
| Example 6 | A | A |
| Example 7 | B | A |
| Example 8 | B | A |

A: >200% vehicle;
B: 100%-200% vehicle;
C: <100% vehicle

Assays

Dendritogenesis Assays. Phenotypic screening has historically proven more successful than target-based approaches for identifying drugs with novel mechanisms of action. Using a phenotypic assay, the compounds provided herein are tested for their ability to increase dendritic arbor complexity in cultures of cortical neurons. Following treatment, neurons are fixed and visualized using an antibody against MAP2—a cytoskeletal protein localized to the somatodendritic compartment of neurons. Sholl analysis is then performed, and the maximum number of crossings ($N_{max}$) is used as a quantitative metric of dendritic arbor complexity. For statistical comparisons between specific compounds, the raw $N_{max}$ values are compared. Percent efficacies are determined by setting the $N_{max}$ values for the vehicle (DMSO) and positive (ketamine) controls equal to 0% and 100%, respectively.

Animals. For the dendritogenesis experiments, timed pregnant Sprague Dawley rats are obtained from Charles River Laboratories (Wilmington, MA). In some instances, male and female C57BL/6J mice are obtained from Jackson Laboratory (Sacramento, C.A.). In some instances, mice are housed in a temperature and humidity-controlled room maintained on a 12-h light/dark cycle in groups of 4-5 (same sex).

Dendritogenesis—Sholl Analysis. Neurons are plated in 96-well format (200 μL of media per well) at a density of approximately 15,000 cells/well in Neurobasal (Life Technologies) containing 1% penicillin-streptomycin, 10% heat-inactivated fetal bovine serum, and 0.5 mM glutamine. After 24 h, the medium is replaced with Neurobasal containing 1×B27 supplement (Life Technologies), 1% penicillin-streptomycin, 0.5 mM glutamine, and 12.5 μM glutamate. After 3 days in vitro (DIV3), the cells are treated with compounds. Compounds tested in the dendritogenesis assays are treated at 10 μM unless noted otherwise. Stock solutions of the compounds in DMSO are first diluted 100-fold in Neurobasal before an additional 10-fold dilution into each well (total dilution=1:1000; 0.1% DMSO concentration). Treatments are randomized. After 1 h, the media is removed and replaced with new Neurobasal media containing 1×B27 supplement, 1% penicillin-streptomycin, 0.5 mM glutamine, and 12.5 μM glutamate. The cells grow for an additional 71 h. At that time, neurons are fixed by removing 80% of the media and replacing it with a volume of 4% aqueous paraformaldehyde (Alfa Aesar) equal to 50% of the working volume of the well. Then, the cells are incubated at room temperature for 20 min before the fixative is aspirated and each well washed twice with DPBS. Cells are permeabilized using 0.2% Triton X-100 (ThermoFisher) in DPBS for 20 minutes at room temperature without shaking. Plates are blocked with antibody diluting buffer (ADB) containing 2% bovine serum albumin (BSA) in DPBS for 1 h at room temperature. Then, plates are incubated overnight at 4° C. with gentle shaking in ADB containing a chicken anti-MAP2 antibody (1:10,000; EnCor, CPCA-MAP2). The next day, plates are washed three times with DPBS and once with 2% ADB in DPBS. Plates are incubated for 1 h at room temperature in ADB containing an anti-chicken IgG secondary antibody conjugated to Alexa Fluor 488 (Life Technologies, 1:500) and washed five times with DPBS. After the final wash, 100 μL of DPBS is added per well and imaged on an ImageXpress Micro XL High-Content Screening System (Molecular Devices, Sunnyvale, CA) with a 20× objective.

Images are analyzed using ImageJ Fiji (version 1.51W). First, images corresponding to each treatment are sorted into individual folders that are then blinded for data analysis. Plate controls (both positive and negative) are used to ensure that the assay is working properly as well as to visually determine appropriate numerical values for brightness/contrast and thresholding to be applied universally to the remainder of the randomized images. Next, the brightness/contrast settings are applied, and approximately 1-2 individual pyramidal-like neurons per image (i.e., no bipolar neurons) are selected using the rectangular selection tool and saved as separate files. Neurons are selected that did not overlap extensively with other cells or extend far beyond the field of view. The threshold settings are then applied to the individual images. The paintbrush tool is used to eliminate artifacts and dendritic processes originating from adjacent neurons (cleanup phaseNext, the point tool is used to select the center of the neuron, and the images are saved and processed using the following Sholl analysis batch macro:

run("Sholl Analysis . . . ", "starting=0 ending=NaN radius_step=2 #_samples=1 integration=Mean enclosing=1 #_primary=4 infer fit linear polynomial=[Best fitting degree] most semi-log normalizer=Area create background=228 save do");

Sholl analysis circle radii=2 pixel increments=0.67 μm. All images are taken and analyzed by an experimenter blinded to treatment conditions. The number of crossings for each neuron at each distinct radius is averaged to produce an average Sholl plot for each treatment. The $N_{max}$ values are simply determined by identifying the maximum of each plot. For each treatment, neurons are selected from at least 6 wells spread across 2 plates (9 sites/well×3 wells/plate×2 plates). Each plate is prepared using neurons obtained from independent pregnant dams).

Spinogenesis Experiments. Spinogenesis experiments are performed as previously described with the exception that cells are treated on DIV19 and fixed 24 h after treatment on DIV20. (Ly, C. et al., 2018) The images are taken on a Nikon HCA Confocal microscope a with a 100×/NA 1.45 oil objective. DMSO and ketamine (10 μM) are used as vehicle and positive controls, respectively.

Ketanserin Blocking Experiments. On DIV 3, neurons are first treated with ketanserin (10 μM) for 1 h followed by a 1 h incubation with drug (1 μM) and ketanserin (10 μM) (final concentration of DMSO=0.2%). After 1 h, the media is removed and replaced with new Neurobasal media containing 1×B27 supplement, 1% penicillin-streptomycin, 0.5 mM glutamine, and 12.5 μM glutamate. The cells are allowed to grow for an additional 71 h before being fixed, stained, and imaged.

hERG Inhibition Studies. Experiments are conducted manually using an EPC-10 amplifier (HEKA, Lambrecht/Pfalz, Germany) at room temperature in the whole-cell mode of the patch-clamp technique. Cells are cultured in DMEM containing 10% fetal bovine serum, 2 mM glutamine, 1 mM sodium pyruvate, 100 U/mL penicillin, 100 μg/mL streptomycin, and 500 mg/ml G418. Before experiments, cells are cultured to 60-80% confluency and lifted using TrypLE and plated onto poly-L-lysine-coated coverslips. Patch pipettes are pulled from soda lime glass (micro-hematocrit tubes) and have resistances of 2-4 MO. For the external solution, normal sodium Ringer is used (160 mM NaCl, 4.5 mM KCl, 2 mM $CaCl_2$), 1 mM $MgCl_2$, 10 mM HEPES, pH 7.4 and 290-310 mOsm). The internal solution is potassium fluoride with ATP (160 mM KF, 2 mM $MgCl_2$, 10 mM EGTA, 10 mM HEPES, 4 mM NaATP, pH=7.2 and 300-320 mOsm). A 2-step pulse (applied every 10 sec) from −80 mV first to 40 mV for 2 sec and then to −60 mV for 4 sec, is used to elicit hERG currents. The percent reduction of tail current amplitude by the drugs is determined and data are shown as mean+/−SD. Solutions of the drugs are prepared fresh from 10 mM stock solutions in DMSO.

Serotonin and Opioid Receptor Functional Assays. Functional assay screens at 5-HT and opioid receptors are performed in parallel using the same compound dilutions and 384-well format high-throughput assay platforms. Receptor constructs in pcDNA vectors are generated from the Presto-Tango GPCR library with minor modifications. Compounds are serially diluted in drug buffer (HBSS, 20 mM HEPES, pH 7.4 supplemented with 0.1% bovine serum albumin and 0.01% ascorbic acid) and dispensed into 384-well assay plates using a $FLIPR^{TETRA}$ (Molecular Devices). Every plate includes a positive control, such as 5-HT (for all 5-HT receptors), DADLE (DOR), salvinorin A (KOR), and DAMGO (MOR). For measurements of 5-HT2A, 5-HT2B, and 5-HT2C Gq-mediated calcium flux function, HEK Flp-In 293 T-Rex stable cell lines (Invitrogen) are loaded with Fluo-4 dye for one hour, stimulated with compounds and read for baseline (0-10 seconds) and peak fold-over-basal fluorescence (5 minutes) at 25° C. on the $FLIPR^{TETRA}$. For measurement of 5-HT6 and 5-HT7a functional assays, Gs-mediated cAMP accumulation is detected using the split-luciferase GloSensor assay in HEKT cells measuring luminescence on a Microbeta Trilux (Perkin Elmer) with a 15 min drug incubation at 25° C. For 5-HT1A, 5-HT1B, 5-HT1F, MOR, KOR, and DOR functional assays, Gi/o-mediated cAMP inhibition is measured using the split-luciferase GloSensor assay in HEKT cells, conducted similarly as above, but in combination with either 0.3 μM isoproterenol (5-HT1A, 5-HT1B, 5-HTIF) or 1 μM forskolin (MOR, KOR, and DOR) to stimulate endogenous cAMP accumulation. For measurement of 5-HT1D, 5-HT1E, 5-HT4, and 5-HT5A functional assays, 0-arrestin2 recruitment is measured by the Tango assay utilizing HTLA cells expressing TEV fused-o-arrestin2, as described previously with minor modifications. Data for these assays are plotted and non-linear regression is performed using "log(agonist) vs. response" in Graphpad Prism to yield Emax and $EC_{50}$ parameter estimates.

Serotonin 5-HT$_{2A}$ In Vitro Radioligand Binding Competition Assay. The 5-HT2A radioligand binding competition assay was performed at Epics Therapeutics S.A. (Belgium, FAST-0505B) using conventional methods. Briefly, competition binding is performed in duplicate in the wells of a 96 well plate (Master Block, Greiner, 786201) containing binding buffer (optimized for each receptor), membrane extracts (amount of protein/well optimized for each receptor), radiotracer [$^3$H]-DOI (final concentration optimized for each receptor) and test compound. Nonspecific binding is determined by co-incubation with 200-fold excess of cold competitor. The samples are incubated in a final volume of 0.1 ml at a temperature and for a duration optimized for each receptor and then filtered over filter plates. Filters are washed six times with 0.5 ml of ice-cold washing buffer (optimized for each receptor) and 50 μl of Microscint 20 (Packard) are added in each well. The plates are incubated 15 min on an orbital shaker and then counted with a TopCount™ for 1 min/well.

Serotonin 5-HT$_{2A}$ In Vitro Cellular IPOne Agonism Assay. The 5-HT$_{2A}$ IPOne HTRF assay was performed at Epics Therapeutics S.A. (Belgium, FAST-0505I) using conventional methods. Briefly, CHO-K1 cells expressing human recombinant 5-HT$_{2A}$ receptor grown to mid-log phase in culture media without antibiotics were detached with PBS-EDTA, centrifuged, and resuspended in medium without antibiotics buffer. 20,000 cells are distributed in a 96 well plate and incubated overnight at 37° C. with 5% $CO_2$.

For agonist testing, the medium is removed and 20 μl of assay buffer plus 20 μl of test compound or reference agonist are added in each well. The plate is incubated for 60 min. at 37° C. with 5% $CO_2$.

After addition of the lysis buffer containing IP1-d2 and anti-IP1 cryptate detection reagents, plates are incubated 1-hour at room temperature, and fluorescence ratios are measured according to the manufacturer specification, with the HTRF kit.

Serotonin 5-HT2C In Vitro Radioligand Binding Competition Assay. The 5-HT2C edited (accession number AAF35842.1) radioligand binding competition assay was performed at Epics Therapeutics S.A. (Belgium, FAST-0507B) using conventional methods. Briefly, competition binding is performed in duplicate in the wells of a 96 well plate (Master Block, Greiner, 786201) containing binding buffer (optimized for each receptor), membrane extracts (amount of protein/well optimized for each receptor), radiotracer [3H]-DOI (final concentration optimized for each receptor) and test compound. Nonspecific binding is determined by co-incubation with 200-fold excess of cold competitor. The samples are incubated in a final volume of 0.1 ml at a temperature and for a duration optimized for each receptor and then filtered over filter plates. Filters are washed six times with 0.5 ml of ice-cold washing buffer (optimized for each receptor) and 50 1 of Microscint 20 (Packard) are added in each well. The plates are incubated 15 min on an orbital shaker and then counted with a TopCount™ for 1 min/well.

Serotonin 5-HT2C In Vitro Cellular IPOne Agonism Assay. The 5-HT2C IPOne HTRF assay was performed at Epics Therapeutics S.A. (Belgium, FAST-0507I) using conventional methods. Briefly, CHO-K1 cells expressing human recombinant 5-HT2C edited receptor (accession number AAF35842.1) grown to mid-log phase in culture media without antibiotics were detached with PBS-EDTA, centrifuged, and resuspended in medium without antibiotics buffer. 20,000 cells are distributed in a 96 well plate and incubated overnight at 37° C. with 5% $CO_2$.

For agonist testing, the medium is removed and 20 μl of assay buffer plus 20 μl of test compound or reference agonist are added in each well. The plate is incubated for 60 min. at 37° C. with 5% $CO_2$.

After addition of the lysis buffer containing IP1-d2 and anti-IP1 cryptate detection reagents, plates are incubated 1-hour at room temperature, and fluorescence ratios are measured according to the manufacturer specification, with the HTRF kit.

The compounds provided herein were tested in the Serotonin 5-HT$_{2A}$ and 5-HT2C in vitro radioligand binding and cellular IPOne agonism assays. The binding and agonism functional potencies of several compound provided herein compounds (as indicated by their $IC_{50}$s or $EC_{50}$s) are shown in Table 11.

TABLE 11

| | 5-HT2A Radioligand Binding Activity | 5-HT2A IPOne Agonism Activity | 5-HT2C Radioligand Binding Activity | 5-HT2C IPOne Agonism Activity |
|---|---|---|---|---|
| Example 1 | E | E | D | E |
| Example 2 | E | E | D | E |
| Example 3 | C | E | C | E |
| Example 4 | D | E | C | E |
| Example 5 | C | E | C | E |
| Example 6 | D | E | D | E |
| Example 7 | E | E | E | E |
| Example 8 | E | E | D | E |
| Example 9 | C | E | C | E |
| Example 10 | D | E | D | D |
| Example 11 | C | E | C | E |
| Example 12 | E | E | E | E |
| Example 13 | E | D | D | D |
| Example 14 | E | E | E | E |
| Example 15 | E | E | E | E |
| Example 16 | E | E | E | E |
| Example 17 | E | E | E | E |
| Example 18 | E | E | E | E |
| Example 19 | E | E | E | E |
| Example 20 | E | E | E | E |
| Example 21 | E | E | E | E |
| Example 22 | E | E | E | E |
| Example 23 | E | E | E | E |
| Example 24 | E | E | D | E |
| Example 25 | E | E | D | E |
| Example 26 | E | D | D | D |
| Example 27 | E | E | E | E |
| Example 28 | E | E | E | D |
| Example 29 | E | E | E | E |
| Example 30 | E | E | E | E |
| Example 31 | D | D | C | C |
| Example 32 | E | E | D | D |
| Example 33 | E | E | E | E |
| Example 34 | E | D | D | D |
| Example 35 | E | E | E | D |
| Example 36 | E | E | D | D |
| Example 37 | E | E | E | D |
| Example 38 | E | E | E | E |
| Example 39 | E | E | E | E |
| Example 40 | D | D | C | C |
| Example 41 | D | D | C | C |
| Example 42 | E | D | D | D |
| Example 43 | E | E | E | E |
| Example 44 | E | E | E | E |

TABLE 11-continued

| | 5-HT2A Radioligand Binding Activity | 5-HT2A IPOne Agonism Activity | 5-HT2C Radioligand Binding Activity | 5-HT2C IPOne Agonism Activity |
|---|---|---|---|---|
| Example 45 | E | E | E | E |
| Example 46 | E | E | D | E |
| Example 47 | E | E | E | E |
| Example 48 | E | E | D | E |

Table legend:
A: IC50 or EC50 is < 0.010 μM;
B: IC50 or EC50 is 0.010 μM-0.100 μM;
C: IC50 or EC50 is 0.101 μM-1 μM;
D: IC50 or EC50 is 1.001 μM-10 μM; E: IC50 or EC50 is > 10 μM Neurite Outgrowth Assay (Procedure A). Rat cortical neurons (20,000 cells/well) were freshly isolated from embryonic day 18 rats and cultured in Neurobasal Medium (+B27). The cultured cells were plated in 96 well-plates (avoiding external wells). At DIV 4, the neurons were treated with compound or control (10 μM) for 1 hour followed by complete washout of the compound. At DIV 7, the neurons were analyzed. The experiments were performed in triplicate. Neurite outgrowth was measured analyzing the following parameters: Number of Cell Bodies, total neurite length (pixels), Root Count, Segments, Extremities Count and node points. Changes in the pattern of neurite outgrowth of the neurons were analyzed by immunocytochemistry against 3-III-tubulin. Pictures were acquired by the CellInsight CX7 from Thermo Fisher and analyzed using its software. Results generated in the equipment were maximum neurite length, extremity count, root count, dendrite branch points, and total neurite length. The results were compared the percent of DMSO control, representing the percentage of outgrowth compare to vehicle control in neuronal outgrowth.

Neurite Outgrowth in Primary Neuronal Cultures Assay (Procedure B). Changes in the pattern of neurite outgrowth have been implicated in psychiatric and neurodegenerative disorders as well as traumatic injuries. The discovery of new compounds that can positively affect neuritogenesis are important for developing new therapeutics for neurological diseases. Measurement of neurite outgrowth of rat cortical neurons using an automated image-based assay was used to determine the neuroplastic effects of the compounds of the present invention. The neurite outgrowth assay was performed at Neurofit SAS (France) as described below.

Pregnant Wistar rats (Janvier; France) were used for the study. They were delivered 6 days before their use. Upon arrival at Neurofit animal facility, they were housed one per cage and maintained in a room with controlled temperature (21-22° C.) and a reversed light-dark cycle (12 h/12 h; lights on: 17:30-05:30; lights off: 05:30-17:30) with food and water available ad libitum.

Female Wistar rats of 17 days gestation were killed by cervical dislocation and the fetuses were removed from the uterus. Their brains were placed in ice-cold medium of Leibovitz (L15, Gibco, Fisher bioblock, France). Cortices were dissected and meninges were carefully removed. The cortical neurons were dissociated by trypsinization for 30 min at 37° C. (trypsin-EDTA, Gibco) in presence of 0.1 mg/ml DNAse I (Roche, France). The reaction was stopped by addition of Dulbecco's Modified Eagle Medium (DMEM; Gibco) with 10% of fetal bovine serum (FBS; Gibco). The suspension was triturated with a 10-ml pipette and using a needle syringe 21G and centrifuged at 350×g for 10 min at room temperature. The pellet of dissociated cells was resuspended in a medium consisting of Neurobasal (Gibco) supplemented with 2% B27 supplement (Gibco), 0.5 mM L-Glutamine (Gibco), an antibiotic-antimicotic mixture. Viable cells were counted in a Neubauer cytometer using the trypan blue exclusion test (Sigma). Cells were seeded at a density of 10000 cells per well in 96-well plate (Costar) precoated with poly-L-lysine. Test compound at different concentrations were added to the cultures. Donepezil (positive control) was tested at 250 nM.

After 72 h (3 days) of plating, cultures were fixed with paraformaldehyde in PBS (4%, Sigma) for 30 min at 4° C. Then, cells were successively permeabilized with 0.1% Triton X100 for 30 min, saturated with PBS containing 3% of BSA and were incubated 1 h with anti-beta III tubulin antibody (Sigma) at 1/10 000 in PBS containing 0.5% of BSA. Cells were washed three times with PBS containing 0.5% of BSA, and they were incubated 1 h with goat anti-mouse antibody coupled with AF488 (Invitrogen A11001) diluted at 1/1000 in PBS containing 0.5% of BSA. Finally, nuclei were staining with DAPI 1 mg/ml at 1/1000 in PBS containing 0.5% of BSA. After rinsing with PBS, the plate was filmed and neurite networks were examined and analyzed using High-Content Screening (CellInsight, Thermo Scientific). The average number of neurites per neuron and the average total length of neurites per neuron were the main parameters analyzed. Analysis of data was performed using analysis of variance (ANOVA). The Fisher's Protected Least Significant Difference test was used for multiple comparisons. A p value$<0.05$ was considered significant. The software used is StatView 5.0 from SAS Institut.

In some embodiments, a compound of the present invention increases the pattern of neurite outgrowth. In some embodiments, a compound of the present invention increases neurite average length compared to a control. In some embodiments, a compound of the present invention increases neurite branch points compared to a control. In some embodiments, a compound of the present invention significantly increases the number of new neurites and/or the average neurite length compared to a control.

Plastogenic potential (as measured by Neurite Outgrowth Procedure B) of several compounds provided herein is shown in Table 12.

TABLE 12

| | Increase in Neurite Number | Increase in Neurite Length |
|---|---|---|
| Example 1 | A | A |
| Example 2 | B | B |
| Example 3 | B | A |
| Example 4 | A | A |
| Example 5 | B | B |
| Example 6 | B | B |
| Example 7 | B | A |
| Example 8 | B | A |
| Example 9 | B | B |
| Example 24 | B | A |
| Example 25 | B | A |
| Example 27 | B | A |
| Example 28 | B | A |
| Example 29 | B | A |
| Example 30 | A | A |
| Example 31 | B | B |
| Example 32 | B | B |
| Example 33 | B | A |
| Example 36 | B | B |

TABLE 12-continued

| | Increase in Neurite Number | Increase in Neurite Length |
|---|---|---|
| Example 39 | B | B |
| Example 45 | B | B |
| Example 47 | B | B |

Figure legend:
A: Statistically significant mean increase as a percent of DMSO control at 10 μM or less;
B: No statistically significant mean increase as a percent of DMSO control at 10 μM or less $5HT_{2A}$ Sensor Assays. HEK293T (ATCC) 5HT2A sensor stable line (sLight1.3s) was generated via lentiviral transduction of HIV-EF1α-sLight1.3 and propagated from a single colony. Lentivirus was produced using $2^{nd}$ generation lentiviral plasmids pHIV-EF1α-sLight1.3, pHCMV-G, and pCMV-deltaR8.2.

For the screening, sLight1.3s cells were plated in 96-well plates at a density of 40000 24-hours prior to imaging. On the day of imaging, compounds solubilized in DMSO were diluted from the 100 mM stock solution to working concentrations of 1 mM, 100 μM and 1 μM with a DMSO concentration of 1%. Immediately prior to imaging, cells growing in DMEM (Gibco) were washed 2× with HBSS (Gibco) and in agonist mode 180 μL of HBSS or in antagonist mode 160 μL of HBSS was added to each well after the final wash. For agonist mode, images were taken before and after the addition of the 20 μL compound working solution into the wells containing 180 μL HBSS. This produced final compound concentrations of 100 μM, 10 μM and 100 nM with a DMSO concentration of 0.1%. For antagonist mode, images were taken before and after addition of 20 μL of 900 nM 5-HT and again after 20 μL of the compound working solutions to produce final concentrations of 100 nM for 5HT and 100 μM, 10 μM and 100 nM for the compounds with a DMSO concentration of 0.1%. Compounds were tested in triplicates (3 wells) for each concentration (100 μM, 10 μM and 100 nM). Additionally, within each plate, 100 nM 5HT and 0.1% DMSO controls were also imaged.

Imaging was performed using the Leica DMi8 inverted microscope with a 40× objective using the FITC preset with an excitation of 460 nm and emission of 512-542 nm. For each well, the cellular membrane where the $5HT_{2A}$ sensor is targeted was autofocused using the adaptive focus controls and 5 images from different regions within the well were taken with each image processed from a 2×2 binning.

For data processing, the membranes from each image were segmented and analyzed using a custom algorithm written in MATLAB producing a single raw fluorescence intensity value. For each well the 5 raw fluorescence intensity values generated from the 5 images were averaged and the change in fluorescence intensity (dFF) was calculated as:

$$dFF = (F_{sat} - F_{apo})/F_{apo}$$

For both agonist and antagonist modes, the fluorescence intensity values before compound addition in HBSS only were used as the $F_{apo}$ values while the fluorescence intensity values after compound addition were used as the $F_{sat}$ values.

For agonist mode, data were as percent activation relative to 5HT, where 0 is the average of the DMSO wells and 100 is the average of the 100 uM 5HT wells. For antagonist mode, the inactivation score was calculated as:

$$\text{Inactivation score} = (dFFF(\text{Compound} + 5HT) - dFF(5HT))/dFF(5HT)$$

Calcium Secondary Messenger Pathway. Cell lines were expanded from freezer stocks according to standard procedures. Cells were seeded in a total volume of 20 μL into black-walled, clear-bottom, Poly-D-lysine coated 384-well microplates and incubated at 37° C. for the appropriate time prior to testing. Assays were performed in 1× Dye Loading Buffer consisting of 1× Dye, 1× Additive A and 2.5 mM Probenecid in HBSS/20 mM Hepes. Probenicid was prepared fresh. Cells were loaded with dye prior to testing. Media was aspirated from cells and replaced with 20 μL Dye Loading Buffer. Cells are incubated for 30-60 minutes at 37° C.

For agonist determination, cells were incubated with sample to induce response. After dye loading, cells were removed from the incubator and 10 μL HBSS/20 mM Hepes was added. 3× vehicle was included in the buffer when performing agonist dose curves to define the ECso for subsequent antagonist assays. Cells were incubated for 30 minutes at room temperature in the dark to equilibrate plate temperature. Intermediate dilution of sample stocks was performed to generate 4× sample in assay buffer. Compound agonist activity was measured on a FLIPR Tetra (MDS). Calcium mobilization is monitored for 2 minutes and 10 μL 4× sample in HBSS/20 mM Hepes was added to the cells 5 seconds into the assay.

Compound activity was analyzed using CBIS data analysis suite (ChemInnovation, CA). For agonist mode assays, percentage activity was calculated using the following formula:

$$\% \text{ Activity} = 100\% \times (\text{mean } RFU \text{ of test sample} - \text{mean } RFU \text{ of vehicle control})/(\text{mean MAX} RFU \text{ control ligand} - \text{mean} RFU \text{ of vehicle control}).$$

Head twitch response (HTR) experiments. C57BL/6J Mice (9-10 weeks old) are housed following an IACUC approved protocol. The mice are habituated in the test cage for at least 30 min, injected intraperitoneally with compound (injection volume 5 ml/kg), returned to the empty test cage, and filmed for 20 minutes. Each video is scored for the number of head-twitches by a trained observer blinded to treatment condition.

Forced Swim Test (FST) (Procedure A). Male C57/BL6J mice are obtained from the Jackson Lab and housed 4-5 mice/cage in a UCD vivarium following an IACUC approved protocol. After 1 week in the vivarium each mouse is handled for approximately 1 minute by an experimenter for 3 consecutive days leading up to the first FST. Experiments are carried out by the same experimenter who performed handling. During the FST, mice undergo a 6 min swim session in a clear Plexiglas cylinder 40 cm tall, 20 cm in diameter, and filled with 30 cm of 24±1° C. water. Fresh water is used for every mouse. After handling and habituation to the experimenter, drug-naïve mice first undergo a pretest swim to more reliably induce a depressive phenotype in the subsequent FST sessions. Immobility scores for mice are determined after the pre-test and mice are randomly assigned to treatment groups to generate groups with similar average immobility scores to be used for the following two FST sessions. The next day, the animals receive intraperitoneal injections of experimental compounds (20 mg/kg), a positive control (ketamine, 3 mg/kg), or vehicle (saline). The animals are subjected to the FST 30 mins after injection and then returned to their home cages. Immobility time-defined as passive floating or remaining motionless with no activity other than that needed to keep the mouse's head above water—is scored for the last 4 min of the 6 min trial.

Forced Swim Test (FST) (Procedure B). Male Sprague Dawley rats from Envigo (Indianapolis, IN) are obtained and housed 3 rats per cage following an IACUC approved protocol. All experiments are carried out at ambient temperatures (20 and 23° C.) under artificial lighting during the light-on part of the light/dark cycle in a Forced Swim chamber constructed of clear acrylic (height=40 cm; diameter=20.3 cm). Only one rat is placed in the swim chamber at a time for each swim test. The water is changed and the chamber cleaned between each animal. All rats are exposed to two swim sessions. The water depth is 16 cm in the first swim session and 30 cm in the second swim session, and the water temperature is maintained at 23±1° C. for all swim sessions. During the FST, animals undergo a 15 min swim session (pre-swim), lasting for 15 minutes, dried with paper towels, and returned to the home cage. Rats are injected with either saline, ketamine (positive control), or test compound after the habituation session, returned to home cage, and then tested in a second FST lasting 5 minutes ~24 hours (second swim test) later. The second swim test is video recorded for scoring. Body weights are measured on both days. Scoring of the second swim test is performed by trained technicians using a time sampling technique in which the animal in the video recorded test is viewed every 5 seconds and the behavior seen is noted. The measures noted are immobility, climbing, and swimming behaviors.

Statistical analysis. Treatments are randomized, and data are analyzed by experimenters blinded to treatment conditions. Statistical analyses are performed using GraphPad Prism (version 8.1.2). Comparisons are planned prior to performing each experiment.

The examples and embodiments described herein are for illustrative purposes only and various modifications or changes suggested to persons skilled in the art are to be included within the spirit and purview of this application and scope of the appended claims.

What is claimed is:

1. A compound having the structure of Formula (VI), or a pharmaceutically acceptable salt:

Formula (VI)

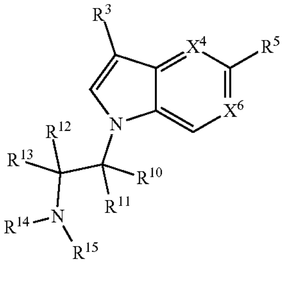

wherein:

$R^3$ is hydrogen or $C_1$-$C_3$ alkyl;

$X^4$ is N or $CR^4$;

$R^4$ is hydrogen or halo;

$X^6$ is N or CH;

$R^5$ is halo or $C_1$-$C_3$ alkoxy;

$R^{10}$ and $R^{11}$ are each hydrogen;

$R^{12}$ and $R^{13}$ are each independently hydrogen or $C_1$-$C_3$ alkyl;

or $R^{12}$ and $R^{13}$ are taken together with the atoms to which they are attached to form a cyclopropyl ring;

$R^{14}$ is hydrogen or $C_1$-$C_3$ alkyl; and $R^{15}$ is $C_1$-$C_3$ alkyl, provided that:

(a) $X^4$ or $X^6$ is N; and (b) one or both of $R^{12}$ and $R^{13}$ are $C_1$-$C_3$ alkyl; or $R^{12}$ and $R^{13}$ are taken together with the atoms to which they are attached to form a cyclopropyl ring.

2. The compound of claim 1, or a pharmaceutically acceptable salt thereof, wherein $X^4$ is N.

3. The compound of claim 1, or a pharmaceutically acceptable salt thereof, wherein $X^4$ is $CR^4$; and $R^4$ is hydrogen or fluorine.

4. The compound of claim 1, or a pharmaceutically acceptable salt thereof, wherein $X^6$ is N.

5. The compound of claim 1, or a pharmaceutically acceptable salt thereof, wherein $R^{10}$ and $R^{11}$ are hydrogen.

6. The compound of claim 1, or a pharmaceutically acceptable salt thereof, wherein $R^{10}$ and $R^{11}$ are hydrogen; $X^4$ is N; and $R^5$ is —$OCH_3$.

7. The compound of claim 1, or a pharmaceutically acceptable salt thereof, wherein $R^{10}$ and $R^{11}$ are hydrogen; and $X^6$ is N.

8. The compound of claim 1, or a pharmaceutically acceptable salt thereof, wherein $R^{10}$ and $R^{11}$ are hydrogen; $X^6$ is N; and $R^5$ is —$OCH_3$.

9. The compound of claim 1, or a pharmaceutically acceptable salt thereof, wherein $R^{12}$ is hydrogen; and $R^{13}$ is $CH_3$.

10. The compound of claim 1, or a pharmaceutically acceptable salt thereof, wherein $R^{12}$ is hydrogen; $R^{13}$ is $CH_3$; $X^4$ is N; and $R^5$ is —$OCH_3$.

11. The compound of claim 1, or a pharmaceutically acceptable salt thereof, wherein $R^{12}$ and $R^{13}$ are $CH_3$.

12. The compound of claim 1, or a pharmaceutically acceptable salt thereof, wherein $R^{12}$ and $R^{13}$ are taken together with the atoms to which they are attached to form a cyclopropyl ring.

13. The compound of claim 1, or a pharmaceutically acceptable salt thereof, wherein $R^{14}$ is hydrogen and $R^{15}$ is —$CH_3$.

14. The compound of claim 1, or a pharmaceutically acceptable salt thereof, wherein $R^{14}$ and $R^{15}$ are —$CH_3$.

15. The compound of claim 1, or a pharmaceutically acceptable salt thereof, wherein the compound is:

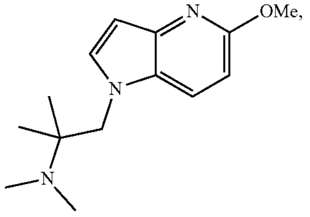

-continued
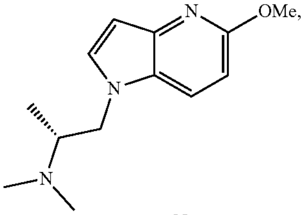
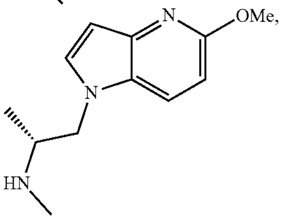
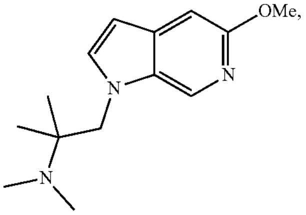
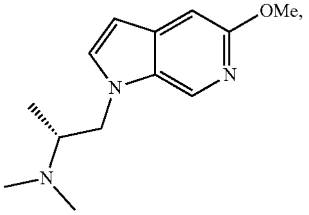
or
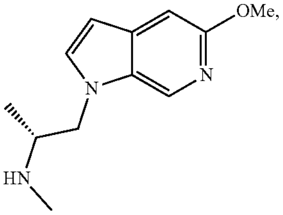
or a pharmaceutically acceptable salt or thereof.
16. A pharmaceutical composition comprising a compound of claim 1, or a pharmaceutically acceptable salt thereof, and at least one pharmaceutically acceptable excipient.
* * * * *